(12) United States Patent
Cashman

(10) Patent No.: US 7,887,803 B2
(45) Date of Patent: Feb. 15, 2011

(54) METHODS AND COMPOSITIONS TO TREAT MISFOLDED-SOD1 MEDIATED DISEASES

(75) Inventor: Neil R. Cashman, Vancouver (CA)

(73) Assignee: Amorfix Life Sciences, Mississauga, Ontario (CA)

( * ) Notice: Subject to any disclaimer, the term of this patent is extended or adjusted under 35 U.S.C. 154(b) by 357 days.

(21) Appl. No.: 11/850,502

(22) Filed: Sep. 5, 2007

(65) Prior Publication Data

US 2008/0206251 A1 Aug. 28, 2008

Related U.S. Application Data

(63) Continuation-in-part of application No. 11/682,217, filed on Mar. 5, 2007, which is a continuation-in-part of application No. 11/565,967, filed on Dec. 1, 2006, now Pat. No. 7,794,692, said application No. 11/682,217 and a continuation-in-part of application No. 11/367,609, filed on Mar. 3, 2006, now Pat. No. 7,439,324.

(60) Provisional application No. 60/741,462, filed on Dec. 2, 2005, provisional application No. 60/798,727, filed on May 9, 2006, provisional application No. 60/798,728, filed on May 9, 2006, provisional application No. 60/778,379, filed on Mar. 3, 2006.

(51) Int. Cl.
    A61K 39/395 (2006.01)
    A61K 35/30 (2006.01)
    C07K 16/00 (2006.01)

(52) U.S. Cl. .................. 424/139.1; 514/18.2; 530/387.1
(58) Field of Classification Search ........................ None
    See application file for complete search history.

(56) References Cited

U.S. PATENT DOCUMENTS

| | | | |
|---|---|---|---|
| 4,806,627 | A | 2/1989 | Wisniewski et al. |
| 4,910,133 | A | 3/1990 | Uda et al. |
| 4,940,659 | A | 7/1990 | Warrington et al. |
| 5,834,457 | A | 11/1998 | Bredesen et al. |
| 5,849,290 | A | 12/1998 | Brown et al. |
| 6,270,954 | B1 | 8/2001 | Welch et al. |
| 6,406,864 | B2 | 6/2002 | Prusiner et al. |
| 6,541,195 | B2 | 4/2003 | Welch et al. |
| 6,677,125 | B2 | 1/2004 | Prusiner et al. |
| 6,743,771 | B2 | 6/2004 | Douglas et al. |
| 6,765,088 | B1 | 7/2004 | Korth et al. |
| 7,041,807 | B1 | 5/2006 | Cashman et al. |
| 7,439,324 | B2 | 10/2008 | Cashman |
| 7,510,430 | B2 | 3/2009 | Zhang et al. |
| 2002/0123072 | A1 | 9/2002 | Prusiner et al. |
| 2003/0022243 | A1 | 1/2003 | Kondejewski et al. |
| 2006/0194821 | A1 | 8/2006 | Lansbury et al. |
| 2006/0211079 | A1 | 9/2006 | Hazen et al. |
| 2006/0280733 | A1 | 12/2006 | Kayed et al. |
| 2007/0003977 | A1 | 1/2007 | Cashman et al. |
| 2007/0292410 | A1 | 12/2007 | Cashman et al. |
| 2008/0132685 | A1 | 6/2008 | Chakrabartty et al. |

FOREIGN PATENT DOCUMENTS

| | | |
|---|---|---|
| AU | 2004266324 | 8/2004 |
| CA | 2408762 | 4/2003 |
| CA | 2452946 | 6/2004 |
| CA | 2437999 | 2/2005 |
| CA | 2536305 | 3/2005 |
| CA | 2642848 | 3/2007 |
| EP | 04761667.7 A1 | 6/2006 |
| EP | 07710682.1 | 5/2007 |

(Continued)

OTHER PUBLICATIONS

Kabashi et al. Annals of Neurology, 62(6): 553-559, Dec. 2007.*

(Continued)

*Primary Examiner*—Lorraine Spector
*Assistant Examiner*—Stacey MacFarlane
(74) *Attorney, Agent, or Firm*—Bereskin & Parr LLP; Noel Courage; Carmela DeLuca

(57) ABSTRACT

The invention provides a method for treating a medical condition, disease, or disorder mediated by a misfolded form of superoxide dismutase (SOD) in a subject in need of treatment. The method optionally comprises administering to the subject a composition comprising a pharmaceutically acceptable vehicle and an agent selected from (1) an exogenous antibody or fragment thereof that binds selectively to the misfolded form of SOD, and/or (2) an immunogen that elicits production of an endogenous antibody that binds selectively to the misfolded form of SOD, and/or (3) a nucleic acid sequence encoding (1) or (2). In certain embodiments, the invention provides methods of treating diseases such as Alzheimer's Disease, Parkinson's Disease or amyotrophic lateral sclerosis and macular degeneration, glaucoma, ischemia, cerebral infarction, myocardial infarction, atherosclerosis, multiple sclerosis, inflammatory bowel disease, ulcerative colitis, Crohn's disease or necrotizing enterocolitis using disease-specific epitopes, and compositions including these epitopes. The invention also provides antibodies that bind to monomeric or misfolded SOD1, and not on the molecular surface of native homodimeric SOD1. In addition, the invention includes methods of diagnosing Alzheimer's Disease, Parkinson's Disease or amyotrophic lateral sclerosis in a subject. Also, the invention provides methods of identifying substances for the treatment or prevention of Alzheimer's Disease, Parkinson's Disease or amyotrophic lateral sclerosis and kits using the binding proteins of the invention.

11 Claims, 10 Drawing Sheets

FOREIGN PATENT DOCUMENTS

| | | |
|---|---|---|
| JP | 2006-523496 | 8/2004 |
| WO | WO 00/12718 | 3/2000 |
| WO | WO00/22438 A1 | 4/2000 |
| WO | WO00/78344 A1 | 12/2000 |
| WO | WO01/06989 A2 | 2/2001 |
| WO | WO 2004/024090 | 3/2004 |
| WO | WO 2005/019828 | 3/2005 |
| WO | WO 2005/077040 | 8/2005 |
| WO | WO 2007/025385 | 3/2007 |
| WO | WO 2007/067900 | 6/2007 |
| WO | WO2007/098607 A1 | 9/2007 |

OTHER PUBLICATIONS

Le Pecheur et al., FEBS Letters, 579(17): 3613-3618, 2005.*
Haenggeli et al., Neurobiology of Disease, 26:146-152, 2007.*
Kayed, R. et al.; Common Structure of Soluble Amyloid Oligomers Implies Common Mechanism of Pathogenesis; Science, Apr. 18, 2003, p. 486-489, vol. 300; AAAS, New York, USA.
Rakhit, R. et al.; Monomeric Cu,Zn-superoxide Dismutase Is a Common Misfolding Intermediate in the Oxidation Models of Sporadic and Familial ALS; JBC, Apr. 9, 2004, p. 15499-15504, vol. 279, No. 15; ASBMB, Bethesda, USA.
Paramithiotis, E. et al.; A prion protein epitope selective for the pathologically misfolded conformation; Nature Medicine, Jul. 2003, vol. 9, No. 7; NPG, London, UK.
Kim, J.S.M. and Cashman, N.R.; Non-Specific Binding of Aggregated SOD1 to Antibodies. Abstract for Poster Presentation presented at the 15$^{th}$ International Symposium on ALS/MND, Dec. 2-4, 2004, Philadelphia, U.S.A. and published in ALS and other Motor Neuron Disorders 2004 (suppl 2) pp. 83-84 (Abstract p41).
Chakrabartty, Avijit.; Oxidation-induced misfolding monomerization and aggregation of SOD1 and its role in ALS, Slides and abstract, presented at the 15$^{th}$ International Symposium on ALS/MND, Dec. 2-4, 2004, Philadelphia, U.S.A. and abstract published in ALS and other Motor Neuron Disorders 2004 (suppl 2) 48-49 (Abstract c72.).
Deng, et al.: Amyotrophic lateral sclerosis and structural defects in Cu,Zn superoxide dismutase; Science, Aug. 20, 1993, pp. 1047-1051, vol. 261. AAAS, New York, U.S.A.
Rakhit, R., et al.; Oxidation-induced misfolding and aggregation of superoxide dismutase and its implications for amyotrophic lateral sclerosis. J Biol Chem. Dec. 6, 2002, pp. 47551-47556, vol. 277, No. 49. ASBMB, Bethesda, U.S.A.
Khare, et al.; Sequence and structural determinants of Cu, Zn superoxide dismutase aggregation. Proteins. Nov. 15, 2005, pp. 617-632, vol. 61, No. 3. Wiley-Liss, New York, U.S.A.
Elam J.S., et al.; Amyloid-like filaments and water-filled nanotubes formed by SOD1 mutant proteins linked to familial ALS. Nature Struct. Biol. Jun. 2003, pp. 461-467, vol. 10, No. 6. Nature Pub. Co., New York, U.S.A.
Bolton, et al.; Molecular location of a Species-specific epitope on the hampster scrapie agent protein, J. of Virology, Jul. 1991, pp. 3667-3675, vol. 65, No. 7.
Safar, et al.; Measuring prions causing bovine spongiform enecephalopathy or chronic wasting disease by immunoassays and transgenic mice, Natural Biotechnol. Nov. 2002, pp. 1147-1150, vol. 20, No. 11.
Choi, et al.; Oxidative modifications and Aggregation of Cu, Zn-superoxide dismutase associated with Alzheimer and Parkinson diseases. The Journal of Biological Chemistry. Mar. 25, 2005. pp. 11648-11655, vol. 280, No. 12. Published online Jan. 19, 2005.
Pardo, Carlos, et al. "Superoxide dismutase is an abundant component in cell bodies, dendrites, and axons of motor neurons and in a subset of other neurons", Proc. Natl. Acad. Sci., Feb. 1995, vol. 92, pp. 954-958.
Urushitani, et al.; Chromogranin-mediated secretion of mutant superoxide dismutase proteins linked to amyotrophic lateral sclerosis. Nature Neurosci. Jan. 2006, pp. 108-118, vol. 9, No. 1. Nature Publishing Group, New York, U.S.A.
Sendtner, M.; Damaging secretions: chromogranins team up with mutant SOD1. Nature Neurosci. Jan. 2006, pp. 12-14, vol. 9, No. 1. Nature Publishing Group, New York, U.S.A.
McCaffrey, P.; SOD1 mutant protein gets loose in ALS. Lancet Neurology, Feb. 2006, p. 119, vol. 5, No. 2. Lancet Publishing Gropup, New York, U.S.A.
Deng H.X., et al.; Conversion to the amyotrophic lateral sclerosis phenotype is associated with intermolecular linked insoluble aggregates of SOD1 in mitochondria. Proc. Natl. Acad. Sci., May 2, 2006, pp. 7142-7147, vol. 103, No. 18. National Academy of Sciences, D.C, U.S.A.
Furukawa Y, et al.; Disulfide cross-linked protein represents a significant fraction of ALS-associated Cu, Zn-superoxide dismutase aggregates in spinal cords of model mice. Proc. Natl. Acad. Sci. May 2, 2006, pp. 7148-7153, vol. 103, No. 18. National Academy of Sciences, D.C, U.S.A.
Soto, C.; Diagnosing prion diseases: needs, challenges and hopes, Nature Rev. Microbial., Oct. 2004, pp. 809-819, vol. 2, No. 10.
Urushitani et al; Therapeutic effects of immunization with mutant superoxide dismutase in mice models of amyotrophic lateral sclerosis, Proc. Natl. Acad. Sci., Feb. 13, 2007, pp. 2495-2500, vol. 104, No. 7. National Academy of Sciences, D.C., U.S.A.
Lehto, et al.; Peroxynitrite as a probe for the structure of normal and misfolded prion protein, poster and abstract presented at the Society for Neuroscience 32$^{nd}$ Annual Meeting, Nov. 2-7, 2002, Orlando, Florida.
Griffin, et al; Isomorphic recruitment of superoxide dismutase in amyotrophic lateral sclerosis, Poster presented at the 13$^{th}$ International Symposium on ALS/MND, Nov. 2002.
Jonsson et al; Minute quantities of misfolded mutant superoxide dismutase-1 cause amyotrophic lateral sclerosis. Brain Jan. 2004, vol. 127, pp. 73-88. Oxford University Press, England.
Kalnine, N. et al.; UniProt Accession No. Q6NR8. Superoxide dismutase 1. [online] May 10, 2005.
Gelinas, D.S. et al.; Immunotherapy for Alzheimer's disease. Proceedings for the National Academy of Sciences of the United States of America. Oct. 5, 2004. vol. 101, Suppl. 2, pp. 14657-14662.
Griffin and Cashman.; Progress in prion vaccines and immunotherapies. Expert Opinion on Biological Therapies. Jan. 6, 2005. vol. 5, No. 1, pp. 97-110.
Rakhit R, et al. An Immunological epitope selective for pathological monomer-misfolded SOD1 in ALS, nature medicine Jun. 2007, vol. 13, No. 6, pp. 754-759.
Liu, et al., Lack of evidence of monomer/misfolded superoxide dismutase-1 in sporadic amyotrophic lateral sclerosis. Ann. Neurol., 66:75-80, 2009.
Gruzman et al., Common molecular signature in SOD1 for both sporadic and familial amyotrophic lateral sclerosis, PNAS, Jul. 24, 2007, 104(30): 12524-12529.
Jacobsson et al., Brain, 124:1461, 2001.
Urushitani et al.,The endoplasmic reticulum-Golgi pathway is a target for translocation and aggregation of mutant superoxide dismutes linked to ASL, The FASEB Journal vol. 22, pp. 2476-2487, Jul. 2008.
Brettschneider et al., Axonal damage markers in cerebrospinal fluid are increased in ALS, Neurology, 2006, May 2008, 66(6): 852-6.
Ezzi et al., Wild—type superoxide dismutase acquires binding and toxic properties of ALS-linked mutant forms through oxidation, J Neurochem, Jul. 2007; 102, 107-178.
Burgess et al., Possible Dissociation of the Herapin-binding and Mitogenic Activities of Heparin-bidning (Acid Fibroplast) Growth-Factor-1 from Its Receptor-binding Activities by Site-directed Mutagenesis of a Single Lysine Residue, The Journalof. Cell Bioology 1990, 111:2129-2138.
Bowie et al., Deciphering the Message in Protein Sequences: Tolerance to Amino Acid Substitutions, Science, 1990, 247:1306-1310.
Pawson et al., Assembly of Cell Regulatory Systems Through Protein Interaction Domains, 2003, Science 300:445-452.
Kim et al.; Aggregation of Alfa-Synclucein induced by the Cu,Zn-Superoxide dismutase and hydrogen peroxide system, Free Rad Biol. Med. 2002. 32:544-550.
Product No. S-2147 Product Information Sheet [online] published 1996-08.

UniProtKB/Swiss-Prot entry P00441, SODC_HUMAN, Jul. 21, 1986.

Harris et al., Keyhole limpet hemocyanin (KLH): a biomedical review, Micron, Dec. 1999, 30: 597-623.

Johnston et al., Formation of high molecular weight complexes of mutant Cu, Zn-superoxide dismutase in a mouse model for familial amyotrophic lateral sclerosis, PNAS, Nov. 2000, 97(23): 12571-12576.

Kunst et al., Mutations in SOD1 associated with amyotrophic lateral sclerosis cause novel; protein interactions, Nature Genetics, Jan. 1997,15:91-94.

Julien, Mouse models of amyotrophic lateral sclerosis, Elsevier Disease Models, 2006, 3(4): 331-339.

Goodall E.F. et al., Amyotrophic later sclerosis (motor neuron disease): proposed mechanism and pathways to treatment, Expert Reviews in Molecular Reviews, 2006, 8(11): 1-24.

Valentine J.S. et al, Copper-Zinc Superoxide dismutase and amytrophoc lateral sclerosis, Annual Rev. Biochem. 2005, 74: 563-593.

Watanabe et al., Adherent Monomer-Misfolded SOD1, PLos One, Oct. 2008; vol. 3, issue 10, e:3497.

Kerman A, et al., P163 Investigation of CuZn superoxide dismutase misfolding and aggregation in ALS using conformation-specific antibodies. Amyotrophic Lateral Sclerosis 2007 (Suppl 1); 8:156-177, Abstract p. 164.

Liu H.S. et al., P139 An immunization strategy for treating amyotrphic lateral sclerosis that targets misfolded SOD1, Amyotrophic Lateral Sclerosis 2007 (Suppl 1); 8:140-155, Abstract p. 150.

Session 7A protein folding and degradation effects: Function of the proteasome in cell regulation and neuromuscular disease, Amytrophic Lateral Sclerosis, 2005, 6: 33-35.

Bruijn L. et al, ALS-linked SOD1 mutant G85R mediates damage to astrocytes and promotes rapidly progressive disease with SOD1-containg inclusions, Neuron 1997, vol. 18(2): 327-338.

Otvos et al. Curr. Protein Pept. Sci. Dec. 2002; 3:643-52.

* cited by examiner

A

B

C

D

E

F

A                                B

1: 10ug G93A mouse brain homogenate
2: 10ug WT mouse brain homogenate
3: 100ng hSOD1

SEQUENCE LISTING

<160> NUMBER OF SEQ ID NOS: 80

<210> SEQ ID NO 1
<211> LENGTH: 9
<212> TYPE: PRT
<213> ORGANISM: Homo sapiens

<400> SEQUENCE: 1

Arg Leu Ala Cys Gly Val Ile Gly Ile
1               5

<210> SEQ ID NO 2
<211> LENGTH: 18
<212> TYPE: PRT
<213> ORGANISM: Homo sapiens

<400> SEQUENCE: 2

Asp Leu Gly Lys Gly Gly Asn Glu Glu Ser Thr Lys Thr Gly Asn Ala
1               5                   10                  15

Gly Ser

<210> SEQ ID NO 3
<211> LENGTH: 14
<212> TYPE: PRT
<213> ORGANISM: Homo sapiens

<400> SEQUENCE: 3

Asn Pro Leu Ser Arg Lys His Gly Gly Pro Lys Asp Glu Glu
1               5                   10

```
<210> SEQ ID NO 4
<211> LENGTH: 7
<212> TYPE: PRT
<213> ORGANISM: Homo sapiens

<400> SEQUENCE: 4

Lys Ala Val Cys Val Leu Lys
1               5

<210> SEQ ID NO 5
<211> LENGTH: 11
<212> TYPE: PRT
<213> ORGANISM: Homo sapiens

<400> SEQUENCE: 5

Ile Lys Gly Leu Thr Glu Gly Leu His Gly Phe
1               5                   10

<210> SEQ ID NO 6
<211> LENGTH: 11
<212> TYPE: PRT
<213> ORGANISM: Homo sapiens

<400> SEQUENCE: 6

His Cys Ile Ile Gly Arg Thr Leu Val Val His
1               5                   10

<210> SEQ ID NO 7
<211> LENGTH: 8
<212> TYPE: PRT
<213> ORGANISM: Homo sapiens

<400> SEQUENCE: 7

Gly Leu His Gly Phe His Val His
1               5

<210> SEQ ID NO 8
<211> LENGTH: 9
<212> TYPE: PRT
<213> ORGANISM: Homo sapiens
<220> FEATURE:
<221> NAME/KEY: MISC_FEATURE
<222> LOCATION: (4)..(4)
<223> OTHER INFORMATION: Cysteine oxidized to cysteic acid

<400> SEQUENCE: 8

Arg Leu Ala Cys Gly Val Ile Gly Ile
1               5

<210> SEQ ID NO 9
<211> LENGTH: 7
<212> TYPE: PRT
<213> ORGANISM: Homo sapiens

<400> SEQUENCE: 9

Ala Cys Gly Val Ile Gly Ile
1               5

<210> SEQ ID NO 10
<211> LENGTH: 14
<212> TYPE: PRT
<213> ORGANISM: Homo sapiens
<220> FEATURE:
<221> NAME/KEY: MOD_RES
<222> LOCATION: (1)..(1)
<223> OTHER INFORMATION: ACETYLATION
```

```
<400> SEQUENCE: 10

Gly Gly Arg Leu Ala Cys Gly Val Ile Gly Gly Lys Gly
1               5                   10

<210> SEQ ID NO 11
<211> LENGTH: 19
<212> TYPE: PRT
<213> ORGANISM: Homo sapiens

<400> SEQUENCE: 11

Cys Asp Leu Gly Lys Gly Gly Asn Glu Glu Ser Thr Lys Thr Gly Asn
1               5                   10                  15

Ala Gly Ser

<210> SEQ ID NO 12
<211> LENGTH: 15
<212> TYPE: PRT
<213> ORGANISM: Homo sapiens

<400> SEQUENCE: 12

Cys Asn Pro Leu Ser Arg Lys His Gly Gly Pro Lys Asp Glu Glu
1               5                   10                  15

<210> SEQ ID NO 13
<211> LENGTH: 7
<212> TYPE: PRT
<213> ORGANISM: Homo sapiens
<220> FEATURE:
<221> NAME/KEY: MISC_FEATURE
<222> LOCATION: (2)..(2)
<223> OTHER INFORMATION: Cysteine oxidized to cysteic acid

<400> SEQUENCE: 13

Ala Cys Gly Val Ile Gly Ile
1               5

<210> SEQ ID NO 14
<211> LENGTH: 12
<212> TYPE: PRT
<213> ORGANISM: Homo sapiens

<400> SEQUENCE: 14

Cys Ile Lys Gly Leu Thr Glu Gly Leu His Gly Phe
1               5                   10

<210> SEQ ID NO 15
<211> LENGTH: 16
<212> TYPE: PRT
<213> ORGANISM: Homo sapiens
<220> FEATURE:
<221> NAME/KEY: MISC_FEATURE
<222> LOCATION: (8)..(8)
<223> OTHER INFORMATION: Cysteine oxidized to cysteic acid

<400> SEQUENCE: 15

Cys Gly Gly Gly Arg Leu Ala Cys Gly Val Ile Gly Ile Gly Ser Gly
1               5                   10                  15

<210> SEQ ID NO 16
<211> LENGTH: 9
<212> TYPE: PRT
<213> ORGANISM: Homo sapiens

<400> SEQUENCE: 16
```

```
Gly Ser Gly Lys Ala Val Cys Leu Lys
1               5
```

<210> SEQ ID NO 17
<211> LENGTH: 154
<212> TYPE: PRT
<213> ORGANISM: Homo sapiens

<400> SEQUENCE: 17

```
Met Ala Thr Lys Ala Val Cys Val Leu Lys Gly Asp Gly Pro Val Gln
1               5                   10                  15

Gly Ile Ile Asn Phe Glu Gln Lys Glu Ser Asn Gly Pro Val Lys Val
            20                  25                  30

Trp Gly Ser Ile Lys Gly Leu Thr Glu Gly Leu His Gly Phe His Val
        35                  40                  45

His Glu Phe Gly Asp Asn Thr Ala Gly Cys Thr Ser Ala Gly Pro His
    50                  55                  60

Phe Asn Pro Leu Ser Arg Lys His Gly Pro Lys Asp Glu Glu Arg
65                  70                  75                  80

His Val Gly Asp Leu Gly Asn Val Thr Ala Asp Lys Asp Gly Val Ala
                85                  90                  95

Asp Val Ser Ile Glu Asp Ser Val Ile Ser Leu Ser Gly Asp His Cys
            100                 105                 110

Ile Ile Gly Arg Thr Leu Val Val His Glu Lys Ala Asp Asp Leu Gly
        115                 120                 125

Lys Gly Gly Asn Glu Glu Ser Thr Lys Thr Gly Asn Ala Gly Ser Arg
    130                 135                 140

Leu Ala Cys Gly Val Ile Gly Ile Ala Gln
145                 150
```

<210> SEQ ID NO 18
<211> LENGTH: 981
<212> TYPE: DNA
<213> ORGANISM: Homo sapiens

<400> SEQUENCE: 18

```
gtttggggcc agagtgggcg aggcgcggag gtctggccta taaagtagtc gcggagacgg    60
ggtgctggtt tgcgtcgtag tctcctgcag cgtctggggt ttccgttgca gtcctcggaa   120
ccaggacctc ggcgtggcct agcgagttat ggcgacgaag gccgtgtgcg tgctgaaggg   180
cgacggccca gtgcagggca tcatcaattt cgagcagaag gaaagtaatg gaccagtgaa   240
ggtgtgggga agcattaaag gactgactga aggcctgcat ggattccatg ttcatgagtt   300
tggagataat acagcaggct gtaccagtgc aggtcctcac tttaatcctc tatccagaaa   360
acacggtggg ccaaaggatg aagagaggca tgttggagac ttgggcaatg tgactgctga   420
caaagatggt gtggccgatg tgtctattga agattctgtg atctcactct caggagacca   480
ttgcatcatt ggccgcacac tggtggtcca tgaaaaagca gatgacttgg gcaaaggtgg   540
aaatgaagaa agtacaaaga caggaaacgc tggaagtcgt ttggcttgtg gtgtaattgg   600
gatcgcccaa taaacattcc cttggatgta gtctgaggcc ccttaactca tctgttatcc   660
tgctagctgt agaaatgtat cctgataaac attaaacact gtaatcttaa aagtgtaatt   720
gtgtgacttt ttcagagttg ctttaaagta cctgtagtga gaaactgatt tatgatcact   780
tggaagattt gtatagtttt ataaaactca gttaaaatgt ctgtttcaat gacctgtatt   840
ttgccagact taaatcacag atgggtatta aacttgtcag aatttctttg tcattcaagc   900
```

```
ctgtgaataa aaaccctgta tggcacttat tatgaggcta ttaaaagaat ccaaattcaa    960
actaaaaaaa aaaaaaaaaa a                                              981
```

<210> SEQ ID NO 19
<211> LENGTH: 27
<212> TYPE: DNA
<213> ORGANISM: Homo sapiens

<400> SEQUENCE: 19

```
agguuagcuu gugguguuau agguaua                                         27
```

<210> SEQ ID NO 20
<211> LENGTH: 54
<212> TYPE: DNA
<213> ORGANISM: Homo sapiens

<400> SEQUENCE: 20

```
gauuuaggua aaggugguaa ugaagaaagu acuaaaacug guaaugcugg uagu           54
```

<210> SEQ ID NO 21
<211> LENGTH: 42
<212> TYPE: DNA
<213> ORGANISM: Homo sapiens

<400> SEQUENCE: 21

```
aauccuuuaa gucguaaaca cggaggaccg aaggacgagg ag                        42
```

<210> SEQ ID NO 22
<211> LENGTH: 33
<212> TYPE: DNA
<213> ORGANISM: Homo sapiens

<400> SEQUENCE: 22

```
auaaagggga aaacagaagg acuccacggc uuu                                  33
```

<210> SEQ ID NO 23
<211> LENGTH: 33
<212> TYPE: DNA
<213> ORGANISM: Homo sapiens

<400> SEQUENCE: 23

```
cacuguauua uuggcaggac ccucguuguu cac                                  33
```

<210> SEQ ID NO 24
<211> LENGTH: 27
<212> TYPE: DNA
<213> ORGANISM: Homo sapiens

<400> SEQUENCE: 24

```
cguuuggcuu gugguguaau ugggauc                                         27
```

<210> SEQ ID NO 25
<211> LENGTH: 21
<212> TYPE: DNA
<213> ORGANISM: Homo sapiens

<400> SEQUENCE: 25

```
gcuuguggug uaauugggau c                                               21
```

<210> SEQ ID NO 26
<211> LENGTH: 54
<212> TYPE: DNA
<213> ORGANISM: Homo sapiens

```
<400> SEQUENCE: 26
gacuugggca aaggugaaaa ugaagaaagu acaaagacag gaaacgcugg aagu        54

<210> SEQ ID NO 27
<211> LENGTH: 42
<212> TYPE: DNA
<213> ORGANISM: Homo sapiens

<400> SEQUENCE: 27
aauccucuau ccagaaaaca cgguggggcca aaggaugaag ag                    42

<210> SEQ ID NO 28
<211> LENGTH: 21
<212> TYPE: DNA
<213> ORGANISM: Homo sapiens

<400> SEQUENCE: 28
aaggccgugu gcgugcugaa g                                            21

<210> SEQ ID NO 29
<211> LENGTH: 33
<212> TYPE: DNA
<213> ORGANISM: Homo sapiens

<400> SEQUENCE: 29
auuaaaggac ugacugaagg ccugcaugga uuc                               33

<210> SEQ ID NO 30
<211> LENGTH: 33
<212> TYPE: DNA
<213> ORGANISM: Homo sapiens

<400> SEQUENCE: 30
cauugcauca uuggccgcac acuggugguc cau                               33

<210> SEQ ID NO 31
<211> LENGTH: 24
<212> TYPE: DNA
<213> ORGANISM: Homo sapiens

<400> SEQUENCE: 31
ggccugcaug gauuccaugu ucau                                         24

<210> SEQ ID NO 32
<211> LENGTH: 3
<212> TYPE: PRT
<213> ORGANISM: Artificial Sequence
<220> FEATURE:
<223> OTHER INFORMATION: Synthetic Construct - Flanking sequence

<400> SEQUENCE: 32

Gly Ser Gly
1

<210> SEQ ID NO 33
<211> LENGTH: 4
<212> TYPE: PRT
<213> ORGANISM: Artificial Sequence
<220> FEATURE:
<223> OTHER INFORMATION: Synthetic Construct - Flanking sequence

<400> SEQUENCE: 33

Gly Gly Lys Gly
```

-continued

```
<210> SEQ ID NO 34
<211> LENGTH: 16
<212> TYPE: PRT
<213> ORGANISM: Artificial sequence
<220> FEATURE:
<223> OTHER INFORMATION: Synthetic Construct - DSE analog
<220> FEATURE:
<221> NAME/KEY: MISC_FEATURE
<222> LOCATION: (1)..(1)
<223> OTHER INFORMATION: Xaa=G or acetyl G

<400> SEQUENCE: 34

Xaa Gly Gly Arg Leu Ala Cys Gly Val Ile Gly Ile Gly Gly Lys Gly
1               5                   10                  15

<210> SEQ ID NO 35
<211> LENGTH: 13
<212> TYPE: PRT
<213> ORGANISM: Artificial Sequence
<220> FEATURE:
<223> OTHER INFORMATION: Synthetic Construct - DSE analog

<400> SEQUENCE: 35

Gly Gly Arg Leu Ala Cys Gly Val Ile Gly Ile Ala Gln
1               5                   10

<210> SEQ ID NO 36
<211> LENGTH: 15
<212> TYPE: PRT
<213> ORGANISM: Artificial Sequence
<220> FEATURE:
<223> OTHER INFORMATION: Synthetic Construct - DSE analog
<220> FEATURE:
<221> NAME/KEY: MISC_FEATURE
<222> LOCATION: (1)..(1)
<223> OTHER INFORMATION: Xaa=acetyl G when G at position 2 is present;
      or G; or absent
<220> FEATURE:
<221> NAME/KEY: MISC_FEATURE
<222> LOCATION: (2)..(2)
<223> OTHER INFORMATION: Xaa=G or absent
<220> FEATURE:
<221> NAME/KEY: MISC_FEATURE
<222> LOCATION: (3)..(3)
<223> OTHER INFORMATION: Xaa=R or absent
<220> FEATURE:
<221> NAME/KEY: MISC_FEATURE
<222> LOCATION: (4)..(4)
<223> OTHER INFORMATION: Xaa=L; or absent when R at position 3 is absent
<220> FEATURE:
<221> NAME/KEY: MISC_FEATURE
<222> LOCATION: (12)..(13)
<223> OTHER INFORMATION: Xaa=G; or upto 2 residues may be absent
<220> FEATURE:
<221> NAME/KEY: MISC_FEATURE
<222> LOCATION: (14)..(14)
<223> OTHER INFORMATION: Xaa=K when G is present at position 12 and 13;
      or absent when G at position 15 is absent
<220> FEATURE:
<221> NAME/KEY: MISC_FEATURE
<222> LOCATION: (15)..(15)
<223> OTHER INFORMATION: Xaa=G when K at position 14 is present; or
      absent

<400> SEQUENCE: 36

Xaa Xaa Xaa Xaa Ala Cys Gly Val Ile Gly Ile Xaa Xaa Xaa Xaa
1               5                   10                  15

<210> SEQ ID NO 37
<211> LENGTH: 15
```

```
<212> TYPE: PRT
<213> ORGANISM: Artificial Sequence
<220> FEATURE:
<223> OTHER INFORMATION: Synthetic Construct - DSE analog
<220> FEATURE:
<221> NAME/KEY: MISC_FEATURE
<222> LOCATION: (1)..(1)
<223> OTHER INFORMATION: Xaa=acetyl G when G at position 2 is present;
      or G; or absent
<220> FEATURE:
<221> NAME/KEY: MISC_FEATURE
<222> LOCATION: (2)..(2)
<223> OTHER INFORMATION: Xaa=G; or absent
<220> FEATURE:
<221> NAME/KEY: MISC_FEATURE
<222> LOCATION: (3)..(3)
<223> OTHER INFORMATION: Xaa=R; or absent
<220> FEATURE:
<221> NAME/KEY: MISC_FEATURE
<222> LOCATION: (4)..(4)
<223> OTHER INFORMATION: Xaa=L; or absent when R at position 3 is absent
<220> FEATURE:
<221> NAME/KEY: MISC_FEATURE
<222> LOCATION: (6)..(6)
<223> OTHER INFORMATION: Cysteine oxidized to cysteic acid
<220> FEATURE:
<221> NAME/KEY: MISC_FEATURE
<222> LOCATION: (12)..(13)
<223> OTHER INFORMATION: Xaa= G; or upto 2 residues may be absent
<220> FEATURE:
<221> NAME/KEY: MISC_FEATURE
<222> LOCATION: (14)..(14)
<223> OTHER INFORMATION: Xaa= K when G is present at positions 12 and
      13; or absent when G at position 15 is absent
<220> FEATURE:
<221> NAME/KEY: MISC_FEATURE
<222> LOCATION: (15)..(15)
<223> OTHER INFORMATION: Xaa= G when K at position 14 is present; or
      absent

<400> SEQUENCE: 37

Xaa Xaa Xaa Xaa Ala Cys Gly Val Ile Gly Ile Xaa Xaa Xaa Xaa
1               5                   10                  15

<210> SEQ ID NO 38
<211> LENGTH: 14
<212> TYPE: PRT
<213> ORGANISM: Artificial Sequence
<220> FEATURE:
<223> OTHER INFORMATION: Synthetic Construct - DSE analog
<220> FEATURE:
<221> NAME/KEY: MOD_RES
<222> LOCATION: (1)..(1)
<223> OTHER INFORMATION: ACETYLATION

<400> SEQUENCE: 38

Arg Leu Ala Cys Gly Val Ile Val Ile Val Gly Gly Lys Gly
1               5                   10

<210> SEQ ID NO 39
<211> LENGTH: 9
<212> TYPE: PRT
<213> ORGANISM: Artificial Sequence
<220> FEATURE:
<223> OTHER INFORMATION: Synthetic Construct - DSE analog
<220> FEATURE:
<221> NAME/KEY: MISC_FEATURE
<222> LOCATION: (2)..(2)
<223> OTHER INFORMATION: Cysteine oxidized to cysteic acid

<400> SEQUENCE: 39

Ala Cys Gly Val Ile Val Ile Val Gly
1               5
```

```
<210> SEQ ID NO 40
<211> LENGTH: 16
<212> TYPE: PRT
<213> ORGANISM: Artificial Sequence
<220> FEATURE:
<223> OTHER INFORMATION: Synthetic Construct - DSE analog
<220> FEATURE:
<221> NAME/KEY: MISC_FEATURE
<222> LOCATION: (8)..(8)
<223> OTHER INFORMATION: Cysteine oxidized to cysteic acid

<400> SEQUENCE: 40

Cys Gly Gly Gly Arg Leu Ala Cys Gly Val Ile Gly Ile Gly Ser Gly
1               5                   10                  15

<210> SEQ ID NO 41
<211> LENGTH: 12
<212> TYPE: PRT
<213> ORGANISM: Artificial Sequence
<220> FEATURE:
<223> OTHER INFORMATION: Synthetic Construct - DSE analog
<220> FEATURE:
<221> NAME/KEY: MISC_FEATURE
<222> LOCATION: (4)..(4)
<223> OTHER INFORMATION: Cysteine oxidized to cysteic acid

<400> SEQUENCE: 41

Arg Leu Ala Cys Gly Val Ile Gly Ile Gly Ser Gly
1               5                   10

<210> SEQ ID NO 42
<211> LENGTH: 13
<212> TYPE: PRT
<213> ORGANISM: Artificial Sequence
<220> FEATURE:
<223> OTHER INFORMATION: Synthetic Construct - DSE analog
<220> FEATURE:
<221> NAME/KEY: MISC_FEATURE
<222> LOCATION: (5)..(5)
<223> OTHER INFORMATION: Cysteine oxidized to cysteic acid

<400> SEQUENCE: 42

Cys Arg Leu Ala Cys Gly Val Ile Gly Ile Gly Ser Gly
1               5                   10

<210> SEQ ID NO 43
<211> LENGTH: 18
<212> TYPE: PRT
<213> ORGANISM: Artificial Sequence
<220> FEATURE:
<223> OTHER INFORMATION: Synthetic Construct - DSE Analog
<220> FEATURE:
<221> NAME/KEY: MISC_FEATURE
<222> LOCATION: (1)..(1)
<223> OTHER INFORMATION: Xaa=D; or absent
<220> FEATURE:
<221> NAME/KEY: MISC_FEATURE
<222> LOCATION: (2)..(2)
<223> OTHER INFORMATION: Xaa=L; or absent when D at position 1 is absent
<220> FEATURE:
<221> NAME/KEY: MISC_FEATURE
<222> LOCATION: (3)..(3)
<223> OTHER INFORMATION: Xaa=G; or absent when L at position 2 is absent
<220> FEATURE:
<221> NAME/KEY: MISC_FEATURE
<222> LOCATION: (4)..(4)
<223> OTHER INFORMATION: Xaa=K; or carbonylated K; or absent when G at
      position 3 is absent
<220> FEATURE:
<221> NAME/KEY: MISC_FEATURE
<222> LOCATION: (12)..(12)
<223> OTHER INFORMATION: Xaa=K; or carbonylated K
```

```
<220> FEATURE:
<221> NAME/KEY: MISC_FEATURE
<222> LOCATION: (15)..(15)
<223> OTHER INFORMATION: Xaa=N; or absent when A at position 16 is
      absent
<220> FEATURE:
<221> NAME/KEY: MISC_FEATURE
<222> LOCATION: (16)..(16)
<223> OTHER INFORMATION: Xaa=A; or absent when G at position 17 is
      absent
<220> FEATURE:
<221> NAME/KEY: MISC_FEATURE
<222> LOCATION: (17)..(17)
<223> OTHER INFORMATION: Xaa=G; or absent when S at position 18 is
      absent
<220> FEATURE:
<221> NAME/KEY: MISC_FEATURE
<222> LOCATION: (18)..(18)
<223> OTHER INFORMATION: Xaa=S; or absent

<400> SEQUENCE: 43

Xaa Xaa Xaa Xaa Gly Gly Asn Glu Glu Ser Thr Xaa Thr Gly Xaa Xaa
1               5                   10                  15

Xaa Xaa

<210> SEQ ID NO 44
<211> LENGTH: 24
<212> TYPE: PRT
<213> ORGANISM: Artificial Sequence
<220> FEATURE:
<223> OTHER INFORMATION: Synthetic Construct - DSE analog
<220> FEATURE:
<221> NAME/KEY: MISC_FEATURE
<222> LOCATION: (1)..(2)
<223> OTHER INFORMATION: Xaa=G; or upto 2 residues may be absent
<220> FEATURE:
<221> NAME/KEY: MISC_FEATURE
<222> LOCATION: (3)..(3)
<223> OTHER INFORMATION: Xaa=C; or G; or absent
<220> FEATURE:
<221> NAME/KEY: MISC_FEATURE
<222> LOCATION: (4)..(4)
<223> OTHER INFORMATION: Xaa=D when L at position 5 is present; or
      absent
<220> FEATURE:
<221> NAME/KEY: MISC_FEATURE
<222> LOCATION: (5)..(5)
<223> OTHER INFORMATION: Xaa=L when G at position 6 is present; or
      absent when D at position 4 is absent
<220> FEATURE:
<221> NAME/KEY: MISC_FEATURE
<222> LOCATION: (6)..(6)
<223> OTHER INFORMATION: Xaa=G when K at position 7 is present; or
      absent when L at position 5 is absent
<220> FEATURE:
<221> NAME/KEY: MISC_FEATURE
<222> LOCATION: (7)..(7)
<223> OTHER INFORMATION: Xaa=K; or carbonylated K; or absent when G at
      position 6 is absent
<220> FEATURE:
<221> NAME/KEY: MISC_FEATURE
<222> LOCATION: (15)..(15)
<223> OTHER INFORMATION: Xaa=K; or carbonylated K
<220> FEATURE:
<221> NAME/KEY: MISC_FEATURE
<222> LOCATION: (18)..(18)
<223> OTHER INFORMATION: Xaa=N; or absent when A at position 19 is
      absent
<220> FEATURE:
<221> NAME/KEY: MISC_FEATURE
<222> LOCATION: (19)..(19)
<223> OTHER INFORMATION: Xaa=A when N at position 18 is present; or
      absent when G at position 20 is absent
<220> FEATURE:
<221> NAME/KEY: MISC_FEATURE
<222> LOCATION: (20)..(20)
```

```
<223> OTHER INFORMATION: Xaa=G when A at position 19 is present; or
      absent when S at position 21 is absent
<220> FEATURE:
<221> NAME/KEY: MISC_FEATURE
<222> LOCATION: (21)..(21)
<223> OTHER INFORMATION: Xaa=S when G at position 20 is present; or
      absent
<220> FEATURE:
<221> NAME/KEY: MISC_FEATURE
<222> LOCATION: (22)..(22)
<223> OTHER INFORMATION: Xaa=G; or absent
<220> FEATURE:
<221> NAME/KEY: MISC_FEATURE
<222> LOCATION: (23)..(23)
<223> OTHER INFORMATION: Xaa=G when G at position 22 is present; or S
      when G at position 22 is present; or absent when G at position 24
      is absent
<220> FEATURE:
<221> NAME/KEY: MISC_FEATURE
<222> LOCATION: (24)..(24)
<223> OTHER INFORMATION: Xaa=G; or absent

<400> SEQUENCE: 44

Xaa Xaa Xaa Xaa Xaa Xaa Xaa Gly Gly Asn Glu Glu Ser Thr Xaa Thr
1               5                   10                  15

Gly Xaa Xaa Xaa Xaa Xaa Xaa Xaa
            20

<210> SEQ ID NO 45
<211> LENGTH: 19
<212> TYPE: PRT
<213> ORGANISM: Artificial Sequence
<220> FEATURE:
<223> OTHER INFORMATION: Synthetic Construct - DSE analog
<220> FEATURE:
<221> NAME/KEY: MISC_FEATURE
<222> LOCATION: (5)..(5)
<223> OTHER INFORMATION: Xaa=K; or cabonylated K
<220> FEATURE:
<221> NAME/KEY: MISC_FEATURE
<222> LOCATION: (13)..(13)
<223> OTHER INFORMATION: Xaa=K; or cabonylated K

<400> SEQUENCE: 45

Cys Asp Leu Gly Xaa Gly Gly Asn Glu Glu Ser Thr Xaa Thr Gly Asn
1               5                   10                  15

Ala Gly Ser

<210> SEQ ID NO 46
<211> LENGTH: 17
<212> TYPE: PRT
<213> ORGANISM: Homo sapiens
<220> FEATURE:
<221> NAME/KEY: MISC_FEATURE
<222> LOCATION: (3)..(3)
<223> OTHER INFORMATION: Xaa=K; or carbonylated K
<220> FEATURE:
<221> NAME/KEY: MISC_FEATURE
<222> LOCATION: (11)..(11)
<223> OTHER INFORMATION: Xaa=K; or carbonylated K

<400> SEQUENCE: 46

Leu Gly Xaa Gly Gly Asn Glu Glu Ser Thr Xaa Thr Gly Asn Ala Gly
1               5                   10                  15

Ser

<210> SEQ ID NO 47
<211> LENGTH: 17
<212> TYPE: PRT
<213> ORGANISM: Homo sapiens
```

```
-continued

<220> FEATURE:
<221> NAME/KEY: MISC_FEATURE
<222> LOCATION: (4)..(4)
<223> OTHER INFORMATION: Xaa=K; or cabonylated K
<220> FEATURE:
<221> NAME/KEY: MISC_FEATURE
<222> LOCATION: (12)..(12)
<223> OTHER INFORMATION: Xaa=K; or cabonylated K

<400> SEQUENCE: 47

Asp Leu Gly Xaa Gly Gly Asn Glu Glu Ser Thr Xaa Thr Gly Asn Ala
1               5                   10                  15

Gly

<210> SEQ ID NO 48
<211> LENGTH: 16
<212> TYPE: PRT
<213> ORGANISM: Homo sapiens
<220> FEATURE:
<221> NAME/KEY: MISC_FEATURE
<222> LOCATION: (2)..(2)
<223> OTHER INFORMATION: Xaa=K; or carbonylated K
<220> FEATURE:
<221> NAME/KEY: MISC_FEATURE
<222> LOCATION: (10)..(10)
<223> OTHER INFORMATION: Xaa=K; or carbonylated K

<400> SEQUENCE: 48

Gly Xaa Gly Gly Asn Glu Glu Ser Thr Xaa Thr Gly Asn Ala Gly Ser
1               5                   10                  15

<210> SEQ ID NO 49
<211> LENGTH: 16
<212> TYPE: PRT
<213> ORGANISM: Homo sapiens
<220> FEATURE:
<221> NAME/KEY: MISC_FEATURE
<222> LOCATION: (4)..(4)
<223> OTHER INFORMATION: Xaa=K; or carbonylated K
<220> FEATURE:
<221> NAME/KEY: MISC_FEATURE
<222> LOCATION: (12)..(12)
<223> OTHER INFORMATION: Xaa=K; or carbonylated K

<400> SEQUENCE: 49

Asp Leu Gly Xaa Gly Gly Asn Glu Glu Ser Thr Xaa Thr Gly Asn Ala
1               5                   10                  15

<210> SEQ ID NO 50
<211> LENGTH: 15
<212> TYPE: PRT
<213> ORGANISM: Homo sapiens
<220> FEATURE:
<221> NAME/KEY: MISC_FEATURE
<222> LOCATION: (1)..(1)
<223> OTHER INFORMATION: Xaa=K; or cabonylated K
<220> FEATURE:
<221> NAME/KEY: MISC_FEATURE
<222> LOCATION: (9)..(9)
<223> OTHER INFORMATION: Xaa=K; or cabonylated K

<400> SEQUENCE: 50

Xaa Gly Gly Asn Glu Glu Ser Thr Xaa Thr Gly Asn Ala Gly Ser
1               5                   10                  15

<210> SEQ ID NO 51
<211> LENGTH: 15
<212> TYPE: PRT
<213> ORGANISM: Homo sapiens
<220> FEATURE:
```

```
<221> NAME/KEY: MISC_FEATURE
<222> LOCATION: (4)..(4)
<223> OTHER INFORMATION: Xaa=K; or cabonylated K
<220> FEATURE:
<221> NAME/KEY: MISC_FEATURE
<222> LOCATION: (12)..(12)
<223> OTHER INFORMATION: Xaa=K; or cabonylated K

<400> SEQUENCE: 51

Asp Leu Gly Xaa Gly Gly Asn Glu Glu Ser Thr Xaa Thr Gly Asn
1               5                   10                  15

<210> SEQ ID NO 52
<211> LENGTH: 14
<212> TYPE: PRT
<213> ORGANISM: Homo sapiens
<220> FEATURE:
<221> NAME/KEY: MISC_FEATURE
<222> LOCATION: (8)..(8)
<223> OTHER INFORMATION: Xaa=K; or carbonylated K

<400> SEQUENCE: 52

Gly Gly Asn Glu Glu Ser Thr Xaa Thr Gly Asn Ala Gly Ser
1               5                   10

<210> SEQ ID NO 53
<211> LENGTH: 14
<212> TYPE: PRT
<213> ORGANISM: Homo sapiens
<220> FEATURE:
<221> NAME/KEY: MISC_FEATURE
<222> LOCATION: (4)..(4)
<223> OTHER INFORMATION: Xaa=K; or carbonylated K
<220> FEATURE:
<221> NAME/KEY: MISC_FEATURE
<222> LOCATION: (12)..(12)
<223> OTHER INFORMATION: Xaa=K; or carbonylated K

<400> SEQUENCE: 53

Asp Leu Gly Xaa Gly Gly Asn Glu Glu Ser Thr Xaa Thr Gly
1               5                   10

<210> SEQ ID NO 54
<211> LENGTH: 16
<212> TYPE: PRT
<213> ORGANISM: Homo sapiens
<220> FEATURE:
<221> NAME/KEY: MISC_FEATURE
<222> LOCATION: (3)..(3)
<223> OTHER INFORMATION: Xaa=K; or carbonylated K
<220> FEATURE:
<221> NAME/KEY: MISC_FEATURE
<222> LOCATION: (11)..(11)
<223> OTHER INFORMATION: Xaa=K; or carbonylated K

<400> SEQUENCE: 54

Leu Gly Xaa Gly Gly Asn Glu Glu Ser Thr Xaa Thr Gly Asn Ala Gly
1               5                   10                  15

<210> SEQ ID NO 55
<211> LENGTH: 14
<212> TYPE: PRT
<213> ORGANISM: Homo sapiens
<220> FEATURE:
<221> NAME/KEY: MISC_FEATURE
<222> LOCATION: (2)..(2)
<223> OTHER INFORMATION: Xaa=K; or carbonylated K
<220> FEATURE:
<221> NAME/KEY: MISC_FEATURE
<222> LOCATION: (10)..(10)
<223> OTHER INFORMATION: Xaa=K; or carbonylated K
```

```
<400> SEQUENCE: 55

Gly Xaa Gly Gly Asn Glu Glu Ser Thr Xaa Thr Gly Asn Ala
1               5                   10

<210> SEQ ID NO 56
<211> LENGTH: 12
<212> TYPE: PRT
<213> ORGANISM: Homo sapiens
<220> FEATURE:
<221> NAME/KEY: MISC_FEATURE
<222> LOCATION: (1)..(1)
<223> OTHER INFORMATION: Xaa=K; or carbonylated K
<220> FEATURE:
<221> NAME/KEY: MISC_FEATURE
<222> LOCATION: (9)..(9)
<223> OTHER INFORMATION: Xaa=K; or carbonylated K

<400> SEQUENCE: 56

Xaa Gly Gly Asn Glu Glu Ser Thr Xaa Thr Gly Asn
1               5                   10

<210> SEQ ID NO 57
<211> LENGTH: 14
<212> TYPE: PRT
<213> ORGANISM: Artificial Sequence
<220> FEATURE:
<223> OTHER INFORMATION: Synthetic Construct - DSE analog
<220> FEATURE:
<221> NAME/KEY: MISC_FEATURE
<222> LOCATION: (1)..(1)
<223> OTHER INFORMATION: Xaa=N; or absent
<220> FEATURE:
<221> NAME/KEY: MISC_FEATURE
<222> LOCATION: (2)..(2)
<223> OTHER INFORMATION: Xaa=P; or absent when N at position 1 is absent
<220> FEATURE:
<221> NAME/KEY: MISC_FEATURE
<222> LOCATION: (3)..(3)
<223> OTHER INFORMATION: Xaa=L; or absent whe P at position 2 is absent
<220> FEATURE:
<221> NAME/KEY: MISC_FEATURE
<222> LOCATION: (7)..(7)
<223> OTHER INFORMATION: Xaa=H; or carbonylated H
<220> FEATURE:
<221> NAME/KEY: MISC_FEATURE
<222> LOCATION: (12)..(12)
<223> OTHER INFORMATION: Xaa=D; or absent
<220> FEATURE:
<221> NAME/KEY: MISC_FEATURE
<222> LOCATION: (13)..(14)
<223> OTHER INFORMATION: Xaa=E; or absent when D at position 12 is
      absent

<400> SEQUENCE: 57

Xaa Xaa Xaa Ser Arg Lys Xaa Gly Gly Pro Lys Xaa Xaa Xaa
1               5                   10

<210> SEQ ID NO 58
<211> LENGTH: 20
<212> TYPE: PRT
<213> ORGANISM: Artificial Sequence
<220> FEATURE:
<223> OTHER INFORMATION: Synthetic Construct - DSE analog
<220> FEATURE:
<221> NAME/KEY: MISC_FEATURE
<222> LOCATION: (1)..(2)
<223> OTHER INFORMATION: Xaa=G; or upto 2 residues may be absent
<220> FEATURE:
<221> NAME/KEY: MISC_FEATURE
<222> LOCATION: (3)..(3)
<223> OTHER INFORMATION: Xaa=G; or C when G at position 1 and 2 absent;
      or absent
```

```
<220> FEATURE:
<221> NAME/KEY: MISC_FEATURE
<222> LOCATION: (4)..(4)
<223> OTHER INFORMATION: Xaa=N; or absent
<220> FEATURE:
<221> NAME/KEY: MISC_FEATURE
<222> LOCATION: (5)..(5)
<223> OTHER INFORMATION: Xaa=P; or absent when N at position 4 is absent
<220> FEATURE:
<221> NAME/KEY: MISC_FEATURE
<222> LOCATION: (6)..(6)
<223> OTHER INFORMATION: Xaa=L; or absent when P at position 5 is absent
<220> FEATURE:
<221> NAME/KEY: MISC_FEATURE
<222> LOCATION: (10)..(10)
<223> OTHER INFORMATION: Xaa=H; or carbonylated H
<220> FEATURE:
<221> NAME/KEY: MISC_FEATURE
<222> LOCATION: (15)..(15)
<223> OTHER INFORMATION: Xaa=D; or absent
<220> FEATURE:
<221> NAME/KEY: MISC_FEATURE
<222> LOCATION: (16)..(16)
<223> OTHER INFORMATION: Xaa=E when D at position 15 is present; or
     absent when E at position 17 is absent
<220> FEATURE:
<221> NAME/KEY: MISC_FEATURE
<222> LOCATION: (17)..(17)
<223> OTHER INFORMATION: Xaa=E when E at position 16 is present; or
     absent
<220> FEATURE:
<221> NAME/KEY: MISC_FEATURE
<222> LOCATION: (18)..(18)
<223> OTHER INFORMATION: Xaa=G; or absent
<220> FEATURE:
<221> NAME/KEY: MISC_FEATURE
<222> LOCATION: (19)..(19)
<223> OTHER INFORMATION: Xaa=G when G at position 18 is present; or S
     when G at position 18 is present; or absent when G at position 20
     is absent
<220> FEATURE:
<221> NAME/KEY: MISC_FEATURE
<222> LOCATION: (20)..(20)
<223> OTHER INFORMATION: Xaa=G; or absent

<400> SEQUENCE: 58

Xaa Xaa Xaa Xaa Xaa Xaa Ser Arg Lys Xaa Gly Gly Pro Lys Xaa Xaa
1               5                   10                  15

Xaa Xaa Xaa Xaa
            20

<210> SEQ ID NO 59
<211> LENGTH: 15
<212> TYPE: PRT
<213> ORGANISM: Artificial Sequence
<220> FEATURE:
<223> OTHER INFORMATION: Synthetic Construct - DSE analog
<220> FEATURE:
<221> NAME/KEY: MISC_FEATURE
<222> LOCATION: (8)..(8)
<223> OTHER INFORMATION: Xaa=H; or carbonylated H

<400> SEQUENCE: 59

Cys Asn Pro Leu Ser Arg Lys Xaa Gly Gly Pro Lys Asp Glu Glu
1               5                   10                  15

<210> SEQ ID NO 60
<211> LENGTH: 12
<212> TYPE: PRT
<213> ORGANISM: Artificial Sequence
<220> FEATURE:
<223> OTHER INFORMATION: Synthetic Construct - DSE analog
<220> FEATURE:
<221> NAME/KEY: MISC_FEATURE
```

```
<222> LOCATION: (1)..(1)
<223> OTHER INFORMATION: Xaa=C; or absent

<400> SEQUENCE: 60

Xaa Ile Lys Gly Leu Thr Glu Gly Leu His Gly Phe
1               5                   10

<210> SEQ ID NO 61
<211> LENGTH: 11
<212> TYPE: PRT
<213> ORGANISM: Artificial Sequence
<220> FEATURE:
<223> OTHER INFORMATION: Synthetic Construct - DSE analog
<220> FEATURE:
<221> NAME/KEY: MISC_FEATURE
<222> LOCATION: (1)..(1)
<223> OTHER INFORMATION: Xaa=H; or absent
<220> FEATURE:
<221> NAME/KEY: MISC_FEATURE
<222> LOCATION: (2)..(2)
<223> OTHER INFORMATION: Xaa=C; or absent when H at position 1 is absent
<220> FEATURE:
<221> NAME/KEY: MISC_FEATURE
<222> LOCATION: (10)..(10)
<223> OTHER INFORMATION: Xaa=V; or absent when H is at position 11 is
      absent
<220> FEATURE:
<221> NAME/KEY: MISC_FEATURE
<222> LOCATION: (11)..(11)
<223> OTHER INFORMATION: Xaa=H; or absent

<400> SEQUENCE: 61

Xaa Xaa Ile Ile Gly Arg Thr Leu Val Xaa Xaa
1               5                   10

<210> SEQ ID NO 62
<211> LENGTH: 16
<212> TYPE: PRT
<213> ORGANISM: Artificial Sequence
<220> FEATURE:
<223> OTHER INFORMATION: Synthetic Construct - DSE analog
<220> FEATURE:
<221> NAME/KEY: MISC_FEATURE
<222> LOCATION: (1)..(1)
<223> OTHER INFORMATION: Xaa=G; or absent
<220> FEATURE:
<221> NAME/KEY: MISC_FEATURE
<222> LOCATION: (2)..(2)
<223> OTHER INFORMATION: Xaa=G; or S when G at position 3 is present; or
      absent
<220> FEATURE:
<221> NAME/KEY: MISC_FEATURE
<222> LOCATION: (3)..(3)
<223> OTHER INFORMATION: Xaa=G; or absent
<220> FEATURE:
<221> NAME/KEY: MISC_FEATURE
<222> LOCATION: (4)..(4)
<223> OTHER INFORMATION: Xaa=H; or absent
<220> FEATURE:
<221> NAME/KEY: MISC_FEATURE
<222> LOCATION: (5)..(5)
<223> OTHER INFORMATION: Xaa=C; or absent when H at position 4 is absent
<220> FEATURE:
<221> NAME/KEY: MISC_FEATURE
<222> LOCATION: (13)..(13)
<223> OTHER INFORMATION: Xaa=V; or absent when H at position 14 is
      absent
<220> FEATURE:
<221> NAME/KEY: MISC_FEATURE
<222> LOCATION: (14)..(14)
<223> OTHER INFORMATION: Xaa=H; when V at position 13 is present; or
      absent when E at position 15 is absent
<220> FEATURE:
<221> NAME/KEY: MISC_FEATURE
<222> LOCATION: (15)..(15)
```

```
<223> OTHER INFORMATION: Xaa=E when H at position 14 is present; or
      absent when K at position 16 is absent
<220> FEATURE:
<221> NAME/KEY: MISC_FEATURE
<222> LOCATION: (16)..(16)
<223> OTHER INFORMATION: Xaa=K when E at 15 present; or absent

<400> SEQUENCE: 62

Xaa Xaa Xaa Xaa Xaa Ile Ile Gly Arg Thr Leu Val Xaa Xaa Xaa Xaa
1               5                   10                  15

<210> SEQ ID NO 63
<211> LENGTH: 17
<212> TYPE: PRT
<213> ORGANISM: Artificial Sequence
<220> FEATURE:
<223> OTHER INFORMATION: Synthetic Construct - DSE analog

<400> SEQUENCE: 63

Gly Gly Gly His Cys Ile Ile Gly Arg Thr Leu Val Val His Gly Ser
1               5                   10                  15

Gly

<210> SEQ ID NO 64
<211> LENGTH: 5
<212> TYPE: PRT
<213> ORGANISM: Artificial Sequence
<220> FEATURE:
<223> OTHER INFORMATION: Synthetic Construct - Spacer

<400> SEQUENCE: 64

Gly Gly Gly Gly Ser
1               5

<210> SEQ ID NO 65
<211> LENGTH: 15
<212> TYPE: PRT
<213> ORGANISM: Artificial Sequence
<220> FEATURE:
<223> OTHER INFORMATION: Synthetic Construct - DSE analog
<220> FEATURE:
<221> NAME/KEY: MISC_FEATURE
<222> LOCATION: (7)..(7)
<223> OTHER INFORMATION: Cysteine oxidized to cysteic acid

<400> SEQUENCE: 65

Gly Gly Gly Arg Leu Ala Cys Gly Val Ile Gly Ile Gly Ser Gly
1               5                   10                  15

<210> SEQ ID NO 66
<211> LENGTH: 15
<212> TYPE: PRT
<213> ORGANISM: Artificial Sequence
<220> FEATURE:
<223> OTHER INFORMATION: Synthetic Construct - DSE analog

<400> SEQUENCE: 66

Gly Gly Gly Arg Leu Ala Cys Gly Val Ile Gly Ile Gly Ser Gly
1               5                   10                  15

<210> SEQ ID NO 67
<211> LENGTH: 10
<212> TYPE: PRT
<213> ORGANISM: Artificial Sequence
<220> FEATURE:
<223> OTHER INFORMATION: Synthetic Construct - DSE analog

<400> SEQUENCE: 67
```

```
Gly Ser Gly Lys Ala Val Cys Val Leu Lys
1               5                   10

<210> SEQ ID NO 68
<211> LENGTH: 9
<212> TYPE: PRT
<213> ORGANISM: Artificial Sequence
<220> FEATURE:
<223> OTHER INFORMATION: Synthetic Construct - DSE analog

<400> SEQUENCE: 68

Cys Gly Leu His Gly Phe His Val His
1               5

<210> SEQ ID NO 69
<211> LENGTH: 8
<212> TYPE: PRT
<213> ORGANISM: Homo sapiens

<400> SEQUENCE: 69

Ala Val Cys Val Leu Lys Gly Asp
1               5

<210> SEQ ID NO 70
<211> LENGTH: 7
<212> TYPE: PRT
<213> ORGANISM: Homo sapiens

<400> SEQUENCE: 70

Gly Pro Val Lys Val Trp Gly
1               5

<210> SEQ ID NO 71
<211> LENGTH: 7
<212> TYPE: PRT
<213> ORGANISM: Homo sapiens

<400> SEQUENCE: 71

Leu His Gly Phe His Val His
1               5

<210> SEQ ID NO 72
<211> LENGTH: 29
<212> TYPE: PRT
<213> ORGANISM: Homo sapiens

<400> SEQUENCE: 72

Gly Val Ala Asp Val Ser Ile Glu Asp Ser Val Ile Ser Leu Ser Gly
1               5                   10                  15

Asp His Cys Ile Ile Gly Arg Thr Leu Val Val His Glu
            20                  25

<210> SEQ ID NO 73
<211> LENGTH: 9
<212> TYPE: PRT
<213> ORGANISM: Homo sapiens
<220> FEATURE:
<221> NAME/KEY: MISC_FEATURE
<222> LOCATION: (4)..(4)
<223> OTHER INFORMATION: Xaa=C; or cysteine sulfinic acid; or cysteic
      acid

<400> SEQUENCE: 73

Arg Leu Ala Xaa Gly Val Ile Gly Ile
1               5
```

```
<210> SEQ ID NO 74
<211> LENGTH: 18
<212> TYPE: PRT
<213> ORGANISM: Homo sapiens
<220> FEATURE:
<221> NAME/KEY: MISC_FEATURE
<222> LOCATION: (4)..(4)
<223> OTHER INFORMATION: Xaa=K; or carbonylated K
<220> FEATURE:
<221> NAME/KEY: MISC_FEATURE
<222> LOCATION: (12)..(12)
<223> OTHER INFORMATION: Xaa=K; or carbonylated K

<400> SEQUENCE: 74

Asp Leu Gly Xaa Gly Gly Asn Glu Glu Ser Thr Xaa Thr Gly Asn Ala
1               5                   10                  15

Gly Ser

<210> SEQ ID NO 75
<211> LENGTH: 14
<212> TYPE: PRT
<213> ORGANISM: Homo sapiens
<220> FEATURE:
<221> NAME/KEY: MISC_FEATURE
<222> LOCATION: (5)..(5)
<223> OTHER INFORMATION: Xaa=R; or carbonylated R
<220> FEATURE:
<221> NAME/KEY: MISC_FEATURE
<222> LOCATION: (6)..(6)
<223> OTHER INFORMATION: Xaa=K; or carbonylated K
<220> FEATURE:
<221> NAME/KEY: MISC_FEATURE
<222> LOCATION: (7)..(7)
<223> OTHER INFORMATION: Xaa=H; or carbonylated H
<220> FEATURE:
<221> NAME/KEY: MISC_FEATURE
<222> LOCATION: (11)..(11)
<223> OTHER INFORMATION: Xaa=K; or carbonylated K

<400> SEQUENCE: 75

Asn Pro Leu Ser Xaa Xaa Xaa Gly Gly Pro Xaa Asp Glu Glu
1               5                   10

<210> SEQ ID NO 76
<211> LENGTH: 7
<212> TYPE: PRT
<213> ORGANISM: Homo sapiens
<220> FEATURE:
<221> NAME/KEY: MISC_FEATURE
<222> LOCATION: (1)..(1)
<223> OTHER INFORMATION: Xaa=K; or carbonylated K
<220> FEATURE:
<221> NAME/KEY: MISC_FEATURE
<222> LOCATION: (4)..(4)
<223> OTHER INFORMATION: Xaa=C; or cysteine sulfinic acid or cysteic
      acid
<220> FEATURE:
<221> NAME/KEY: MISC_FEATURE
<222> LOCATION: (7)..(7)
<223> OTHER INFORMATION: Xaa=K; or carbonyalted K

<400> SEQUENCE: 76

Xaa Ala Val Xaa Val Leu Xaa
1               5

<210> SEQ ID NO 77
<211> LENGTH: 11
<212> TYPE: PRT
<213> ORGANISM: Homo sapiens
<220> FEATURE:
```

```
<221> NAME/KEY: MISC_FEATURE
<222> LOCATION: (2)..(2)
<223> OTHER INFORMATION: Xaa=K; or carbonylated K
<220> FEATURE:
<221> NAME/KEY: MISC_FEATURE
<222> LOCATION: (9)..(9)
<223> OTHER INFORMATION: Xaa=H; or carbonylated H
<220> FEATURE:
<221> NAME/KEY: MISC_FEATURE
<222> LOCATION: (11)..(11)
<223> OTHER INFORMATION: Xaa=F; or nitrophenylalanine

<400> SEQUENCE: 77

Ile Xaa Gly Leu Thr Glu Gly Leu Xaa Gly Xaa
1               5                   10

<210> SEQ ID NO 78
<211> LENGTH: 11
<212> TYPE: PRT
<213> ORGANISM: Homo sapiens
<220> FEATURE:
<221> NAME/KEY: MISC_FEATURE
<222> LOCATION: (1)..(1)
<223> OTHER INFORMATION: Xaa=H; or carbonylated H
<220> FEATURE:
<221> NAME/KEY: MISC_FEATURE
<222> LOCATION: (2)..(2)
<223> OTHER INFORMATION: Xaa=C; or cysteine sulfinic acid or cysteic
      acid
<220> FEATURE:
<221> NAME/KEY: MISC_FEATURE
<222> LOCATION: (6)..(6)
<223> OTHER INFORMATION: Xaa=R; or carbonylated R
<220> FEATURE:
<221> NAME/KEY: MISC_FEATURE
<222> LOCATION: (11)..(11)
<223> OTHER INFORMATION: Xaa=H; or carbonylated H

<400> SEQUENCE: 78

Xaa Xaa Ile Ile Gly Xaa Thr Leu Val Val Xaa
1               5                   10

<210> SEQ ID NO 79
<211> LENGTH: 8
<212> TYPE: PRT
<213> ORGANISM: Homo sapiens
<220> FEATURE:
<221> NAME/KEY: MISC_FEATURE
<222> LOCATION: (3)..(3)
<223> OTHER INFORMATION: Xaa=H; or carbonylated H
<220> FEATURE:
<221> NAME/KEY: MISC_FEATURE
<222> LOCATION: (5)..(5)
<223> OTHER INFORMATION: Xaa=F; or nitrophenylalanine
<220> FEATURE:
<221> NAME/KEY: MISC_FEATURE
<222> LOCATION: (6)..(6)
<223> OTHER INFORMATION: Xaa=H; or carbonylated H
<220> FEATURE:
<221> NAME/KEY: MISC_FEATURE
<222> LOCATION: (8)..(8)
<223> OTHER INFORMATION: Xaa=H; or carbonylated H

<400> SEQUENCE: 79

Gly Leu Xaa Gly Xaa Xaa Val Xaa
1               5

<210> SEQ ID NO 80
<211> LENGTH: 8
<212> TYPE: PRT
<213> ORGANISM: Homo sapiens

<400> SEQUENCE: 80
```

-continued

```
Ser Arg Leu Ala Cys Gly Val Ile
1               5
```

METHODS AND COMPOSITIONS TO TREAT MISFOLDED-SOD1 MEDIATED DISEASES

This application is a continuation-in-part of U.S. non-provisional patent application Ser. No. 11/682,217 filed Mar. 5, 2007. The entire content of the above-referenced patent application is herein incorporated by reference. Application Ser. No. 11/682,217 is a continuation-in-part of U.S. non-provisional patent application Ser. No. 11/565,967 filed Dec. 1, 2006 now U.S. Pat. No. 7,794,692; application Ser. No. 11/565,967 claims the benefit of U.S. provisional application Ser. No. 60/741,462, filed Dec. 2, 2005. Application Ser. No. 11/682,217 is also a continuation-in-part of U.S. non-provisional application Ser. No. 11/367,609 filed Mar. 3, 2006 now U.S. Pat. No. 7,439,324. Application Ser. No. 11/682,217 claims the benefit of U.S. provisional application Ser. No. 60/798,727 filed May 9, 2006, U.S. provisional application Ser. No. 60/798,728, filed May 9, 2006, and U.S. provisional application Ser. No. 60/778,379, filed Mar. 3, 2006.

FIELD OF THE INVENTION

The invention relates to methods and compositions for treating and detecting conditions, diseases and disorders mediated by non-native SOD1, including amyotrophic lateral sclerosis, Alzheimer's disease and Parkinson's disease, macular degeneration, glaucoma, ischemia, cerebral infarction, myocardial infarction, atherosclerosis, multiple sclerosis, inflammatory bowel disease, ulcerative colitis, Crohn's disease or necrotizing enterocolitis.

BACKGROUND OF THE INVENTION

Protein Misfolding and Aggregation

Proteins can fold into complex and close-packed structures. Folding is not only crucial for biological activity but failure of proteins to fold properly or remain folded can give rise to disease (reviewed in 48). Misfolding can in some cases cause protein aggregation which can further give rise to discrete deposits extracellularly (e.g., plaques) or intracellularly (e.g., inclusions in the cytosol or nucleus).

Neurodegenerative diseases such as Alzheimer's disease (AD), Parkinson's disease (PD), Huntington's disease (HD), amyotrophic lateral sclerosis (ALS) and prion diseases are characterized by neural deposits of misfolded aggregated protein (reviewed in 49).

Neurodegenerative diseases, such as Alzheimer's disease (AD), Huntington's disease, amyotrophic lateral sclerosis (ALS) and Parkinson's disease/Lewy body dementia (PD, LBD) also pose major challenges to our aging population and health care system.

Sporadic AD, ALS, and PD/LBD are all associated with neural accumulation of pathological multimers of misfolded polypeptides (these could potentially be fibrils, protofilaments, and amorphous aggregates), including the amyloid-beta (Abeta) fragment of the amyloid precursor protein (APP) in AD; superoxide dismutase-1 (SOD1) in ALS, AD, and PD, and alpha-synuclein in PD and LBD. Additionally familial amyloidotic polyneuropathy (FAP) results from the aggregation of transthyretin to form amyloid deposits. As with prion diseases, mutations in genes encoding these polypeptides are associated with autosomal dominant familial forms of AD, ALS, and PD.

ALS and Protein Misfolding

Amyotrophic lateral sclerosis (ALS) is a fatal neuromuscular disease which afflicts about 30,000 patients in North America, with 5,000 new cases per year. In ALS, also known as "Lou Gehrig's disease," muscles of the limbs, speech and swallowing, and respiration weaken and atrophy, due to degeneration of motor nerve cells that supply them from the spinal cord and brain. Half of affected patients are dead within 3 years, with survival over 5 years being less than 20%.

ALS belongs to a family of fatal neurodegenerative disorders, which includes prion illnesses, Alzheimer's and Parkinson's diseases, and in which aggregated misfolded proteins are thought to cause progressive killing of brain cells. About 20% of familial (inherited) ALS is associated with mutations in the gene encoding superoxide dismutase 1 (SOD1), an intracellular free radical defense enzyme (see 73 and Table 1 for listing of known mutations). Intracellular deposits of aggregated misfolded SOD1 have been observed in familial ALS, and also in the more common non-familial (sporadic) ALS, suggesting that SOD1 aggregation may underlie all ALS.

Experiments performed in cell culture and mice transgenic for human mutant SOD1 have established that extracellular misfolded SOD1 is highly toxic for motor neurons (1), in part by activation of killing pathways by local immune cells (microglia). Recently, it has also become clear that misfolded SOD1 is exported from the cell by both secretory and constitutive mechanisms (1, 2).

Aggregation of SOD1 may progress through a protein-based template-directed misfolding mechanism (3) similar to that proposed for the prion diseases (4). Thus, misfolded SOD1 in the extracellular space is not only directly toxic for motor neurons, but may also participate in the cell-to-cell propagation of disease throughout the nervous system by a prion-like templated misfolding process.

TABLE 1

Detected Mutations in SOD1 in FALS.

| Amino Acid | Mutation |
| --- | --- |
| 4 | A -> S (in FALS). |
| 4 | A -> T (in FALS). |
| 4 | A -> V (in FALS). |
| 6 | C -> F (in FALS). |
| 7 | V -> E (in FALS). |
| 8 | L -> Q (in FALS). |
| 8 | L -> V (in FALS). |
| 12 | G -> R (in FALS). |
| 14 | V -> G (in FALS). |
| 14 | V -> M (in FALS). |
| 16 | G -> S (in ALS). |
| 21 | E -> G (in FALS). |
| 21 | E -> K (in FALS). |
| 37 | G -> R (in FALS. |
| 38 | L -> R (in FALS). |
| 38 | L -> V (in FALS). |
| 41 | G -> D (in FALS). |
| 41 | G -> S (in FALS). |
| 43 | H -> R (in FALS). |
| 45 | F -> C (in FALS). |
| 46 | H -> R (in FALS). |
| 48 | H -> Q (in FALS). |
| 49 | E -> K (in FALS). |
| 65 | N -> S (in FALS). |
| 67 | L -> R (in FALS). |
| 72 | G -> S (in FALS). |
| 76 | D -> Y (in FALS). |
| 80 | H -> A (in ALS). |
| 84 | L -> F (in FALS). |
| 84 | L -> V (in FALS). |
| 85 | G -> R (in FALS). |

TABLE 1-continued

Detected Mutations in SOD1 in FALS.

| Amino Acid | Mutation |
|---|---|
| 86 | N -> S (in FALS). |
| 89 | A -> V (in FALS). |
| 90 | D -> A (in FALS). |
| 90 | D -> V (in FALS). |
| 93 | G -> A (in FALS). |
| 93 | G -> C (in FALS). |
| 93 | G -> D (in FALS). |
| 93 | G -> R (in FALS). |
| 93 | G -> V (in FALS). |
| 100 | E -> G (in FALS). |
| 100 | E -> K (in FALS). |
| 101 | D -> G (in FALS). |
| 101 | D -> N (in FALS). |
| 104 | I -> F (in FALS). |
| 105 | S -> L (in FALS). |
| 106 | L -> V (in FALS). |
| 108 | G -> V (in FALS). |
| 112 | I -> M (in FALS). |
| 112 | I -> T (in FALS). |
| 113 | I -> T (in FALS). |
| 114 | G -> A (in FALS). |
| 115 | R -> G (in FALS). |
| 118 | V -> VFLQ (in FALS). |
| 124 | D -> V (in FALS). |
| 125 | D -> H (in FALS). |
| 126 | L -> S (in FALS). |
| 133 | Missing (in ALS). |
| 134 | S -> N (in FALS). |
| 139 | N -> K (in FALS). |
| 144 | L -> F (in FALS). |
| 144 | L -> S (in FALS). |
| 145 | A -> T (in FALS). |
| 146 | C -> R (in FALS). |
| 148 | V -> G (in FALS). |
| 148 | V -> I (in FALS). |
| 149 | I -> T (in FALS). |
| 151 | I -> T (in FALS). |

Alzheimer's Disease

AD is a common dementing (disordered memory and cognition) neurodegenerative disease associated with brain accumulation of extracellular plaques composed predominantly of the Abeta (1-40), Abeta (1-42) and Abeta (1-43) peptides, all of which are proteolytic products of APP (reviewed in 50) In addition, neurofibrillary tangles, composed principally of abnormally phosphorylated tau protein (a neuronal microtubule-associated protein), accumulate intracellularly in dying neurons (reviewed in 49). Familial forms of AD can be caused by mutations in the APP gene, or in the presenilin 1 or 2 genes (reviewed in 51), the protein products of which are implicated in the processing of APP to Abeta. Apolipoprotein E allelic variants also influence the age at onset of both sporadic and familial forms of AD (reviewed in 52). Abeta, tau and phosphorylated tau has been detected in the blood and CSF of AD patients and in normal controls (53-55). Immunization of Alzheimer's disease patients with Abeta has shown some promising preliminary treatment results, although limited by autoimmune meningoencephalitis in humans (56-58)

Parkinson's Disease

PD is a neurodegenerative movement disorder, second only to AD in prevalence (~350 per 100,000 population; reviewed in 59). It is clinically characterized by rigidity, slowness of movement, and tremor. Most cases of Parkinson's disease are sporadic, but both sporadic and familial forms of the disease are characterized by intracellular Lewy bodies in dying neurons of the substantia nigra, a population of midbrain neurons (~60,000) that are selectively decimated in PD. Lewy bodies are predominantly composed of alpha-synuclein (60). Mutations in, and duplication of, the gene encoding alpha-synuclein have been found in patients with familial Parkinson's disease (reviewed in 61). Another gene associated with autosomal recessive PD is parkin, which is involved in alpha-synuclein degradation (61). Diffuse cortical Lewy bodies composed of alpha-synuclein are observed in Lewy body disease (LBD), a dementing syndrome associated with parkinsonian tone changes, hallucinations, and rapid symptom fluctuation (62). LBD may be the second most common form of neurodegenerative dementia after AD, accounting for 20 to 30 percent of cases among persons over the age of 60 years. Similar to the vaccine approach to Alzheimer's disease (58-60) promising results in a mouse model of Parkinson's/Lewy body disease have been obtained by immunization with alpha synuclein (63). Other dementing syndromes include frontotermporal dementias, Pick's disease, and corticobasal dementia, and others known to neurological medicine.

SOD1 has been Detected in AD and PD Protein Aggregates

Oxidative stress has been implicated in several neurodegenerative diseases, including ALS, PD and AD. Reactive oxygen and nitrogen species (ROS and RNS respectively) generated in these environments may participate in cell injury including the abnormal oxidation of proteins or lipids. Other pathological hallmarks of such disease include cytoskeletal debris accumulations and selective neuronal death, frequently attributed to oxidative stress and the accumulated insoluble protein (74-81). Several enzymes including SOD1 have antioxidant roles. Alterations in the activity of such enzymes may contribute to a neurodegenerative disease state.

Recently, Choi et al. (64) reported that SOD1 is a major target of oxidative damage in AD and PD brains. They noted that the total level of SOD1 is increased in both AD and PD and that SOD1 forms proteinaceous aggregates that are associated with amyloid senile plaques and neurofibrillary tangles in AD brains. Choi et al. (64) have suggested that AD, PD and ALS may share a common pathogenic mechanism. It has also recently been shown that SOD1 is secreted into the extracellular space, in a form which is toxic to neurons, but more accessible by extracellular therapeutic agents (1).

The implication that extracellular misfolded SOD1 plays a role in ALS pathogenesis provides an opportunity for the antibody treatment of neurodegenerative diseases, as this compartment is accessible to antibody neutralization. In normal humans, IgGs can cross the blood brain barrier to levels between 1/100 and 1/1000 that of circulating concentrations; and transudation of immunoglobulins is often increased in diseases affecting the blood brain barrier. However, treatment of human patients with antibodies or vaccines targeted to accessible extracellular epitopes on ubiquitous proteins may lead to deleterious autoimmune effects such as those seen with Abeta in Alzheimer disease. Thus, there remains a need in the art for compositions and methods for diagnosis and treatment of misfolded SOD1-related diseases, such as ALS, AD and PD.

SUMMARY OF THE INVENTION

Misfolded SOD1 is toxic to neurons (1) and is believed to participate in neuronal cell death and dysfunction in amyotrophic lateral sclerosis and other neurodegenerative diseases. The present invention uses SOD1 disease-specific epitopes (DSEs) as a target for vaccines or immunotherapy for these diseases, including amyotrophic lateral sclerosis (ALS), Alzheimer's (AD), Parkinson's (PD) and Lewy body diseases (LBD). Non-native forms of SOD1 also participate in other diseases including non-neurodegenerative diseases. Other diseases in which non-native forms of SOD1 is believed to participate include macular degeneration, glaucoma, ischemia, cerebral infarction, myocardial infarction, atherosclerosis, multiple sclerosis, inflammatory bowel disease, ulcerative colitis, Crohn's disease or necrotizing enterocolitis. The invention isolates and targets epitopes that are presented selectively by non-native forms of SOD1 that are associated with SOD1-mediated conditions, diseases and disorders such as ALS and other neurodegenerative and non-neurodegenerative diseases. These epitopes are not presented or accessible in native forms of SOD1. For example, disease specific epitopes such as ALS-specific, AD-specific and PD-specific epitopes are not presented by the native dimeric forms of SOD1. However, disease specific epitopes are presented or accessible when the SOD1 monomer either fails to associate or dissociates from its normal, homodimeric state, and in other non-native forms of SOD1, including misfolded SOD1 monomers, misfolded SOD1 dimers and SOD1 aggregates. These epitopes are selectively presented or accessible in non-native forms of SOD1, and are characteristic of non-native-SOD1 related conditions, diseases and disorders.

In this application, "ALS-specific" epitopes refers to epitopes that are presented on the ALS-associated forms of SOD1, "AD-specific" epitopes refers to epitopes that are presented on the AD-associated forms of SOD1, and "PD-specific" epitopes refers to epitopes that are presented on the PD-associated forms of SOD1 that arise from processes such as misfolding, aggregation or dissociation. Misfolded SOD1 presents many of the same epitopes in each of ALS, AD and PD however, for convenience herein, the epitopes are described as "specific" to that disease because, within the body of a particular subject, the epitopes are specifically presented only on the non-native toxic SOD1 that causes, underlies or is associated with the neurodegenerative disease. Such disease-specific epitopes thus include the epitopes on SOD1 monomer that are revealed when the SOD1 monomer dissociates from its normal, homodimeric state, the epitopes selectively presented or accessible in non-native SOD1 forms including misfolded SOD1 monomer, misfolded SOD1 dimer, and the epitopes selectively presented or accessible in SOD1 aggregates.

In certain embodiments, the epitopes which are presented by or accessible on non-native forms of SOD1 include:

DLGKGGNEESTKTGNAGS, (DSE2) (WO 2005/019828); (SEQ ID NO: 2)

NPLSRKHGGPKDEE, (DSE3) (WO 2005/019828); (SEQ ID NO: 3)

IKGLTEGLHGF, (DSE5) (8); (SEQ ID NO: 5)

HCIIGRTLVVH, (DSE6) (8); (SEQ ID NO: 6)
and

GLHGFHVH, (DSE7), (SEQ ID NO: 7)

as well as the additional epitopes which are presented by or accessible only on monomeric forms of SOD1, which include:

RLACGVIGI, (DSE1); (SEQ ID NO: 1)

and

KAVCVLK, (DSE4). (SEQ ID NO: 4)

The present invention uses these epitopes, and/or antigenic determinants contained within these epitopes, and similarly any epitope selectively presented or accessible in non-native forms of SOD1, as targets for immunotherapeutic intervention. For example, isolated peptides corresponding to these epitopes are useful to reduce or inhibit participation of monomeric, dimeric or misfolded SOD1 in SOD1 aggregation, which is characteristic of misfolded-SOD1 related disorders, such as amyotrophic lateral sclerosis, Alzheimer's disease and/or Parkinson's disease. These peptides are also useful for in other diseases such as macular degeneration, glaucoma, ischemia, cerebral infarction, myocardial infarction, atherosclerosis, multiple sclerosis, inflammatory bowel disease, ulcerative colitis, Crohn's disease or necrotizing enterocolitis. Accordingly, isolated peptides corresponding to these epitopes can be used to treat amyotrophic lateral sclerosis, Alzheimer's disease and/or Parkinson's disease and/or macular degeneration, glaucoma, ischemia, cerebral infarction, myocardial infarction, atherosclerosis, multiple sclerosis, inflammatory bowel disease, ulcerative colitis, Crohn's disease or necrotizing enterocolitis. and can be used to elicit a selective immune response in an animal against the monomeric, aggregated or misfolded SOD1 molecules, and to inhibit or neutralize the toxic effect of these misfolded SOD1 species on neurons. In the case where the isolated peptide corresponding to a disease specific epitope is used in a vaccine, the isolated peptide can be any analog of the noted isolated peptides that yields endogenous antibody to that epitope. In addition, the inventor provides binding proteins such as antibodies and fragments that bind to the amyotrophic lateral sclerosis-specific epitopes, antibodies and fragments that bind Alzheimer's disease-specific epitopes and antibodies and fragments that bind Parkinson's disease-specific epitopes. These antibodies can be used to detect or treat amyotrophic lateral sclerosis, Alzheimer's disease, and Parkinson's disease.

Accordingly, the invention includes a composition useful for inhibiting SOD1 aggregation mediated by monomeric, or misfolded SOD1, and thus for treating SOD1 disorders including neurodegenerative diseases such as amyotrophic lateral sclerosis, Alzheimer's disease and/or Parkinson's disease.

Accordingly, one aspect of the invention is a composition for treating a neurodegenerative disease such as ALS, AD or PD in a subject comprising an effective amount of an isolated peptide corresponding to an epitope selectively presented or accessible in non-native forms of SOD1 (optionally referred to as a disease-specific epitope), or an immunogen comprising such an peptide, in admixture with a suitable, such as a pharmaceutically acceptable, diluent or carrier. Another aspect of the invention is a composition for treating ALS in a subject comprising an effective amount of an isolated peptide corresponding to an epitope selectively presented or accessible in non-native forms of SOD1, or an analog thereof that elicits endogenous antibody that binds that epitope or an immunogen comprising such isolated peptide, in admixture with a suitable, such as a pharmaceutically acceptable, diluent or carrier. A further aspect of the invention is a composition for treating AD in a subject, comprising an effective amount of an isolated peptide corresponding to an epitope selectively presented or associated with non-native forms of SOD1, or an analog thereof that elicits endogenous antibody that binds that epitope or an immunogen comprising such isolated peptide or analog, in admixture with a suitable, such as a pharmaceutically acceptable, diluent or carrier. Yet a further aspect of the invention is a composition for treating PD in a subject, comprising an effective amount of an isolated peptide corresponding to an epitope selectively presented or accessible in non-native forms of SOD1, or an immunogen comprising such peptide, in admixture with a suitable, such as a pharmaceutically acceptable, diluent or carrier. Other aspects include a composition for treating macular degeneration, glaucoma, ischemia, cerebral infarction, myocardial infarction, atherosclerosis, multiple sclerosis, inflammatory bowel disease, ulcerative colitis, Crohn's disease or necrotizing enterocolitis in a subject, comprising an effective amount of an isolated peptide corresponding to an epitope selectively presented or accessible in non-native forms of SOD1, or an immunogen comprising such peptide, in admixture with a suitable, such as a pharmaceutically acceptable, diluent or carrier.

In a preferred embodiment, the isolated peptide corresponding to an epitope selectively presented or accessible in non-native forms of SOD1 is selected from the group consisting of the isolated peptides in Table 2 or in Table 2A (described below), or an analog thereof.

TABLE 2

Isolated Peptides Corresponding to Epitopes Selectively Accessible in Non-native Forms of SOD1

| Sequence | ID |
|---|---|
| RLACGVIGI | (SEQ ID NO: 1, DSE1): |
| DLGKGGNEESTKTGNAGS | (SEQ ID NO: 2, DSE2); |
| NPLSRKHGGPKDEE; | (SEQ ID NO: 3, DSE3): |
| IKGLTEGLHGF; | SEQ ID NO: 5, DSE5); |
| HCIIGRTLVVH; | SEQ ID NO: 6, DSE6); |
| RLA[Cysteic acid]GVIGI (DSE1a); | SEQ ID NO: 8, DSE1a); |
| KAVCVLK (DSE4); and | SEQ ID NO: 4, DSE4) |
| GLHGFHVH (DSE7) | SEQ ID NO: 7, DSE7). |

These isolated peptides listed in Table 2 are referred to herein as the "Table 2 isolated peptides".

One aspect of the invention is a pharmaceutical composition for treating amyotrophic lateral sclerosis in a subject comprising an effective amount of an isolated amyotrophic lateral sclerosis-specific epitope, or an immunogen comprising such epitope, in admixture with a suitable, such as a pharmaceutically acceptable, diluent or carrier. In one embodiment, the epitope or an immunogenic form thereof is selectively presented or accessible in the monomeric form of SOD1. Such epitopes include those which recognize a SOD1 monomer epitope that lies normally in the SOD1 dimer interface. Other such epitopes are those accessible on the surface of SOD1 when the SOD1 monomers are in their normal associated state, e.g., when SOD is in its dimer form, or when in its aggregated form. In particular embodiments, the isolated peptide corresponding to an amyotrophic lateral sclerosis-specific epitope is selected from the group consisting of the isolated peptides in Table 2 or Table 2A, or an analog thereof.

Another aspect of the invention is a pharmaceutical composition for treating Alzheimer's disease in a subject comprising an effective amount of an isolated Alzheimer's disease-specific epitope, or an immunogen comprising such epitope, in admixture with a suitable, such as a pharmaceutically acceptable, diluent or carrier. In one embodiment, the epitope or an immunogenic form thereof is selectively presented or accessible in the monomeric form of SOD. Such epitopes include those which recognize a SOD monomer epitope that lies normally in the SOD dimer interface. Other such SOD epitopes are those accessible on the surface of SOD when in its dimer form, or when in its aggregated form. In particular embodiments, the isolated peptide corresponding to an Alzheimer's disease-specific epitope is selected from the group consisting of the Table 2 or Table 2A isolated peptides.

A further aspect of the invention is a pharmaceutical composition of the present invention, for treating Parkinson's disease in a subject.

Analogs of the isolated peptides and modified isolated peptides are also useful. Analogs and modified isolated peptides comprise in vivo occurring and molecularly engineered peptides corresponding to the epitopes presented or accessible in non-native forms of SOD1 which retain the capacity to elicit production of antibodies that specifically recognize the corresponding epitopes in monomeric, misfolded or aggregated forms of SOD1. In one embodiment the isolated peptide analog comprises a cysteic acid. In one embodiment the analog isolated peptide corresponding to an epitope comprises RLAC*GVIGI (DSE1a) (SEQ ID NO: 8), wherein * denotes an oxidized cysteine, in the form of cysteic acid.

An additional aspect of the invention is a composition for treating a SOD1 mediated disorder, disease or condition comprising an effective amount of an isolated nucleic acid that encodes for a peptide or analog corresponding to an epitope selectively presented or accessible in non-native forms of SOD1 in admixture with a suitable diluent or carrier. Another aspect of the invention is a composition for treating amyotrophic lateral sclerosis comprising an effective amount of an isolated nucleic acid that encodes for a peptide corresponding to an epitope selectively presented or accessible in non-native forms of SOD1 in admixture with a suitable diluent or carrier. A further aspect of the invention is a composition for treating Alzheimer's disease or Parkinson's disease comprising an effective amount of an isolated nucleic acid that encodes for a peptide corresponding to an epitope selectively presented or accessible in non-native forms of SOD1 in admixture with a suitable diluent or carrier.

In a preferred embodiment, the nucleic acid encodes an isolated peptide corresponding to an epitope selected from the group consisting of the isolated peptides in Table 2 or Table 2A, or an analog thereof.

One particular aspect of the invention is a composition for treating amyotrophic lateral sclerosis comprising an effective amount of a nucleic acid that encodes for an isolated peptide corresponding to an amyotrophic lateral sclerosis-specific epitope in admixture with a suitable diluent or carrier, wherein the isolated peptide corresponding to the amyotrophic lateral sclerosis-specific epitope is selected from the group consisting of the isolated peptides in Table 2 or Table 2A, or an analog thereof.

These compositions can be used to treat amyotrophic lateral sclerosis, Alzheimer's disease and/or Parkinson's disease and in methods to treat amyotrophic lateral sclerosis, Alzheimer's disease and/or Parkinson's disease.

The compositions are useful particularly for treating a neurodegenerative disease using immunotherapy directed at an epitope presented in misfolded SOD1, wherein the treatment comprises either active immunotherapy i.e., vaccine-based therapy in which the isolated peptide corresponding to an epitope is used in an immunogen to elicit antibodies which recognize monomeric or misfolded SOD1 in the recipient, or comprise passive immunotherapy in which an antibody to the isolated peptide corresponding to the epitope is administered to the recipient. The compositions are also useful for treating non-native forms of SOD1 mediated diseases. Other diseases for which the compositions are useful include treating macular degeneration, glaucoma, ischemia, cerebral infarction, myocardial infarction, atherosclerosis, multiple sclerosis, inflammatory bowel disease, ulcerative colitis, Crohn's disease or necrotizing enterocolitis. The composition is typically a pharmaceutical composition.

Accordingly, one aspect of the invention includes a composition for eliciting an immune response in an animal comprising an effective amount of an isolated peptide corresponding to an epitope presented in non-native forms of SOD1 in admixture with a suitable diluent or carrier. The medical condition, disease or disorder includes, but is not limited to, amyotrophic lateral sclerosis, Alzheimer's disease and Parkinson's disease. Other medical conditions, diseases or disorders include macular degeneration, glaucoma, ischemia, cerebral infarction, myocardial infarction, atherosclerosis, multiple sclerosis, inflammatory bowel disease, ulcerative colitis, Crohn's disease or necrotizing enterocolitis.

Another aspect of the invention is a composition for eliciting an immune response in an animal comprising an effective amount of an isolated peptide corresponding to an amyotrophic lateral sclerosis-specific epitope in admixture with a suitable diluent or carrier, wherein the isolated peptide corresponding to the amyotrophic lateral sclerosis-specific epitope is selected from the group consisting of the isolated peptides in Table 2 or Table 2A, or an analog thereof.

In one aspect, the composition is a pharmaceutical composition for treating amyotrophic lateral sclerosis in a subject by active immunization, comprising an effective amount of an isolated peptide corresponding to an amyotrophic lateral sclerosis-specific epitope, or an immunogen comprising such an isolated peptide corresponding to said epitope, in admixture with a suitable vehicle, such as a pharmaceutically acceptable, diluent or carrier. In one embodiment, the isolated peptide or an immunogenic form thereof corresponds to an epitope selectively presented or accessible in the monomeric form of SOD1. Such epitopes include those epitopes in SOD1 monomer which normally lie in the SOD1 dimer interface. Other such epitopes are those accessible on the surface of SOD1 when in its dimer form, or when SOD1 is in its aggregated form. In particular embodiments, the isolated peptide corresponding to an amyotrophic lateral sclerosis-specific epitope is selected from the group consisting of the isolated peptides in Table 2 or Table 2A, or an analog thereof.

Another aspect of the invention is a pharmaceutical composition for treating Alzheimer's disease in a subject by active immunization, comprising an effective amount of an isolated peptide corresponding to an Alzheimer's disease-specific epitope, or an immunogen comprising such isolated peptide, in admixture with a suitable, such as a pharmaceutically acceptable, diluent or carrier. In one embodiment, the isolated peptide or an immunogenic form thereof corresponds to an epitope selectively presented or accessible in the monomeric form of SOD1. Such epitopes include those epitopes in SOD1 monomer which normally lie in the SOD1 dimer interface. Other such epitopes are those accessible on the surface of SOD1 when in its dimer form, or when in its aggregated form. In particular embodiments, the isolated peptide corresponding to an Alzheimer's disease-specific epitope is selected from the group consisting of the isolated peptides in Table 2 or Table 2A, or an analog thereof.

A further aspect of the invention is a pharmaceutical composition for treating Parkinson's disease in a subject by active immunization, comprising an effective amount of an isolated peptide corresponding to a Parkinson's disease-specific epitope, or an immunogen comprising such isolated peptide, in admixture with a suitable, such as a pharmaceutically acceptable, diluent or carrier. In one embodiment, the isolated peptide or an immunogenic form thereof corresponds to an epitope selectively presented or accessible in the monomeric form of SOD1. Such epitopes include those which recognize a SOD1 monomer epitope that lies normally in the SOD1 dimer interface. Other such epitopes are those accessible on the surface of SOD1 when in its dimer form, or when in its aggregated form. In particular embodiments, the isolated peptide corresponding to a Parkinson's disease-specific epitope is selected from the group consisting of the isolated peptides in Table 2 or Table 2A, or an analog thereof.

One aspect of the invention includes a composition for eliciting an immune response in an animal comprising an effective amount of a nucleic acid encoding a peptide corresponding to anepitope selectively presented or accessible in non-native forms of SOD1, in admixture with a suitable diluent or carrier. The medical condition, disease or disorder is a SOD1 disorder such as a neurodegenerative disease that includes, but is not limited to, amyotrophic lateral sclerosis, Alzheimer's disease and Parkinson's disease.

A further aspect of the invention is a composition for eliciting an immune response in an animal comprising an effective amount of a nucleic acid encoding an isolated peptide corresponding to an amyotrophic lateral sclerosis-specific epitope in admixture with a suitable diluent or carrier, wherein the isolated peptide corresponding to a amyotrophic lateral sclerosis-specific epitope is selected from the group consisting of the isolated peptides in Table 2 or Table 2A, or an analog thereof.

These compositions are useful to elicit an immune response in an animal and are useful in methods to elicit an immune response in an animal against non-native forms of SOD1, including an immune response against amyotrophic lateral sclerosis-specific epitopes, Alzheimer's disease-specific epitopes and/or Parkinson's disease-specific epitopes.

These compositions are useful to generate binding proteins such as antibodies against non-native forms of SOD1, including antibodies that bind amyotrophic lateral sclerosis-specific epitopes, Alzheimer's disease-specific epitopes and/or Parkinson's disease-specific epitopes.

Accordingly, the invention includes exogenous antibodies specific for non-native forms of SOD1, including amyotrophic lateral sclerosis-specific epitopes, Alzheimer's disease-specific epitopes and/or Parkinson's disease-specific epitopes.

In one embodiment, the antibodies specific for non-native forms of SOD1 are produced using a composition comprising an isolated peptide corresponding to a disease-specific epitope selected from the group consisting of the isolated peptides in Table 2 or Table 2A, or an analog thereof.

In one embodiment, the antibody binds to the epitope RLACGVIGI (SEQ ID NO: 1). In another embodiment the antibody binds to the epitope DLGKGGNEESTKTGNAGS (SEQ ID NO: 2). In another embodiment the antibody binds to the epitope NPLSRKHGGPKDEE (SEQ ID NO: 3). In yet another embodiment the antibody binds to the epitope IKGLTEGLHGF (SEQ ID NO: 5). In another embodiment the antibody binds to the epitope HCIIGRTLVVH (SEQ ID NO: 6). In another embodiment the antibody binds to the epitope RLAC*GVIGI (SEQ ID NO: 8). In another embodiment the antibody binds to the epitope KAVCVLK (SEQ ID NO: 4). In yet another embodiment the antibody binds to the epitope GLHGFHVH (SEQ ID NO: 7).

The antibodies of the invention may be polyclonal antibodies, monoclonal antibodies, chimeric antibodies, humanized antibodies, human antibodies, and/or epitope binding fragments and analogs thereof. The invention further comprises hybridomas that produce antibodies to DSE1a, DSE2 and DSE5. Embodiments of the present invention include the hybridomas per se, as well as progeny thereof, subsequent fusions therewith, and endogenous DNA and RNA that encodes the SOD1 antibody. In related aspects, the invention thus further provides a method for producing SOD1 antibodies, comprising the step of culturing the hybridomas. These antibodies are useful to treat amyotrophic lateral sclerosis by passive immunization. In another embodiment, these antibodies are useful to treat Alzheimer's disease. In a further embodiment, these antibodies are useful to treat Parkinson's disease. For example, they inhibit or neutralize the toxic effect of these misfolded SOD1 species on neurons, and/or they prevent disease progression by immunological clearing of toxic SOD aggregates, by inhibiting SOD1 aggregation mediated by misfolded SOD1, and/or by blocking the SOD1 template directed misfolding process. Thus, the invention includes compositions useful to treat amyotrophic lateral sclerosis, Alzheimer's disease and/or Parkinson's disease in a subject comprising an effective amount of an antibody specific for an amyotrophic lateral sclerosis-specific epitope, Alzheimer's disease-specific epitope or Parkinson's disease-specific epitope respectively, in admixture with a suitable diluent or carrier. The invention in other embodiments provides compositions useful to treat treating macular degeneration, glaucoma, ischemia, cerebral infarction, myocardial infarction, atherosclerosis, multiple sclerosis, inflammatory bowel disease, ulcerative colitis, Crohn's disease or necrotizing enterocolitis.

In addition to antibodies, other agents that bind specifically to epitopes presented or accessible on non-native forms of SOD1 and not presented or accessible on native forms of SOD1 are also provided. Agents that bind include polypeptides, small molecules, nucleic and peptide aptamers, affibodies and anticalins.

More generally, the invention thus comprises a method for treating a subject having a medical condition, disease, or disorder mediated by a non-native form of superoxide dismutase (SOD), the method comprising the step of administering to the subject a composition comprising a pharmaceutically acceptable vehicle and an agent selected from (1) a protein in the form of an antibody or fragment thereof that binds selectively to the monomeric or misfolded form of SOD1, and/or (2) an immunogen that elicits production of said antibody by said subject, and/or (3) a nucleic acid sequence encoding (1) or (2).

The methods of the present invention thus relate to immunotherapeutic applications of SOD1 antibodies that bind selectively to epitopes accessible on the monomeric or misfolded forms of SOD1 present in disease states. The method can be conducted as monotherapy, in which any one antibody or any one epitope is administered to the subject. In the alternative, the method can be conducted as a combination therapy, in which the subject is treated to receive both a selected antibody or peptide corresponding to an epitope and another agent useful in the treatment or management of the disease.

These antibodies are useful to detect non-native forms of monomeric, dimeric or aggregated forms of SOD1, and thereby are useful to diagnose amyotrophic lateral sclerosis, Alzheimer's disease or Parkinson's disease. In one embodiment, the invention includes a method of detecting or diagnosing amyotrophic lateral sclerosis in a subject comprising the steps of:

(a) contacting a test sample of said subject with an antibody specific for an amyotrophic lateral sclerosis-specific epitope, wherein the antibody binds to an amyotrophic lateral sclerosis-specific epitope to produce an antibody-antigen complex;

(b) measuring the amount of the antibody-antigen complex in the test sample; and (c) comparing the amount of antibody-antigen complex in the test sample to a control wherein a difference in the amount of antibody-antigen complex in the test sample as compared to the control is indicative of amyotrophic lateral sclerosis. Optionally, and in the case where the misfolded SOD1 epitope is masked within a SOD1 aggregation, the method provides for the step of treating the sample to promote disaggregation of the SOD1 aggregate to expose the target epitope prior to step (a). In an alternate embodiment, the invention provides a method of detecting or diagnosing Alzheimer's disease. In another embodiment, the invention provides a method for detecting or diagnosing Parkinson's disease.

These antibodies and/or binding fragments thereof are usefully conjugated to labels to produce a diagnostic agent.

The invention also includes kits comprising the compositions and antibodies of the invention to treat neurogenerative diseases such as amyotrophic lateral sclerosis, Alzheimer's disease and Parkinson's disease for instance to inhibit SOD1 aggregation; to elicit an immune response in an animal; or to detect misfolded SOD1, and thereby to diagnose a neurodegenerative disease such as amyotrophic lateral sclerosis, Alzheimer's disease or Parkinson's disease.

In a further aspect the invention provides novel isolated peptides. In one embodiment the novel isolated peptides comprise peptides comprising an amino acid sequence selected from the group consisting of:

| | |
|---|---|
| RLACGVIGI | (SEQ ID NO: 1, DSE1) |
| ACGVIGI | (SEQ ID NO: 9, DSE1 analog) |
| Ac-GG-RLACGVIG-GGKG | (SEQ ID NO: 10, DSE1 analog) |
| CDLGKGGNEESTKTGNAGS | (SEQ ID NO: 11, DSE2 analog) |
| CNPLSRKHGGPKDEE | (SEQ ID NO: 12, DSE3 analog) |
| CIKGLTEGLHGF | (SEQ ID NO: 14, DSE5 analog) |
| RLA[Cysteic acid]GVIGI | (SEQ ID NO: 8, DSE1a) |
| A[Cysteic acid]GVIGI | (SEQ ID NO: 13, DSE1a analog) |
| C-GGG-RLA[Cysteic acid]GVIGI- GSG | (SEQ ID NO: 15, DSE1a analog) |
| KAVCVLK | (SEQ ID NO: 4, DSE4); |
| GSGKAVCLK and | (SEQ ID NO: 16, DSE4 analog); |
| GLHGFHVH | (SEQ ID NO: 7, DSE7). |

In another embodiment the invention comprises novel modified isolated peptides comprising RLA[Cysteic acid] GVIGI (SEQ ID NO:8, DSE1a), where cysteine residue is cysteic acid.

In related aspects, these peptides are provided in labeled form, or as conjugates or fusions e.g. "immunogens" useful to raise antibodies or detect SOD1 and for other diagnostic and therapeutic uses. Such immunogens comprise the peptides coupled, for instance, to KLH or to MAP antigen.

Certain embodiments of the invention relate to a method of i) eliciting an immune response in a subject and/or ii) treating a medical condition, disease, or disorder mediated by a misfolded form of superoxide dismutase (SOD) in a subject in need of treatment, by comprising administering a composition comprising a nucleic acid that encodes for an isolated amyotrophic lateral sclerosis-specific immunogen (e.g. peptide) of the invention in admixture with a suitable diluent or carrier to the subject. Of course, such nucleic acids will encode only those forms of the epitopes and peptides that consist of genetically encoded amino acids, but the nucleic acids may also yield, endogenously, analogs of the encoded epitopes that, after being expressed as such, become modified in vivo such as by nitration, oxidation, carbonylation and the like by the endogenous environment. Suitable RNA and DNA nucleotide sequences are set out in this application (other DNA sequences having sequence identity or synonymous codon equivalents are also useful in the methods). Examples of medical conditions, diseases, or disorders include ALS, Parkinson's Disease, Lewy Body Disease or Alzheimer's Disease. Other examples include treating macular degeneration, glaucoma, ischemia, cerebral infarction, myocardial infarction, atherosclerosis, multiple sclerosis, inflammatory bowel disease, ulcerative colitis, Crohn's disease or necrotizing enterocolitis. The invention also includes composition for treating Alzheimer's disease comprising an effective amount of an isolated nucleic acid that encodes for an epitope selectively presented or accessible in non-native forms of SOD1 in admixture with a suitable diluent or carrier.

The invention also relates to a method for i) increasing immunological clearing of SOD aggregates, ii) reducing SOD1 aggregation mediated by misfolded SOD1, and/or iii) reducing SOD1 template directed misfolding, comprising administering to the subject a composition comprising a pharmaceutically acceptable vehicle and an agent selected from (1) an isolated exogenous antibody that binds selectively to the misfolded form of SOD, and/or (2) an immunogen that elicits production of an endogenous antibody that binds selectively to the monomer or misfolded form of SOD, and/or (3) a nucleic acid sequence encoding (1) or (2).

Another aspect of the invention relates to a method for treating a medical condition, disease, or disorder mediated by a misfolded form of superoxide dismutase (SOD) in a subject in need of treatment, the method comprising administering to the subject in need of treatment an agent (such as an exogenous antibody or immunogen (e.g. peptide) of the invention that i) causes immunological clearing of SOD aggregates, ii) reduces SOD1 aggregation mediated by misfolded SOD1 and/or iii) reduces SOD1 template directed misfolding and/or SOD1 cytotoxicity. The invention also includes methods of treating medical conditions, diseases, or disorders described herein by administering to a subject an effective amount of an antibody specific for epitopes described herein that are selectively presented or accessible in non-native forms of SOD1.

Other features and advantages of the present invention will become apparent from the following detailed description. It should be understood, however, that the detailed description and the specific examples while indicating preferred embodiments of the invention are given by way of illustration only, since various changes and modifications within the spirit and scope of the invention will become apparent to those skilled in the art from this detailed description.

BRIEF DESCRIPTION OF THE FIGURES

Embodiments of the invention will be described in relation to the drawings in which.

DETAILED DESCRIPTION OF THE INVENTION

Figure 1:
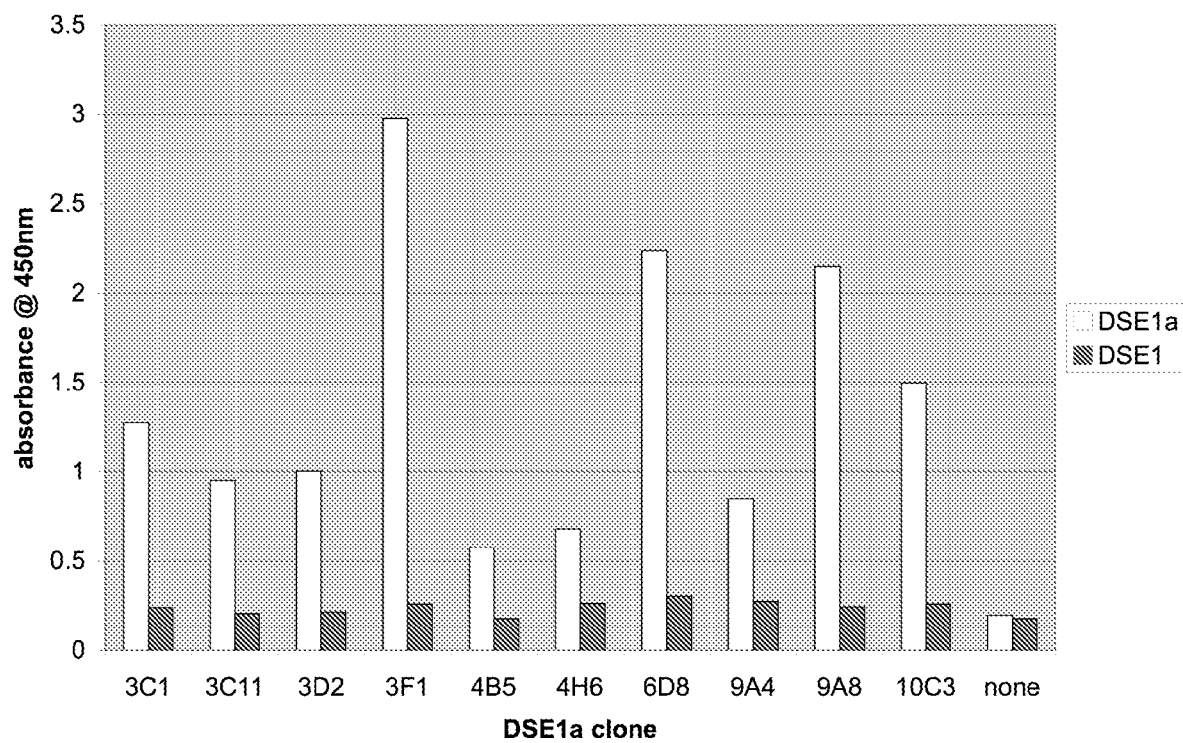
FIG. 1 is a graph demonstrating that anti-DSE1a antibody preferentially recognizes DSE1a over DSE1.

The invention provides the first immunotherapeutic compositions and methods which specifically target toxic SOD1 species, including those SOD1 confomers which may be associated with neurodegenerative diseases, such as ALS, AD and PD, by identifying and taking therapeutic advantage of immunological epitopes (antibody binding sites) exposed on the molecular surface of misfolded and aggregated SOD1. These epitopes are not presented in native, normally-folded SOD1. The invention identifies previously-unknown epitopes that are useful as targets to design compounds or elicit antibodies for therapy or diagnostics. The invention also provides the first immunotherapeutic use of epitopes previously identified as presented in misfolded and aggregated forms of SOD1 but not presented in native forms of SOD1 (see 3 and WO 2005/019828, which are incorporated by reference herein). These epitopes are useful targets for passive or active immunotherapy to prevent disease progression. Without wishing to be bound by theory, these epitopes prevent disease progression by immunological clearing or sequestering of toxic SOD1 aggregates, blocking the SOD1 template-directed misfolding process, neutralizing the toxic effect of these misfolded SOD1 species on neurons, and/or inhibition of oxidative stress mediated by misfolded SOD1.

Compositions and Uses of the Disease Specific Epitopes

The inventors have determined that there are epitopes selectively presented by, or accessible on, monomeric SOD1 or misfolded forms of SOD1 in monomeric, dimeric or aggregated forms, but not on the native, properly-folded homodimeric form of SOD1. The misfolded forms of SOD1 are characterized by the adoption of a conformation, particularly a secondary or tertiary conformation that is different from the conformation adopted by a wild type SOD1 dimer, and/or participates in the formation of SOD1 aggregates that are characteristic of SOD1 disorders including neurodegenerative diseases such as amyotrophic lateral sclerosis, Alzheimer's disease and Parkinson's disease. Such misfolded SOD1 can have a wild type sequence or a mutated sequence. In certain embodiments, the epitopes are those selectively presented by or accessible on misfolded SOD1 having a wild type, or native, sequence. In other embodiments, the epitopes are these selectively presented by or accessible on misfolded SOD1 having mutated or non-wild type sequence. In other embodiments, the epitope is presented by SOD1 monomer (in any form including wild type, mutant, misfolded and native), and becomes accessible on the SOD1 monomer upon dissociation of the monomer from the SOD1 homodimer. Immunological recognition of only misfolded SOD1 will reduce or eliminate autoimmune manifestations caused by antibody binding to normal native SOD1. Immunological recognition of misfolded SOD1 that is wild type, in particular, will be useful particularly in the treatment of sporadic ALS The term "SOD1" as used herein means superoxide dismutase-1 and includes all analog and mutant forms from all species, particularly human SOD1 (i.e. hSOD1) and is optionally referred to as SOD. The amino acid sequence of human SOD1 (e.g. UniProtKB/TrEMBL Accession Number Q6NR85; Genbank Accession number CAG46542; SEQ ID NO:17) and the mRNA nucleotide sequence (e.g. Genbank Accession number NM_000454; SEQ ID NO:18) of human SOD1 have been previously characterized.

"Wild type" refers to the primary amino acid sequence of a native or non-mutant protein, and wild type SOD1 refers to SOD1, and particularly human SOD1, which may be optionally referred to as hSOD1, having a native or naturally occurring amino acid sequence. The amino acid sequence of human SOD1 is provided in SEQ ID NO:17 and the nucleic acid sequence is provided in SEQ ID NO:18. "Wild type" can also refer to the normal native structure of a specific protein (e.g.

the atomic level coordinates of the crystal structure of native dimeric SOD1 protein is available at Protein Data Bank Accession Number 1PUO). Wild type folded SOD1 is optionally referred to as "natively folded" SOD1, "normally folded" SOD1 and/or "properly folded" SOD1.

"Mutant SOD" refers to forms of SOD, and particularly endogenous forms of SOD, that occur as a result of genetic mutation that result for instance in amino acid substitution, such as those substitutions characteristic for instance of familial ALS. Such substitutions include those listed in Table 1.

"Misfolded" as used herein refers to the secondary and tertiary structure of a protein, and indicates that the protein has adopted a conformation that is not normal for that protein in its properly functioning state. Although misfolding can be caused by mutations in a protein, such as amino acid deletion, substitution, or addition, wild-type sequence protein can also be misfolded in disease, and expose disease-specific epitopes for instance, as a result of microenvironmental conditions and/or amino acid modification such as nitration, oxidation, carbonylation or other modification. Other post-translational modifications include non-enzymatic glycation, and ubiquitylation.

In certain embodiments, in the case where the non-native SOD1 is a mutant SOD1 such as a form of SOD1 that comprises sequence variations characteristic of familial ALS, the non-native SOD1 mutant is other than a mutant where one or more of the amino acids A4, G37, G85, or G93 is mutated.

An "epitope" as used herein means a region of a protein that is recognized by a B cell or T-cell receptor, or an antibody or a binding fragment thereof. The epitope is optionally represented herein by the linear amino acid sequence or the region of the protein recognized by the antibody. The "isolated peptides corresponding to an epitope" are optionally themselves referred to as an "epitope".

An epitope is "accessible" in the context of the present specification when it is accessible to binding by an antibody or a binding fragment thereof. A disease-specific epitope of the invention may be partially or completely exposed on the molecular surface of a misfolded protein in a form accessible to antibody binding, and partially or completely obscured from antibody recognition in the natively folded isoform of the protein. Said epitope is presented or accessible selectively in a misfolded or non-native conformation of a protein and not presented or accessible in the native conformation of the protein. "Selectively presented or accessible" is used contextually, to indicate that the referenced epitope is available for binding to an antibody or other binding protein in misfolded SOD1 and not available for antibody binding in native forms of SOD1. The disease-specific epitope is sufficiently different from a corresponding portion of native, properly-folded SOD1 (ie. SOD1 having normal, non-pathogenic SOD1 activity), usually in terms of its conformation, so that an antibody can bind selectively to the epitope. A misfolded SOD1 epitope or disease specific epitope therefore is an epitope that is not accessible on native SOD1, and can be any epitope that is associated with disease and that results from altered conformation and/or from post-translational modification of an amino acid such as oxidation, nitration, carbonylation, non-enzymatic glycation, and ubiquitylation or other modification.

An epitope comprises one or more antigenic determinants. For example an antibody generated against an isolated peptide corresponding to a specific disease-specific epitope recognizes part or all of said epitope sequence. Accordingly, in one embodiment a part of an isolated peptide corresponding to an epitope presented or accessible in misfolded SOD1 that retains an antigenic determinant is used to raise antibodies to said epitope.

When referring to epitopes of SOD1 selectively presented in ALS the epitopes are optionally referred to as ALS-specific epitopes; when referring to epitopes selectively presented in Alzheimer's disease, the epitopes are optionally referred to as AD-specific epitopes and similarly when referring to epitopes selectively presented in Parkinson's disease, the epitopes are optionally referred to as PD-specific epitopes for ease of reference to the named disease. However it is understood that ALS-specific epitopes of SOD1 are not limited to ALS, but are optionally presented in other neurodegenerative diseases such as AD and PD; AD-specific epitopes of SOD1 are not limited to AD, but are optionally presented in other neurodegenerative diseases such as ALS and PD; and PD-specific SOD1 epitopes are not limited to PD, but are optionally presented in other neurodegenerative diseases such as AD and ALS. Epitopes that are accessible selectively on forms of SOD1 that are associated with SOD1-mediated conditions, diseases and disorders are optionally referred to as disease specific epitopes. Disease specific epitopes are present in SOD1 mediated conditions including macular degeneration, glaucoma, ischemia, cerebral infarction, myocardial infarction, atherosclerosis, multiple sclerosis, inflammatory bowel disease, ulcerative colitis, Crohn's disease or necrotizing enterocolitis.

An epitope may be selectively recognized by an antibody in one conformation of a protein and not in a second conformation of the protein. "Selective" is used contextually, to characterize the binding properties of an antibody. An antibody that binds selectively to a given epitope will bind to that epitope either with greater avidity or with more specificity, relative to other, different epitopes presented by the same molecule. For example, an antibody selectively binds a disease specific epitope if it binds misfolded SOD1 in which the disease-specific epitope is accessible, two fold more efficiently than it binds native SOD1 wherein the disease-specific epitope is not accessible. In other embodiments, the antibody binds 3-5 fold, 5-7 fold, 7-10, 10-15, 5-15, or 5-30 fold more efficiently.

Epitopes that are "disease specific", in the context of the present specification, are epitopes that are presented or accessible selectively by one or more misfolded forms of SOD1 that are characteristic of a particular disease or of a disease category.

Because of the SOD1 disease specificity of these epitopes, they are useful targets to treat SOD1 mediated disorders, diseases and conditions such as amyotrophic lateral sclerosis, Alzheimer's disease or Parkinson's disease as well as macular degeneration, glaucoma, ischemia, cerebral infarction, myocardial infarction, atherosclerosis, multiple sclerosis, inflammatory bowel disease, ulcerative colitis, Crohn's disease or necrotizing enterocolitis or to elicit an immune response in an animal. For example, vaccination of subjects diagnosed with amyotrophic lateral sclerosis, Alzheimer's disease or Parkinson's disease with a composition comprising isolated peptides corresponding to the amyotrophic lateral sclerosis-specific epitopes, Alzheimer's disease-specific epitopes or Parkinson's disease-specific epitopes, respectively, inhibits SOD1 aggregate formation in the disease by blocking participation of misfolded SOD1 molecular species in the aggregation process and/or by blocking SOD1 templated directed misfolding, or by inducing immune complex-based clearing of antibody-bound forms of the misfolded neurotoxic SOD1 and/or aggregates.

The epitopes selectively presented or accessible in non-native forms of SOD1 are found in SOD1 associated with neurodegenerative diseases and are useful to treat, diagnose or prevent misfolded-SOD1 related diseases, including Alzheimer's disease, Parkinson's disease and/or amyotrophic lateral sclerosis.

The term "epitope selectively presented or accessible in non-native forms of SOD1" as used herein refers to an epitope that is selectively presented or accessible on monomeric SOD1 or misfolded SOD1 in monomeric, dimeric or aggregated forms, but not on the molecular surface of the native, correctly folded, homodimeric form of SOD1. In other terms, the epitopes can be characterized as those giving rise to antibodies that bind selectively to forms of SOD1 associated with misfolded-SOD1 related diseases, including Alzheimer's disease, Parkinson's disease and/or amyotrophic lateral sclerosis, relative to the native homodimeric form of SOD1.

The following 7 epitopes have been identified as epitopes selectively presented or accessible in non-native forms of SOD1:

```
RLACGVIGI           (SEQ ID NO: 1, DSE1);

DLGKGGNEESTKTGNAGS  (SEQ ID NO: 2, DSE2)
                    (WO 2005/019828);

NPLSRKHGGPKDEE      (SEQ ID NO: 3, DSE3)
                    (WO 2005/019828);

IKGLTEGLHGF         (SEQ ID NO: 5, DSE5) (8);

HCIIGRTLVVH         (SEQ ID NO: 6, DSE6) (8)

KAVCVLK             (SEQ ID NO: 4, DSE4);
and

GLHGFHVH            (SEQ ID NO: 7, DSE7).
```

A person skilled in the art will appreciate that the epitopes selectively presented or accessible in non-native forms of SOD1 can be all or part of the above sequences. The term "part of" as used herein refers to the sequence that retains the epitope activity of binding an antibody selective for non-native forms of SOD1 and wherein the antibody is optionally generated by immunization with an isolated peptide corresponding to said epitope in an animal. The invention also includes analogs of the above sequences, such as RLA[Cysteic Acid]GVIGI (SEQ ID NO: 8), (DSE1a), which has an oxidized cysteine.

The term "Alzheimer's disease-specific epitope" as used herein refers to an epitope that is selectively present or accessible on monomeric SOD1 or misfolded SOD1 in monomeric, dimeric or aggregated form, but not on the native homodimeric form of SOD1. In other terms, the epitopes can be characterized as those wherein immunization with an immunogen comprising isolated peptides corresponding to said epitopes gives rise to antibodies that bind selectively to Alzheimer's disease-associated forms of SOD1, relative to the native homodimeric form of SOD1.

A person skilled in the art will appreciate that the Alzheimer's disease-specific epitope can be all or part of the above sequences. The term "part of" as used herein refers to the sequence that retains the epitope activity of binding an antibody selective for non-native forms of SOD1 wherein the antibody is optionally generated by immunization with an isolated peptide corresponding to all or part of said epitope in an animal. The invention also includes analogs of the above sequences.

The term "Parkinson's disease-specific epitope" as used herein refers to an epitope that is present or accessible on monomeric SOD1 or misfolded SOD1 in monomeric, dimeric or aggregated form, but not on the native homodimeric form of SOD1. In other terms, the epitopes can be characterized as those wherein immunization with an immunogen comprising isolated peptides corresponding to said epitopes gives rise to antibodies that bind selectively to Parkinson's disease-associated forms of SOD1, relative to the native homodimeric form of SOD1.

A person skilled in the art will appreciate that the Parkinson's disease-specific epitope can be all or part of the above sequences. The term "part of" as used herein refers to the sequence that retains the epitope activity of binding an antibody selective for non-native forms of SOD1 wherein the antibody is optionally generated by immunization with an isolated peptide corresponding to said epitope in an animal. The invention also includes analogs of the above sequences.

The term "amyotrophic lateral sclerosis-specific epitope" as used herein refers to an epitope that is selectively present or accessible on monomeric SOD1 or misfolded SOD1 in monomeric, dimeric or aggregated form, but not on the native homodimeric form of SOD1. In other terms, the epitopes can be characterized as those giving rise to antibodies that bind selectively to ALS-associated forms of SOD1, relative to the native homodimeric form of SOD1. A person skilled in the art will appreciate that the amyotrophic lateral sclerosis-specific epitope can be all or part of the above sequences. The term "part of" as used herein refers to the sequence that retains the epitope activity of binding an antibody selective for non-native forms of SOD1 wherein the antibody is optionally generated by immunization with an isolated peptide corresponding to said epitope in an animal. The invention also includes analogs of the above sequences.

The term "analog" as used herein includes parts, extensions, substitutions, variants, modifications or chemical equivalents and derivatives thereof of the amino acid and nucleotide sequences of the present invention that perform substantially the same function as the peptide, protein or nucleic acid molecules of the invention in substantially the same way. For example, analogs of peptides and proteins of the invention include, without limitation, conservative amino acid substitutions. Analogs of peptides also include cysteic acid modification of an amino acid, as in RLAC*GVIGI (SEQ ID NO: 8), (DSE1a). For example, an amino acid is optionally acetylated (Ac-). Analogs of the peptides and proteins of the invention also include additions and deletions to the peptides and proteins of the invention. Analogs of nucleic acids include degenerate nucleotide substitutions that encode an isolated peptide of the invention. In addition, analog peptides and analog nucleotide sequences include derivatives thereof.

A "conservative amino acid substitution", as used herein, is one in which one amino acid residue is replaced with another amino acid residue without abolishing the peptide's desired properties.

The term "derivative of a peptide" refers to a peptide having one or more residues chemically derivatized by reaction of a functional side group. Such derivatized molecules include for example, those molecules in which free amino groups have been derivatized to form amine hydrochlorides, p-toluene sulfonyl groups, carbobenzoxy groups, t-butyloxycarbonyl groups, chloroacetyl groups or formyl groups. Free carboxyl groups may be derivatized to form salts, methyl and ethyl esters or other types of esters or hydrazides. Free hydroxyl groups may be derivatized to form O-acyl or O-alkyl derivatives. The imidazole nitrogen of histidine may be derivatized to form N-im-benzylhistidine. Also included as derivatives are those peptides which contain one or more naturally occurring amino acid derivatives of the twenty standard amino acids. For examples: 4-hydroxyproline may be substituted for proline; 5-hydroxylysine may be substituted for lysine; 3-methylhistidine may be substituted for histidine; homoserine may be substituted for serine; and ornithine may be substituted for lysine. A derivative of a peptide also optionally includes peptides comprising forms of amino acids that are oxidized.

Oxidative stress can lead to damage to cellular protein, DNA and lipids. Oxidative stress has been reported in AD and PD (64). The inventors have shown that antibodies selective for DSE1a comprising an oxidized cysteine in the form cysteic acid, has high affinity for misfolded SOD1. Other amino acids can also be oxidized or nitrated as a result of oxidative stress. For example histidine, arginine and lysine can form carbonyl groups, methionine may be oxidized to methionesulfoxide and phenylalanine can by nitrated to nitrotryptophan. Additionally cysteine can be oxidized to cysteine sulfinic acid.

Accordingly, the epitopes in one embodiment comprise one or more oxidized or nitrated amino acids. In specific embodiments of the invention, the SOD1 epitope may comprise an oxidized or nitrated amino acid, particularly oxidized cysteine, i.e., cysteic acid.

The isolated peptides corresponding to epitopes selectively presented in non-native SOD1, in one embodiment comprise one or more oxidized or nitrated amino acids. In specific embodiments of the invention, the SOD1 epitope may comprise an oxidized or nitrated amino acid, particularly oxidized cysteine, i.e., cysteic acid.

The isolated peptides corresponding to epitopes which are useful in the present invention thus are optionally peptides that incorporate sequence corresponding to contiguous amino acid stretches within the human SOD1 sequence that form epitopes selectively accessible either only in the monomeric forms of SOD, or in any form of SOD1 that has misfolded or is non-native. Epitopes that have been identified as selectively accessible in non-native SOD1 comprise the following amino acid stretches in hSOD1:

| | |
|---|---|
| RLACGVIGI | (SEQ ID NO: 1 at SOD1 SEQ ID NO: 17 residues 143-151) |
| DLGKGGNEESTKTGNAGS | (SEQ ID NO: 2 at SOD1 SEQ ID NO: 17 residues 125-142); |
| NPLSRKHGGPKDEE; | (SEQ ID NO: 3 at SOD1 SEQ ID NO: 17 residues 65-78); |
| IKGLTEGLHGF | (SEQ ID NO: 5 at SOD1 SEQ ID NO: 17 residues 35-45); |
| HCIIGRTLVVH | (SEQ ID NO: 6 at SOD1 SEQ ID NO: 17 residues 110-120); |
| KAVCVLK and | (SEQ ID NO: 4 at SOD SEQ ID NO: 17 residues 3-9) |
| GLHGFHVH | (SEQ ID NO: 7 at SOD SEQ ID NO: 17 residues 41-48) |

To serve as a useful immunogen either for active immunotherapy or to raise antibodies for use for instance in passive immunotherapy, the peptide desirably incorporates a minimum of about 3, 4, 5, 6, or 7 SOD1 disease specific epitope residues. In one embodiment, the isolated peptide corresponding to an epitope desirably comprises at least 8 SOD1 residues Typically, the peptide will not require more than about 50 SOD1 residues, and more usually will be accommodated within a SOD1 stretch that is less than about 40 residues, e.g., about 30 residues and even more usually less than about 20 residues. It is possible to use peptides comprising an even larger portion of SOD1, possibly resulting in multiple antibodies, requiring selection for those that bind selectively to an epitope characteristic of misfolded SOD1.

SOD1 sequence useful to be targeted in accordance with embodiments of the present invention include the hSOD1 regions incorporating residues 3-9, residues 35-45, residues 41-48, residues 65-78, residues 125-142, residues 143-151 and residues 145-151. As noted, such peptide sequence corresponding to misfolded SOD1 epitopes can be truncated to incorporate a minimum of any 5, 6, or 7 residues from the regions noted. For example DSE1, having sequence RLACGVIGI (SEQ ID NO: 1) can be truncated by removing the first two amino acids "RL". In addition, these regions can be extended, as noted, to incorporate additional flanking SOD1 residues to a maximum number of residues that strikes any desired balance between the cost of peptide or vaccine production and the desired specificity and other properties of the resulting antibody.

In a preferred embodiment, the isolated peptide corresponding to a disease specific epitope comprises all or part of the sequence of an isolated peptide selected from the group consisting of peptides in Table 2 or Table 2A, or an analog thereof.

The peptides corresponding to these epitopes can further comprise additional non-SOD1 amino acid residues particularly at the N- and C-terminal flanks thereof, which may be useful in conjugating the peptide with an agent useful for instance in eliciting an immune response, or an agent serving as a tag useful in the production of the peptide or to monitor its presence. For instance, the peptide may further comprise an N-terminal Cys residue to assist with coupling to KLH or the like. The peptide may further comprise one, two, three or more flanking glycine residues, or a glycine/serine or glycine/lysine combination such as GSG (SEQ ID NO: 32) or GGKG (SEQ ID NO: 33), to improve the immune response by increasing the length of the peptide without changing the specificity of antibodies that are formed. The peptide corresponding to the epitope may further comprise a linker effective to couple the peptide tandemly to another copy of the same or a different peptide corresponding to the same or a different epitope. Alternatively, the peptide corresponding to an epitope may further comprise a polyhistidine or Flag tag. In another embodiment, the peptides may comprise additional amino acids that enhance the immunogenecity or solubility of the peptide. In one embodiment, the additional amino acids number from 1 to about 10, preferably 1 to 8, more preferably 1 to 5. Importantly the additional residues do not materially affect the conformation of the peptide. In one embodiment, the isolated peptide corresponding to the amyotrophic lateral sclerosis-specific epitope comprises 6 additional amino acids and comprises the sequence GGR-LACGVIGIGGKG (SEQ ID NO: 34). In one embodiment, the isolated peptide corresponding to the amyotrophic lateral sclerosis-specific epitope comprises 4 additional amino acids and comprises the sequence GGRLACGVIGIAQ (SEQ ID NO: 35).

In one embodiment, the analog amino acid sequences of the isolated peptide corresponding to disease specific epitopes selectively presented or accessible in non-native forms of SOD1 typically have at least: 60%, 70%, 80% or 90% sequence identity to the above sequences. In another embodiment, the analog amino acid sequences of the isolated peptide corresponding to ALS-specific epitopes, PD-specific epitopes or AD-specific epitopes have at least: 60%, 70%, 80% or 90% sequence identity to the above sequences. The term "sequence identity" as used herein refers to the percentage of sequence identity between two polypeptide sequences. In order to determine the percentage of identity between two polypeptide sequences, the amino acid sequences of such two sequences are aligned, preferably using the Clustal W algorithm (9), together with BLOSUM 62 scoring matrix (10) and a gap opening penalty of 10 and gap extension penalty of 0.1, so that the highest order match is obtained between two sequences wherein at least 50% of the total length of one of the sequences is involved in the alignment. Other methods that may be used to align sequences are the alignment method of Needleman and Wunsch (11), as revised by Smith and Waterman (12) so that the highest order match is obtained between the two sequences and the number of identical amino acids is determined between the two sequences. Other methods to calculate the percentage identity between two amino acid sequences are generally art recognized and include, for example, those described by Carillo and Lipton (13) and those described in Computational Molecular Biology (14). Generally, computer programs will be employed for such calculations. Computer programs that may be used in this regard include, but are not limited to, GCG (15) BLASTP, BLASTN and FASTA (16).

Thus, while the preferred epitope targets comprise sequence that is found in hSOD1, it will be appreciated that the present invention also embraces analogs of these epitope sequences that, as noted above, include, derivatives, extensions, truncations, modified amino acids and the like. Such forms of the isolated peptides corresponding to disease specific epitopes are embraced by the term "analogs". Such analogs are also useful to raise antibodies that will bind to the epitopes present on misfolded or monomeric SOD, for instance, to one of the seven epitopes identified hereinabove.

Thus, relative to the preferred epitopes identified above, useful isolated peptides corresponding to an epitope analogs, include isolated peptides that comprise but are not limited to:

For RLACGVIGI: (SEQ ID NO: 36 and 37)
  N-terminal truncation of R or RL; N-terminal extension with G or GG or acetyl-GG and/or C-terminal extension with G, GG, GGK or GGKG (SEQ ID NO: 33), for instance to arrive at acetyl-RLACGVIVIVGGKG (SEQ ID NO: 38); with or without oxidation of C to yield cysteic acid, to arrive at AC*GVIVIVG (SEQ ID NO: 39), including CGGGRLAC*GVIGIGSG (SEQ ID NO: 40); RLAC*GVIGIGSGSEQ ID NO: 41) and CRLAC*GVIGIGSG (SEQ ID NO: 42); (wherein C* denotes cysteic acid)

For DLGKGGNEESTKTGNAGS; (SEQ ID NO: 43 and 44)
  N-terminal truncation of D, DL, DLG, DLGK and/or C-terminal truncation of S, GS, AGS, NAGS (residues 15-18 of SEQ ID NO:2); N-terminal extension with C or with G, GG or GGG; C-terminal extension with G, GG, GS or GSG; for instance to arrive at CDLGKG-GNEESTKTGNAGS (SEQ ID NO: 45), with or without internal modification by carbonylation of one or two K residues, for instance; and including such peptides as LGKGGNEESTKTGNAGS (SEQ ID NO: 46), DLGKGGNEESTKTGNAG (SEQ ID NO: 47), GKG-GNEESTKTGNAGS, (SEQ ID NO: 48), DLGKG-GNEESTKTGNA (SEQ ID NO: 49), KGGNEESTKT-GNAGS (SEQ ID NO: 50), DLGKGGNEESTKTGN (SEQ ID NO: 51), GGNEESTKTGNAGS (SEQ ID NO: 52), DLGKGGNEESTKTG (SEQ ID NO: 53), LGKG-GNEESTKTGNAG (SEQ ID NO: 54), GKGGNEEST-KTGNA (SEQ ID NO: 55), or KGGNEESTKTGN (SEQ ID NO: 56).

For NPLSRKHGGPKDEE; (SEQ ID NOS: 57 and 58)
N-terminal truncation of N, NP, NPL and/or C-terminal truncation of E, EE, DEE; N-terminal extension with C or with G, GG or GGG; C-terminal extension with G, GG, GS or GSG; for instance to arrive at CNPLSRKHG-GPKDEE (SEQ ID NO: 59), with or without internal modification by carbonylation of one or two H residues, for instance;

For IKGLTEGLHGF;
N-terminal addition of C, to arrive at CIKGLTEGLHGF (SEQ ID NO: 60)

And for HCIIGRTLWH (SEQ ID NOS: 61 and 62);
N-terminal truncation of H or HC and/or C-terminal truncation of H, or VH, N-terminal extension to include SOD sequence at residues 109 or 108/109 and/or to include G, GG, or GGG and/or C-terminal extension by one or two SOD residues such as residues 121 or 121/122, for instance to arrive at GGGHCIIGRTLVVHGSG (SEQ ID NO: 63).

Examples of the above described peptides are summarized in Table 2A.

TABLE 2A

Isolated DSE Peptides and Analogs

| | |
|---|---|
| ACGVIGI | (SEQ ID NO: 9, DSE1 analog); |
| Ac-GG-RLACGVIG-GGKG | (SEQ ID NO: 10, DSE1 analog); |
| CDLGKGGNEESTKTGNAGS | (SEQ ID NO: 11, DSE2 analog); |
| CNPLSRKHGGPKDEE | (SEQ ID NO: 12; DSE3 analog); |
| CIKGLTEGLHGF | (SEQ ID NO: 14, DSE5 analog); |
| RLA[Cysteic acid]GVIGI | (SEQ ID NO: 8, DSE1a); |
| A[Cysteic acid]GVIGI | (SEQ ID NO: 13, DSE1a analog); |
| C-GGG- RLA[Cysteic acid]GVIGI- GSG and | (SEQ ID NO: 15, DSE1a analog); |
| GSGKAVCLK | (SEQ ID NO: 16, DSE4 analog). |

As noted above, the invention also includes a DSE1 epitope, isolated peptide corresponding to the epitope and an antibody directed against the epitope. Experiments further characterized DSE1. In one embodiment of the invention, the inventors prepared antibodies directed against epitopes found on non-native forms of SOD1. In another embodiment of the invention, the inventors detected misfolded SOD1 from the spinal tissues of G85R, G93A and G37R ALS mouse models by immunoprecipitation using the SED1 antibody. In a further embodiment of the invention, the inventors detected misfolded SOD1 in spinal sections from G93A, G37R ALS mouse models and from a human patient with ALS, using the SED1 antibody as a probe. In another embodiment of the invention, the inventors used SED1 to determine the subcellular localization of misfolded SOD1 where it was determined that the major site of misfolded SOD1 deposition is vacuolated mitochondria within the motor neurons of the ventral horn. Further, misfolded SOD1 was detected in both the mitochondrial and cytoplasmic spinal cord fractions but only minor amounts were immunoprecipitated from similar fractions from liver and brain tissues of G93A mouse. In G85R mice, misfolded SOD1 was enriched in spinal cord and brain mitochondria compared to the amount recovered from the cytosol. In another embodiment of the invention, the inventors showed that misfolded SOD1 was initially absent but was detected prior to disease onset and correlates with motor neuron loss in ALS model mice.

In the case where the isolated peptide corresponding to an epitope per se or its analog is not sufficiently immunogenic, even when administered with standard adjuvants, the isolated peptide or isolated peptide analog can be administered in the form of an "immunogen", in which the isolated peptide corresponding to the epitope or analog is fused to or conjugated with an agent that enhances the immunogenicity of the peptide. Thus, the immunogenicity or effectiveness of the composition to treat amyotrophic lateral sclerosis, Alzheimer's disease and/or Parkinson's disease or elicit an immune response can also be enhanced by conjugating the isolated peptide corresponding to a disease specific epitope (e.g. such as an amyotrophic lateral sclerosis-specific epitope) either directly, such as through an amide bond, or indirectly through a chemical linker such as carbodiimide or any peptide spacer sequence such as a glycine or glycine-serine sequence including Gly4-S (SEQ ID NO: 64), to a molecule that enhances the immunogenicity of the peptide corresponding to the epitope. For example, an isolated peptide corresponding to an amyotrophic lateral sclerosis-specific epitope can be conjugated to MAP antigen, or keyhole limpet hemocyanin (KLH). KLH is a respiratory protein found in mollusks. Its large size makes it very immunogenic, and the large number of lysine residues available for conjugation make it very useful to attach to a polypeptide, such as an isolated peptide corresponding to an amyotrophic lateral sclerosis-specific epitope. Conjugation of KLH can be done through an N-terminal Cys residues added to the isolated peptide corresponding to the epitope, if no other convenient site is available on the peptide for KLH conjugation.

Thus, the composition for eliciting an immune response may comprise an immunogen. An "immunogen" as used herein means a substance which provokes an immune response and/or causes production of an antibody. In addition to the isolated peptides, conjugates and fusions described herein, peptide mimetics which elicit cross-reactive antibodies to disease specific epitopes of SOD1 are useful (see 82).

A person skilled in the art will appreciate that there may be other epitopes selectively presented or accessible in non-native forms of SOD1, such as other amyotrophic lateral sclerosis-specific epitopes, other Alzheimer's disease-specific epitopes, and/or other Parkinson's disease-specific epitopes. For example, other disease specific epitopes may be identified using the epitope protection assay described in WO 2005/019828 which is specifically incorporated by reference herein. In another example, other disease specific epitopes may be identified using the method disclosed in Khare et al. (8). Furthermore, useful epitopes can be identified as those presenting selectively in SOD1 that is denatured, or SOD1 that is subjected to denaturing conditions such as chaotropic agents, heat, pH extremes, or detergents known to those practiced in the art, or otherwise treated to induce adoption of a misfolded conformation, relative to a pH neutral control SOD1.

In one embodiment, the invention provides a method of identifying disease specific epitopes in disease associated non-native proteins. The rationale for selecting disease specific epitopes is based on several considerations. The selected linear peptide epitopes should be obscured in an antibody inaccessible state in the normal isoform of the targeted protein, but exposed at the surface in the disease-misfolded isoform such that the linear peptide epitopes may be bound by an antibody specific for the normally obscured epitope. Other considerations include the predicted or experimentally defined role of the defined specific epitope in the formation of aggregates, and the adequate length and immunogenicity of a peptide corresponding to the epitope as a target for immunization or immunotherapy, The optimal disease specific epitopes benefit from the safety of immune response against a non-native antigen, with minimization of autoimmunity and the comparative effectiveness of minimal adjuvant regimens for therapeutic vaccines. The optimal disease-specific epitopes also benefit from the efficacy of neutralization and inhibition of the toxic and template-directed activity of misfolded proteins by antibody binding. Neutralization may also accelerate the degradation of the misfolded protein species by systems such as the reticulo-endothelial system and by the resident CNS immune effector cells such as microglia.

Compositions Comprising Epitopes for Treating SOD1 Mediated Neurodegenerative Diseases One aspect of the invention is a composition for treating Alzheimer's disease in a subject comprising an effective amount of an isolated peptide corresponding to an epitope selectively presented or accessible in a non-native form of SOD1 in admixture with a suitable, such as a pharmaceutically acceptable, diluent or carrier. Another aspect of the invention is a composition for treating Parkinson's disease in a subject comprising an effective amount of an isolated peptide corresponding to epitope selectively presented or accessible in a non-native form of SOD1 in admixture with a suitable, such as a pharmaceutically acceptable, diluent or carrier. A further aspect of the invention is a composition for treating amyotrophic lateral sclerosis in a subject comprising an effective amount of an isolated peptide corresponding to an epitope selectively presented or accessible in a non-native form of SOD1 in admixture with a suitable, such as a pharmaceutically acceptable, diluent or carrier. The term "Isolated peptide" refers to peptide that has been produced, for example, by recombinant or synthetic techniques, and removed from the source that produced the peptide, such as recombinant cells or residual peptide synthesis reactants. The isolated peptide is optionally "purified", which means at least: 80%, 85%, 90%, 95%, 98% or 99% purity and optionally pharmaceutical grade purity.

An "isolated peptide corresponding to an epitope" as used herein refers to the produced peptide that comprises the epitope or a region of the epitope and is the same or similar in sequence to a disease specific epitope in non-native SOD1. "Epitope" is optionally used to refer to the produced isolated peptide that corresponds to the epitope on SOD1 selectively presented or accessible in non-native forms of SOD1.

In the case where the isolated peptide corresponding to disease specific epitope, per se is not sufficiently immunogenic, even when administered with standard adjuvants, the isolated peptide can be administered in the form of an immunogen, in which the isolated peptide is fused to or conjugated with an agent that enhances the immunogenicity of said peptide.

In certain embodiments, the isolated peptide corresponding to an epitope selectively presented or accessible in a non-native form of SOD1 comprises all or part of a Table 2 or Table 2A isolated peptide referenced herein above.

As used herein, the property of inhibiting or reducing SOD1 aggregate formation is revealed as a reduction in the formation rate, number or size of neurotoxic SOD1 aggregates, as revealed using assays established for this purpose, and as exemplified herein.

One aspect of the invention is a composition useful for treating amyotrophic lateral sclerosis in a subject comprising an effective amount of an isolated peptide corresponding to amyotrophic lateral sclerosis-specific epitope in admixture with a suitable, such as a pharmaceutically acceptable, diluent or carrier, such as pharmaceutically acceptable carriers. In other embodiments, the isolated peptide corresponding to an amyotrophic lateral sclerosis-specific epitope comprises an having the sequence of a Table 2 or Table 2A isolated peptide referenced above.

As used herein, the phrase "treating amyotrophic lateral sclerosis" as used herein includes inhibiting the disease, preventing the disease or reducing the symptoms associated with the disease.

A further aspect of the invention is a composition useful for treating Alzheimer's disease in a subject comprising an effective amount of an isolated peptide corresponding to an Alzheimer's disease-specific epitope in admixture with a suitable vehicle, such as a pharmaceutically acceptable, diluent or carrier. In embodiments, the isolated peptide corresponding to Alzheimer's disease-specific epitope comprises an isolated peptide selected from the group consisting of the isolated peptides in Table 2 or Table 2A, or an analog thereof.

As used herein, the phrase "treating Alzheimer's disease" as used herein includes inhibiting the disease, preventing the disease or reducing the symptoms associated with the disease.

Another aspect of the invention is a composition useful for treating Parkinson's disease in a subject comprising an effective amount of an isolated peptide corresponding to a Parkinson's disease-specific epitope in admixture with a suitable, such as a pharmaceutically acceptable, diluent or carrier, such as pharmaceutically acceptable carriers. In embodiments, the isolated peptide corresponding to a Parkinson's disease-specific epitope comprises an isolated peptide selected from the group consisting of the isolated peptides in Table 2 or Table 2A, or an analog thereof.

As used herein, the phrase "treating Parkinson's disease" as used herein includes inhibiting the disease, preventing the disease or reducing the symptoms associated with the disease.

The compositions described herein are also useful for treating other diseases, disorders and conditions such as macular degeneration, glaucoma, ischemia, cerebral infarction, myocardial infarction, atherosclerosis, multiple sclerosis, inflammatory bowel disease, ulcerative colitis, Crohn's disease or necrotizing enterocolitis.

Compositions Comprising Epitopes for Eliciting Immune Response

An aspect of the invention is a composition for eliciting an immune response in an animal comprising an effective amount of an isolated epitope selectively presented or accessible in non-native forms of SOD1 in admixture with a suitable diluent or carrier. In a preferred embodiment, the epitope selectively presented or accessible in non-native forms of SOD1 comprises an isolated peptide selected from the group consisting of the isolated peptides in Table 2 or Table 2A, or an analog thereof.

One aspect of the invention is a composition for eliciting an immune response in an animal comprising an effective amount of an isolated peptide corresponding to an amyotrophic lateral sclerosis-specific epitope in admixture with a suitable diluent or carrier, wherein the amyotrophic lateral sclerosis-specific epitope comprises an isolated peptide selected from the group consisting of the isolated peptides in Table 2 or Table 2A, or an analog thereof.

Another aspect of the invention is a composition for eliciting an immune response in an animal comprising an effective amount of an isolated peptide corresponding to an Alzheimer's disease-specific epitope in admixture with a suitable diluent or carrier, wherein the isolated peptide corresponding to an Alzheimer's disease-specific epitope comprises an isolated peptide selected from the group consisting of the isolated peptides in Table 2 or Table 2A, or an analog thereof.

A further aspect of the invention is a composition for eliciting an immune response in an animal comprising an effective amount of an isolated the isolated peptide corresponding to a Parkinson's disease-specific epitope in admixture with a suitable diluent or carrier, wherein the isolated peptide corresponding to a Parkinson's disease-specific epitope comprises an isolated peptide selected from the group consisting of the isolated peptides in Table 2 or Table 2A, or an analog thereof.

The phrase "eliciting an immune response" is defined as initiating, triggering, causing, enhancing, improving or augmenting any response of the immune system, for example, of either a humoral or cell-mediated nature. The initiation or enhancement of an immune response can be assessed using assays known to those skilled in the art including, but not limited to, antibody assays (for example ELISA assays), antigen specific cytotoxicity assays and the production of cytokines (for example ELISPOT assays).

The composition for eliciting an immune response may comprise an immunogen. An "immunogen" as used herein means a substance which provokes an immune response and/or causes production of an antibody. In certain embodiments, the immunogen comprises an isolated peptide selected from the isolated peptides provided in Table 2 or Table 2A. The isolated peptide is, in some embodiments, conjugated to a suitable carrier such as KLH. In addition to the isolated peptides described herein, peptide mimetics which elicit cross-reactive antibodies to disease specific epitopes of SOD1 are useful. The term "animal" or "subject" as used herein includes all members of the animal kingdom including mammals, preferably humans.

As used herein, the phrase "effective amount" means an amount effective, at dosages and for periods of time necessary to achieve a desired result. Effective amounts may vary according to factors such as the disease state, age, sex, weight of the animal. Dosage regime may be adjusted to provide the optimum therapeutic response.

Pharmaceutical Compositions Comprising Isolated Peptides Corresponding to Disease Specific Epitopes The compositions described herein can be prepared by per se known methods for the preparation of pharmaceutically acceptable compositions that can be administered to subjects, optionally as a vaccine, such that an effective quantity of the active substance is combined in a mixture with a pharmaceutically acceptable vehicle. Suitable vehicles are described, for example, in Remington's Pharmaceutical Sciences (17). On this basis, the compositions include, albeit not exclusively, solutions of the substances in association with one or more pharmaceutically acceptable vehicles or diluents, and contained in buffered solutions with a suitable pH and iso-osmotic with the physiological fluids.

Pharmaceutical compositions include, without limitation, lyophilized powders or aqueous or non-aqueous sterile injectable solutions or suspensions, which may further contain antioxidants, buffers, bacteriostats and solutes that render the compositions substantially compatible with the tissues or the blood of an intended recipient. Other components that may be present in such compositions include water, surfactants (such as Tween), alcohols, polyols, glycerin and vegetable oils, for example. Extemporaneous injection solutions and suspensions may be prepared from sterile powders, granules, tablets, or concentrated solutions or suspensions. The composition may be supplied, for example but not by way of limitation, as a lyophilized powder which is reconstituted with sterile water or saline prior to administration to the patient.

Pharmaceutical compositions of the invention may comprise a pharmaceutically acceptable carrier. Suitable pharmaceutically acceptable carriers include essentially chemically inert and nontoxic compositions that do not interfere with the effectiveness of the biological activity of the pharmaceutical composition. Examples of suitable pharmaceutical carriers include, but are not limited to, water, saline solutions, glycerol solutions, ethanol, N-(1(2,3-dioleyloxy)propyl)N,N,N-trimethylammonium chloride (DOTMA), diolesylphosphotidyl-ethanolamine (DOPE), and liposomes. Such compositions should contain a therapeutically effective amount of the compound, together with a suitable amount of carrier so as to provide the form for direct administration to the patient.

The composition may be in the form of a pharmaceutically acceptable salt which includes, without limitation, those formed with free amino groups such as those derived from hydrochloric, phosphoric, acetic, oxalic, tartaric acids, etc., and those formed with free carboxyl groups such as those derived from sodium, potassium, ammonium, calcium, ferric hydroxides, isopropylamine, triethylamine, 2-ethylamino ethanol, histidine, procaine, etc.

Immunogenicity can be significantly improved if the immunizing agent(s) or immunogen (e.g. isolated peptide corresponding to an amyotrophic lateral sclerosis-specific epitope or a fusion or conjugate thereof with an immune enhancing agent) and/or composition is, regardless of administration format, co-immunized with an adjuvant. Commonly, adjuvants are used as a 0.05 to 1.0 percent solution in phosphate-buffered saline. Adjuvants enhance the immunogenicity of an immunogen but are not necessarily immunogenic themselves. Adjuvants may act by retaining the immunogen locally near the site of administration to produce a depot effect facilitating a slow, sustained release of immunogen to cells of the immune system. Adjuvants can also attract cells of the immune system to an immunogen depot and stimulate such cells to elicit immune responses. As such, embodiments of this invention encompass compositions further comprising adjuvants.

Adjuvants have been used for many years to improve the host immune responses to, for example, vaccines. Intrinsic adjuvants (such as lipopolysaccharides) normally are the components of killed or attenuated bacteria used as vaccines. Extrinsic adjuvants are immunomodulators which are typically non-covalently linked to antigens and are formulated to enhance the host immune responses. Thus, adjuvants have been identified that enhance the immune response to antigens delivered parenterally. Some of these adjuvants are toxic, however, and can cause undesirable side effects making them unsuitable for use in humans and many animals. Indeed, only aluminum hydroxide, aluminum sulfate and aluminum phosphate (collectively commonly referred to as alum) are routinely used as adjuvants in human and veterinary vaccines. Alum may be used with immunostimulating agents such as MPL or 3-DMP; QS21; and monomeric or polymeric amino acids such as polyglutamic acid or polylysine. The efficacy of alum in increasing antibody responses to diphtheria and tetanus toxoids is well established. Notwithstanding, it does have limitations. For example, alum is ineffective for influenza vaccination and inconsistently elicits a cell mediated immune response with other immunogens. The antibodies elicited by alum-adjuvanted antigens are mainly of the IgG1 isotype in the mouse, which may not be optimal for protection by some vaccinal agents.

A wide range of extrinsic adjuvants can provoke potent immune responses to immunogens. These include saponins such as Stimulons (QS21, Aquila, Worcester, Mass.) or particles generated therefrom such as ISCOMs and (immunostimulating complexes) and ISCOMATRIX, complexed to membrane protein antigens (immune stimulating complexes), pluronic polymers with mineral oil, killed mycobacteria and mineral oil, Freund's complete adjuvant, bacterial products such as muramyl dipeptide (MDP) and lipopolysaccharide (LPS), as well as lipid A, and liposomes.

In one aspect of this invention, adjuvants useful in any of the embodiments of the invention described herein are as follows. Adjuvants for parenteral immunization include aluminum compounds (such as aluminum hydroxide, aluminum phosphate, and aluminum hydroxy phosphate). The antigen can be precipitated with, or adsorbed onto, the aluminum compound according to standard protocols. Other adjuvants such as RIBI (ImmunoChem, Hamilton, Mont.) can also be used in parenteral administration.

Adjuvants for mucosal immunization include bacterial toxins (e.g., the cholera toxin (CT), the *E. coli* heat-labile toxin (LT), the *Clostridium difficile* toxin A and the pertussis toxin (PT), or combinations, subunits, toxoids, or mutants thereof). For example, a purified preparation of native cholera toxin subunit B (CTB) can be of use. Fragments, homologs, derivatives, and fusion to any of these toxins are also suitable, provided that they retain adjuvant activity. Preferably, a mutant having reduced toxicity is used. Suitable mutants have been described (e.g., in WO 95/17211 (Arg-7-Lys CT mutant), WO 96/6627 (Arg-192-Gly LT mutant), and WO 95/34323 (Arg-9-Lys and Glu-129-Gly PT mutant)). Additional LT mutants that can be used in the methods and compositions of the invention include, for example Ser-63-Lys, Ala-69-Gly, Glu-110-Asp, and Glu-112-Asp mutants. Other adjuvants (such as a bacterial monophosphoryl lipid A (MPLA) of various sources (e.g., *E. coli, Salmonella minnesota, Salmonella typhimurium*, or *Shigella flexneri*, saponins, or polylactide glycolide (PLGA) microspheres) can also be used in mucosal administration.

Other adjuvants include cytokines such as interleukins for example IL-1, IL-2 and IL-12, chemokines, for example CXCL10 and CCL5, macrophage stimulating factor, and/or tumor necrosis factor. Other adjuvants that may be used include CpG oligonucleotides (Davis. Curr Top Microbiol Immunol., 247:171-183, 2000).

Oil in water emulsions include squalene; peanut oil; MF59 (WO 90/14387); SAF (Syntex Laboratories, Palo Alto, Calif.); and Ribi™ (Ribi Immunochem, Hamilton, Mont.). Oil in water emulsions may be used with immunostimulating agents such as muramyl peptides (for example, N-acetylmuramyl-L-threonyl-D-isoglutamine (thr-MDP), -acetyl-nor-muramyl-L-alanyl-D-isoglutamine (nor-MDP), N-acetylmuramyl-L-alanyl-D-isoglutamyl-L-alanine-2-(1'-2'dipalmitoyl-sn-glycero-3-hydroxyphosphoryloxy)-ethylamine (MTP-PE), N-acetylglucsaminyl-N-acetylmuramyl-L-Al-D-isoglu-L-Ala-dipalmitoxy propylamide (DTP-DPP) theramide (TM)), or other bacterial cell wall components.

Adjuvants useful for both mucosal and parenteral immunization include polyphosphazene (for example, WO 95/2415), DC-chol (3 b-(N—(N',N'-dimethyl aminomethane)-carbamoyl) cholesterol (for example, U.S. Pat. No. 5,283,185 and WO 96/14831) and QS-21 (for example, WO 88/9336).

An adjuvant may be coupled to an immunogen for administration (Livingston. J Immunol., 159: 1383-1392, 1997). For example, a lipid such as palmitic acid, may be coupled directly to one or more peptides such that the change in conformation of the peptides comprising the immunogen does not affect the nature of the immune response to the immunogen.

The choice of an adjuvant may depend on a number of factors including the route of administration, the efficacy of the adjuvant, the dosing regimen, the stability of the vaccine containing the adjuvant and the species being vaccinated. The adjuvant may be administered with an immunogen as a single composition. Further, an adjuvant may be administered before, concurrent or after administration of the immunogen.

The immunogenicity or effectiveness of the composition to treat amyotrophic lateral sclerosis, Alzheimer's disease and/or Parkinson's disease as well as to treat macular degeneration, glaucoma, ischemia, cerebral infarction, myocardial infarction, atherosclerosis, multiple sclerosis, inflammatory bowel disease, ulcerative colitis, Crohn's disease or necrotizing enterocolitis or elicit an immune response can also be enhanced by conjugating the isolated peptide corresponding to a disease specific epitope (e.g. such as an amyotrophic lateral sclerosis-specific epitope) either directly, such as through an amide bond, or indirectly through a chemical linker such as carbodiimide or any peptide spacer sequence such as a glycine or glycine-serine sequence including Gly4-S (SEQ ID NO:64), to a molecule that enhances the immunogenicity of the epitope. For example, an isolated peptide corresponding to an amyotrophic lateral sclerosis-specific epitope can be conjugated to keyhole limpet hemocyanin (KLH). KLH is a respiratory protein found in mollusks. Its large size makes it very immunogenic, and the large number of lysine residues available for conjugation make it very useful to attach to an protein, such as an isolated peptide corresponding to an amyotrophic lateral sclerosis-specific epitope.

Other guidance on peptide vaccination technique is found in the work showing that a disease-specific epitope for misfolded prion protein (6) provides a target for prion-infected neuroblastoma cells in vitro (7), and that peptide vaccination of mice with this epitope is protective against inoculation of infectious prions.

Isolated peptides corresponding to the epitopes or analogs thereof selectively presented or accessible in non-native forms of SOD1, including amyotrophic lateral sclerosis-specific, Alzheimer's disease-specific and Parkinson's disease-specific epitopes are readily prepared using a variety of methods known to one skilled in the art. Accordingly, peptides that correspond to disease specific epitopes such as amyotrophic lateral sclerosis-specific epitopes may be prepared by chemical synthesis using techniques well known in the chemistry of proteins such as solid phase synthesis (18) or synthesis in homogenous solution (19).

Peptides corresponding to the epitopes selectively presented or accessible in non-native forms of SOD1 (disease specific epitopes), including amyotrophic lateral sclerosis-specific, Alzheimer's disease-specific and Parkinson's disease-specific epitopes may also be produced by recombinant DNA technology. To prepare peptides corresponding to the amyotrophic lateral sclerosis-specific epitopes by recombinant DNA techniques, a DNA sequence encoding the peptide corresponding to amyotrophic lateral sclerosis-specific epitope must be prepared. Consequently, the present invention also includes the use of purified and isolated nucleic acids comprising a nucleotide sequence coding for amyotrophic lateral sclerosis-specific epitopes to treat amyotrophic lateral sclerosis or to elicit an immune response.

In one embodiment the nucleic acid sequence encoding the peptides corresponding to epitopes selectively presented or accessible in non-native forms of SOD1 is incorporated into an expression vector adapted for transfection or transformation of a host cell. In another embodiment the nucleic acid sequence encoding the peptides corresponding to amyotrophic lateral sclerosis-specific epitopes is incorporated into an expression vector adapted for transfection or transformation of a host cell. In a further embodiment, the nucleic acid sequence encoding the peptides corresponding to Alzheimer's disease specific epitopes is incorporated into an expression vector adapted for transfection or transformation. In another embodiment, the nuclei acid sequence encoding the peptides corresponding to Parkinson's disease specific epitopes is incorporated into an expression vector adapted for transfection or transformation. The nucleic acid molecules may be incorporated in a known manner into an appropriate expression vector which ensures expression of the protein. Possible expression vectors include but are not limited to cosmids, plasmids, or modified viruses (e.g. replication defective retroviruses, adenoviruses and adeno-associated viruses). The vector should be compatible with the host cell used. The expression vectors are "suitable for transformation of a host cell", which means that the expression vectors contain a nucleic acid molecule encoding the peptides corresponding to epitopes selectively presented or accessible in non-native forms of SOD1, including amyotrophic lateral sclerosis-specific epitopes, Alzheimer's disease-specific epitopes and Parkinson's disease specific epitopes, and regulatory sequences selected on the basis of the host cells to be used for expression, which is operatively linked to the nucleic acid molecule. "Operatively linked" is intended to mean that the nucleic acid is linked to regulatory sequences in a manner which allows expression of the nucleic acid.

Suitable regulatory sequences may be derived from a variety of sources, including bacterial, fungal, viral, mammalian, or insect genes (For example, see the regulatory sequences described in Goeddel (20)). Selection of appropriate regulatory sequences is dependent on the host cell chosen as discussed below, and may be readily accomplished by one of ordinary skill in the art. Examples of such regulatory sequences include: a transcriptional promoter and enhancer or RNA polymerase binding sequence, a ribosomal binding sequence, including a translation initiation signal. Additionally, depending on the host cell chosen and the vector employed, other sequences, such as an origin of replication, additional DNA restriction sites, enhancers, and sequences conferring inducibility of transcription may be incorporated into the expression vector.

The recombinant expression vectors may also contain a marker gene which facilitates the selection of host cells transformed or transfected with a recombinant molecule of the invention. Examples of selectable marker genes are genes encoding a protein such as G418 and hygromycin which confer resistance to certain drugs, β-galactosidase, chloramphenicol acetyltransferase, firefly luciferase, or an immunoglobulin or portion thereof such as the Fc portion of an immunoglobulin preferably IgG. Transcription of the selectable marker gene is monitored by changes in the concentration of the selectable marker protein such as β-galactosidase, chloramphenicol acetyltransferase, or firefly luciferase. If the selectable marker gene encodes a protein conferring antibiotic resistance such as neomycin resistance transformant cells can be selected with G418. Cells that have incorporated the selectable marker gene will survive, while the other cells die. This makes it possible to visualize and assay for expression of recombinant expression vectors of the invention and in particular to determine the effect of a mutation on expression and phenotype. It will be appreciated that selectable markers can be introduced on a separate vector from the nucleic acid of interest.

Recombinant expression vectors can be introduced into host cells to produce a transformant host cell. The term "transformant host cell" is intended to include prokaryotic and eukaryotic cells which have been transformed or transfected with a recombinant expression vector encoding the amyotrophic lateral sclerosis-specific epitopes. The terms "transformed with", "transfected with", "transformation" and "transfection" are intended to encompass introduction of nucleic acid (e.g. a vector) into a cell by one of many possible techniques known in the art. Prokaryotic cells can be transformed with nucleic acid by, for example, electroporation or calcium-chloride mediated transformation. Nucleic acid can be introduced into mammalian cells via conventional techniques such as calcium phosphate or calcium chloride co-precipitation, DEAE-dextran mediated transfection, lipofectin, electroporation or microinjection. Suitable methods for transforming and transfecting host cells can be found in Sambrook et al. (21), and other laboratory textbooks.

Suitable host cells include a wide variety of prokaryotic and eukaryotic host cells. For example, the proteins of the invention may be expressed in bacterial cells such as *E. coli*, insect cells (using baculovirus), yeast cells or mammalian cells. Other suitable host cells can be found in Goeddel (20).

More particularly, bacterial host cells suitable for carrying out the present invention include *E. coli, B. subtilis, Salmonella typhimurium*, and various species within the genus *Pseudomonas, Streptomyces*, and *Staphylococcus*, as well as many other bacterial species well known to one of ordinary skill in the art. Suitable bacterial expression vectors preferably comprise a promoter which functions in the host cell, one or more selectable phenotypic markers, and a bacterial origin of replication. Representative promoters include the β-lactamase (penicillinase) and lactose promoter system (see Chang et al. (22)), the trp promoter (23) and the tac promoter (24). Representative selectable markers include various antibiotic resistance markers such as the kanamycin or ampicillin resistance genes. Suitable expression vectors include but are not limited to bacteriophages such as lambda derivatives or plasmids such as pBR322 (see Bolivar et al. (25)), the pUC plasmids pUC18, pUC19, pUC118, pUC119 (see Messing (26) and Vieira and Messing (27)), and pNH8A, pNH16a, pNH18a, and Bluescript M13 (Stratagene, La Jolla, Calif.). Typical fusion expression vectors which may be used are discussed above, e.g. pGEX (Amrad Corp., Melbourne, Australia), pMAL (New England Biolabs, Beverly, Mass.) and pRIT5 (Pharmacia, Piscataway, N.J.). Examples of inducible non-fusion expression vectors include pTrc (28) and pET 11d (29).

Yeast and fungi host cells suitable for carrying out the present invention include, but are not limited to *Saccharomyces cerevisiae, Schizosaccharomyces pombe*, the genera *Pichia* or *Kluyveromyces* and various species of the genus *Aspergillus*. Examples of vectors for expression in yeast *S. cerevisiae* include pYepSec1 (30), pMFa (31), pJR88 (32), and pYES2 (Invitrogen Corporation, San Diego, Calif.). Protocols for the transformation of yeast and fungi are well known to those of ordinary skill in the art (see Hinnen et al. (33); Itoh et al. (34), and Cullen et al. (35).

Mammalian cells suitable for carrying out the present invention include, among others: COS (e.g., ATCC No. CRL 1650 or 1651), BHK (e.g. ATCC No. CRL 6281), CHO (ATCC No. CCL 61), HeLa (e.g., ATCC No. CCL 2), 293 (ATCC No. 1573) and NS-1 cells. Suitable expression vectors for directing expression in mammalian cells generally include a promoter (e.g., derived from viral material such as polyoma, Adenovirus 2, cytomegalovirus and Simian Virus 40), as well as other transcriptional and translational control sequences. Examples of mammalian expression vectors include pCDM8 (36) and pMT2PC (37).

Given the teachings provided herein, promoters, terminators, and methods for introducing expression vectors of an appropriate type into plant, avian, and insect cells may also be readily accomplished. For example, within one embodiment, the proteins of the invention may be expressed from plant cells (see Sinkar et al. (38)), which reviews the use of *Agrobacterium rhizogenes* vectors; see also Zambryski et al. (39), which describes the use of expression vectors for plant cells, including, among others, pAS2022, pAS2023, and pAS2034).

Insect cells suitable for carrying out the present invention include cells and cell lines from *Bombyx* or *Spodotera* species. Baculovirus vectors available for expression of proteins in cultured insect cells (SF 9 cells) include the pAc series (40) and the pVL series (41). Some baculovirus-insect cell expression systems suitable for expression of recombinant proteins are described in PCT/US/02442.

The recombinant expression vectors containing the nucleotide sequences encoding the peptide corresponding to epitopes selectively presented or accessible in non-native forms of SOD1, including amyotrophic lateral sclerosis-specific epitopes, Alzheimer's disease specific epitopes and Parkinson's disease specific epitopes may also contain genes which encode a fusion moiety (i.e. a "fusion protein") which provides increased expression of the recombinant peptide; increased solubility of the recombinant peptide; and aid in the purification of the target recombinant peptide by acting as a ligand in affinity purification. For example, a proteolytic cleavage site may be added to the target recombinant protein to allow separation of the recombinant protein from the fusion moiety subsequent to purification of the fusion protein. Typical fusion expression vectors include pGEX (Amrad Corp., Melbourne, Australia), pMAL (New England Biolabs, Beverly, Mass.) and pRIT5 (Pharmacia, Piscataway, N.J.) which fuse glutathione S-transferase (GST), maltose E binding protein, or protein A, respectively, to the recombinant protein.

Nucleic Acid Compositions for Treating SOD1 Mediated Neurodegenerative Diseases

One aspect of the invention is a composition for treating Alzheimer's disease comprising an effective amount of an isolated nucleic acid that encodes for a peptide corresponding to an epitope selectively presented or accessible in non-native forms of SOD1 in admixture with a suitable diluent or carrier. An further aspect of the invention is a composition for treating Parkinson's disease comprising an effective amount of an isolated nucleic acid that encodes for a peptide corresponding to an epitope selectively presented or accessible in non-native forms of SOD1 in admixture with a suitable diluent or carrier. Another aspect of the invention is a composition for treating amyotrophic lateral sclerosis comprising an effective amount of an isolated nucleic acid that encodes for an peptide corresponding to an epitope selectively presented or accessible in non-native forms of SOD1 in admixture with a suitable diluent or carrier.

In a preferred embodiment, the isolated peptide is selected from the group consisting of the peptides in Table 2 or Table 2A, or an analog thereof.

Another aspect of the invention is a composition for eliciting an immune response in an animal comprising an effective amount of a nucleic acid encoding an peptide corresponding to an epitope selectively presented or accessible in non-native forms of SOD1 in admixture with a suitable diluent or carrier, wherein the peptide corresponds to an epitope selectively presented or accessible in non-native forms of SOD1 selected from the group consisting of the peptides in Table 2 or Table 2A, or an analog thereof.

In embodiments, isolated nucleic acids encoding the peptides corresponding to the epitopes selectively presented or accessible in non-native forms of SOD1 include the following RNA molecules, synonymous codon equivalents thereof, and their DNA counterparts and complements:

```
For RLACGVIGI (SEQ ID NO: 1);
                                            (SEQ ID NO: 19)
AGGUUAGCUUGUGGUGUUAUAGGUAUA.

For DLGKGGNEESTKTGNAGS (SEQ ID NO: 2);
                                            (SEQ ID NO: 20)
GAUUUAGGUAAAGGUGGUAAUGAAGAAAGUACUAAAACUGGUAAUGCUGG
UAGU.

For NPLSRKHGGPKDEE (SEQ ID NO: 3);
                                            (SEQ ID NO: 21)
AAUCCUUUAAGUCGUAAACACGGAGGACCGAAGGACGAGGAG.

For IKGLTEGLHGF (SEQ ID NO: 5);
                                            (SEQ ID NO: 22)
AUAAAGGGGAAAACAGAAGGACUCCACGGCUUU.

For HCIIGRTLVVH (SEQ ID NO: 6);
                                            (SEQ ID NO: 23)
CACUGUAUUAUUGGCAGGACCCUCGUUGUUCAC.
```

Other useful nucleic acids include:

Other useful nucleic acids include:

```
For RLACGVIGI (SEQ ID NO: 1), (DSE1: 143-151);
                                            (SEQ ID NO: 24)
CGUUUGGCUUGUGGUGUAAUUGGGAUC.

For ACGVIGI (SEQ ID NO: 9), (DSE1: 145-151);
                                            (SEQ ID NO: 25)
GCUUGUGGUGUAAUUGGGAUC.

For DLGKGGNEESTKTGNAGS (SEQ ID NO: 2),
(DSE2: 125-142);
                                            (SEQ ID NO: 26)
GACUUGGGCAAAGGUGGAAAUGAAGAAAGUACAAAGACAGGAAACGCUGG
AAGU.

For NPLSRKHGGPKDEE (SEQ ID NO: 3), (DSE3: 65-78);
                                            (SEQ ID NO: 27)
AAUCCUCUAUCCAGAAAACACGGUGGGCCAAAGGAUGAAGAG.
```

```
                         -continued
For KAVCVLK (SEQ ID NO: 4), (DSE4: 3-9);
                                         (SEQ ID NO: 28)
AAGGCCGUGUGCGUGCUGAAG.

For IKGLTEGLHGF (SEQ ID NO: 5), (DSE5: 35-45);
                                         (SEQ ID NO: 29)
AUUAAAGGACUGACUGAAGGCCUGCAUGGAUUC.

For HCIIGRTLVVH (SEQ ID NO: 6), (DSE6: 110-120);
                                         (SEQ ID NO: 30)
CAUUGCAUCAUUGGCCGCACACUGGUGGUCCAU.

For GLHGFHVH (SEQ ID NO: 7), (DSE7: 41-48);
                                         (SEQ ID NO: 31)
GGCCUGCAUGGAUUCCAUGUUCAU.
```

The nucleic acids are referred to herein as "Table 2C nucleic acids".

One aspect of the invention is a composition for treating amyotrophic lateral sclerosis in a subject comprising an effective amount of an isolated nucleic acid that encodes for an isolated amyotrophic lateral sclerosis-specific epitope in admixture with a suitable diluent or carrier, wherein the amyotrophic lateral sclerosis-specific epitope comprises an isolated peptide selected from the group consisting of the peptides in Table 2 or Table 2A, or an analog thereof.

Another aspect of the invention is a composition for eliciting an immune response in an animal comprising an effective amount of an isolated nucleic acid encoding an isolated amyotrophic lateral sclerosis-specific epitope in admixture with a suitable diluent or carrier, wherein the amyotrophic lateral sclerosis-specific epitope comprises an isolated peptide selected from the group consisting of the peptides in Table 2 or Table 2A, or an analog thereof.

In embodiments, isolated nucleic acids encoding the peptides corresponding to amyotrophic lateral sclerosis-specific epitopes include the following RNA molecules, synonymous codon equivalents thereof, and their DNA counterparts listed in Table 2C nucleic acids.

A further aspect of the invention is a composition for treating Alzheimer's disease in a subject comprising an effective amount of an isolated nucleic acid that encodes for an isolated Alzheimer's disease-specific epitope in admixture with a suitable diluent or carrier, wherein the Alzheimer's disease-specific epitope comprises a peptide selected from the group consisting of the peptides in Table 2 or Table 2A, or an analog thereof.

Another aspect of the invention is a composition for eliciting an immune response in an animal comprising an effective amount of an isolated nucleic acid encoding an isolated Alzheimer's disease-specific epitope in admixture with a suitable diluent or carrier, wherein the Alzheimer's disease-specific epitope comprises an peptide selected from the group consisting of the peptides in Table 2 or Table 2A, or an analog thereof.

In embodiments, isolated nucleic acids encoding the Alzheimer's disease-specific epitopes include the following RNA molecules, synonymous codon equivalents thereof, and their DNA counterparts and complements listed in the Table 2C nucleic acids.

Another aspect of the invention is a composition for treating Parkinson's disease in a subject comprising an effective amount of an isolated nucleic acid that encodes for a peptide corresponding to a Parkinson's disease-specific epitope in admixture with a suitable diluent or carrier, wherein the Parkinson's disease-specific epitope comprises an isolated peptide selected from the group consisting of the isolated peptides in Table 2 or Table 2A, or an analog thereof.

Another aspect of the invention is a composition for eliciting an immune response in an animal comprising an effective amount of an isolated nucleic acid encoding an isolated Parkinson's disease-specific epitope in admixture with a suitable diluent or carrier, wherein the Parkinson's disease-specific epitope comprises an isolated peptide selected from the group consisting of the isolated peptides in Table 2 or Table 2A, or an analog thereof.

In embodiments, nucleic acids encoding the Parkinson's disease-specific epitopes include the following RNA molecules, synonymous codon equivalents thereof, and their DNA counterparts listed in the Table 2C nucleic acids.

A person skilled in the art will appreciate that there are several modes of administration available when using a composition containing an isolated nucleic acid molecule encoding a peptide corresponding to an epitope selectively presented or accessible in non-native forms of SOD1, including an isolated amyotrophic lateral sclerosis-specific epitope, an isolated Alzheimer's disease-specific epitope and an isolated Parkinson's disease-specific epitope. The recombinant molecules described above may be directly introduced into cells or tissues in vivo using delivery vehicles such as retroviral vectors, adenoviral vectors and DNA virus vectors. They may also be introduced into cells in vivo using physical techniques such as microinjection and electroporation or chemical methods such as coprecipitation and incorporation of DNA into liposomes. Recombinant molecules may also be delivered in the form of an aerosol or by lavage. The nucleic acid molecules of the invention may also be applied extracellularly such as by direct injection into cells.

Method of Medical Treatment of Disease Using Nucleic Acids

Vectors containing the nucleic acid molecules of the invention are optionally administered to the CNS of mammals, preferably humans, in gene therapy using techniques described below. The polypeptides produced from the nucleic acid molecules are readily administered to the CNS of mammals, preferably humans. The invention relates to a method of medical treatment of a mammal, preferably a human, by administering to the mammal a vector of the invention or a cell containing a vector of the invention. Neural diseases such as Parkinson's disease, Alzheimer's disease and amyotrophic lateral sclerosis are treated as described in this application or using methods known in the art (U.S. Pat. Nos. 7,175,840, 7,157,098, 7,141,044, 6,309,634; 6,936,594; US Application Nos. 20060731 19; 2004265283; 2002107213; 2006122116). Diseases, such as blood diseases or neural diseases (neurodegenerative), are treated as described in this application and known in the art Stem cell nerve diseases to be treated by neural stem cell transplantation include diseases resulting in neural cell damage or loss, eg. paralysis, Parkinson's disease, Alzheimer's disease, ALS, multiple sclerosis). The vector of the invention is useful as a stem cell marker and to express genes that cause stem cells to differentiate (e.g. growth factor).

The nucleic acid molecules described herein and vectors comprising said nucleic acid molecules are also useful for treating non-neurodegenerative diseases. Said nucleic acid molecules are in one embodiment used to treat a disease, disorder, condition selected from macular degeneration, glaucoma, ischemia, cerebral infarction, myocardial infarction, atherosclerosis, multiple sclerosis, inflammatory bowel disease, ulcerative colitis, Crohn's disease or necrotizing enterocolitis.

Gene Therapy

The invention includes compositions and methods for providing a coding nucleic acid molecule to a subject such that expression of the molecule in the cells provides the biological activity of the polypeptide encoded by the coding nucleic acid molecule to those cells. A coding nucleic acid as used herein means a nucleic acid that comprises nucleotides which specify the amino acid sequence, or a portion thereof, of the corresponding protein. A coding sequence may comprise a start codon and/or a termination sequence.

The invention includes methods and compositions for providing a coding nucleic acid molecule to the cells of an individual such that expression of the coding nucleic acid molecule in the cells provides the biological activity or phenotype of the polypeptide encoded by the coding nucleic acid molecule. The method also relates to a method for providing an individual having a disease, disorder or abnormal physical state with a biologically active polypeptide by administering a nucleic acid molecule of the present invention. The methods may be performed ex vivo or in vivo. Gene therapy methods and compositions are demonstrated, for example, in U.S. Pat. Nos. 5,869,040, 5,639,642, 5,928,214, 5,911,983, 5,830,880, 5,910,488, 5,854,019, 5,672,344, 5,645,829, 5,741,486, 5,656,465, 5,547,932, 5,529,774, 5,436,146, 5,399,346 and 5,670,488, 5,240,846. The amount of polypeptide will vary with the subject's needs. The optimal dosage of vector is readily determined using empirical techniques, for example by escalating doses (see U.S. Pat. No. 5,910,488 for an example of escalating doses).

Various approaches to gene therapy are used. The invention includes a process for providing a human with a therapeutic polypeptide including: introducing human cells into a human, said human cells having been treated in vitro or ex vivo to insert therein a vector of the invention, the human cells expressing in vivo in said human a therapeutically effective amount of said therapeutic polypeptide.

The method also relates to a method for producing a stock of recombinant virus by producing virus suitable for gene therapy comprising modified DNA encoding globinan epitope selectively presented or accessible in non-native forms of SOD1. This method preferably involves transfecting cells permissive for virus replication (the virus containing an epitope selectively presented or accessible in non-native forms of SOD1 modified globin) and collecting the virus produced. The most efficient systems for the transfer of genes into neurons both in vitro and in vivo are vectors based on viruses, most notably Herpes Simplex Virus (Geller et al., 1995; During et al., 1994), Adenovirus (Davidson et al., 1993; La Gal La Salle, 1993), Adeno-associated virus (AAV) (Kaplitt and During, 1995; During and Leone, 1996) and Lentiviruses (Naldini et al., 1996). Alternative approaches for gene delivery in humans include the use of naked, plasmid DNA as well as liposome-DNA complexes (Ulrich et al., 1996; Gao and Huang, 1995). Another approach is the use of AAV plasmids in which the DNA is polycation-condensed and lipidentrapped and introduced into the brain by intracerebral gene delivery (Leone et al. US Application No. 2002076394). It should be understood that more than one transgene could be expressed by the delivered viral vector. Alternatively, separate vectors, each expressing one or more different transgenes, can also be delivered to the CNS.

Cotransfection (DNA and marker on separate molecules) are optionally employed (see eg U.S. Pat. No. 5,928,914 and U.S. Pat. No. 5,817,492). As well, a marker (such as Green Fluorescent Protein marker or a derivative) is useful within the vector itself (preferably a viral vector).

Other in vivo gene therapy approaches to the treatment of neurodegenerative diseases, such as ALS, AD and PD, include transduction with virus expressing aromatic L-amino acid decarboxylatse (ASDC), suthalamic glutamic acid decarboxylase (GAD) ((Marutso, Nippon Naika Gakkai Zasshi, 2003, 92 (8), 1461-1466; Howard, Nature Biotechnology, 2003, 21 (10), 1117-18).

A vector is optionally administered by direct injection. Methods for injection into the brain (in particular the striatum) are well known in the art (Bilang-Bleuel et al (1997) Proc. Acad. Natl. Sci. USA 94:8818-8823; Choi-Lundberg et al (1998) Exp. Neurol. 154:261-275; Choi-Lundberg et al (1997) Science 275:838-841; and Mandel et al (1997)) Proc. Acad. Natl. Sci. USA 94:14083-14088). Stereotaxic injections may be given. Vectors are optionally delivered to the brain by convection-enhanced delivery (CED) achieved by infusion pumps or by osmotic pumps (U.S. Pat. No. 6,309,634). The convection-enhanced delivery device is optionally an osmotic pump or an infusion pump. (e.g. Alzet Corporation, Hamilton Corporation, Alza, Inc., Palo Alto, Calif.). A catheter, cannula or other injection device is inserted into CNS tissue in the chosen subject to deliver the vector. A person skilled in the art could readily determine which general area of the CNS is an appropriate target for vector delivery. For example, the cholinergic basal forebrain (particularly, the Ch4 region of the basal forebrain) is a suitable target tissue for the delivery of vectors in the treatment of a number of neurodegenerative diseases including, Alzheimer's disease, Parkinson's disease, and amyotrophic lateral sclerosis.

The compositions can be used to treat amyotrophic lateral sclerosis, Alzheimer's disease and/or Parkinson's disease, in methods to treat amyotrophic lateral sclerosis Alzheimer's disease and/or Parkinson's disease, and be used in the manufacture of a medicament to treat amyotrophic lateral sclerosis, Alzheimer's disease and/or Parkinson's disease. The compositions can also be used to treat macular degeneration, glaucoma, ischemia, cerebral infarction, myocardial infarction, atherosclerosis, multiple sclerosis, inflammatory bowel disease, ulcerative colitis, Crohn's disease or necrotizing enterocolitis in methods to treat macular degeneration, glaucoma, ischemia, cerebral infarction, myocardial infarction, atherosclerosis, multiple sclerosis, inflammatory bowel disease, ulcerative colitis, Crohn's disease or necrotizing enterocolitis and be used in the manufacture of a medicament to treat macular degeneration, glaucoma, ischemia, cerebral infarction, myocardial infarction, atherosclerosis, multiple sclerosis, inflammatory bowel disease, ulcerative colitis, Crohn's disease or necrotizing enterocolitis.

Methods of Treatment Using Isolated Peptides Corresponding to Disease Specific Epitopes Accordingly, one aspect of the invention is a method of treating Alzheimer's disease in a subject in need thereof, comprising administering to the subject an isolated peptide corresponding to an epitope selectively presented or accessible in non-native forms of SOD1 in admixture with a suitable diluent or carrier. Another aspect of the invention is a method of treating Parkinson's disease in a subject in need thereof, comprising administering to the subject an isolated peptide corresponding to an epitope selectively presented or accessible in non-native forms of SOD1 in admixture with a suitable diluent or carrier. An additional aspect of the invention is a method of treating amyotrophic lateral sclerosis in a subject in need thereof, comprising administering to the subject an isolated peptide corresponding to an epitope selectively presented or accessible in non-native forms of SOD1 in admixture with a suitable diluent or carrier. A further aspect of the invention is a method of treating macular degeneration, glaucoma, ischemia, cerebral infarction, myocardial infarction, atherosclerosis, multiple sclerosis, inflammatory bowel disease, ulcerative colitis, Crohn's disease or necrotizing enterocolitis in a subject in need thereof, comprising administering to the subject an isolated peptide corresponding to an epitope selectively presented or accessible in non-native forms of SOD1 in admixture with a suitable diluent or carrier.

In a preferred embodiment, the epitope comprises an isolated peptide selected from the group consisting of the isolated peptides in Table 2 or Table 2A, or an analog thereof.

One embodiment of the invention is a method of treating amyotrophic lateral sclerosis in a subject in need thereof, comprising administering to the subject one of the compositions of the invention.

Another embodiment of the invention is a method of treating amyotrophic lateral sclerosis in a subject in need thereof, comprising administering to the subject a composition comprising an amyotrophic lateral sclerosis-specific epitope, in admixture with a suitable diluent or carrier.

In a further embodiment, the amyotrophic lateral sclerosis-specific epitope comprises an isolated peptide selected from the group consisting of the isolated peptides in Table 2 or Table 2A, or an analog thereof.

One embodiment of the invention is a method of treating Alzheimer's disease in a subject in need thereof, comprising administering to the subject one of the compositions of the invention.

Another embodiment of the invention is a method of treating Alzheimer's disease in a subject in need thereof, comprising administering to the subject a composition comprising an isolated peptide corresponding to an Alzheimer's disease-specific epitope in admixture with a suitable diluent or carrier.

In a further embodiment, the isolated peptide corresponding to an Alzheimer's disease-specific epitope comprises an isolated peptide selected from the group consisting of the isolated peptides in Table 2 or Table 2A, or an analog thereof.

One embodiment of the invention is a method of treating Parkinson's disease in a subject in need thereof, comprising administering to the subject one of the compositions of the invention.

Another embodiment of the invention is a method of treating Parkinson's disease in a subject in need thereof, comprising administering to the subject a composition comprising an isolated peptide corresponding to Parkinson's disease-specific epitope in admixture with a suitable diluent or carrier.

In a further embodiment, the isolated peptide corresponding to a Parkinson's disease-specific epitope comprises an isolated peptide selected from the group consisting of the isolated peptides in Table 2 or Table 2A, or an analog thereof.

Methods of treatment Using Isolated Nucleic Acids

An additional aspect of the invention is a method of treating Alzheimer's disease in a subject in need thereof, comprising administering to the subject an isolated nucleic acid that encodes for a peptide corresponding to an epitope selectively presented or accessible in non-native forms of SOD1 in admixture with a suitable diluent or carrier. A further aspect of the invention is a method of treating Parkinson's disease in a subject in need thereof, comprising administering to the subject an isolated nucleic acid that encodes for a peptide corresponding to an epitope selectively presented or accessible in non-native forms of SOD1 in admixture with a suitable diluent or carrier. An additional aspect of the invention is a method of treating amyotrophic lateral sclerosis in a subject in need thereof, comprising administering to the subject an isolated nucleic acid that encodes for a peptide corresponding to an epitope selectively presented or accessible in non-native forms of SOD1 in admixture with a suitable diluent or carrier. A further aspect of the invention is a method of treating macular degeneration, glaucoma, ischemia, cerebral infarction, myocardial infarction, atherosclerosis, multiple sclerosis, inflammatory bowel disease, ulcerative colitis, Crohn's disease or necrotizing enterocolitis comprising administering to the subject an isolated nucleic acid that encodes for a peptide corresponding to an epitope selectively presented or accessible in non-native forms of SOD1 in admixture with a suitable diluent or carrier.

In certain embodiments the nucleic acids comprise nucleic acids selected from the group of Table 2C nucleic acids.

In a preferred embodiment, the epitope comprises an isolated peptide selected from the group consisting of the isolated peptides in Table 2 or Table 2A, or an analog thereof.

One embodiment of the invention is a method of treating amyotrophic lateral sclerosis in a subject in need thereof, comprising administering to the subject a composition comprising a nucleic acid that encodes for a peptide corresponding to an amyotrophic lateral sclerosis-specific epitope in admixture with a suitable diluent or carrier. In one embodiment the nucleic acid comprises a nucleic acid selected from the group of Table 2C nucleic acids.

In a further embodiment, the amyotrophic lateral sclerosis-specific epitope comprises an isolated peptide selected from the group consisting of the isolated peptides in Table 2 or Table 2A, or an analog thereof.

A further embodiment of the invention is a method of treating Alzheimer's disease in a subject in need thereof, comprising administering to the subject a composition comprising a nucleic acid that encodes for an isolated Alzheimer's disease-specific epitope in admixture with a suitable diluent or carrier. In one embodiment the nucleic acid comprises a nucleic acid selected from the group of Table 2C nucleic acids.

In a further embodiment, the Alzheimer's disease-specific epitope comprises an isolated peptide selected from the group consisting of the isolated peptides in Table 2 or Table 2A, or an analog thereof.

Another embodiment of the invention is a method of treating Parkinson's disease in a subject in need thereof, comprising administering to the subject a composition comprising a nucleic acid that encodes a peptide corresponding to a Parkinson's disease-specific epitope in admixture with a suitable diluent or carrier. In one embodiment the nucleic acid comprises a nucleic acid selected from the group of Table 2C nucleic acids.

In a further embodiment, the Parkinson's disease-specific epitope comprises an isolated peptide selected from the group consisting of the isolated peptides in Table 2 or Table 2A, or an analog thereof.

In one embodiment the invention also provides a method for treating a subject having a medical condition, disease, or disorder mediated by a misfolded form of superoxide dismutase (SOD), the method comprising the step of administering to the subject a composition comprising a pharmaceutically acceptable vehicle and an agent selected from (1) an antibody that binds selectively to the misfolded form of SOD, and/or (2) an immunogen that elicits production of said antibody by said subject, and/or (3) a nucleic acid sequence encoding (1) or (2).

Methods of Eliciting an Immune Response Using an Isolated Peptide Corresponding to a Disease Specific Epitope These compositions can be used to elicit an immune response in an animal and can be used in methods to elicit an immune response in an animal against an epitope selectively presented or accessible in non-native SOD1, including the amyotrophic lateral sclerosis-specific epitope, Alzheimer's disease specific epitope or Parkinson's disease-specific epitope.

Another embodiment of the invention is a method of eliciting an immune response in an animal using one of the compositions of the invention. An aspect of the invention includes a method of eliciting an immune response in an animal, using a composition comprising an isolated peptide corresponding to an epitope selectively presented or accessible in non-native forms of SOD1 in admixture with a suitable diluent or carrier. In a preferred embodiment, the isolated peptide corresponding to an epitope selectively presented or accessible in non-native forms of SOD1 is a peptide selected from the group consisting of the isolated peptides in Table 2 or Table 2A, or an analog thereof.

One embodiment includes a method of eliciting an immune response in an animal, using a composition comprising an isolated peptide corresponding to an amyotrophic lateral sclerosis-specific epitope in admixture with a suitable diluent or carrier.

In a further embodiment, the isolated peptide corresponding to an amyotrophic lateral sclerosis-specific epitope is an isolated peptide selected from the group consisting of the isolated peptides in Table 2 or Table 2A, or an analog thereof.

Another embodiment includes a method of eliciting an immune response in an animal, using a composition comprising an isolated peptide corresponding to an Alzheimer's disease-specific epitope in admixture with a suitable diluent or carrier.

In a further embodiment, the isolated peptide corresponding to an Alzheimer's disease-specific epitope is an isolated peptide selected from the group consisting of the isolated peptides in Table 2 or Table 2A, or an analog thereof.

A further embodiment includes a method of eliciting an immune response in an animal, using a composition comprising an isolated peptide corresponding to a Parkinson's disease-specific epitope in admixture with a suitable diluent or carrier.

In a further embodiment, the isolated peptide corresponding to Parkinson's disease-specific epitope is an isolated peptide selected from the group consisting of the isolated peptides in Table 2 or Table 2A, or an analog thereof.

Method of Eliciting an Immune Response Using an Isolated Nucleic Acid

Another aspect of the invention includes a method of eliciting an immune response in an animal, using a composition comprising a nucleic acid that encodes for an isolated peptide corresponding to an epitope selectively presented or accessible in non-native forms of SOD1 in admixture with a suitable diluent or carrier to treat Alzheimer's disease. An additional aspect of the invention includes a method of eliciting an immune response in an animal, using a composition comprising a nucleic acid that encodes for an isolated peptide corresponding to an epitope selectively presented or accessible in non-native forms of SOD1 in admixture with a suitable diluent or carrier to treat Parkinson's disease. A further aspect of the invention includes a method of eliciting an immune response in an animal, using a composition comprising a nucleic acid that encodes for an isolated peptide corresponding to an epitope selectively presented or accessible in non-native forms of SOD1 in admixture with a suitable diluent or carrier to treat amyotrophic lateral sclerosis.

In a preferred embodiment, the isolated peptide corresponding to an epitope comprises an isolated peptide selected from the group consisting of the isolated peptides in Table 2 or Table 2A, or an analog thereof.

One embodiment of the invention includes a method of eliciting an immune response in an animal, using a composition comprising a nucleic acid that encodes for an isolated amyotrophic lateral sclerosis-specific epitope in admixture with a suitable diluent or carrier.

In a further embodiment, the isolated peptide corresponding to an amyotrophic lateral sclerosis-specific epitope is an isolated peptide selected from the group consisting of the isolated peptides in Table 2 or Table 2A, or an analog thereof.

A further embodiment of the invention includes a method of eliciting an immune response in an animal, using a composition comprising a nucleic acid that encodes for a peptide corresponding to an Alzheimer's disease-specific epitope in admixture with a suitable diluent or carrier.

In a further embodiment, the peptide corresponding to an Alzheimer's disease-specific epitope is a peptide selected from the group consisting of the peptides in Table 2 or Table 2A, or an analog thereof.

Another embodiment of the invention includes a method of eliciting an immune response in an animal, using a composition comprising a nucleic acid that encodes for an isolated peptide corresponding to an Parkinson's disease-specific epitope in admixture with a suitable diluent or carrier.

In a further embodiment, the isolated peptide corresponding to a Parkinson's disease-specific epitope is an isolated peptide selected from the group consisting of the isolated peptides in Table 2 or Table 2A, or an analog thereof.

Use of an Isolated Peptide Corresponding to a Disease Specific Epitope in the Manufacture of a Medicament A further aspect of the invention is the use of an isolated peptide corresponding to an epitope selectively presented or accessible in non-native forms of SOD1 in the manufacture of a medicament to treat Alzheimer's disease. An additional aspect of the invention is the use of an isolated peptide corresponding to an epitope selectively presented or accessible in non-native forms of SOD1 in the manufacture of a medicament to treat Parkinson's disease. A further aspect of the invention is the use of an isolated isolated peptide corresponding to an epitope selectively presented or accessible in non-native forms of SOD1 in the manufacture of a medicament to treat amyotrophic lateral sclerosis. A further aspect of the invention is the use of an isolated peptide corresponding to an epitope selectively presented or accessible in non-native forms of SOD1 in the manufacture of a medicament to treat a non-native form of SOD1 mediated disease, disorder or condition including macular degeneration, glaucoma, ischemia, cerebral infarction, myocardial infarction, atherosclerosis, multiple sclerosis, inflammatory bowel disease, ulcerative colitis, Crohn's disease or necrotizing enterocolitis.

In a preferred embodiment, the isolated peptide corresponding to an epitope comprises an isolated peptide selected from the group consisting of the isolated peptides in Table 2 or Table 2A, or an analog thereof.

Use of an Isolated Nucleic Acid in the Manufacture of a Medicament

A further aspect of the invention is the use of an isolated nucleic acid that encodes for a peptide corresponding to an epitope selectively presented or accessible in non-native forms of SOD1 in the manufacture of a medicament to treat Alzheimer's disease. An additional aspect of the invention is the use of an isolated nucleic acid that encodes for a peptide that corresponds to an epitope selectively presented or accessible in non-native forms of SOD1 in the manufacture of a medicament to treat Parkinson's disease. A further aspect of the invention is the use of an isolated nucleic acid that encodes for a peptide that corresponds to an epitope selectively presented or accessible in non-native forms of SOD1 in the manufacture of a medicament to treat amyotrophic lateral sclerosis. A further aspect of the invention is the use of an isolated nucleic acid that encodes for a peptide that corresponds to an epitope selectively presented or accessible in non-native forms of SOD1 in the manufacture of a medicament to treat macular degeneration, glaucoma, ischemia, cerebral infarction, myocardial infarction, atherosclerosis, multiple sclerosis, inflammatory bowel disease, ulcerative colitis, Crohn's disease or necrotizing enterocolitis.

In a preferred embodiment, the isolated peptide corresponding to an epitope comprises an isolated peptide selected from the group consisting of the isolated peptides in Table 2 or Table 2A, or an analog thereof.

As described above, immunogenicity and thus the effectiveness of a vaccine can be significantly improved if the immunizing agent (e.g. isolated isolated peptide corresponding to an epitope selectively presented or accessible in non-native forms of SOD1) and/or compositions thereof are co-immunized with an adjuvant. Accordingly, the methods and uses of invention include the use of an adjuvant.

Use of Isolated Nucleic Acids Corresponding to Disease Specific Epitopes to Treat SOD1 Mediated Neurodegenerative Diseases.

Another aspect of the invention is the use of an isolated nucleic acid that corresponds to an epitope selectively presented or accessible in non-native forms of SOD1 in admixture with a suitable diluent or carrier to treat Alzheimer's disease. An additional aspect of the invention is the use of an isolated nucleic acid that corresponds to an epitope selectively presented or accessible in non-native forms of SOD1 in admixture with a suitable diluent or carrier to treat Parkinson's disease. A further aspect of the invention is the use of an isolated nucleic acid that corresponds to an epitope selectively presented or accessible in non-native forms of SOD1 in admixture with a suitable diluent or carrier to treat amyotrophic lateral sclerosis. In alternate embodiments, the invention comprises the use of an isolated nucleic acid that encodes a peptide that corresponds to a disease specific epitope.

In a preferred embodiment, the nucleic acid encodes a peptide that corresponds to a disease specific epitope that comprises a peptide selected from the group consisting of peptides in Table 2 or Table 2A, or an analog thereof.

Another aspect of the invention is the use of an isolated peptide corresponding to an epitope selectively presented or accessible in non-native forms of SOD1, in admixture with a suitable diluent or carrier to treat Alzheimer's disease. An additional aspect of the invention is the use of an isolated peptide corresponding to an epitope selectively presented or accessible in non-native forms of SOD1 in admixture with a suitable diluent or carrier to treat Parkinson's disease. A further aspect of the invention is the use of an isolated peptide corresponding to an epitope selectively presented or accessible in non-native forms of SOD1 in admixture with a suitable diluent or carrier to treat amyotrophic lateral sclerosis.

In a preferred embodiment, the isolated peptide corresponding to an epitope comprises an isolated peptide selected from the group consisting of the isolated peptides in Table 2 or Table 2A, or an analog thereof.

Compositions and Uses of Binding Agents Specific for the Disease Specific Epitopes Agents that Bind Disease Specific Epitopes Epitopes presented on misfolded SOD1 may be bound and/or neutralized by a number of different natural or engineered agents such as antibodies, other polypeptides, small molecules, affibodies (Wahlberg et al., Proc Natl Acad Sci USA, 100:3185-3190, 2003); anticalins (Schlehuber and Skerra, Biophys Chem., 96:213-28, 2002); and nucleic acid and protein aptamers (Cullen et al. Cell, 58: 423-466, 1989). In certain embodiments the agent is an antibody that selectively binds a disease specific epitope or an analog thereof presented or accessible on non-native SOD1.

Generating Antibodies

The epitopes selectively presented or accessible in non-native forms of SOD1 can be used to make antibodies. In a preferred embodiment, the antibodies are specific for misfolded SOD1 molecules, preferably misfolded SOD1 molecules associated with Alzheimer's disease, Parkinson's disease and/or amyotrophic lateral sclerosis.

In one embodiment, the amyotrophic lateral sclerosis-specific epitopes can be used to make antibodies specific for the amyotrophic lateral sclerosis-specific epitopes. In a preferred embodiment, the antibodies are specific for the misfolded SOD1 molecules. In other embodiments, the antibodies are isolated antibodies.

In another embodiment, the isolated antibody specific for the amyotrophic lateral sclerosis-specific epitope is made by administering one of the compositions of the invention to an animal.

Another embodiment includes an isolated antibody for an amyotrophic lateral sclerosis-specific epitope, wherein the amyotrophic lateral sclerosis-specific epitope comprises an isolated peptide selected from the group consisting of the isolated peptides in Table 2 or Table 2A, or an analog thereof.

In one embodiment, the Alzheimer's disease-specific epitopes are useful to make antibodies specific for the Alzheimer's disease-specific epitopes. The antibodies are typically specific for the misfolded SOD1 molecules.

In another embodiment, the isolated antibody specific for the Alzheimer's disease-specific epitope is made by administering one of the compositions of the invention to an animal.

Another embodiment includes an isolated antibody for an Alzheimer's disease-specific epitope, wherein the Alzheimer's disease-specific epitope comprises an isolated peptide selected from the group consisting of the isolated peptides in Table 2 or Table 2A, or an analog thereof.

In one embodiment, the Parkinson's disease-specific epitopes are useful to make antibodies specific for the Parkinson's disease-specific epitopes. In a preferred embodiment, the antibodies are specific for the misfolded SOD1 molecules.

In another embodiment, the isolated antibody specific for the Parkinson's disease-specific epitope is made by administering one of the compositions of the invention to an animal.

Another embodiment includes an isolated antibody for a Parkinson's disease-specific epitope, wherein the isolated peptide corresponding to a Parkinson's disease-specific epitope used to generate the antibody comprises an isolated peptide selected from the group consisting of the isolated peptides in Table 2 or Table 2A, or an analog thereof.

The term "antibody" as used herein is intended to include monoclonal antibodies including chimeric and humanized monoclonal antibodies, polyclonal antibodies, humanized antibodies, human antibodies, and chimeric antibodies. The antibody may be from recombinant sources and/or produced in transgenic animals. The term "antibody fragment" as used herein is intended to include Fab, Fab', F(ab')$_2$, scFv, dsFv, ds-scFv, dimers, minibodies, diabodies, and multimers thereof and bispecific antibody fragments. Antibodies can be fragmented using conventional techniques. For example, F(ab')$_2$ fragments can be generated by treating the antibody with pepsin. The resulting F(ab')$_2$ fragment can be treated to reduce disulfide bridges to produce Fab' fragments. Papain digestion can lead to the formation of Fab fragments. Fab, Fab' and F(ab')$_2$, scFv, dsFv, ds-scFv, dimers, minibodies, diabodies, bispecific antibody fragments and other fragments can also be synthesized by recombinant techniques. The antibodies are optionally in any useful isotype, including IgM which in one embodiment is used for diagnostic applications and IgG, such as IgG1, IgG2, IgG3 and IgG4 which in one embodiment is used for therapeutic applications.

"Isolated antibody" refers to antibody produced in vivo or in vivo that has been removed from the source that produced the antibody, for example, an animal, hybridoma or other cell line (such as recombinant cells that produce antibody). The isolated antibody is optionally "purified", which means at least: 80%, 85%, 90%, 95%, 98% or 99% purity and optionally pharmaceutical grade purity.

"Endogenous antibody" refers to antibody produced by a subject, such as a mammal (eg. human), as part of an immune response in the subject.

"Exogenous antibody" refers to an antibody that is non-self or foreign to a subject, such as a mammal (eg. human). The term "exogenous antibody" encompasses isolated antibody as well as isolated and purified antibody. To produce monoclonal antibodies, antibody producing cells (lymphocytes) can be harvested from a subject immunized with an immunogen comprising an isolated peptide corresponding to a misfolded SOD1-specific epitope, including an amyotrophic lateral sclerosis-specific epitope, an Alzheimer's disease specific epitope or a Parkinson's disease specific epitope, and fused with myeloma cells by standard somatic cell fusion procedures thus immortalizing these cells and yielding hybridoma cells. Such techniques are well known in the art, (e.g. the hybridoma technique originally developed by Kohler and Milstein (42) as well as other techniques such as the human B-cell hybridoma technique (43), the EBV-hybridoma technique to produce human monoclonal antibodies (44), and screening of combinatorial antibody libraries (45). Hybridoma cells can be screened immunochemically for production of antibodies specifically reactive with the amyotrophic lateral sclerosis-specific epitopes and the monoclonal antibodies can be isolated.

Specific antibodies, or antibody fragments, reactive against particular antigens or molecules, such as epitopes selectively presented or accessible in misfolded forms of SOD1, including amyotrophic lateral sclerosis-specific epitopes, Alzheimer's disease specific epitopes or Parkinson's disease specific epitopes may also be generated by screening expression libraries encoding immunoglobulin genes, or portions thereof, expressed in bacteria with cell surface components. For example, complete Fab fragments, VH regions and FV regions can be expressed in bacteria using phage expression libraries (see for example Ward et al. (46); Huse et al. (45); and McCafferty et al. (47)).

The term "humanized antibody" as used herein means that the antibody or fragment comprises human conserved framework regions (alternatively referred to as constant regions) and the hypervariable regions (alternatively referred to as the antigen binding domain) are of non-human origin. For example, the hypervariable region may be from a mouse, rat or other species. The humanization of antibodies from non-human species has been well described in the literature. See for example EP-B1 0 239400 and Carter & Merchant 1997 (Curr Opin Biotechnol 8, 449-454, 1997 incorporated by reference in their entirety herein). Humanized antibodies are also readily obtained commercially (eg. Scotgen Limited, 2 Holly Road, Twickenham, Middlesex, Great Britain.)

Humanized forms of rodent antibodies are readily generated by CDR grafting (Riechmann et al. Nature, 332:323-327, 1988). In this approach the six CDR loops comprising the antigen binding site of the rodent monoclonal antibody are linked to corresponding human framework regions. CDR grafting often yields antibodies with reduced affinity as the amino acids of the framework regions may influence antigen recognition (Foote & Winter. J Mol Biol, 224: 487-499, 1992). To maintain the affinity of the antibody, it is often necessary to replace certain framework residues by site directed mutagenesis or other recombinant techniques and may be aided by computer modeling of the antigen binding site (Co et al. J Immunol, 152: 2968-2976, 1994).

Humanized forms of antibodies are optionally obtained by resurfacing (Pedersen et al. J Mol Biol, 235: 959-973, 1994). In this approach only the surface residues of a rodent antibody are humanized.

The term "human antibodies" as used herein refers to antibodies that are, or correspond to, antibodies that are produced endogenously in a human subject, however, human antibodies are also optionally produced exogenously through biochemical techniques. Human antibodies specific to a particular antigen may be identified by a phage display strategy (Jespers et al. Bio/Technology, 12: 899-903, 1994). In one approach, the heavy chain of a rodent antibody directed against a specific antigen is cloned and paired with a repertoire of human light chains for display as Fab fragments on filamentous phage. The phage is selected by binding to antigen. The selected human light chain is subsequently paired with a repertoire of human heavy chains for display on phage, and the phage is again selected by binding to antigen. The result is a human antibody Fab fragment specific to a particular antigen. In another approach, libraries of phage are produced were members display different human antibody fragments (Fab or Fv) on their outer surfaces (Dower et al., WO 91/17271 and McCafferty et al., WO 92/01047). Phage displaying antibodies with a desired specificity are selected by affinity enrichment to a specific antigen. The human Fab or Fv fragment identified from either approach may be recloned for expression as a human antibody in mammalian cells.

Human antibodies are optionally obtained from transgenic animals (U.S. Pat. Nos. 6,150,584; 6,114,598; and 5,770,429). In this approach the heavy chain joining region ($J_H$) gene in a chimeric or germ-line mutant mouse is deleted. Human germ-line immunoglobulin gene array is subsequently transferred to such mutant mice. The resulting transgenic mouse is then capable of generating a full repertoire of human antibodies upon antigen challenge.

Humanized or human antibodies are selected from any class of immunoglobulins including: IgM, IgG, IgD, IgA or IgE; and any isotype, including: IgG1, IgG2, IgG3 and IgG4. The humanized or human antibody may include sequences from one or more than one isotype or class. Further, these antibodies are typically produced as antigen binding fragments such as Fab, Fab'F(ab')$_2$, Fd, Fv and single domain antibody fragments, or as single chain antibodies in which the heavy and light chains are linked by a spacer. Also, the human or humanized antibodies may exist in monomeric or polymeric form. The humanized antibody optionally comprises one non-human chain and one humanized chain (i.e. one humanized heavy or light chain).

Additionally, antibodies specific for the epitopes of the invention are readily isolated by screening antibody phage display libraries. For example, an antibody phage library is optionally screened by using a disease specific epitope of the current invention to identify antibody fragments specific for the disease specific epitope. Antibody fragments identified are optionally used to produce a variety of recombinant antibodies that are useful with different embodiments of the present invention. Antibody phage display libraries are commercially available, for example, through Xoma (Berkeley, Calif.) Methods for screening antibody phage libraries are well known in the art.

The invention also comprises in one embodiment antibodies that selectively compete with antibodies raised using an immunogen comprising an isolated peptide from Table 2 and Table 2A and analogs thereof. Competition assays are performed to provide a method of determining whether a test antibody displaces an antibody of the invention described herein, comprising contacting an epitope presented in a non-native form of SOD1 with a test antibody and an antibody raised using an immunogen comprising an isolated peptide from Table 2, Table 2A or analogs thereof and next determining whether the test antibody selectively displaces the antibody of the invention from binding the epitope. The test antibody is considered to selectively displace the antibody of the invention if the test antibody has at least 1.5 times or at least 2 times greater binding affinity for the epitope.

These antibodies specific for epitopes selectively presented or accessible in non-native forms of SOD1 can be used to treat Alzheimer's disease, Parkinson's disease and/or amyotrophic lateral sclerosis. In one embodiment, the antibodies of the invention can be used to treat amyotrophic lateral sclerosis. In a further embodiment, the antibodies of the invention can be used to treat Alzheimer's disease. In another embodiment, the antibodies of the invention can be used to treat Parkinson's disease. For example, passive infusion of antibodies specific for amyotrophic lateral sclerosis-specific epitope may inhibit SOD1 aggregate formation and/or may block SOD1 template directed misfolding.

Compositions Comprising Antibodies

Accordingly, one aspect of the invention is a composition to treat Alzheimer's disease comprising an effective amount of an antibody specific for epitopes or analogs thereof selectively presented or accessible in non-native forms of SOD1 in admixture with a suitable diluent or carrier. A further aspect of the invention is a composition to treat Parkinson's disease comprising an effective amount of an antibody specific for epitopes selectively presented or accessible in non-native forms of SOD1 in admixture with a suitable diluent or carrier. An additional aspect of the invention is a composition to treat amyotrophic lateral sclerosis comprising an effective amount of an antibody specific for epitopes selectively presented or accessible in non-native forms of SOD1 in admixture with a suitable diluent or carrier.

In a preferred embodiment, the epitope comprises an isolated peptide selected from the group consisting of the isolated peptides in Table 2 or Table 2A, or an analog thereof.

One aspect of the invention is a composition to treat amyotrophic lateral sclerosis comprising an effective amount of an antibody specific for the amyotrophic lateral sclerosis-specific epitopes in admixture with a suitable diluent or carrier.

In one embodiment, the antibodies are humanized antibodies. In another embodiment, the antibodies are administered into the blood or spinal fluid of a subject with amyotrophic lateral sclerosis.

A further aspect of the invention is a composition to treat Alzheimer's disease comprising an effective amount of an antibody specific for the Alzheimer's disease-specific epitopes in admixture with a suitable diluent or carrier.

In one embodiment, the antibodies are humanized antibodies. In another embodiment, the antibodies are administered into the blood or spinal fluid of a subject with Alzheimer's disease.

Another aspect of the invention is a composition to treat Parkinson's disease comprising an effective amount of an antibody specific for the Parkinson's disease-specific epitopes in admixture with a suitable diluent or carrier.

In one embodiment, the antibodies are humanized antibodies. In another embodiment, the antibodies are administered into the blood or spinal fluid of a subject with Parkinson's disease. Also provided is DSE1a, and immunogens based on it, as well as antibodies. Also provided are hybridomas producing DSE1a, DSE2 and DSE5, their use to produce antibodies.

The invention also includes methods and uses of the antibodies to treat amyotrophic lateral sclerosis, Alzheimer's disease and Parkinson's disease.

Method of Treatment: Passive Immunization

An aspect of the invention is a method of treating Alzheimer's disease in a subject in need thereof, comprising administering to the subject a binding agent such as an antibody that binds to an epitope selectively presented or accessible in non-native forms of SOD1 in admixture with a suitable diluent or carrier. Another aspect of the invention is a method of treating Parkinson's disease in a subject in need thereof, comprising administering to the subject an antibody that binds to an epitope selectively presented or accessible in non-native forms of SOD1 in admixture with a suitable diluent or carrier. A further aspect of the invention is a method of treating amyotrophic lateral sclerosis in a subject in need thereof, comprising administering to the subject an antibody that binds to an epitope selectively presented or accessible in non-native forms of SOD1 in admixture with a suitable diluent or carrier.

In addition to antibodies, epitopes presented on misfolded SOD1 may be bound and/or neutralized by a number of different natural or engineered agents such as other polypeptides, small molecules, affibodies (Wahlberg et al., Proc Natl Acad Sci USA, 100:3185-3190, 2003); anticalins (Schlehuber and Skerra, Biophys Chem., 96:213-28, 2002); and nucleic acid and protein aptamers (Cullen et al. Cell, 58: 423-466, 1989).

Affibodies are engineered binding proteins based on the three-helix scaffold of the Z domain derived from staphylococcal protein A (Wahlberg et al., Proc Natl Acad Sci USA, 100:3185-3190, 2003). The Z domain consists of 58 residues that bind to the Fc portion of IgG from different species (Nygren and Uhlen. Curr Opin Struct Biol., 7:463-469, 1997). By simultaneously randomizing 13 amino acid positions located at the two helices making up the Fc-binding face of the Z domain, a library of binding proteins (affibodies) are created and used to screen for binding to desired targets by phage display technology (Nord, et al. Protein Eng., 8:601-608, 1995; Nord et al. Nat. Biotechnol. 15:772-777, 1997). Affibodies have a secondary structure similar to the native Z domain and have micromolar range dissociation constants (KD) for their respective targets (Nord et al. Nat. Biotechnol., 15:772-777, 1997).

Anticalins are a class of engineered ligand-binding proteins derived from the lipocalin protein scaffold (Schlehuber and Skerra, Biophys Chem., 96:213-28, 2002; Weiss and Lowman. Chem. Biol., 7:R177-R184, 2000; Skerra. J Biotechnol., 74:257-275, 2001). The process of preparing anticalins is described in EP1017814. The ligand-binding site of anticalins may be re-engineered by amino acid substitutions, or other recombinant approaches, to alter the binding specificity of the protein. Anticalins are similar to antibodies in that they possess high affinity and specificity for their prescribed ligands. However, anticalins have a number of advantages over antibodies including a smaller size; single peptide composition; and a binding site that is easily manipulated.

Aptamers are short single-stranded DNA oligonucleotides, RNA oligonucleotides or polypeptides with the capacity to recognize various target molecules with high affinity and specificity (Cullen et al. Cell, 58: 423-466, 1989). Aptamers are optionally identified by an in vitro evolution and selection process called SELEX (systemic evolution of ligands by exponential enrichment), and methods for obtaining aptamers specific for a polypeptide of interest are known in the art. See, e.g., Brody E N, Gold L. J Biotechnol. 2000 March; 74(1):5-13. Methods for efficient selection of aptamers that bind to any polypeptide of interest are described in U.S. Pub. No. 20050142582.

Like antibodies, aptamers assume a specific and stable three-dimensional shape in vivo, which provides for specific binding to target molecules and elicit a biological response. Further, the binding affinities of aptamers are analogous to that of antibodies (reviewed in Nimjee et al. Annu Rev Med, 56: 555-83, 2005). Aptamers have a number of advantages over antibodies including stability at 80° C., long shelf life, low immunogenicity (Retina, 22: 143-152, 2002), low inter-batch variability, broad tissue distribution due to their small size, readily modified to alter its tissue distribution and clearance properties, e.g. by pegylation (Tucker et al. J Chromatogr B Biomed Sci Appl, 732: 203-212, 1999).

In a preferred embodiment, the epitope comprises an isolated peptide selected from the group consisting of the isolated peptides in Table 2 or Table 2A, or an analog thereof.

Use of Antibodies to Treat Disease

A further aspect of the invention is the use of an antibody that binds to an epitope selectively presented or accessible in non-native forms of SOD1 in admixture with a suitable diluent or carrier to treat Alzheimer's disease. An additional aspect of the invention is the use of an antibody that binds to an epitope selectively presented or accessible in non-native forms of SOD1 in admixture with a suitable diluent or carrier to treat Parkinson's disease. A further aspect of the invention is the use of an antibody that binds to an epitope selectively presented or accessible in non-native forms of SOD1 in admixture with a suitable diluent or carrier to treat amyotrophic lateral sclerosis. In other aspects, the invention provides the use of antibody that binds to an epitope selectively presented or accessible in non-native forms of SOD1 in admixture with a suitable diluent or carrier to treat macular degeneration, glaucoma, ischemia, cerebral infarction, myocardial infarction, atherosclerosis, multiple sclerosis, inflammatory bowel disease, ulcerative colitis, Crohn's disease or necrotizing enterocolitis.

In a preferred embodiment, the epitope comprises an isolated peptide selected from the group consisting of the isolated peptides in Table 2 or Table 2A, or an analog thereof.

Use of Antibody in Manufacture of a Medicament

A further aspect of the invention is the use of an antibody that binds to an epitope selectively presented or accessible in non-native forms of SOD1 in the manufacture of a medicament to treat Alzheimer's disease. An additional aspect of the invention is the use of an antibody that binds to an epitope selectively presented or accessible in non-native forms of SOD1 in the manufacture of a medicament to treat Parkinson's' disease. Another aspect of the invention is the use of an antibody that binds to an epitope selectively presented or accessible in non-native forms of SOD1 in the manufacture of a medicament to treat amyotrophic lateral sclerosis.

In a preferred embodiment, the epitope comprises an isolated peptide selected from the group consisting of the isolated peptides in Table 2 or Table 2A, or an analog thereof.

The above disclosure generally describes the present invention. A more complete understanding can be obtained by reference to the following specific examples. These examples are described solely for the purpose of illustration and are not intended to limit the scope of the invention. Changes in form and substitution of equivalents are contemplated as circumstances might suggest or render expedient. Although specific terms have been employed herein, such terms are intended in a descriptive sense and not for purposes of limitation.

Methods of Administering Compositions

The compositions of the invention are readily administered for example, by parenteral, intravenous, subcutaneous, intramuscular, intracranial, intraventricular, intrathecal, intraorbital, ophthalmic, intracapsular, intraspinal, intracisternal, intraperitoneal, intranasal, aerosol or oral administration.

In certain embodiments, the pharmaceutical composition is administered systemically.

In other embodiments, the pharmaceutical composition is administered to the directly to the brain or other portion of the CNS. For example such methods include the use of an implantable catheter and a pump, which would serve to discharge a pre-determined dose through the catheter to the infusion site. A person skilled in the art would further recognize that the catheter may be implanted by surgical techniques that permit visualization of the catheter so as to position the catheter adjacent to the desired site of administration or infusion in the brain. Such techniques are described in Elsberry et al. U.S. Pat. No. 5,814,014 "Techniques of Treating Neurodegenerative Disorders by Brain Infusion", which is herein incorporated by reference. The inventors have also contemplated other methods such as those described in US patent application 20060129126 (Kaplitt and During "Infusion device and method for infusing material into the brain of a patient". Devices for delivering drugs to the brain and other parts of the CNS are commercially available (eg. SynchroMed® EL Infusion System; Medtronic, Minneapolis, Minn.)

In another embodiment, the pharmaceutical composition is administered to the brain using methods such as modifying the compounds of the invention to allow receptor-mediated transport across the blood brain barrier.

Other embodiments contemplate the co-administration of the compounds of the invention with biologically active molecules known to facilitate the transport across the blood brain barrier.

In another embodiment, the compounds of the invention are reformulated as fusion or chimeric proteins in order to enable their transport across the blood brain barrier. Such technologies are described in U.S. Pat. No. 4,902,505, "Chimeric peptides for neuropeptide delivery through the blood-brain barrier".

The invention also contemplates additional methods for administering the compounds across the blood brain barrier such as those directed at transiently increasing the permeability of the blood brain barrier as described in U.S. Pat. No. 7,012,061 "Method for increasing the permeability of the blood brain barrier".

A person skilled in the art will recognize the variety of suitable methods for administering the compounds of the invention directly to the brain or across the blood brain barrier and be able to modify these methods in order to safely administer the products of the invention.

Methods of Treatment

As mentioned previously, SOD 1 is a free radical defense enzyme that is typically found intracellularly in its native forms. Experiments performed in cell culture and with mice transgenic for human mutant SOD1 have established that SOD1 is secreted into the extracellular space in ALS mice in a form that highly toxic for motor neurons (1). The Inventors have now demonstrated that non-native forms of SOD1 are detectable in a number of diseases and disorders in addition to ALS, PD or AD and further that non-native forms of SOD1 are also detectable extracellularly.

Accordingly, in addition to CNS indications such as ALS, AD and PD, the present invention relates to the diagnosis and treatment of other indications, including non-CNS indications, which are marked by the presence of SOD1 in its misfolded, monomeric or aggregated forms (e.g. non-native forms of SOD1) and particularly to the diagnosis and treatment of other indications marked by the extracellular presence of said non-native forms of SOD1. In other embodiments, the treatment method is applied to a subject that has a neurodegenerative disease, disorder or condition other than ALS, AD or PD. In other embodiments, the treatment method is applied to a subject that has a disorder, condition or disease having a neurodegenerative component. In other embodiments, the treatment method is applied to a subject having a non-neurodegenerative condition, disease or disorder that causes neurodegeneration as a secondary component of the condition, disease or disorder and is other than a neurodegenerative disorder selected from ALS, AD or PD. Using antibodies of the present invention and analysis by immunohistochemistry, the presence of misfolded or monomeric SOD1 has been detected in a variety of tissues obtained from subjects having an array of medical diseases, disorders and conditions and particularly diseases disorders and conditions that involve inflammation and cell death and/or neurodegeneration. Results of this analysis indicate that non-native forms of SOD1 are at least present or formed in tissues other than brain tissue, and in diseases other than the neurodegenerative disorders noted above, and is useful in the diagnosis and treatment of such disorders.

Thus, in a further aspect, the present invention relates very generally to a method for inhibiting a cytotoxic activity of non-native forms of SOD1 in a subject in need of such treatment, comprising the step of delivering to the subject a pharmaceutically effective amount of an antibody or binding fragment thereof that binds to non-native forms of SOD1. In one embodiment the present invention provides a method of treating a disorder, condition or disease associated with a non-native form of SOD1 cytotoxic activity. The non-native form of SOD1 is in one embodiment misfolded SOD1. In another embodiment the non-native form of SOD1 is monomeric SOD1.

In embodiments, the treatment method is applied to a subject having a neurodegenerative disorder selected from ALS, AD and PD. In other embodiments, the treatment method is applied to a subject having a neurodegenerative disease, disorder or condition other than ALS, AD, PD. In other embodiments, the treatment method is applied to a subject having a disease, disorder or condition that has a neurodegenerative component. In other embodiments, the treatment method is applied to a subject having a non-neurodegenerative condition, disease or disorder, including a condition, disease or disorder that causes neurodegeneration as a secondary component of the condition, disease or disorder, and is other than neurodegenerative disorder selected from ALS, AD and PD. In particular embodiments of the invention, the treatment method is applied to a subject having a disease, disorder or condition that is marked by presence of a form of SOD1 that is immunoreactive with an antibody that binds selectively to a non-native form of SOD1.

In other embodiments, the non-neurodegenerative disease, disorder or condition is other than a disease of cell proliferation, e.g., cancer. In embodiments of the present invention, the antibodies or fragments that bind selectively to non-native forms of SOD1 are used to treat a subject having, or at risk for, a condition that is associated with a non-native form of SOD1 including a monomeric or misfolded SOD1 form and that is associated also with a higher than normal accumulation or level of reactive nitrogen species (RNS) and/or reactive oxygen species (ROS), also collectively referred to as free radical species. While not wishing to be bound by any particular theory, it is believed that, in an extracellular environment, the misfolded form of SOD1 presents its copper ion in an exposed state that, in the presence of antioxidants such as ascorbate and through redox cycling, assumes a toxic function enabling the non-native forms of SOD1 copper ion to elevate, rather than reduce, the level of ROS and RNS in its environment. The result is accumulation of free radical species to a toxic level that is harmful to neighboring cells. It is believed that the present antibodies and any related agents that bind misfolded SOD1 can act essentially by blocking the exposed copper ion presented by misfolded SOD1, and/or accelerating the degradation of non-native or misfolded SOD1, thereby inhibiting the elevation of ROS and RNS in the local environment.

In embodiments of the present invention, the antibodies, and fragments thereof, that bind selectively to non-native forms of SOD1 including misfolded SOD1 are used to diagnose or treat a subject having a condition that is associated with non-native forms of SOD1 such as misfolded SOD1 and is associated with an elevation of ROS and RNS. In particular embodiments, the condition is macular degeneration or glaucoma. In other related embodiments, the condition associated with an elevation of ROS and RNS is a condition associated with ischemia and/or ischemic cell death. In particular embodiments, the condition is an infarction, and in specific embodiments, the condition is cerebral infarction (stroke) or myocardial infarction (heart attack). In other embodiments of the present invention, the antibodies, and fragments thereof, that bind selectively to non-native forms of SOD1 are used to diagnose or treat a subject having, or at risk for, an inflammatory disorder that may be associated with cell death. The inflammatory disorders include chronic and acute disorders. In particular embodiments, the antibodies and fragments are used to treat a subject having, or at risk for, an arterial inflammatory condition, disease or disorder such as arteriosclerosis including atherosclerosis. In particular embodiments, the antibodies, and fragments thereof, are used to diagnose or treat a subject having, or at risk for, a gastrointestinal condition, disease or disorder that is associated with detectable, misfolded SOD1, and may be selected for instance from inflammatory bowel disease, including ulcerative colitis and Crohn's disease, necrotizing enterocolitis and other gastrointestinal conditions, diseases or disorders that may be associated with ischemia and/or inflammation. Still other indications found to be associated with misfolded SOD1 include, according to the present invention conditions, diseases or disorders that comprise neural cell death and inflammation such as, multiple sclerosis. It will be appreciated that many of the disorders, conditions or diseases described herein are secondary to another disorder, conditions and diseases (for example, neurodegeration may be directly or indirectly caused by another disorder, condition or disease, such as, in tissue near nerve cells). The invention contemplates use of the therapeutic compositions for the treatment of non-native SOD1 meditated disorders, conditions and diseases, when said disorder, condition or disease is secondary to another disorder, condition or disease. It will be appreciated that acute conditions, such as stroke, myocardial infarction and conditions related thereto by ischemia will require the use of passive agents (e.g. passive immunization) such as antibodies or binding fragments rather than vaccines, in their treatment. Moreover, the antibody will preferably be administered to the bloodstream of the subject, rather than by a different parenteral route.

For the treatment of subjects experiencing or at risk for stroke, an antibody or binding fragment thereof that specifically binds to non-native forms of SOD1 is administered in an amount effective to reduce the cytotoxic activity of the misfolded SOD1. Reduction of cytotoxicity results from reduction of non-native forms of SOD1 levels and/or from reduction of non-native forms of SOD1 cytotoxicity. Reduction of non-native forms of SOD1 is optionally determined using antibodies specific for non-native forms of SOD1 of the present invention, to confirm that the level of misfolded SOD1 is reduced as a result of treatment. The reduction in cytotoxic misfolded SOD1 activity is alternatively determined by detecting the level or generation rate of toxic species in the misfolded SOD1 environment, such as reactive oxygen species (ROS) and/or reactive nitrogen species (RNS) or by detecting an alteration in markers affected by such reactive species before and after treatment. The effect of antibody on the level of these free radical toxins and markers can be determined experimentally using an in vitro system in which selected antibodies specific for non-native forms of SOD1 are assayed for their ability to block, completely or partially, the generation of ROS and RNS by misfolded SOD1 in the presence of proper substrates for the generation reactions, such as nitric oxide, ascorbate and molecular oxygen. Therapeutic antibodies may function by blocking completely or partially, ROS and RNS generation. Alternatively, therapeutic antibodies may also reduce the cytotoxic activity of misfolded SOD1 by accelerating its clearance and degradation. It is also possible that therapeutic antibodies function through both of these and/or other mechanisms. Inhibition or reducing non-native SOD1 cytotoxic by antibodies of the invention includes inhibition of each or any of the above mechanisms or any other mechanisms. Titration curves are optionally employed to determine an effective dose of antibody required to reduce a given quantity of cytotoxic misfolded SOD1.

An effective antibody dose can also be determined using animal models of stroke, such as those accomplished with carotid occlusion, with or without reperfusion after an ischemic period. Outcome measures of therapeutic efficacy of antibody therapy would include measurable aspects of motor behavior (such as increased use of the impaired limbs) and neuropathology (reduced infarct volume). Administration of antibodies specific for non-native forms of SOD1, is optionally prior to ischemia, or during the phase of reperfusion which mimics the likely treatment window during human stroke.

Similarly, for the treatment of subjects experiencing, or at risk for, myocardial infarction (MI), the antibody or misfolded SOD1-binding fragment thereof is administered in an amount effective to reduce the cytotoxic activity of the misfolded SOD1. A reduction in the misfolded SOD1 is optionally determined using antibodies specific for non-native forms of SOD1 of the present invention, to confirm that the level of misfolded SOD1 is reduced as a result of treatment. The reduction in cytotoxic misfolded SOD1 activity is alternatively determined by detecting the level or generation rate of toxic species in the misfolded SOD1 environment, such as reactive oxygen species (ROS) and/or reactive nitrogen species (RNS), or detecting an alteration in markers affected by such reactive species, before and after treatment. The effect of antibody on the level of these free radical species or markers can be determined experimentally using an in vitro system in which selected antibodies specific for non-native forms of SOD1 are assayed for their ability to block, completely or partially, the generation of ROS and RNS by misfolded SOD1 in the presence of proper substrates for the generation reactions, such as nitric oxide, ascorbate and molecular oxygen. Titration curves are optionally employed to determine an effective dose of antibody required to reduce a given quantity of cytotoxic misfolded SOD1.

An effective antibody dose can also be determined using animal models of MI, such as those accomplished by occlusion of a coronary artery, with or without reperfusion after an ischemic period. Outcome measures of therapeutic efficacy of antibody therapy would include assessment of cardiac enzymes and cardiopathology (reduced infarct volume). Administration of antibodies specific for non-native forms of SOD1 is optionally prior to ischemia, or during the phase of reperfusion to mimic a treatment window during human myocardial infarction.

The method of treatment is optionally provided in combination with other therapies. For example, a treatment regimen optionally combines administration of an antibody or fragment thereof that binds non-native forms of SOD1 with administration of an effective amount of tissue plasminogen activator (TPA) for the treatment of stroke and/or MI. In certain embodiments, the antibody and or fragment thereof and TPA are administered intravenously. In other embodiments the antibody and/or fragment thereof and TPA are administered intraarterially.

For the treatment of other indications that are not acute in nature, and particularly for the treatment of chronic indications, such as the majority of gastrointestinal disorders, it will be appreciated that treatment can be achieved using either antibodies or fragments that bind non-native forms of SOD1, or vaccines that elicit such antibodies in the subject, to provide a prolonged antibody effect. Treatment with either antibody or vaccine is useful, in embodiments of the present invention, to treat subjects presenting with a gastrointestinal disorder that is marked by the presence of misfolded SOD1 and by an elevation in the level of, ROS and RNS, at the disease site.

In one embodiment, antibody that binds selectively to non-native forms of SOD1, fragments thereof, or a vaccine useful in the production thereof, is administered to a subject diagnosed with inflammatory bowel disease (IBD). In a specific embodiment, the subject is a subject diagnosed with ulcerative colitis. Examination of tissues extracted from subjects presenting with ulcerative colitis are found to be positive for misfolded SOD1 immunoreactivity (DSE2 epitope), including the surface epithelium of the colon (strongly positive) and mast cells resident in the small intestine. Also positive for immunoreactivity are the absorptive and paneth cells of the small intestine. In another specific embodiment, the subject is a subject diagnosed with Crohn's disease. Examination of tissues extracted from subjects presenting with Crohn's disease are found to be positive for misfolded SOD1 immunoreactivity (DSE2 epitope), including the reactive epithelial mucosa particularly adjacent to ulcers (strongly positive). The effect of treatment is assessed by reduction in the frequency and severity of clinical attacks of IBD, for example, as determined by pain, diarrhea, weight loss, and other clinical parameters.

In another embodiment, antibody or fragments thereof that bind selectively to non-native forms of SOD1, or a vaccine useful in the production thereof, is administered to a subject diagnosed with multiple sclerosis (MS). Examination of tissues extracted from subjects presenting with MS are found to be positive for misfolded SOD1 immunoreactivity (DSE2 epitope), including glial cells and endothelia with increases in both nuclear and paranuclear staining. The effect of treatment can be assessed by a reduction in the frequency and severity of MS relapses, as determined by the commonly applied disability scales, and/or by neuroimaging evidence of amelioration, such as reduced plaque burden by magnetic resonance imaging, or enhanced neuronal function as evidenced by brain N-acetylaspartate levels by magnetic resonance spectroscopy.

In another embodiment, antibody or fragments thereof that bind selectively to misfolded or monomeric SOD1, or a vaccine useful in the production thereof, is administered to a subject diagnosed with atherosclerosis, Examination of tissues extracted from subjects presenting with atherosclerosis are found to be positive for misfolded SOD1 immunoreactivity (DSE2 epitope), including histocytes, subsets of myointimal cells. The effect of treatment can be assessed by reduction in vascular events, such as infarction, thrombosis and/or embolus, or by evidence of improved artery lumina by formal angiography, computerized tomography angiography, magnetic resonance angiography, and/or Doppler ultrasound assessment of accessible arteries such as the extracranial carotid arteries.

Subjects that are candidates for treatment with the antibodies and vaccines of the present invention can be identified using a variety of techniques that enable in situ detection of misfolded SOD1 using antibodies of the present invention for that detection. For example, misfolded SOD1 may be detected in situ using diagnostic scanning methods such as positron emission tomography (PET) or single photon emission computed tomography (SPECT). As well, it will be appreciated that well established methods can be applied to arrive at a diagnosis for each particular indication noted herein. Such diseases are marked by presence of a form of SOD1 that is immunoreactive with an antibody that binds selectively to non-native forms of SOD1.

Doses and Formulations

The dosage form is optionally a liquid dosage form. The term "liquid dosage form" refers to non-solid dosage forms suitable for, but not limited to, parenteral, intravenous, subcutaneous, intramuscular, intracranial, intraventricular, intrathecal, intraorbital, ophthalmic, intracapsular, intraspinal, intracisternal, intraperitoneal, intranasal, aerosol or oral administration. Solutions of a compound of the invention can be prepared in water suitably mixed with a surfactant such as hydroxypropylcellulose. Dispersions can also be prepared in glycerol, liquid polyethylene glycols, DMSO and mixtures thereof with or without alcohol, and in oils. Under ordinary conditions of storage and use, these preparations contain a preservative to prevent the growth of microorganisms. A person skilled in the art would know how to prepare suitable formulations. Conventional procedures and ingredients for the selection and preparation of suitable formulations are described, for example, in Remington's Pharmaceutical Sciences (2003-20th edition) and in The United States Pharmacopeia: The National Formulary (USP 24 NF19) published in 1999. Formulations optionally contain excipients including, but not limited to, a buffering agents, an anti-oxidant, a stabilizer, a carrier, a diluent, and an agent for pH adjustment.

The pharmaceutical forms suitable for injectable use include sterile aqueous solutions or dispersion and sterile powders for the extemporaneous preparation of sterile injectable solutions or dispersions. In all cases the form must be sterile and must be fluid to the extent that easy syringability exists.

A person skilled in the art would recognize that the dosage form and formulation chosen depends on characteristics of the composition. For example a person skilled in the art would know that a composition comprising an antibody may require a different formulation than a composition comprising a nucleic acid and would choose a formulation and dosage form suitable to the composition.

Additional factors that affect the effective dose of a formulation include the route of administration, the target site, the physiological state of the subject, the species of the subject, whether the treatment is prophylactic or therapeutic, whether other medications were are administered, and whether an adjuvant is also administered.

The timing of the immunizations optionally vary from once a day, to once a week, to once a month, to once a year, to once a decade. A typical regimen includes an immunization followed by booster injections at 6 weekly intervals. Another regimen consists of immunization followed by booster injections 1, 2 and 12 months later. Alternatively, booster injections will vary depending on the immune response and the physiological condition of the subject.

For passive immunization using an antibody directed against an epitope derived from a non-native form of SOD1, the dose optionally ranges from about 0.0001 mg/kg to about 100 mg/kg, about 0.01 mg/kg to about 5 mg/kg, about 0.15 mg/kg to about 3 mg/kg, 0.5 mg/kg to about 2 mg/kg and about 1 mg/kg to about 2 mg/kg of the subject's body weight. In other embodiments the dose ranges from about 100 mg/kg to about 5 g/kg, about 500 mg/kg to about 2 mg/kg and about 750 mg/kg to about 1.5 g/kg of the subject's body weight.

For active immunization using immunogens comprising isolated peptides or related molecules corresponding to disease specific epitopes of non-native forms of SOD1, the dose optionally ranges from about 0.0001 microgram to 10 grams, about 0.01 microgram to about 1 gram, about 1 microgram to about 1 mg, and about 100 to 250 micrograms per treatment. In one embodiment the timing of administering treatment is at one or more of the following: 0 months, 2 months, 6 months, 9 months, and/or 12 months. In one regimen, the dosing is at 2, 6, 9, and 12 months following the first immunization. In another regimen, the dosing is at 2 and 4 weeks following the first immunization, and then monthly afterwards. In an alternative regimen, the dosing varies depending on the physiological condition of the subject and/or the response to the subject to prior immunizations. The route of administration optionally includes, but is not limited to, intramuscular and intraperitoneal injections. In one embodiment the composition is injected into the deltoid muscle.

Where an isolated peptide corresponding to an epitope is too small to be immunogenic, or where immunogenicity is improved, the peptide is optionally linked or coupled to a suitable carrier. Suitable carriers include, but are not limited to, keyhole limpet hemocyanin, MAP antigen, serum albumins, immunoglobulin molecules and toxoids from pathogenic bacteria. Peptides may be linked to carriers by chemical crosslinking, for instance to form dendrimers. In the alternative, immunogenic peptides may be expressed as fusion proteins with carriers.

Monoclonal antibodies such as humanized mAb can be used by intravenous infusion. The therapeutic concentration of SOD1 DSE humanized antibody may be 1-10 micrograms per mL local concentration in the CNS. In the setting of a non-disrupted blood brain barrier (BBB) only 1/100 to 1/1000 of IgG penetrates the CNS. Thus, the concentration of therapeutic antibody in the peripheral circulation necessary to reach this concentration in the CNS would be on the order of 100 micrograms/ml to maximally 10 mg/ml, close to the pre-treatment level of IgG in human plasma. Considering the human blood volume to be about 5 liters, dosing of 50 grams would be the upper limit, which is similar to the dose of pooled polyclonal intravenous immunoglobulin (IVIG) used to treat many inflammatory and autoimmune disorders. Considering the degradation of human IgG requires 3-4 weeks, dosing once per 3 weeks should constitute an effective regimen. However, dosing of humanized anti-DSE monoclonal antibodies could be much lower than the above calculation, based on mouse treatment experiments provided in the examples below. We have found that dosing G93A mice intraperitoneally with 1 mg of DSE2 antibody was therapeutically effective. Considering the volume of blood in a mouse is 6-7 mL per 100 grams body weight, circulating concentration of the DSE2 mAb was on the order of 1 mg/mL. For dosing of a human being with ALS, this would translate to 1/10 of the circulating normal IgG (ordinarily about 10 mg/mL). Human blood volume is on the order of 5 liters, which would suggest an effective therapeutic dose of humanized DSE2 antibody on the order of 5 grams via IV infusion. Moreover, mild disruption of the BBB has been noted in ALS, which is presumably maximal in regions of greatest neuroinflammation, i.e., those regions in which the disease is most manifest, such as the anterior horn motor neurons, and the cortical motor neurons, as well as certain fiber tracts that are subserved by cortical motor neurons. Thus, it is possible that selective BBB disruption in regions of maximal disease will permit therapeutic efficacy for lower circulating concentrations of anti-DSE SOD1 antibodies.

Humanized DSE mAbs can be used for direct infusion into the CNS via the intraventricular route or by the intrathecal route. Examples of medical devices which are used for this purpose are manufactured by MedTronic. As the CSF recirculates several times daily, ongoing infusion is required, rather than a 3-4 week dosing regimen. The end concentration of 1-10 micrograms per mL will be achieved by infusion of as much as 5 mg per day in the 500 mL per day CSF.

Combination Therapies

The present methods thus provide for the immunotherapeutic application of SOD1 antibodies in the treatment of conditions, disorders or diseases marked by the presence of misfolded or monomeric SOD1.

The treatment of an afflicted subject can be conducted by monotherapy, in the manner just described, by administering a selected antibody or epitope-based vaccine. In embodiments of the present invention, the present method can also be conducted by administering more than one antibody species, or more than one epitope species. For instance, the method can be conducted by administering an antibody to the electrostatic loop structure [DSE 2] and an antibody to an epitope accessible only on the SOD dimer interface [DSE1a]. In one embodiment, the method of the present invention is conducted using antibodies that bind selectively to at least two different epitopes accessible selectively on misfolded SOD1, such as a surface epitope on the SOD dimer, and an interface epitope on the SOD monomer. Similarly, the method can be conducted by administering two different epitopes, in the form of vaccines useful to raise antibodies to those two different epitopes on misfolded or monomeric SOD1. In one embodiment, the method entails administration of two or more epitopes, for instance DSE1a and DSE2. In another embodiment, the method entails administration of three or more epitopes, for instance DSE1a, DSE2 and DSE5. Furthermore, the method can be conducted using a combination of both passive immunotherapy and active immunotherapy, in which the subject is treated to receive both a selected antibody and a selected epitope-based vaccine.

The method can also be conducted as a combination therapy in which the selected SOD1 antibody and/or epitope is administered in combination with another agent useful therapeutically in the treatment or management of the particular disease. For Alzheimer's disease, for instance, useful combination therapies include administration of agents that control or reduce accumulation of Abeta aggregates, fibrils or protofibrils. In embodiments, such agents include vaccines based on Abeta and Abeta fragments. Other agents useful in combination with the present therapy for treatment of Alzheimer's disease include deprenyl, the cholinesterase inhibitors donepezil, rivastigmine and galantimine, as well as memantine and vitamin E.

Similarly, in combination therapies for the treatment of Parkinson's disease, the present therapeutics can be used in combination with inhibitors of alpha-synuclein aggregation, such as vaccines based thereon, as well as levodopa, carbidopa and entacapone, dopamine agonists such as pergolide and rotigotine, amantadine, anticholinergics such as procyclidine, COMT inhibitors, and MOA-B inhibitors such as selegiline and rasagiline.

In combination therapies for the treatment of ALS, the present therapeutics can be used in combination with riluzole and other glutamate inhibitors.

The inventors have also found that copper is retained in metal-catalyzed oxidized SOD1, which is a DSE-2 immunoreactive aggregated species. The inventors also find that SOD1 oxidized by treatment with hydrogen peroxide displays DSE2 immunoreactivity (FIG. 2). The DSE2 antibody, which reacts against the SOD1 electrostatic loop of the active site, may be physically blocking access to the retained copper of the misfolded species, and thus reducing the catalysis of reactive oxygen and nitrogen species via the Haber-Weiess reaction, the Fenton reaction, and others. Notably, high concentrations of ascorbate in the CNS may be facilitating redox cycling of the copper bound by misfolded SOD1, enhancing its ability to generate ROS and RNS. The aggregated state of SOD1, which has been preferentially secreted from neurons (1), impairs its clearance and degradation, "trapping" copper in a catalytically active neurotoxic form in close proximity to motor neurons in ALS, and hippocampal and other neurons in AD. The possibility that Abeta may contribute to this toxic redox cycling of copper in AD (83), is noted.

Accordingly In a particularly useful combination therapy, the present therapeutics are used in combination with an antioxidant, for the treatment of ALS, AD and PD as well as other disorders in which dysfunctional SOD1 and/or SOD1 aggregation results in the toxic accumulation of reactive oxygen species (ROS) or reactive nitrogen species (RNS). The antioxidants are a well known group of readily available agents, and include vitamins ascorbic acid and alpha-tocopherol, and pharmacological agents such as N-acetylcysteine. In embodiments of the present method, the antioxidant is a functional SOD synthetic, which mimics the enzymatic action of endogenous SOD to reduce accumulation of superoxide radicals. Related useful drugs include those which stabilize the SOD dimer, as described for instance by Lansbury et al in US 2006/0194821, incorporated herein by reference. Other drugs having the same effect are useful as well. In particular embodiments, the antioxidant is a copper chelator, such as penicillamine, clioquinol, 8-hydroxyquinoline and derivatives such as those described US2006/0089380, cuprizone, picolinic acid-based compounds, molybdenum compounds, L-taurine or other drug having the effect of inhibiting the redox cycling mediated by copper ion. Still other useful antioxidants include superoxide scavengers, peroxide scavengers, and scavengers of RNS. In a particular embodiment of the invention, the present therapeutics are used in combination with resveritrol, an antioxidant present in red grapes and wine. In a specific embodiment, the DSE2 antibody or epitope is used in combination with resveritrol.

Antioxidants such as ascorbate are useful in combination with the present therapeutics even though as mentioned elsewhere, misfolded SOD1 and anti-oxidant can cooperate through redox cycling to elevate, rather than reduce, the level of toxins such as ROS and RNS. By introducing antibody to misfolded SOD1 or a related agent, participation of misfolded SOD1 in the redox cycling can be reduced or eliminated, ostensibly as a result of blocking the copper ion exposed in misfolded SOD1 and/or by increasing SOD1 degradation, thus allowing the antioxidant to function normally to reduce accumulation of the free radical toxins.

When used in combination with the present therapeutics, the combination agent is administered in the manner prescribed for that agent, in accordance with standard practice.

Diagnostics

The antibodies specific for SOD1 disease specific epitopes such as amyotrophic lateral sclerosis-specific epitopes can also be used to diagnose amyotrophic lateral sclerosis. Thus, one aspect of the invention is a method of detecting or diagnosing amyotrophic lateral sclerosis in a subject comprising the steps of:
  (a) contacting a test sample of said subject with an antibody of the invention, wherein the antibody binds to an amyotrophic lateral sclerosis-specific epitope to produce an antibody-antigen complex;
  (b) measuring the amount of the antibody-antigen complex in the test sample; and
  (c) comparing the amount of antibody-antigen complex in the test sample to a control wherein a difference in the amount of antibody-antigen complex in the test sample as compared to the control is indicative of amyotrophic lateral sclerosis.

Optionally, in the case where the epitope is masked within the SOD1 aggregate, the method comprises the further step of treating the sample under disaggregation conditions, using for instance guanidinium hydrochloride, to liberate the misfolded SOD for subsequent detection.

The phrase "detecting or monitoring amyotrophic lateral sclerosis" refers to a method or process of determining if a subject has or does not have amyotrophic lateral sclerosis or the extent of the amyotrophic lateral sclerosis. In addition, the antibodies of the invention can be used to detect or monitor the appearance and progression of SOD1 aggregation, and hence progression of the disease. The antibodies are further useful to monitor progression of the disease during treating with a method of the invention.

The term "control" as used herein refers to a sample from a subject or a group of subjects who are either known as having amyotrophic lateral sclerosis or not having amyotrophic lateral sclerosis. A person skilled in the art will appreciate that the difference in the amount of antibody-antigen complex will vary depending on the control. For example, if the control is known to have amyotrophic lateral sclerosis, then less measurable antibody-antigen complex in the test sample as compared to the control indicates that the subject does not have amyotrophic lateral sclerosis or that they have less of an extent of amyotrophic lateral sclerosis. If the control is known to have amyotrophic lateral sclerosis, then equal or greater measurable antibody-antigen complex in the test sample as compared to the control indicates that the subject has amyotrophic lateral sclerosis. If the control is known not to have amyotrophic lateral sclerosis, then less or equal measurable antibody-antigen complex in the test sample as compared to the control indicates that the subject does not have amyotrophic lateral sclerosis. If the control is known not to have amyotrophic lateral sclerosis, then greater measurable antibody-antigen complex in the test sample as compared to the control indicates that the subject has amyotrophic lateral sclerosis.

The term "sample" as used herein refers to any fluid, cell or tissue sample from a subject which can be assayed for misfolded SOD1. In one embodiment, the sample comprises, without limitation, cerebrospinal fluid, plasma, blood serum, whole blood, spinal cord tissue, brain cells, motor neurons, a portion of the dorsal horn, or peripheral blood cells, such as erythrocytes, mononuclear cells, lymphocytes, monocytes and granulocytes. In another embodiment, invention is a method of detecting or diagnosing Alzheimer's disease in a subject comprising the steps of:
  (a) contacting a test sample of said subject with an antibody of the invention, wherein the antibody binds to an Alzheimer's disease-specific epitope to produce an antibody-antigen complex;
  (b) measuring the amount of the antibody-antigen complex in the test sample; and
  (c) comparing the amount of antibody-antigen complex in the test sample to a control wherein a difference in the amount of antibody-antigen complex in the test sample as compared to the control is indicative of Alzheimer's disease.

Optionally, in the case where the epitope is masked within the SOD1 aggregate, the method comprises the further step of treating the sample under disaggregation conditions, using for instance guanidinium hydrochloride, to liberate the misfolded SOD for subsequent detection. In a further embodiment, invention is a method of detecting or diagnosing Parkinson's disease in a subject comprising the steps of:
  (a) contacting a test sample of said subject with an antibody of the invention, wherein the antibody binds to a Parkinson's disease-specific epitope to produce an antibody-antigen complex;
  (b) measuring the amount of the antibody-antigen complex in the test sample; and
  (c) comparing the amount of antibody-antigen complex in the test sample to a control wherein a difference in the amount of antibody-antigen complex in the test sample as compared to the control is indicative of Parkinson's disease.

Optionally, in the case where the epitope is masked within the SOD1 aggregate, the method comprises the further step of treating the sample under disaggregation conditions, using for instance guanidinium hydrochloride, to liberate the misfolded SOD for subsequent detection.

A further aspect of the invention is a method of detecting or diagnosing Lewy Body disease in a subject comprising the steps of:
(a) contacting a test sample from said subject with an antibody that binds to an epitope selectively presented or accessible in non-native forms of SOD1, wherein the antibody binds to the epitope to produce an antibody-antigen complex;
(b) measuring the amount of the antibody-antigen complex in the test sample; and
(c) comparing the amount of antibody-antigen complex in the test sample to a control, wherein a difference in the amount of antibody-antigen complex in the test sample as compared to the control is indicative of Lewy body disease.

Optionally, and in the case where the misfolded SOD1 epitope is masked within a SOD1 aggregation, the method provides for the step of treating the sample to promote disaggregation of the SOD1 aggregates to expose the target epitope prior to step (a).

In the case where the epitope is masked within the SOD1 aggregate, the method comprises the further step of treating the sample under disaggregation conditions, using for instance guanidinium hydrochloride, to liberate the misfolded SOD1 for subsequent detection. A person skilled in the art will appreciate that "disaggregation conditions" refers to conditions that promote the dissociation of the aggregate into smaller units, such as dimers or monomers of SOD1. This is different than denaturing the protein. Accordingly, a person skilled in the art will appreciate that concentrations of guanidinium hydrochloride (for example) can be used that dissociate, but do not denature, the SOD1 aggregates.

The phrase "detecting or monitoring Alzheimer's disease" refers to a method or process of determining if a subject has or does not have Alzheimer's disease or the extent of the Alzheimer's disease. In addition, the antibodies of the invention can be used to detect or monitor the appearance and progression of SOD1 aggregation, and hence progression of the disease.

The phrase "detecting or monitoring Parkinson's disease" refers to a method or process of determining if a subject has or does not have Parkinson's disease or the extent of the Parkinson's disease. In addition, the antibodies of the invention can be used to detect or monitor the appearance and progression of SOD1 aggregation, and hence progression of the disease.

The phrase "detecting or monitoring Lewy Body disease" refers to a method or process of determining if a subject has or does not have Lewy Body disease or the extent of the Lewy Body disease. In addition, the antibodies of the invention can be used to detect or monitor the appearance and progression of SOD1 aggregation, and hence progression of the disease.

In one embodiment of the invention, the antibodies are used to determine if misfolded SOD1 is present in the sample. In another embodiment, the antibodies are labeled with a detectable marker.

In another embodiment, the epitopes are used to monitor the appearance and titre of antibodies introduced into or raised within a recipient. In this embodiment, a patient sample is mixed with the epitope, and preferably a labeled epitope, and the presence or quantity of bound antibody is determined.

The label is preferably capable of producing, either directly or indirectly, a detectable signal. For example, the label may be radio-opaque or a radioisotope, such as $^3H$, $^{14}C$, $^{32}P$, $^{35}S$, $^{123}I$, $^{125}I$, $^{131}I$; a fluorescent (fluorophore) or chemiluminescent (chromophore) compound, such as fluorescein isothiocyanate, rhodamine or luciferin; an enzyme, such as alkaline phosphatase, beta-galactosidase or horseradish peroxidase; an imaging agent; or a metal ion.

In another embodiment, the detectable signal is detectable indirectly. For example, a secondary antibody that is specific for the antibody of the invention and contains a detectable label can be used to detect the antibody of the invention.

A person skilled in the art will appreciate that a number of methods can be used to determine if misfolded SOD1 is present in a sample using the antibodies of the invention, including immunoassays such as flow cytometry, Western blots, ELISA, and immunoprecipitation followed by SDS-PAGE immunocytochemistry.

In one embodiment of the invention, a misfolded-SOD1 related disease, such as Alzheimer's disease, Parkinson's disease, Lewy Body and/or amyotrophic lateral sclerosis is detected or monitored in a subject using flow cytometry of a sample from the subject, including peripheral blood cells, such as erythrocytes, mononuclear cells, lymphocytes, monocytes and/or granulocytes, or mononuclear cells found in cerebrospinal fluid. In a further embodiment, the cells assayed using flow cytometry can be permeablized using reagents known to persons skilled in the art including, without limitation, detergents, ethanol, methanol and paraformaldehyde.

In one embodiment of the invention, a misfolded-SOD1 related disease, such as Alzheimer's disease, Parkinson's disease and/or Lewy body disease can be detected or monitored in a subject using flow cytometry of a sample from the subject, including peripheral blood cells, such as erythrocytes, mononuclear cells, lymphocytes, monocytes and/or granulocytes, or mononuclear cells found in cerebrospinal fluid. In a further embodiment, the cells assayed using flow cytometry can be permeablized using reagents known to persons skilled in the art including, without limitation, detergents, ethanol, methanol and paraformaldehyde.

In another embodiment, a misfolded-SOD1 related disease, such as Alzheimer's disease, Parkinson's disease and/or Lewy Body disease can be detected or monitored using the epitope protection assay described in WO 2005/019828 entitled "Epitope Protection Assay and Method for Detecting Protein Conformations", which entered national phase in the United States on Feb. 17, 2006. In another embodiment, amyotrophic lateral sclerosis is detected or monitored using the epitope protection assay described in WO 2005/019828.

Any of the methods of the invention to diagnose, detect or monitor SOD1 aggregation and development of a misfolded-SOD1 related disease can be used in addition or in combination with traditional diagnostic techniques for misfolded-SOD1 related diseases.

Any of the methods of the invention to diagnose, detect or monitor SOD1 aggregation and development of amyotrophic lateral sclerosis can be used in addition or in combination with traditional diagnostic techniques for amyotrophic lateral sclerosis. Traditional diagnostic techniques for amyotrophic lateral sclerosis include physical and neurological examinations, and can include electromyography tests, nerve conduction velocity tests, and magnetic resonance imaging.

Traditional diagnostic techniques for Alzheimer's disease include physical and neurological examinations, and can include brain scans, mental status examinations, and memory function tests. Traditional diagnostic techniques for Parkinson's disease include physical and neurological examinations, and include brain scans. Traditional diagnostic techniques for Lewy Body disease include physical and neurological examinations, and include brain scans.

The diagnosis of neurodegenerative disease, and the monitoring of progression of these disorders, is unsatisfactory at this time. Definite diagnosis can only be made by tissue examination on necropsy evaluation after death, or by biopsy (almost never utilized in neurodegenerative diseases). It is not an exaggeration to state that antemortem presumptive diagnosis of ALS, AD, and PD is made on the basis of clinical features, which are often shared with other diseases, and by attempting to exclude other disorders that mimic the disease in question. "Diagnosis by exclusion" is conducted through neuroimaging (MRI and CAT scans) and blood tests to rule out confounding diagnoses (such as thyroid function tests). Specialized testing for the separate neurodegenerative disorders (such as neuropsychological assessment for AD, PET scanning for PD, and electromyography for ALS, along with the clinical exam, are predictive of autopsy diagnosis 70-90% of AD and PD patents, and usually greater than 90% of ALS patients.

The antibodies of the invention are useful for diagnosis and may optionally be used for concentrating low quantities of misfolded proteins present in patient fluids and tissues by concentrating methods such as immunoprecipitation. In one embodiment, an antibody that recognizes an epitope selectively presented in non-native forms of SOD1 is used to immunoprecipitate SOD1 from peripheral blood. The presence of immunoprecipitated SOD1 may optionally be detected by ELISA.

The invention also includes kits for diagnosing amyotrophic lateral sclerosis comprising an antibody of the invention and instructions for use thereof. A person skilled in the art will appreciate that the antibody may be labeled with a detectable marker.

The invention also includes kits for diagnosing misfolded-SOD1 related diseases, such as Alzheimer's disease, Parkinson's disease and/or Lewy Body disease comprising an antibody that binds to an epitope specific for an epitope selectively presented or accessible in non-native forms of SOD1 and instructions for use thereof. A person skilled in the art will appreciate that the antibody may be labeled with a detectable marker.

The invention additionally includes kits for diagnosing ALS, AD, and/or PD comprising one or more isolated peptides corresponding to disease-specific epitopes. In one embodiment, the kit comprises an isolated peptide corresponding to the disease specific epitopes selected from the group comprising, DSE1, DSE1a, DSE2, DSE3, DSE4, DSE5, DSE6 and DSE7. The isolated peptides may be included in addition to an antibody that binds said epitope. In one embodiment the isolated peptide is a positive control. In the alternative, the isolated peptide can be useful per se to screen a sample to detect any DSE antibodies present, for example, in a patient undergoing either active or passive immunotherapy based on such peptides and antibodies.

Non-Native SOD1 Inhibitor Screening Assays

The invention also includes, in one aspect, screening assays for detecting substances that reduce or inhibit the toxin production or generation activity of non-native SOD1. As mentioned previously, non-native forms of SOD1 can lead to the elevation of free radical toxins such as reactive nitrogen species (RNS) and reactive oxygen species (ROS). Reduction of the toxin production or generation activity of non-native forms of SOD1 is accomplished, for example, by i) substances that reduce the toxic enzymatic activity of non-native forms of SOD1, ii) substances that increase the degradation of non-native forms of SOD1 which produce toxic free radicals and/or iii) substances that prevent the misfolding or aggregation of non-native forms of SOD1 which allow for the production or generation of toxic free radicals. These assays are in vitro or in vivo. In an embodiment, the application provides an in vitro assay for evaluating whether a candidate substance is capable of inhibiting non-native SOD1 toxic enzymatic activity. Substances that reduce SOD1 toxic enzymatic activity are typically identified based on their ability to bind SOD1.

Accordingly, the application provides a method of identifying an inhibitor of a non-native form of SOD1 comprising the steps of:

a) providing non-native form of SOD1;
b) contacting the non-native form of SOD1 with a test substance; and
c) determining whether the test substance binds to the non-native form of SOD1, the binding being an indication that the test substance is an inhibitor of non-native form of SOD1.

The purified non-native form of SOD1 is optionally purified from a cell overexpressing a non-native form of SOD1. Alternatively, binding to non-native forms of SOD1 is readily assessed using a non-native form of SOD1 or test substance that is insolubilized. For example, a non-native form of SOD1 or a test substance may be bound to a suitable carrier. Examples of suitable carriers are agarose, cellulose, dextran, Sephadex, Sepharose, carboxymethyl cellulose polystyrene, filter paper, ion-exchange resin, plastic film, plastic tube, glass beads, polyamine-methyl vinyl-ether-maleic acid copolymer, amino acid copolymer, ethylene-maleic acid copolymer, nylon, silk, etc. The carrier may be in the shape of, for example, a tube, test plate, beads, disc, sphere etc. The insolubilized protein or substance may be prepared by reacting the material with a suitable insoluble carrier using known chemical or physical methods, for example, cyanogen bromide coupling.

In one embodiment the test substance is an antibody. In a further embodiment, the antibody binds a non-native form of SOD1. In one embodiment the non-native form of SOD1 is monomeric SOD1. In another embodiment, the non-native form of SOD1 is misfolded SOD1. In a further embodiment, the misfolded form of SOD1 is a monomeric form of SOD1. In yet a further embodiment, the misfolded form of SOD1 is a dimeric form of SOD1. In another embodiment, the misfolded form of SOD1 is an aggregated form of SOD1. In an alternative embodiment, the test substance is an agent that competes with an antibody known to have a desired effect in the assay such as an antibody exemplified herein.

In another aspect the application provides an in vivo assay for evaluating whether a candidate substance is capable of inhibiting a non-native form of SOD1. Substances that reduce SOD1 toxic enzymatic activity are typically identified based on their ability to bind SOD1. Accordingly, the application provides a method of identifying an inhibitor of a non-native form of SOD1 comprising the steps of:

a) contacting a cell expressing the non-native form of SOD1 with a test substance; and
b) determining whether the test substance binds to the non-native form of SOD1 polypeptide, the binding being an indication that the test substance is an inhibitor of a non-native form of SOD1.

The test substance is optionally contacted with the cell by direct delivery into the cell using a variety of techniques known in the art. For example the test substance can be delivered by microinjection, electroporation, and the use of cationic lipids.

Bound complexes of the substance and non-native form of SOD1 may be isolated by conventional isolation techniques, for example, salting out, chromatography, electrophoresis, gel filtration, fractionation, absorption, polyacrylamide gel electrophoresis, agglutination, or combinations thereof. To facilitate the assay of the components, an antibody the binds or the substance, or a labelled non-native forms of SOD1, or a labelled substance may be utilized. The antibodies, proteins, or substances may be labelled with a detectable substance as described elsewhere.

An inhibitor of a non-native form of SOD1 is also identified by detecting a reduction or inhibition of non-native forms of SOD1 production or generation of toxic free radical species. As mentioned above, non-native forms of SOD1 can result in elevation of cytotoxic free radical species such as reactive oxygen species (ROS) and reactive nitrogen species (RNS). A substance that binds a non-native form of SOD1 is also optionally tested for its ability to inhibit or reduce non-native SOD1 production or generation of toxic free radical species. In one embodiment, the method is in vitro.

Accordingly, the application provides a method of identifying an inhibitor of a non-native form of SOD1 comprising the steps of:
 a) providing non-native form of SOD1;
 b) contacting the non-native form of SOD1 with a test substance; and
 c) determining whether the test substance inhibits or reduces the production of free radical species, the reduction in free radical species production being an indication that the test substance is an inhibitor of a non-native form of SOD1.

In one embodiment the test substance is an antibody. In a further embodiment, the antibody is specific for a non-native form of SOD1. In one embodiment the non-native form of SOD1 is monomeric SOD1. In another embodiment, the non-native form of SOD1 is misfolded SOD1. In a further embodiment, the misfolded form of SOD1 is a monomeric form of SOD1. In yet a further embodiment, the misfolded form of SOD1 is a dimeric form of SOD1. In another embodiment, the misfolded form of SOD1 is an aggregated form of SOD1.

In another embodiment the method is in vivo. In one embodiment, cells are cultured in the presence of at least one compound whose ability to inhibit non-native forms of SOD1 activity is sought to be determined and the cells are assayed for a decrease in the level of free radical production. Accordingly, the application provides a method of identifying an inhibitor of a non-native form of SOD1 comprising the steps of:
 a) contacting a cell expressing a non-native form of SOD1 with a test substance, under conditions which allow for formation of a complex between the non-native form of SOD1 and the test substance, and
 b) determining whether the test substance inhibits or reduces the production of free radical species, the reduction in free radical species production being an indication that the test substance is an inhibitor of a non-native form of SOD1.

The term "free radical species" as used herein includes reactive oxygen species (ROS) and reactive nitrogen species (RNS) and are chemical species having an unpaired electron which renders them highly reactive and cytotoxic.

Methods for detecting free radical species production by well known in the art. For example For example, Estevez A G et al. Induction of nitric oxide-dependent apoptosis in motor neurons by zinc-deficient superoxide dismutase. Science, 1999 286:2498-500 provides an assay for detection of superoxide and peroxynitrite formed by Zn deficient forms of SOD1 (See also Pacher et al Nitric Oxide and Peroxynitrite in Health and Disease Physiol Rev, 2007, 87:315-424; and Singh et al. PNAS 1998, 95:6675-6680). A person skilled in the art will readily recognize that the aforementioned methods are adaptable for determining free radical production by non-native forms of SOD1.

Drug Screening

The antibodies of the invention can also be used to identify and screen for substances useful for the treatment or prevention of amyotrophic lateral sclerosis or the formation of misfolded SOD1, which is associated with amyotrophic lateral sclerosis. For example, the method of identifying substances for treating, inhibiting or preventing of amyotrophic lateral sclerosis can include:
 (a) contacting a sample from a subject treated with a substance with any one of the antibodies of the invention, wherein binding is indicative of the presence of misfolded SOD1 in the sample,
 (b) detecting the level of binding in the sample, and
 (c) comparing the level of binding in the sample to the level of binding in a control,
 wherein an altered level of binding in the sample compared to the control is indicative of a substance for the treatment or prevention of amyotrophic lateral sclerosis.

A person skilled in the art will appreciate that the control can be a sample from a subject not treated with a substance or treated with a substance that is known not to treat or prevent amyotrophic lateral sclerosis. Thus, if the "altered level of binding" is a reduced level of binding in the sample compared to the control, then this is indicative of a substance useful for the treatment or prevention of amyotrophic lateral sclerosis. In addition, the control can be a sample from the same subject, but before treatment with the substance to be tested or samples from the subject taken at different points of time during treatment with the substance to be tested.

Substances for the treatment or prevention of amyotrophic lateral sclerosis can also be identified using cells or cell lines. For example, cells or cell lines can be contacted with a substance and then the presence of misfolded SOD1 on the cells can be detected using the binding proteins of the invention and compared to a control.

A person skilled in the art will appreciate that a library of molecules can be screened by monitoring the effect of the candidate compounds on the inhibition of the conversion of SOD1 to a misfolded or disease-specific conformation.

The invention also includes the substances identified using the methods of the invention, which are useful for the treatment of amyotrophic lateral sclerosis or the formation of misfolded and/or aggregated SOD1, which is associated with amyotrophic lateral sclerosis.

In embodiments that apply to all aspects of the invention, the misfolded SOD1 epitope is an epitope other than DSE 1. In related embodiments, the misfolded SOD1 epitope is other than DSE 4. In related embodiments, the misfolded SOD1 epitope is other than DSE 7. In further related embodiments, the misfolded SOD1 epitope is other than DSE 1, DSE 4 and DSE 7.

The following non-limiting examples are illustrative of embodiments of the present invention:

EXAMPLES

Immunogens comprising isolated peptides corresponding to disease specific epitopes, for example DSE1a, may in the following examples refer to analog DSE sequences (e.g. DSE1a analog GGGRLAC*GVIGIGSG comprising additional Nterminal G sequences) as the DSE number (e.g. DSE1) that is related to the analog.

Example 1

DSE2 Monoclonal Antibody Generation

An isolated peptide corresponding to amyotrophic lateral sclerosis-specific epitope (DLGKGGNEESTKTGNAGS) (SEQ ID NO: 2) bearing an N-terminal Cys residue was conjugated to KLH for immunization of BALB/c mice, and to BSA for ELISA screening. Multiple injections were given to each mouse at 21-day intervals. The adjuvant for first injection was Complete Freund's Adjuvant (Sigma, Cat#F5881-6×10 mL). Incomplete Freund's Adjuvant (Sigma, Cat#F5506-6×10 mL) was the adjuvant used for the remaining injections. Blood was collected from the mice 7-10 days after the 3rd injection. The cell fusion was done 3-4 days after the final boost without any adjuvant.

The fusion partner used was Sp 2/0-Ag14 (ATCC#CRL-1581). The fusion between fusion partner SP2/0 and spleen cells was done at 1:5 ratio ($2.0 \times 10^7 : 1.0 \times 10^8$) in 1 ml pre-warmed PEG (MW1450: Sigma, Cat#P7181). Fusion cells were re-suspended into 50 ml of DMEM with 10% FBS and plated into 5 96-well plates at 100 µl/well. 100 µl/well of 2×HAT DMEM media was added to the fusion cells after 24 hours. Media was changed on days 5 and 7 with fresh 1×HAT media. On day 10-12, 50 µl of supernatant was collected from each well for first ELISA screening. Positive clones were transferred to 24 well plates. Upon confluence, antibody supernatants were screened by ELISA with the antigen used to immunize the mice and a non-related antigen (human transferrin). Positive clones were transferred to 6-well plates for expansion or hybridoma subcloning. The subcloning was done by limiting dilution at 50-70 cells/96-well plate.

Example 2

Large Scale Monoclonal Antibody Production

For large scale antibody production, 0.2-0.5 ml of Pristane (Sigma, Cat#T-7640) or IFA was injected to each mouse (BALB/c) by i.p. for priming. On day 7-14, 500,000 to 5,000,000 hybridoma cells in 0.5 ml 1×PBS at log phase were injected to each mouse by i.p. The ascitic fluid was allowed to accumulate for 1-2 weeks. 2-5 ml of ascites can be harvested from each mouse, with an IgG concentration around 1-9 mg/ml. Protein A was used for the IgG2 and 3 purification, and Protein G for IgG1.

The IgG mAb clone was designated 10E11C1. This antibody displays properties consistent with its recognition of a disease-specific epitope for misfolded SOD1. This mAb binds to denatured SOD1 on immunoblot membranes, recognizing monomeric denatured SOD1 (unstructured). The mAb does not recognize the dimeric SOD1 on immunoblotting. On immunoprecipitations mediated by 10E11C11 conjugated magnetic beads, there is no detectable binding of native SOD1 from normal human brain or mouse brain and spinal cord. The mAb does efficiently immunoprecipitate SOD1 deliberately misfolded by low pH, the chaotrope guanidine, or both. Most importantly, 10E11C11 efficiently immunoprecipitates misfolded SOD1 in a mouse model of ALS caused by transgenic overexpression of mutant SOD1 (G93A). Notably, mouse endogenous SOD1 present in the same tissue is not immunoprecipitated, suggesting that the misfolded human mutant SOD1 does not "co-recruit" normal mouse SOD in this disease model.

Antibodies were also raised in a like manner to the epitope NPLSRKHGGPKDEE (SEQ ID NO: 3), bearing an N-terminal Cys residue.

Such antibodies are readily available and can be obtained from Neil Cashman at the Brain Research Centre, UBC Hospital, 2211 Wesbrook Mall, Vancouver, British Columbia, V6T 2B5, Canada (neil.cashman@.utoronto.ca).

Example 3

DSE2 Monoclonal Antibody Generation Method 2

Mouse monoclonal antibody generation: 4 female BALB/c mice were initially immunized by intraperitoneal injections with 25 mg of KLH coupled to peptide corresponding to DSE2 (DLGKGGNEESTKTGNAGS) (SEQ ID NO: 2), plus an N terminal cysteine for coupling to KLH by disulfide bridge formation) per mouse in Complete Freund's Adjuvant. Four subsequent boosts were administered as above, spaced at 3 week intervals, with Incomplete Freund's Adjuvant. When the serum titre had risen more than 10-fold from a pre-immune serum sample, as determined by ELISA, the 2 highest mouse responders were each boosted intravenously with 10 mg of KLH coupled peptide protein antigen, in 100 ml of sterile PBS pH 7.4. Three days later the donor mice were sacrificed and the spleen cells were harvested and pooled. Fusion of the splenocytes with SP2/0 BALB/c parental myeloma cells was performed as previously described (see example 1 above) except that one-step selection and cloning of the hybridomas was performed in Clone EZ medium. This semi-solid medium allows HAT selection and cloning in a single step and eliminates the overgrowth of slower growing desirable clones by faster growing, perhaps undesirable, hybridomas. Clones were picked 11 days post fusion and resuspended in wells of 96-well tissue culture plates in: 200 µl of D-MEM (Invitrogen) medium containing 20% fetal bovine serum. After 4 days, the supernatants were screened by indirect ELISA for antibody activity on plates coated with 1 µg/well of peptide coupled to BSA.

ELISA Conditions:

For screening and testing: DSE-2-BSA antigen was coated onto plate in $dH_2O$ at 1 µg/well and dried down overnight at 37° C.

For testing on negative control antigen: 0.5 µg/well HT (human transferrin) antigen coated onto plate in $dH_2O$ at 50 µL/well and dried down overnight at 37° C.

Blocking: Plates blocked with 3% skim milk powder in PBS (pH 7.4) at 100 µL/well and incubated for 1 hour at room temperature.

1° antibody: Mouse anti-DSE-2 hybridoma tissue culture supernatant and mouse monoclonal controls added at 100 µL neat per well for screening and testing and were incubated for 1 hour at room temperature with shaking.

2° antibody used for screening and testing: 1/10000 Goat anti-mouse IgG Fc HRP conjugated used was used diluted in PBS-Tween (pH 7.4), added at 100 µL/well and incubated for 1 hour at 37° C. with shaking.

Substrate: TMB buffer (BioFx cat#TMBW-1000-01) was added at 50 µL per well and incubated in the dark at room temperature. The reaction was stopped with 50 µL 1M HCl per well after 15 minutes and read at $OD_{450}$ nm.

Table 3 shows the ELISA screening of hybridoma clones for antibodies directed against the disease-specific epitope DLGKGGNEESTKTGNAGS (SEQ ID NO: 2), (DSE2). The antibodies generated by several of the hybridoma clones were highly specific for peptides corresponding to the disease specific eptiope, and did not detectably recognize the control antigen HT (human transferrin). These results show that monoclonal antibodies can be produced against peptides corresponding to epitopes identified as selectively presented or accessible on misfolded forms of SOD1.

TABLE 3

ELISA Screening of Hybridoma Clones for Antibodies Directed to DLGKGGNEESTKTGNAGS (SEQ ID NO: 2), (DSE2)

| Clone | Exp #1 DSE-2-BSA Antigen | Exp #2 DSE-2-BSA Antigen | HT Antigen | Isotype |
|---|---|---|---|---|
| 2A11 | 2.624 | 2.000 | 0.086 | IgG |
| 3H1 | 1.982 | 1.908 | 0.081 | IgG |
| 5G5 | 2.712 | 2.014 | 0.068 | IgG |
| 5G12 | 2.072 | 1.755 | 0.064 | IgG |
| 6C3 | 2.527 | 1.889 | 0.071 | IgG |
| 6G12 | 2.093 | 1.982 | 0.069 | IgG |
| 7E10 | 2.586 | 2.047 | 0.068 | IgG |
| 7F8 | 2.317 | 1.961 | 0.079 | IgG |
| 8C9 | 2.087 | 1.929 | 0.072 | IgG |
| 8D1 | 2.238 | 1.931 | 0.067 | IgG |
| 10C12 | 3.032 | 1.909 | 0.061 | IgG |
| 10F2 | 2.599 | 1.699 | 0.059 | IgG |

Hybridoma clone 3H1 (Accession number 220207-02) was deposited with the International Depository Authority of Canada located in Winnipeg, Canada on Feb. 22, 2007.

Example 4

DSE1 Polyclonal Antibodies

Antibody Generation and Purification

Peptide synthesis was carried out using standard Fmoc-based chemistry on a Perseptives Biosystems 9050 Plus Pep-synthesizer. The multiple antigenic peptide was synthesized on a [Fmoc-Lys(Fmoc)]$_4$-Lys$_2$-Lys-Cys(Acm)-b-Ala-Wang resin (Advanced ChemTech, SM5104, Louisville, Ky.) using Fmoc-protected amino acids (Advanced ChemTech; Novabiochem, San Diego, Calif.; Applied Biosystems, Foster City, Calif.). The sequence was Acetyl-GGRLACGVIGIGGKG- (SEQ ID NO: 34); composition and sequence were verified by amino acid analysis and peptide synthesizer on-line UV-absorbance analysis. This peptide was cleaved and purified by dialysis versus 10 mM Tris, 10 mM sodium acetate (Sigma); dialysis was carried out at pH 8.0 to allow disulfide bond formation between adjacent strands of the peptide dendrimer. The MAP antigen had a molecular weight of ~11 kDa and was used without conjugation to a carrier protein. The antigen was sent to Sigma-Genosys (Oakville, Ontario, Canada) for rabbit antiserum production (manufacturer's 'partial package'). Antiserum production followed standard protocol (Sigma-Genosys) and was in accordance with the Animal Welfare Act (USA).

A linear peptide with identical sequence to the antigen was synthesized on a [non-cleavable] TentaGel-SH resin (Advanced ChemTech). This resin was deprotected and packed into disposable columns (Evergreen Scientific, Los Angeles, Calif.) for antiserum purification. Anti-serum was pre-cleared by centrifugation (16,000×g) and diluted 1:10 in tris-buffered saline (TBS) prior to purification. Dilute anti-serum was re-circulated over the affinity purification column 3× at a flow rate of ~1 ml/min at room temperature for binding. The antibody-bound column was washed with a minimum of 100 ml of TBS (~1 ml/min), until the wash eluent had no protein ($A_{280}$=0). Antibody fractions were eluted with 50 mM glycine, pH 2.8 into ⅕ volume ice-cold 1.5M Tris, 150 mM NaCl, pH 8.0, mixed and immediately placed on ice. These fractions were centrifuged 16,000×g and the concentration of the antibody in the supernatant was determined using an $\epsilon_{280}$=220,000 and an IgG molecular weight of 150,000 Da. Purification column was regenerated by excess washing with 50 mM glycine, pH 2.8, followed by treatment with saturated guanidine-HCl, 50 mM Tris, pH 8.0. Column was equilibrated with TBS prior to application of anti-serum. Only serum from the third bleed or later was used. In all cases, antibody was purified immediately prior to use and stored with 2 mg/ml BSA to stabilize the antibody.

SDS-PAGE and Western Blotting

SDS-PAGE was performed using the Tris-Glycine buffer system with pre-cast 4-20% poly-acrylamide gradient gels (Invitrogen, Carlsbad, Calif.). For partially denaturing gels human erythrocyte SOD1 (Sigma) was either boiled for 15 minutes with 4% beta-mercaptoethanol (Aldrich) in SDS-loading buffer or kept on ice for 15 minutes in SDS-loading buffer. 1-5 µg of SOD1 was run in each lane with equivalent results For Western blotting, gels were transferred onto PVDF membrane, blocked overnight in 5% milk-TBST (tris buffered saline, 0.05% Tween-20). 0.2 µg/ml (note: up to at least 5 µg/ml yielded equivalent results) SEDI SOD antibody (anti-DSE1 polyclonal) diluted in 5% milk-TBST was used as the primary antibody, and 1:5000 dilution of anti-rabbit IgG-HRP (Stressgen, Victoria, Canada) was used as the secondary antibody. Western blots were developed using ECL-Plus (Amersham, Buckinghamshire, UK) and visualized on Kodak film. For peptide competition experiments), diluted SEDI SOD antibody was pre-incubated with a 500× (molar) excess of free linear peptide with the same sequence as the antigen at 4° C. overnight or 1 hr. at room temperature prior to use.

Results

Antibody Design and Validation

Investigating protein conformation in vivo is a challenging problem. One possible strategy is to design an antibody that will recognize specific misfolded conformations but not the native protein. This hypothesis-driven approach has been previously applied to other neurodegenerative disorders involving protein aggregation, but these designs have relied on low resolution biophysical information on the structure of the misfolded protein. The inventors' approach employs the use of detailed X-ray crystal structure data to design an antibody against misfolded SOD1 (6, 71) It was hypothesized that an antibody that recognizes an epitope inaccessible in native dimeric SOD1 but exposed in SOD1 aggregates and aggregation intermediates, would be capable of selectively detecting misfolded SOD1 in vivo. Examination of the X-ray structure of the native SOD1 dimer (pdb code: 1SPD) (72) shows that residues 145-151 (ACGVIGI) are sequestered in the SOD1 dimer interface and are inaccessible in native SOD1. An antibody raised against this epitope is hypothesized to recognize misfolded forms of SOD1 where the native dimer interface is disrupted and exposed, such as in monomers and non-native oligomers. Accordingly, the inventors have named this the SOD1-dimer interface antibody (SEDI antibody, also referred to as anti-DSE1 polyclonal antibody). The inventors synthesized a multiple antigenic peptide where each branch of the dendrimer had the sequence ggRLACGVIGIggkg (SEQ ID NO: 34); the capitalized sequence is part of the SOD1 sequence (residues 143-151). SOD1 residues 143 and 144 were added to the antigenic peptide to increase its solubility; the N-terminal and C-terminal Gly/Lys linkers were added to contextualize the epitope to an internal sequence, increase solubility, and increase molecular weight for enhanced immunogenicity. Rabbit anti-serum produced from immunization with this antigen was affinity purified using an immobilized linear peptide with identical sequence to the antigen. Western blots were performed to examine whether the antibody could discriminate between dimeric SOD1 and monomeric SOD1 with the selected epitope exposed. Native SOD1 is sufficiently stable that under non-reducing conditions SOD1 runs primarily as a dimer in SDS-PAGE. When reduced under denaturing conditions, it runs predominantly as the monomer, but with some dimer still detectable. In these gels, the SEDI antibody reacts only with monomeric SOD1 and not with native dimeric SOD1 This antibody will thus react with SOD1 conformers where the selected epitope is exposed, but not with native SOD1. This contrasts with commercially available SOD1 antibodies that detect both native and misfolded SOD1 indiscriminately. Competition with the antigenic peptide confirmed the specificity of the antibody. The SEDI antibody thus satisfies the design criteria and provides a selectively presented or accessible inol for testing the in vivo hypotheses.

Example 5

DSE1 Monoclonal Antibody Generation

Mouse monoclonal antibody generation: 4 female BALB/c mice were initially immunized by intraperitoneal injections with 25 µg of protein antigen per mouse in Complete Freund's Adjuvant. Four subsequent boosts were administered as above, spaced at 3 week intervals, with Incomplete Freund's Adjuvant. When the serum titre has risen more than 10-fold from a pre-immune serum sample, as determined by ELISA, the 2 highest responders are each boosted intravenously with 10 µg of protein antigen, in 100 µl of sterile PBS pH 7.4. Three days later the donor mice are sacrificed and the spleen cells are harvested and pooled. Fusion of the splenocytes with SP2/0 BALB/c parental myeloma cells is performed as previously described in example 1 above, except that one-step selection and cloning of the hybridomas is performed in Clone EZ medium. This semi-solid medium allows HAT selection and cloning in a single step and eliminates the overgrowth of slower growing desirable clones by faster growing, perhaps undesirable, hybridomas. Clones are picked 11 days post fusion and are resuspended in wells of 96-well tissue culture plates in: 200 µl of D-MEM (Invitrogen) medium containing 20% fetal bovine serum. After 4 days, the supernatants are screened by indirect ELISA for antibody activity on plates coated with 1 µg/well of protein antigen.

ELISA Conditions:

For screening and testing: DSE-1-BSA antigen is coated onto plate in dH$_2$O at 1 µg/well and dried down overnight at 37° C.

For testing on negative control antigen: 0.5 µg/well HT (human transferrin) antigen is coated onto plate in dH$_2$O at 50 µL/well and dried down overnight at 37° C.

Blocking: Plates are blocked with 3% skim milk powder in PBS (pH 7.4) at 100 µL/well and are incubated for 1 hour at room temperature.

1° antibody: Mouse anti-DSE-1 hybridoma tissue culture supernatant and mouse monoclonal controls are added at 100 µL neat per well for screening and testing. Mouse anti-DSE-1a immune serum and mouse pre-immune serum diluted 1/800 in SP2/0 tissue culture supernatant are added at 100 L/well and incubated for 1 hour at room temperature with shaking.

2° antibody used for screening and testing: 1/10000 Goat anti-mouse IgG Fc HRP conjugated is used. Secondary antibody is diluted in PBS-Tween (pH 7.4), added at 100 µL/well and incubated for 1 hour at 37° C. with shaking.

Substrate: TMB buffer (BioFx cat#TMBW-1000-01) is added at 50 µL per well and incubated in the dark at room temperature. Reaction is stopped with 50 µL 1M HCl per well after 15 minutes and read at OD$_{450}$ nm.

Example 6

DSE1a Antibody Production

The isolated peptide corresponding to the DSE1a epitope (GGGRLAC*GVIGIGSG) (SEQ ID NO: 65) was conjugated to KLH for immunization of BALB/c mice, and to BSA for ELISA screening.

Mouse monoclonal antibody generation: 4 female BALB/c mice were initially immunized by intraperitoneal injections with 25 µg of protein antigen per mouse in Complete Freund's Adjuvant. Four subsequent boosts were administered as above, spaced at 3 week intervals, with Incomplete Freund's Adjuvant. When the serum titre had risen more than 10-fold from a pre-immune serum sample, as determined by ELISA, the 2 highest responders were each boosted intravenously with 10 µg of protein antigen, in 100 µl of sterile PBS pH 7.4. Three days later the donor mice were sacrificed and the spleen cells were harvested and pooled. Fusion of the splenocytes with SP2/0 BALB/c parental myeloma cells was performed as previously described in example 1 above except that onestep selection and cloning of the hybridomas was performed in Clone EZ medium. This semi-solid medium allows HAT selection and cloning in a single step and eliminates the overgrowth of slower growing desirable clones by faster growing, perhaps undesirable, hybridomas. Clones were picked 11 days post fusion and resuspended in wells of 96-well tissue culture plates in: 200 µl of D-MEM (Invitrogen) medium containing 20% fetal bovine serum. After 4 days, the supernatants were screened by indirect ELISA for antibody activity on plates coated with 1 µg/well of protein antigen.

ELISA Conditions:

For screening and testing: DSE-1a-BSA antigen was coated onto plate in dH$_2$O at 1 µg/well and dried down overnight at 37° C.

For testing on negative control antigen: 0.5 µg/well HT (human transferrin) antigen was coated onto plate in dH$_2$O at 50 µL/well and dried down overnight at 37° C.

Blocking: Plates were blocked with 3% skim milk powder in PBS (pH 7.4) at 100 µL/well and incubated for 1 hour at room temperature.

1° antibody: Mouse anti-DSE-1a hybridoma tissue culture supernatant and mouse monoclonal controls were added at 100 µL neat per well for screening and testing. Mouse anti-DSE-1a immune serum and mouse pre-immune serum diluted 1/800 in SP2/0 tissue culture supernatant were added at 100 µL/well and incubated for 1 hour at room temperature with shaking.

2° antibody used for screening and testing: 1/10000 Goat anti-mouse IgG Fc HRP conjugated was used. Secondary antibody was diluted in PBS-Tween (pH 7.4), added at 100 µL/well and incubated for 1 hour at 37° C. with shaking.

Substrate: TMB buffer (BioFx cat#TMBW-1000-01) added at 50 µL per well and incubated in the dark at room temperature. The reaction stopped with 50 µL 1M HCl per well after 15 minutes and read at $OD_{450}$ nm.

Table 4 shows the ELISA screening of hybridoma clones for antibodies directed against the peptide corresponding to the disease-specific epitope GGGRLAC*GVIGIGSG (SEQ ID NO: 65), (DSE1a). The antibodies generated by the hybridoma clones were highly specific for the disease specific eptiope, and did not detectably recognize the control antigen HT (human transferrin). These results show that monoclonal antibodies can be produced against peptides corresponding to epitopes identified as presented or accessible on misfolded forms of SOD1.

TABLE 4

ELISA Screening of Hybridoma Clones for Antibodies directed against epitope GGGRLAC*GVIGIGSG (DSE1a)

| Clone | Exp #1 DSE-1a-BSA Antigen | Exp #2 DSE-1a-BSA Antigen | HT Antigen | Isotype |
|---|---|---|---|---|
| 3C1 | 0.484 | 0.265 | 0.105 | IgG |
| 3C11 | 0.702 | 0.186 | 0.093 | IgG |
| 3D2 | 1.542 | 1.035 | 0.058 | IgG |
| 3F1 | 3.072 | 2.143 | 0.080 | IgG |
| 4B5 | 0.506 | 0.238 | 0.065 | IgG |
| 4H6 | 1.244 | 0.957 | 0.085 | IgG |
| 5F6 | 0.862 | 0.663 | 0.089 | IgG |
| 6D8 | 2.690 | 2.186 | 0.089 | IgG |
| 9A4 | 2.538 | 2.313 | 0.071 | IgG |
| 9A8 | 1.489 | 0.884 | 0.100 | IgG |
| 10C3 | 2.446 | 2.200 | 0.067 | IgG |
| 10C12 | 2.867 | 2.016 | 0.089 | IgG |

Hybridoma clone 6D8 (Accession number 220207-01) was deposited with the International Depository Authority of Canada located in Winnipeg, Canada on Feb. 22, 2007.

Antibodies are generated against DSE 4, 6 and 7 using similar techniques.

Example 7

Antibodies Directed Against DSE1a do not Recognize the DSE1 Peptide

The ability of anti-DSE1a antibody to recognize its cognate peptide sequence (DSE1a) was compared to anti-DSE1a antibody's ability to recognize the non-oxidized peptide (DSE1).

Microtiter plate wells were coated with DSE1 peptide or with DSE1a peptide coupled to BSA. After free binding sites in each was were blocked with BSA, antibody containing tissue culture supernatants from the DSE1a hybridoma clones was added, and antibody allowed to bind to the BSA coupled peptides. Bound antibody was then detected with a peroxidase coupled secondary antibody. FIG. 1 and Table 5 show that all tested antibodies recognize preferentially DSE1a over DSE1.

When mice were immunized with DSE1 peptide, mostly IgM isotype antibody were formed. An IgM antibody likely has a lower affinity for the epitope than the DSE1a antibodies raised as noted above, which are of the IgG isotype. The modification of DSE1 to comprise an oxidized cysteine resulted in the production of antibodies with operationally greater avidity.

TABLE 5

ELISA Showing Anti-DSE1a Antibody Clones Preferentially Recognize Oxidized DSE1a Peptide

| Clone | Peptide DSE1a | Peptide DSE1 |
|---|---|---|
| 3C1 | 1.141 | 0.243 |
|  | 1.405 | 0.234 |
| Average | 1.273 | 0.2385 |
| Rel Dev | 14.66% | 2.67% |
| 3C11 | 1.165 | 0.197 |
|  | 0.732 | 0.216 |
| Average | 0.9485 | 0.2065 |
| Rel Dev | 32.28% | 6.51% |
| 3D2 | 1.073 | 0.219 |
|  | 0.93 | 0.209 |
| Average | 1.0015 | 0.214 |
| Rel Dev | 10.10% | 3.30% |
| 3D9 | 0.195 | 0.223 |
|  | 0.164 | 0.195 |
| Average | 0.1795 | 0.209 |
| Rel Dev | 12.21% | 9.47% |
| 3F1 | 2.948 | 0.247 |
|  | 3.005 | 0.269 |
| Average | 2.9765 | 0.258 |
| Rel Dev | 1.35% | 6.03% |
| 4B5 | 0.671 | 0.185 |
|  | 0.481 | 0.169 |
| Average | 0.576 | 0.177 |
| Rel Dev | 23.32% | 6.39% |
| 4H6 | 0.674 | 0.233 |
|  | 0.685 | 0.29 |
| Average | 0.6795 | 0.2615 |
| Rel Dev | 1.14% | 15.41% |
| 6D8 | 2.303 | 0.366 |
|  | 2.168 | 0.242 |
| Average | 2.2355 | 0.304 |
| Rel Dev | 4.27% | 28.84% |
| 9A4 | 1.006 | 0.203 |
|  | 0.687 | 0.343 |
| Average | 0.8465 | 0.273 |
| Rel Dev | 26.65% | 36.26% |
| 9A8 | 2.101 | 0.21 |
|  | 2.194 | 0.276 |
| Average | 2.1475 | 0.243 |
| Rel Dev | 3.06% | 19.21% |
| 10C3 | 2.227 | 0.233 |
|  | 2.087 | 0.22 |
| Average | 2.157 | 0.2265 |
| Rel Dev | 4.59% | 4.06% |
| PBST | 0.199 | 0.192 |
|  | 0.194 | 0.166 |
| Average | 0.1965 | 0.179 |
| Rel Dev | 1.80% | 10.27% |

Example 8

DSE5 Antibody Production

Mouse monoclonal antibody generation: 4 female BALB/c mice were initially immunized by intraperitoneal injections with 25 mg of immunogen comprising peptide (IKGLTEGL-HGF) (SEQ ID NO: 5) corresponding to DSE5 coupled to KLH by disulfide formation with a cysteine that was added to the N per mouse in Complete Freund's Adjuvant. Four subsequent boosts were administered as above, spaced at 3 week intervals, with Incomplete Freund's Adjuvant. When the serum titre had risen more than 10-fold from a pre-immune serum sample, as determined by ELISA, the 2 highest responders were each boosted intravenously with 10 mg of protein antigen, in 100 ml of sterile PBS pH 7.4. Three days later the donor mice were sacrificed and the spleen cells were harvested and pooled. Fusion of the splenocytes with SP2/0 BALB/c parental myeloma cells was performed as previously described as in example one above except that one-step selection and cloning of the hybridomas was performed in Clone EZ medium. This semi-solid medium allows HAT selection and cloning in a single step and eliminates the overgrowth of slower growing desirable clones by faster growing, perhaps undesirable, hybridomas. Clones were picked 11 days post fusion and resuspended in wells of 96-well tissue culture plates in: 200 µl of D-MEM (Invitrogen) medium containing 20% fetal bovine serum. After 4 days, the supernatants were screened by indirect ELISA for antibody activity on plates coated with 1 µg/well of protein antigen.

ELISA Conditions:

For screening and testing: DSE5-BSA antigen was coated onto plate in dH$_2$O at 1 µg/well and dried down overnight at 37° C.

For testing on negative control antigen: 0.5 µg/well HT (human transferrin) antigen coated onto plate in dH$_2$O at 50 µL/well and dried down overnight at 37° C.

Blocking: Plates were blocked with 3% skim milk powder in PBS (pH 7.4) at 100 µL/well and incubated for 1 hour at room temperature.

1° antibody: Mouse anti-DSE5 hybridoma tissue culture supernatant and mouse monoclonal controls were added at 100 µL neat per well for screening and testing. Mouse anti-DSE-1a immune serum and mouse pre-immune serum diluted 1/800 in SP2/0 tissue culture supernatant were added at 100 µL/well and incubated for 1 hour at room temperature with shaking.

2° antibody used for screening and testing: 1/10000 Goat anti-mouse IgG Fc HRP conjugated was used. Secondary antibody was diluted in PBS-Tween (pH 7.4), added at 100 µL/well and incubated for 1 hour at 37° C. with shaking.

Substrate: TMB buffer (BioFx cat#TMBW-1000-01) was added at 50 µL per well and incubated in the dark at room temperature. The reaction stopped with 50 µL 1M HCl per well after 15 minutes and read at OD$_{450}$ nm.

Table 6 shows the ELISA screening of hybridoma clones for antibodies directed against the disease-specific epitope (IKGLTEGLHGF) (SEQ ID NO: 5). The antibodies generated by several of the hybridoma clones were highly specific for the peptide corresponding to the eptiope, and did not detectably recognize the control antigen HT (human transferrin). These results show that monoclonal antibodies can be produced against peptides corresponding to epitopes identified as selectlively presented or accessible on misfolded forms of SOD1.

TABLE 6

ELISA screening of hybridoma clones for antibodies directed against epitope IKGLTEGLHGF (SEQ ID NO: 5), (DSE5)

| Clone | Exp #1 DSE-5-BSA Antigen | Exp #2 DSE-5-BSA Antigen | HT Antigen | Isotype |
|---|---|---|---|---|
| 5C6 | 2.779 | 1.787 | 0.079 | IgG |

Hybridoma clone 5C6 (accession number 280707-01) was deposited with the International Depository Authority of Canada, National Microbiology Laboratory, Public Health Agency of Canada, Canadian Science Centre for Human and Animal Health, 1015 Arlington Street, Winnipeg, MB, R3E 3R2, Canada on Feb. 28, 2007.

Example 9

Antibody Production to Disease Specific Epitopes (DSEs) and/or DSE Antigenic Determinants An epitope selectively presented or accessible in non-native forms of SOD1 is conjugated to KLH for immunization of BALB/c mice to generate B cells reactive to the epitope. The epitope for immunization is selected from the group of peptides consisting of: GGGRLACGVIGIGSG (SEQ ID NO: 66), (DSE1 analog); GGGRLAC*GVIGIGSG (SEQ ID NO: 65), (DSE1a); CDLGKGGNEESTKTGNAGS (SEQ ID NO: 11), (DSE2); CNPLSRKHGGPKDEE (SEQ ID NO: 12), (DSE3); CIKGLTEGLHGF (SEQ ID NO: 14), (DSE5); GSGKAVCVLK (SEQ ID NO: 67), (DSE4); and CGLHGF-HVH (SEQ ID NO: 68) (DSE7). Alternatively a portion of any of the aforementioned peptides comprising one or more antigenic determinants is conjugated to KLH, minimally comprising 3 or 5 contiguous amino acids of any of the peptide sequence that is immunogenic either alone or when coupled to KLH.

Mouse monoclonal antibody generation: 4 female BALB/c mice are initially immunized by intraperitoneal injections with 25 µg of protein antigen per mouse in Complete Freund's Adjuvant. Four subsequent boosts are administered as above, spaced at 3 week intervals, with Incomplete Freund's Adjuvant. When the serum titre has risen more than 10-fold from a pre-immune serum sample, as determined by ELISA, the 2 highest responders are each boosted intravenously with 10 µg of protein antigen, in 100 µl of sterile PBS pH 7.4. Three days later the donor mice are sacrificed and the spleen cells are harvested and pooled. Fusion of the splenocytes with SP2/0 BALB/c parental myeloma cells is performed as previously described as in example 1 above that one-step selection and cloning of the hybridomas is performed in Clone EZ medium. This semi-solid medium allows HAT selection and cloning in a single step and eliminates the overgrowth of slower growing desirable clones by faster growing, perhaps undesirable, hybridomas. Clones are picked 11 days post fusion and are resuspended in wells of 96-well tissue culture plates in: 200 µl of D-MEM (Invitrogen) medium containing 20% fetal bovine serum. After 4 days, the supernatants are screened by indirect ELISA for antibody activity on plates coated with 1 µg/well of protein antigen.

ELISA Conditions:

For screening and testing: DSE-BSA antigen is coated onto plate in dH$_2$O at 1 µg/well and dried down overnight at 37° C.

For testing on negative control antigen: 0.5 µg/well HT (human transferrin) antigen is coated onto plate in dH$_2$O at 50 µL/well and dried down overnight at 37° C.

Blocking: Plates are blocked with 3% skim milk powder in PBS (pH 7.4) at 100 µL/well and are incubated for 1 hour at room temperature.

1° antibody: Mouse anti-DSE hybridoma tissue culture supernatant and mouse monoclonal controls are added at 100 µL neat per well for screening and testing. Mouse anti-DSE-1a immune serum and mouse pre-immune serum diluted 1/800 in SP2/0 tissue culture supernatant are added at 100 L/well and incubated for 1 hour at room temperature with shaking. 2° antibody used for screening and testing: 1/10000 Goat anti-mouse IgG Fc HRP conjugated is used. Secondary antibody is diluted in PBS-Tween (pH 7.4), added at 100 µL/well and incubated for 1 hour at 37° C. with shaking.

Substrate: TMB buffer (BioFx cat#TMBW-1000-01) is added at 50 µL per well and incubated in the dark at room temperature. The reaction is stopped with 50 µL 1M HCl per well after 15 minutes and read at $OD_{450}$ nm.

specific affinity of the antibody for the natively folded SOD1 (i.e. the affinity of the antibody for SOD1 minus the non-specific binding to the irrelevant protein BSA). Column 11 represents the specific affinity of the antibody for the unfolded SOD1 (i.e. the affinity of the antibody for SOD1 minus the non-specific binding for BSA). Column 12 provides the fold increase of the specific affinity for misfolded SOD1 over natively folded SOD1. These results demonstrate the specific affinity of monoclonal antibodies directed against DSE1a epitope for SOD1 and that the antibodies preferentially target misfolded forms of SOD1 with 2-4 fold higher affinity than for the natively folded form.

Clones 4H6, 6D8, 10C3 were selected for large scale production.

TABLE 7

ELISA testing of DSE1a hybridoma clones to denatured SOD1.

| 1 Clone | 2 SOD1 PBS | 3 GdnHCl | 4 BSA PBS | 5 GdnHCl | 6 SOD1 PBS | 7 GdnHCl | 8 BSA PBS | 9 GdnHCl | 10 S-N (F) | 11 S-N (U) | 12 U/F |
|---|---|---|---|---|---|---|---|---|---|---|---|
| 3C1 | 0.423 | 0.712 | 0.144 | 0.170 | 0.417 | 0.662 | 0.145 | 0.178 | 0.256 | 0.501 | 1.961 |
|  | 0.410 | 0.612 | 0.145 | 0.185 | 2% | 11% | 0% | 6% |  |  |  |
| 3C11 | 0.352 | 0.693 | 0.153 | 0.155 | 0.355 | 0.668 | 0.154 | 0.150 | 0.203 | 0.516 | 2.544 |
|  | 0.357 | 0.642 | 0.155 | 0.144 | 1% | 5% | 1% | 5% |  |  |  |
| 3D2 | 0.364 | 0.727 | 0.134 | 0.130 | 0.357 | 0.690 | 0.127 | 0.125 | 0.231 | 0.564 | 2.442 |
|  | 0.349 | 0.652 | 0.119 | 0.119 | 3% | 8% | 8% | 6% |  |  |  |
| 3D9 | 0.304 | 0.661 | 0.121 | 0.124 | 0.314 | 0.674 | 0.137 | 0.115 | 0.188 | 0.548 | 2.920 |
|  | 0.323 | 0.687 | 0.152 | 0.106 | 4% | 3% | 16% | 11% |  |  |  |
| 3F1 | 0.354 | 0.585 | 0.140 | 0.146 | 0.327 | 0.577 | 0.133 | 0.131 | 0.195 | 0.445 | 2.284 |
|  | 0.299 | 0.568 | 0.125 | 0.116 | 12% | 2% | 8% | 16% |  |  |  |
| 4B5 | 0.352 | 0.643 | 0.145 | 0.140 | 0.338 | 0.637 | 0.137 | 0.137 | 0.201 | 0.500 | 2.491 |
|  | 0.323 | 0.630 | 0.129 | 0.134 | 6% | 1% | 8% | 3% |  |  |  |
| 4H6 | 0.334 | 0.615 | 0.156 | 0.122 | 0.332 | 0.626 | 0.135 | 0.122 | 0.203 | 0.498 | 2.451 |
|  | 0.329 | 0.637 | 0.114 | 0.122 | 1% | 2% | 22% | 0% |  |  |  |
| 6D8 | 0.380 | 0.788 | 0.148 | 0.139 | 0.385 | 0.732 | 0.145 | 0.134 | 0.246 | 0.593 | 2.413 |
|  | 0.390 | 0.676 | 0.142 | 0.129 | 2% | 11% | 3% | 5% |  |  |  |
| 9A4 | 0.305 | 0.634 | 0.144 | 0.127 | 0.302 | 0.604 | 0.133 | 0.125 | 0.173 | 0.475 | 2.740 |
|  | 0.299 | 0.573 | 0.122 | 0.122 | 1% | 7% | 12% | 3% |  |  |  |
| 9A8 | 0.253 | 0.601 | 0.150 | 0.115 | 0.259 | 0.593 | 0.139 | 0.119 | 0.130 | 0.464 | 3.578 |
|  | 0.264 | 0.585 | 0.127 | 0.123 | 3% | 2% | 12% | 5% |  |  |  |
| 10C3 | 0.284 | 0.609 | 0.153 | 0.117 | 0.282 | 0.628 | 0.229 | 0.112 | 0.112 | 0.458 | 4.085 |
|  | 0.280 | 0.646 | 0.304 | 0.106 | 1% | 4% | 47% | 7% |  |  |  |
| 10C12 | 0.326 | 0.562 | 0.121 | 0.115 | 0.313 | 0.551 | 0.121 | 0.122 | 0.191 | 0.429 | 2.244 |
|  | 0.299 | 0.539 | 0.121 | 0.128 | 6% | 3% | 0% | 8% |  |  |  |
| Bkg | 0.112 | 0.142 | 0.117 | 0.151 | 0.122 | 0.143 | 0.118 | 0.147 |  |  |  |
|  | 0.132 | 0.144 | 0.118 | 0.143 | 12% | 1% | 1% | 4% |  |  |  |

S = signal,
N = noise,
F = natively folded,
U = unfolded/misfolded

Example 10

ELISA Testing of Antibody Directed to DSE1a for Affinity to Denatured SOD1

Hybridoma clones producing antibodies directed to DSE1a (GGGRLAC*GVIGIGSG) (SEQ ID NO: 65) were screened by ELISA for specific reactivity to natively folded SOD1 (SOD1 in PBS) denatured or misfolded SOD1 (SOD1 in denaturation buffer with 6M GdnHCl), or natively folded and misfolded BSA control.

Table 7 shows the affinity of hybridoma clones to natively folded and misfolded SOD1. The absorbance of each sample was detected at 450 nm (columns 2-5). Each sample was tested in duplicate. The values in columns 6-9 provide the average values of the affinity of each clone and the % difference between the two samples. Column 10 represents the Example 11

ELISA Testing of Antibody Directed to DSE2 for Affinity to Denatured SOD1

Hybridoma clones producing antibodies directed to DSE2 (DLGKGGNEESTKTGNAGS) (SEQ ID NO: 2) were screened by ELISA for specific reactivity to natively folded SOD1 (SOD1 in PBS) denatured or misfolded SOD1 (SOD1 in denaturation buffer with 6M GdnHCl), or natively folded and misfolded BSA control.

Table 8 shows the affinity of hybridoma clones to natively folded and unfolded SOD1. The absorbance of each sample was detected at 450 nm (columns 2-5). Each sample was tested in duplicate. The values in columns 6-9 provide the average values of the affinity of each clone and the % difference between the two samples. Column 10 represents the specific affinity of the antibody for the natively folded SOD1 (i.e. the affinity of the antibody for SOD1 minus the non-specific binding to BSA). Column 11 represents the specific affinity of the antibody for the misfolded SOD1 (i.e. the affinity of the antibody for SOD1 minus the non-specific binding to BSA). Column 12 provides the fold increase of the specific affinity for misfolded SOD1 over natively folded SOD1. These results demonstrate the specific affinity of monoclonal antibodies directed against DSE2 epitope for SOD1 and that the antibodies preferentially target unfolded forms of SOD1.

Clones 3H1, 5G5 and 8D1 were selected for large scale production.

for specific reactivity to natively folded SOD1 (SOD1 in PBS) denatured or misfolded SOD1 (SOD1 in denaturation buffer GdnHCl), or natively folded and misfolded BSA control.

Table 9 shows the affinity of hybridoma clones to natively folded and misfolded SOD1. The absorbance of each sample was detected at 450 nm (columns 2-5). Each sample was tested in duplicate. The values in columns 6-9 provide the average values of the affinity of each clone and the % difference between the two samples. Column 10 represents the specific affinity of the antibody for the natively folded SOD1 (i.e. the affinity of the antibody for SOD1 minus the non-specific affinity for BSA). Column 11 represents the specific affinity of the antibody for the misfolded SOD1 (i.e. the

TABLE 8

ELISA testing of DSE2 hybridoma clones to denatured SOD1.

| 1 | 2 SOD1 PBS | 3 GdnHCl | 4 BSA PBS | 5 GdnHCl | 6 SOD1 PBS | 7 GdnHCl | 8 BSA PBS | 9 GdnHCl | 10 S-N (F) | 11 S-N (U) | 12 U/F |
|---|---|---|---|---|---|---|---|---|---|---|---|
| 2A9 | 0.321 | 0.593 | 0.125 | 0.137 | 0.316 | 0.589 | 0.116 | 0.141 | 0.187 | 0.460 | 2.460 |
|  | 0.31 | 0.584 | 0.107 | 0.145 | 2% | 1% | 11% | 4% |  |  |  |
| 2A11 | 0.345 | 0.71 | 0.119 | 0.124 | 0.347 | 0.719 | 0.114 | 0.140 | 0.220 | 0.592 | 2.693 |
|  | 0.348 | 0.727 | 0.108 | 0.156 | 1% | 2% | 7% | 16% |  |  |  |
| 3H1 | 0.257 | 2.189 | 0.161 | 0.165 | 0.410 | 2.145 | 0.156 | 0.164 | 0.251 | 1.986 | 7.926 |
|  | 0.563 | 2.101 | 0.15 | 0.162 | 53% | 3% | 5% | 1% |  |  |  |
| 5G5 | 0.308 | 1.032 | 0.22 | 0.145 | 0.307 | 0.879 | 0.171 | 0.149 | 0.147 | 0.719 | 4.881 |
|  | 0.306 | 0.725 | 0.122 | 0.152 | 0% | 25% | 41% | 3% |  |  |  |
| 5G12 | 0.346 | 0.604 | 0.124 | 0.131 | 0.309 | 0.583 | 0.135 | 0.122 | 0.181 | 0.455 | 2.516 |
|  | 0.272 | 0.562 | 0.145 | 0.113 | 17% | 5% | 11% | 10% |  |  |  |
| 6C3 | 0.325 | 0.67 | 0.129 | 0.126 | 0.317 | 0.673 | 0.126 | 0.136 | 0.187 | 0.543 | 2.909 |
|  | 0.309 | 0.676 | 0.122 | 0.145 | 4% | 1% | 4% | 10% |  |  |  |
| 6G12 | 0.29 | 0.414 | 0.125 | 0.114 | 0.293 | 0.558 | 0.112 | 0.111 | 0.181 | 0.446 | 2.462 |
|  | 0.295 | 0.701 | 0.099 | 0.107 | 1% | 36% | 16% | 4% |  |  |  |
| 7E10 | 0.34 | 0.787 | 0.199 | 0.179 | 0.331 | 0.761 | 0.171 | 0.158 | 0.166 | 0.597 | 3.589 |
|  | 0.321 | 0.735 | 0.142 | 0.137 | 4% | 5% | 24% | 19% |  |  |  |
| 7F8 | 0.366 | 0.605 | 0.131 | 0.121 | 0.327 | 0.612 | 0.135 | 0.121 | 0.199 | 0.484 | 2.430 |
|  | 0.288 | 0.619 | 0.138 | 0.121 | 17% | 2% | 4% | 0% |  |  |  |
| 8C9 | 0.354 | 0.701 | 0.131 | 0.132 | 0.347 | 0.713 | 0.122 | 0.135 | 0.218 | 0.584 | 2.679 |
|  | 0.339 | 0.724 | 0.113 | 0.138 | 3% | 2% | 10% | 3% |  |  |  |
| 8D1 | 0.516 | 1.626 | 0.185 | 0.167 | 0.465 | 1.768 | 0.173 | 0.180 | 0.288 | 1.591 | 5.520 |
|  | 0.413 | 1.909 | 0.161 | 0.192 | 16% | 11% | 10% | 10% |  |  |  |
| 10F2 | 0.263 | 0.632 | 0.119 | 0.172 | 0.413 | 0.661 | 0.118 | 0.174 | 0.268 | 0.515 | 1.925 |
|  | 0.563 | 0.689 | 0.116 | 0.175 | 51% | 6% | 2% | 1% |  |  |  |
| Bkg | 0.112 | 0.142 | 0.117 | 0.151 | 0.122 | 0.143 | 0.118 | 0.147 |  |  |  |
|  | 0.132 | 0.144 | 0.118 | 0.143 | 12% | 1% | 1% | 4% |  |  |  |

S = signal,
N = noise,
F = natively folded,
U = unfolded/misfolded

Example 12

ELISA Testing of Antibody Directed to DSE5 for Affinity to Denatured SOD1

Hyrbridoma clones producing antibodies directed to DSE5 (IKGLTEGLHGF) (SEQ ID NO: 5) were screened by ELISA affinity of the antibody for SOD1 minus the non-specific affinity for BSA). And column 12 provides the fold increase of the specific affinity for unfolded SOD1 over natively folded SOD1. These results demonstrate the specific affinity of monoclonal antibodies directed against DSE5 epitope for SOD1 and that the antibodies preferentially target misfolded forms of SOD1.

TABLE 9

ELISA testing of hybridoma clone to denatured SOD1.

| 1 | 2 SOD1 PBS | 3 GdnHCl | 4 BSA PBS | 5 GdnHCl | 6 SOD1 PBS | 7 GdnHCl | 8 BSA PBS | 9 GdnHCl | S-N (F) | S-N (U) | U/F |
|---|---|---|---|---|---|---|---|---|---|---|---|
| DSE5 | 0.272 | 0.622 | 0.122 | 0.188 | 0.279 | 0.626 | 0.113 | 0.163 | 0.141 | 0.488 | 3.457 |
|  | 0.286 | 0.629 | 0.104 | 0.138 | 4% | 1% | 11% | 22% |  |  |  |

TABLE 9-continued

| 1 | 2 SOD1 PBS | 3 GdnHCl | 4 BSA PBS | 5 GdnHCl | 6 SOD1 PBS | 7 GdnHCl | 8 BSA PBS | 9 GdnHCl | S-N (F) | S-N (U) | U/F |
|---|---|---|---|---|---|---|---|---|---|---|---|
| Bkg | 0.112 | 0.142 | 0.117 | 0.151 | 0.122 | 0.143 | 0.118 | 0.147 | | | |
| | 0.132 | 0.144 | 0.118 | 0.143 | 12% | 1% | 1% | 4% | | | |

S = signal,
N = noise,
F = natively folded,
U = unfolded/misfolded

Example 13

Recognition of Oxidized SOD1 by Antibodies Directed Against DSE2

Figure 2:
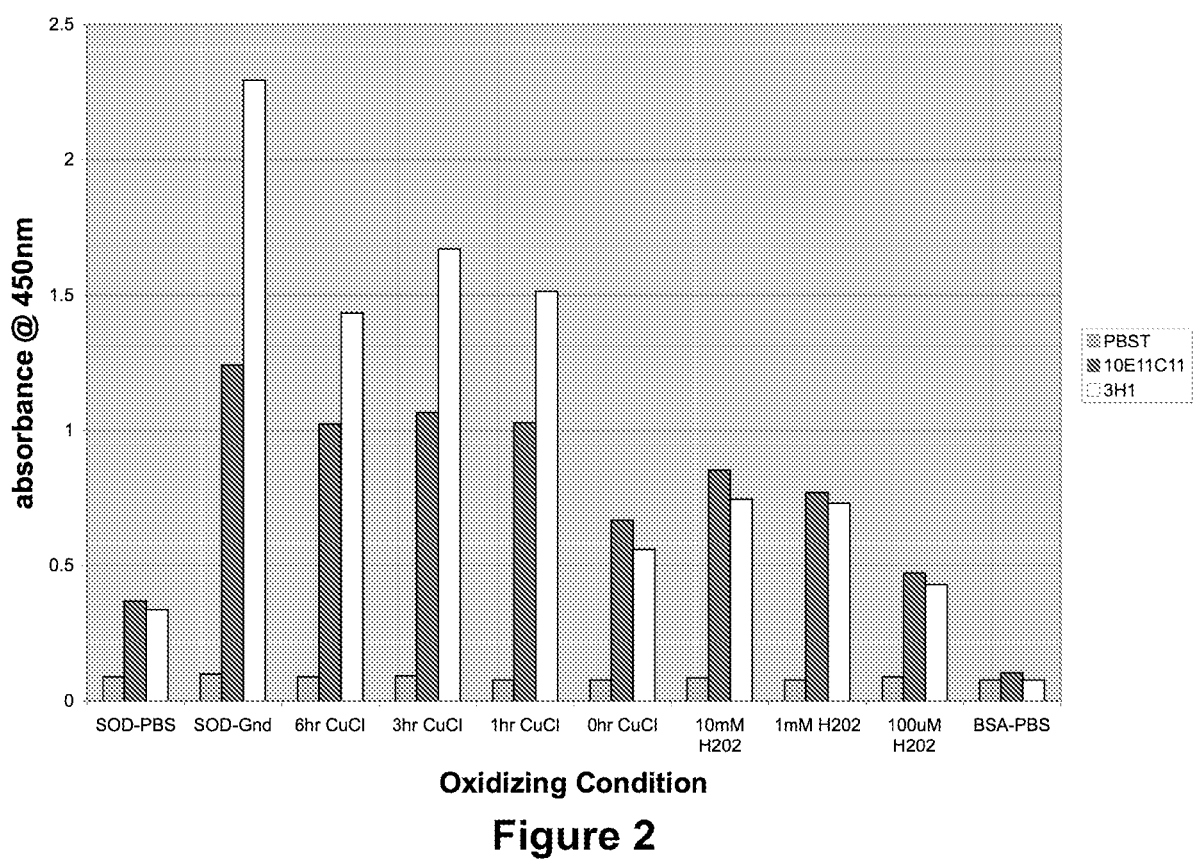
FIG. 2 is a graph illustrating ELISA data showing that anti-DSE2 antibody recognizes oxidized SOD1 protein.

Oxidative damage of enzymes occurs in neurodegenerative diseases, and oxidative damage to SOD1 results in misfolding and formation of aggregated SOD1. The inventors showed that antibodies directed against the DSE2 epitope (hybridoma clones 10E11C11 and 3H1) recognize such oxidatively modified SOD1 by incubating purified SOD1 with either 100 um to 10 mM $H_2O_2$ or with a mixture of ascorbate and copperchloride. Both of these treatments are known to oxidize amino acids in SOD1. Subsequently, we allowed this oxidized SOD1 to bind to microtiter plate wells and added one of two different anti-DSE2 antibodies. For comparison, microtiter wells were coated with untreated and normally folded SOD1 in buffer, or with SOD1 that was denatured with a solution of a chaotropic agent (guanidinium chloride, GdnHCl). As shown in FIG. 2, anti-DSE2 antibodies bind preferentially to misfolded SOD1 in GdnHCl but much less well to natively folded SOD1 in buffer. However, after oxidation, SOD1 is efficiently recognized by the anti-DSE2 antibodies. This demonstrates that anti-DSE2 (both 10E11C11 and 3H1) antibodies recognize the kind of oxidatively modified SOD1 that occurs in patients with neurodegenerative diseases. The results are presented in Table 10 below.

TABLE 10

Recognition of oxidized SOD1 by antibodies directed against DSE2

| | | Clones | | | | Clones | |
|---|---|---|---|---|---|---|---|
| Treatment | PBST | 10E11C11 | 3H1 | Treatment | PBST | 10E11C11 | 3H1 |
| SOD-PBS | 0.088 | 0.357 | 0.34 | SOD-Gnd | 0.118 | 1.243 | 2.29 |
| | 0.094 | 0.362 | 0.335 | | 0.092 | 1.254 | 2.295 |
| | 0.082 | 0.389 | | | 0.086 | 1.225 | |
| Average | 0.088 | 0.369333333 | 0.3375 | Average | 0.098666667 | 1.240666667 | 2.2925 |
| Rel St Dev | 6.82% | 4.66% | 1.05% | Rel St Dev | 17.24% | 1.18% | 0.15% |
| 6 hr CuCl | 0.082 | 1.044 | 1.379 | 3 hr CuCl | 0.087 | 1.061 | 1.717 |
| | 0.093 | 0.987 | 1.489 | | 0.101 | 1.06 | 1.621 |
| | 0.089 | 1.042 | | | 0.088 | 1.076 | |
| Average | 0.088 | 1.024333333 | 1.434 | Average | 0.092 | 1.065666667 | 1.669 |
| Rel St Dev | 6.33% | 3.16% | 5.42% | Rel St Dev | 8.49% | 0.84% | 4.07% |
| 1 hr CuCl | 0.075 | 1.023 | 1.592 | 0 hr CuCl | 0.073 | 0.67 | 0.527 |
| | 0.083 | 1.035 | 1.435 | | 0.087 | 0.669 | 0.59 |
| | 0.072 | 1.026 | | | 0.071 | 0.664 | |
| Average | 0.076666667 | 1.028 | 1.5135 | Average | 0.077 | 0.667666667 | 0.5585 |
| Rel St Dev | 7.42% | 0.61% | 7.34% | Rel St Dev | 11.32% | 0.48% | 7.98% |
| BSA-PBS | 0.073 | 0.12 | 0.078 | 10 uM H202 | 0.071 | 0.489 | 0.436 |
| | 0.083 | 0.098 | 0.076 | | 0.086 | 0.476 | 0.425 |
| | 0.073 | 0.091 | | | 0.107 | 0.453 | |
| Average | 0.076333333 | 0.103 | 0.077 | Average | 0.088 | 0.472666667 | 0.4305 |
| 1 mM h202 | 0.074 | 0.776 | 0.744 | 10 mM H202 | 0.078 | 0.836 | 0.763 |
| | 0.081 | 0.752 | 0.717 | | 0.092 | 0.84 | 0.726 |
| | 0.074 | 0.781 | | | 0.083 | 0.878 | |
| Average | 0.076333333 | 0.769666667 | 0.7305 | Average | 0.084333333 | 0.851333333 | 0.7445 |
| Rel St Dev | 5.29% | 2.01% | 2.61% | Rel St Dev | 8.41% | 2.72% | 3.51% |

Example 14

Epitope Mapping a) ALS-Specific Epitope Prediction, Synthesis, and Refinement Epitopes presented by misfolded SOD1 and not presented by native SOD1 may be determined by analyzing the structure of native SOD1 for sequence regions that are hidden by the normally folded native conformation of SOD1. For example, the DSE2 and DSE3 loops are inaccessible to antibody binding in the native structure of SOD1, but were shown to be extruded from the SOD1 active site in amyloid fibril and nanotube structures (84). Thus, exposure of these loops may be a marker of SOD1 misfolding, but they may also constitute "recruitment domains" of SOD1 that are involved in template directed misfolding of SOD1. The inventors identified DSE1, DSE4 and DSE 7 as putatively hidden sequences that could become accessible upon SOD1 misfolding.

Epitopes presented by misfolded SOD1 and not presented by native SOD1 may be predicted by analyzing sequence regions that have constrained structure. Constrained structures are less able to accommodate any changes in folding resulting in conformational changes in the sequence region and the presentation of accessible epitopes not present in the constrained structure. Epitopes DSE2, 3, 5, and 6 were predicted on this basis.

Peptide targets for misfolded aggregated SOD1 provide immunogens for the development of mouse monoclonal antibodies for biochemical characterization of epitope exposure were synthesized and characterized.

These targets include the sequence:

| | | |
|---|---|---|
| RLACGVIGI | (SEQ ID NO: 1), | (DSE1); |
| DLGKGGNEESTKTGNAGS | (SEQ ID NO: 2), | (DSE2; |
| NPLSRKHGGPKDEE | (SEQ ID NO: 3), | (DSE3); |
| IKGLTEGLHGF | (SEQ ID NO: 5), | (DSE5); |
| HCIIGRTLVVH | (SEQ ID NO: 6), | (DSE6); |
| GSGKAVCVLK and | (SEQ ID NO: 67), | (DSE4); |
| CGLHGFHVH | (SEQ ID NO: 68), | (DSE7). |

DSE peptides were synthesized and conjugated to KLH (keyhole limpet hemocyanin). DSE peptides having an endogenous cysteine (DSE1, DSE1a, DSE4 and DSE6) were conjugated with KLH using the DMS method (Pierce reagent and method) for amino conjugation. DSE peptides not having an endogenous cysteine residue (DSE2, DSE3, DSE5 and DSE7) were conjugated with KLH using the sulfo-MBS method (Pierce reagent and method) for thiol group conjugation.

A "control" epitope exposed on the molecular surface of native normal SOD1 is optionally synthesized and characterized. A control epitope is optionally an epitope that is presented on both natively folded and misfolded SOD1.

The epitopes identified may have multiple antigenic determinants. Epitopes are further analysed to determine subportions of the peptides (e.g. discrete epitopes) that are immunogenic. Immunogenicity analysis of SOD1 including antigenicity plotting is used to identify discrete epitopes, isolated peptides corresponding to these discrete epitopes are synthesized and an immunogen comprising the isolated peptide corresponding to one or more of these discrete epitopes is used to generate antibodies. Antibodies are generated and tested as described in other Examples.

Figure 3:
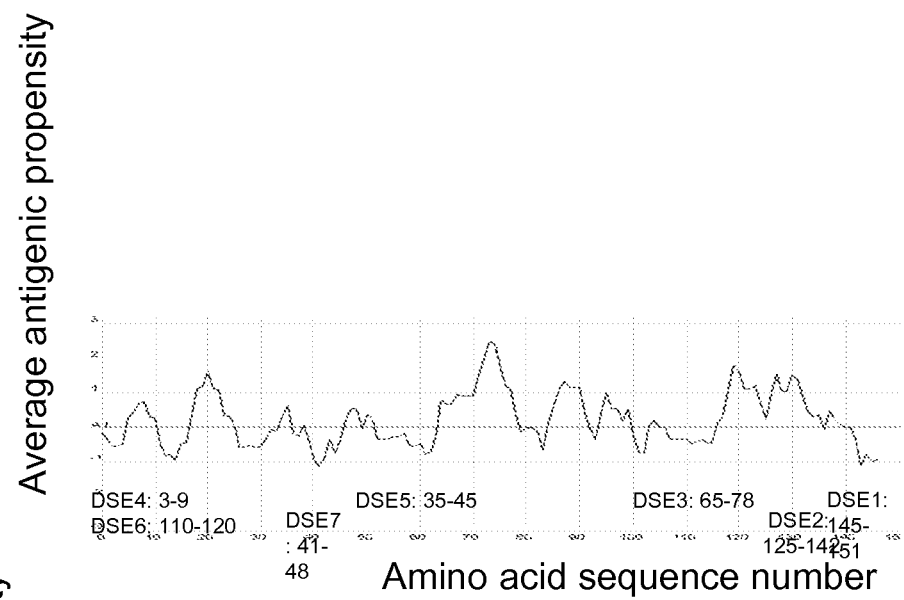
FIG. 3A is an antigenicity plot of SOD1 using the Hopp and Woods method.
FIG. 3B is an antigenicity plot of SOD1 using the Kolaskar and Tongaonkar method.
Figure 3:
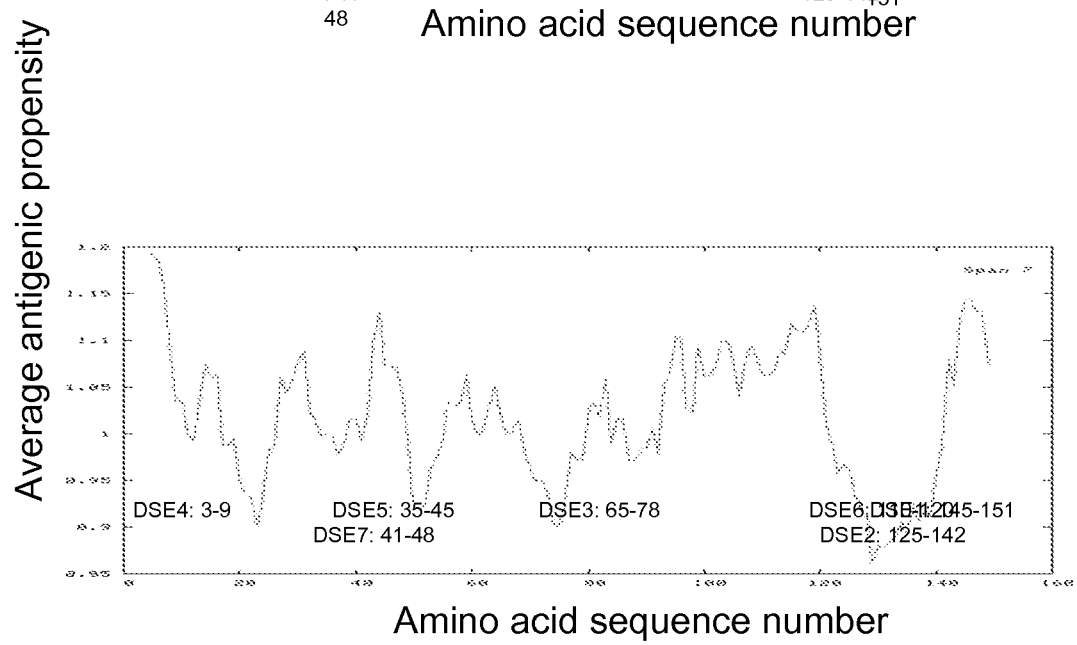

An example of an antigenicity plot is provided in FIG. 3. The SOD1 amino acid sequence was subjected to the publicly available Hopps and Woods computerized method for predicting the locations of protein antigenic determinants (FIG. 3A). In addition, the SOD1 sequence was subjected to the Kolaskar and Tongaonkar method (85) of antigenic determination prediction (FIG. 3B). This latter method identified amino acids 4-11 (AVCVLKGD) (SEQ ID NO: 69), amino acids 27-33 (GPVKVWG) (SEQ ID NO: 70), amino acids 42-48 (LHGFHVH) (SEQ ID NO: 71), amino acids 93-121 GVADVSIEDSVISLSGDHCIIGRTLWHE (SEQ ID NO: 72) and amino acids 142-149 (SRLACGVI) of SOD1 (SEQ ID NO: 80) as antigenic.

Additional modifications to the isolated peptide sequences corresponding to the epitopes of the invention or to the identified discrete epitopes are made to enhance immunogenicity. For example, a cysteine residue within the isolated peptide may be oxidized to cysteic acid. An example is DSE1a where the cysteine present in DSE1 is replaced with oxidized cysteine in the form cysteic acid and used to raise antibodies.

b) DSE Domain Mapping

As disclosed above, the DSE targets represent epitopes that are antibody-accessible when SOD1 is in its monomeric state or misfolded conformation. It will be appreciated that these epitopes can be mapped to identify minimal domains within the epitope that are sufficient for targeting purposes, and for vaccination to raise antibodies either in the subject or in an antibody production host. Moreover, these minimal domains can be useful to identify other antibodies that compete with the specific antibodies of the present invention and are useful in the present invention.

For example, the specific DSE2 epitope set out herein comprises 18 amino acid residues, representing the hSOD1 sequence 125-142. As noted herein, shorter segments of the DSE2 epitope can usefully serve as antigens for the purpose of targeting misfolded SOD1, and can be identified using standard mapping techniques in which representative fragments and derivatives of DSE2 are evaluated for their affinities to antibodies raised against the intact DSE2 epitope.

In one such example, fragments of DSE2 were synthesized as 13-mers using every other residue as the N-terminal starting residue, thus generating 7 different DSE2 fragments that were then assessed for binding to two different DSE2 monoclonal antibodies, 3H1 and 8D1. More particularly, analysis was conducted on a microarray comprising 71 different 13-meric hSOD1-derived peptides displayed on a glass surface. Four additional peptides, derived from the C-terminal end of hSOD1 were synthesized and immobilized exchanging the Cys residue vs. cysteic acid. Coupling to the glass was via Ttds (N-(3-{2-[2-(3-amino-propoxy)-ethoxy]-ethoxy}-propyl)-succinamic acid. The microarrays were pre-treated with blocking buffer (Pierce, Superblock; 2 hours at room temperature) followed by washings with TBS buffer pH 8 and water (3 times each). Each pretreated microarray was scanned using Axon-4000B-microarray scanner for background control (no signals were detected). Individual microarrays were washed with TBS buffer pH 8 followed by incubation with fluorescently labeled secondary antibody. SPOT recognition software package GeneprixPro 6.0 was used for data analysis. The mean of signal intensities from 3 identical subarrays on each array image were used for data evaluation.

In a control incubation, each microarray was incubated with buffer only followed by fluorescently labeled secondary antibody. Immobilized anti-mouse IgG yielded a clear signal. No false positives could be detected. Therefore, secondary antibody was optimal for epitope mapping experiments.

Figure 8:
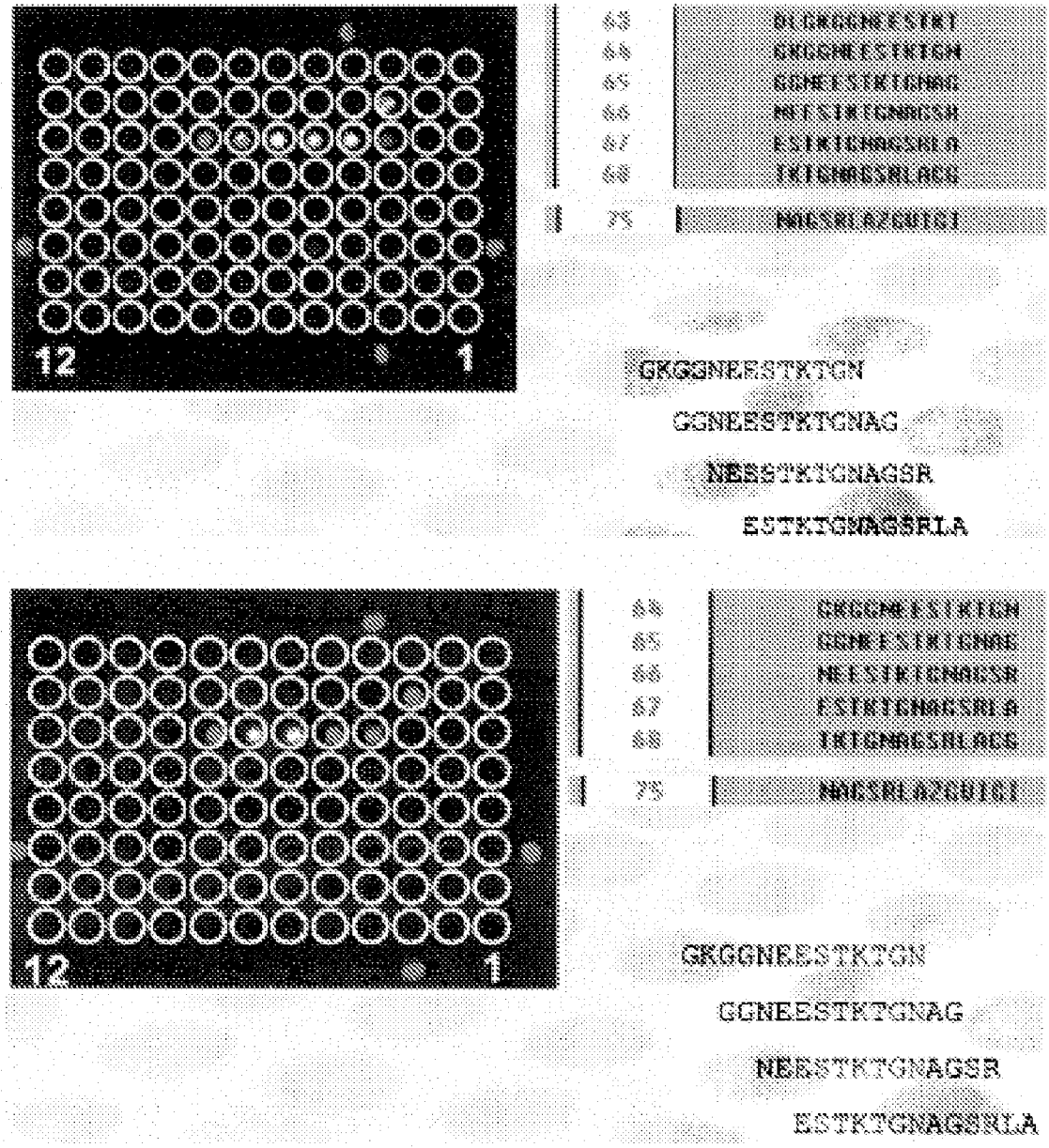
FIG. 8 is a representation of a microarray experiment that demonstrates that monoclonal antibodies raised against the DSE2 peptide recognize a seven residue sequence.
Figure 9:
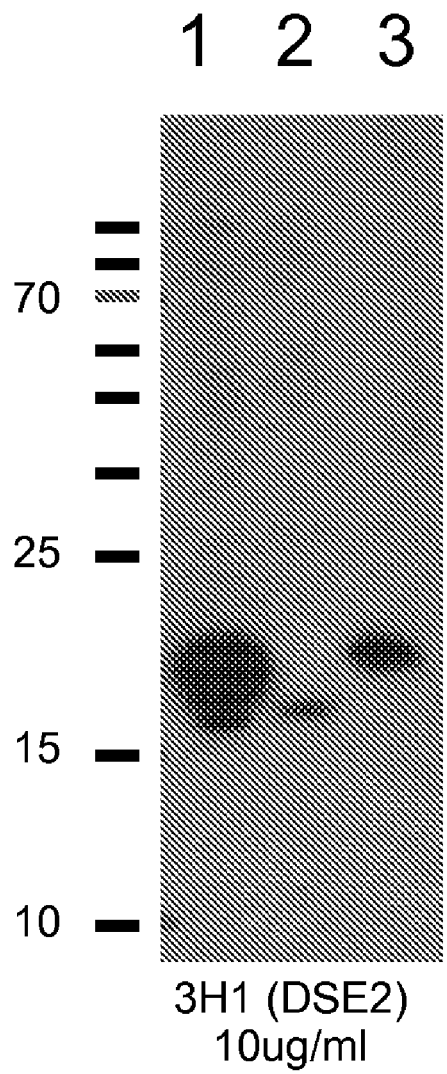
FIG. 9A is an immunoblot demonstrating that the DSE2 3H1 antibody clone which recognizes the DSE2 epitope detects denatured human and mouse SOD1.
FIG. 9B is an immunoblot demonstrating that the DSE2 8D1 antibody clone which recognizes the DSE2 epitope detects denatured human and mouse SOD1.
Figure 9:
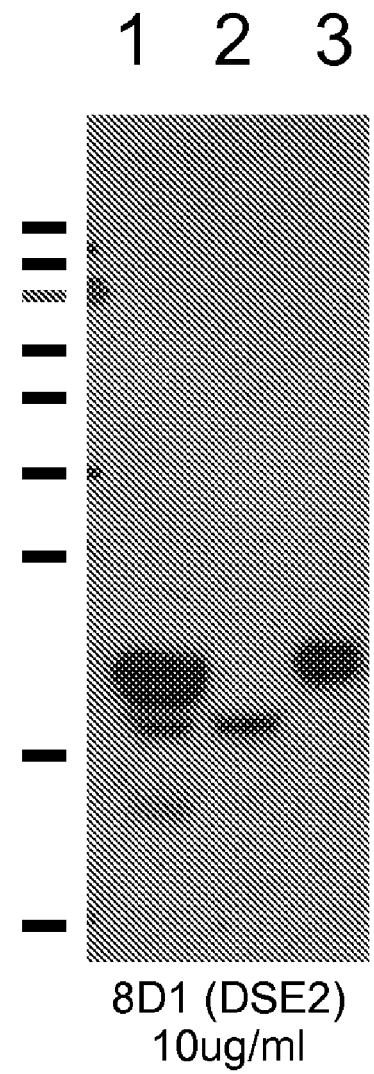
Figure 10:
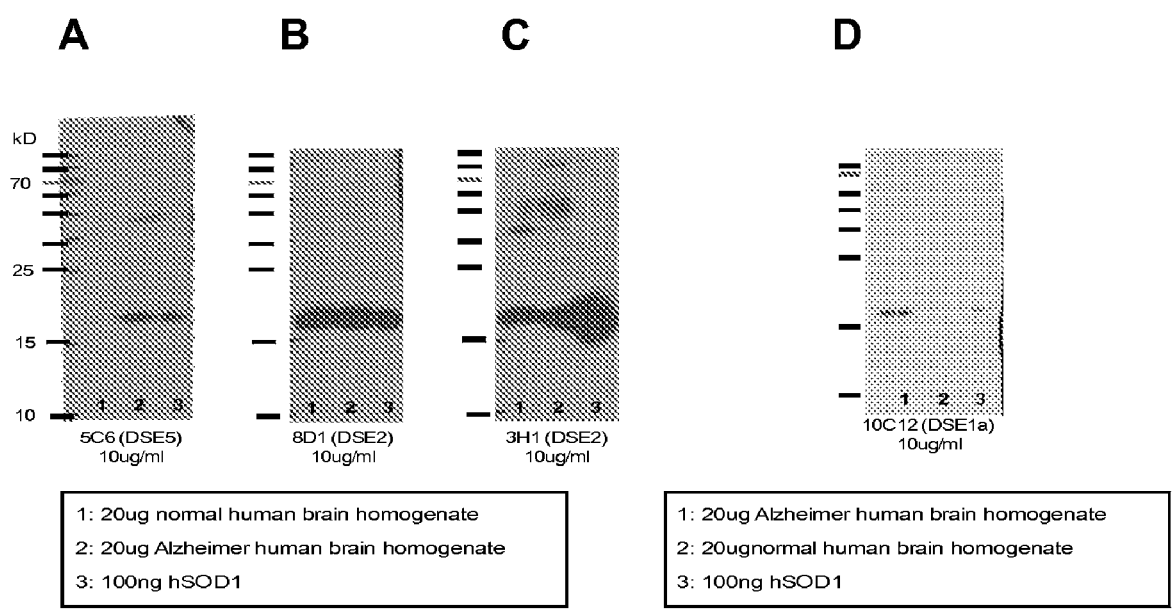
FIG. 10A is an immunoblot demonstrating that DSE5 5C6 antibody clone which recognizes the DSE5 epitope detects non-native SOD1 in AD brain homogenates but not human normal brain.
FIG. 10B is an immunoblot demonstrating that DSE2 8D1 antibody clone which recognizes the DSE2 detects denatured human and mouse SOD1.
FIG. 10C is an immunoblot demonstrating that the DSE2 3H1 antibody clone which recognizes the DSE2 epitope detects denatured human and mouse SOD1.
FIG. 10D is an immunoblot that demonstrates that antibodies raised against DSE1a, an analog of DSE1 that is modified by a cysteic acid, detect non-native forms of SOD1 in AD brain.

As shown in FIG. 8, MAb-binding fragments of the DSE2 epitope all comprise a common 7 residue sequence, namely ESTKTGN (residues 9-15 of SEQ ID NO: 2), which constitutes residues 133-139 of human SOD1. It will thus be appreciated that particular regions or "parts" of a given DSE can usefully be targeted in accordance with the present invention, and can be used to raise antibodies that target the full length form of the given DSE. In particular embodiments, the target is a DSE2 target that comprises at least residues ESTKTGN of DSE2 (residues 9-15 of SEQ ID NO:2), and may comprise additional amino acid sequences that are either heterologous or of DSE2 origin. Minimal useful domains of other DSEs can be identified and exploited in a similar manner.

It will thus be appreciated that the present invention provides, in certain embodiments, an antibody, or fragment thereof, that binds selectively to an epitope presented by misfolded hSOD1, wherein the epitope is defined by the amino acid sequence ESTKTGN (residues 9-15 of SEQ ID NO:2).

Example 15

Analog Epitopes

Analog epitope peptides are synthesized incorporating one or more oxidized or nitrated amino acids according to the list below. The cysteine (C) residue in DSE1 is oxidized to cysteine sulfinic acid or cysteic acid (i.e. DSE1a). The lysine (K) residue in DSE2 is oxidized to a carbonyl group. One or more of the arginine (R), lysine (K) and histidine (H) residues in DSE3 are oxidized to form a carbonyl group. In DSE4 lysine (K) is oxidized to a carbonyl group and/or cysteine (C) is oxidized to cysteine sulfinic acid or cysteic acid. In DSE5 one or more of K and H, are oxidized to a carbonyl group and/of phenylalanine is nitrated to nitrotryptophan. In DSE6, one or more of H or R is oxidized to a carbonyl group and/or C is oxidized to cysteine sulfinic acid or cysteic acid. In DSE7, H is oxidized to a carbonyl group and/or F is nitrated to nitrotryptophan.

| | |
|---|---|
| | (SEQ ID NO: 73) |
| DSE1: 145-151, | RLACGVIGI: C |
| | (SEQ ID NO: 74) |
| DSE2: 125-142, | DLGKGGNEESTKTGNAGS: K |
| | (SEQ ID NO: 75) |
| DSE3: 65-78, | NPLSRKHGGPKDEE: R, K, H |
| | (SEQ ID NO: 76) |
| DSE4: 3-9, | KAVCVLK: K, C |
| | (SEQ ID NO: 77) |
| DSE5: 35-45, | IKGLTEGLHGF: K, H, F |
| | (SEQ ID NO: 78) |
| DSE6: 110-120, | HCIIGRTLVVH: H, C, R |
| | (SEQ ID NO: 79) |
| DSE7: 41-48, | GLHGFHVH: H, F |
| C: | cysteine, is oxidized to cysteine sulfinic acid, and then further oxidized to cysteic acid. |
| H, R, K: | carbonyl formation |
| M: | oxidation, methionesulfoxide |
| F: | nitration, nitrophenylalanine |

Synthesized peptide analogs are used as immunogens to raise antibodies, such as monoclonal antibodies and for treating individuals having a misfolded SOD-1 mediated disease such as ALS, AD and/or PD. Antibodies are screened against the immunizing peptide analog for specificity. Positive clones are further tested for their ability to recognize misfolded SOD1. Antibodies that specifically recognize SOD1 are humanized and used to treat individuals having a misfolded SOD-1 mediated disease such as ALS, AD and/or PD.

Example 16

Immunoprecipitation of Brain Tissue

Brain tissue from patients diagnosed with Alzheimer's disease, Parkinson's disease or ALS, and matched-controls are obtained. The samples are immediately frozen on dry ice and weighed. Frozen tissue is cut into smaller pieces and homogenized (10% w/v) in lysis buffer (100 mM NaCl, 10 mM EDTA, 10 mM Tris, 0.5% deoxycholate, 0.5% NP-40, pH 7.4) and 1× Roche EDTA-free Complete Protease Inhibitor (Roche) solution with a pellet-pestle homogenizer. This homogenate is centrifuged at 2000×g; the supernatant is referred to as the 'soluble fraction' and the pellet fraction is referred to as the 'insoluble fraction'. Tissue homogenates are immediately aliquoted and frozen at −80° C. prior to use. For experiments with the insoluble fraction, the pellet is resuspended in lysis buffer. Protein concentration is determined using the BCA protein assay (Pierce). 100 μg of protein, diluted to 1 ml with PBS containing 1× protease inhibitors is immunoprecipitated with 5-μg of a monoclonal antibody that bind to epitopes selectively presented or accessible in non-native forms of SOD1 coupled to Dynabeads M-280 Tosyl-activated magnetic beads (Dynal Biotech, Oslo, Norway) according to the manufacturer's instructions.

Antibodies that bind to epitopes selectively presented or accessible in non-native forms of SOD1 include SEDI SOD (anti-DSE1) disclosed in U.S. Patent Application No. 60/741,462. This antibody is specific for the epitope comprising the sequence RLACGVIGI (SEQ ID NO: 1).

Briefly, 100 μg of SEDI SOD IgG is dialyzed against 3 changes of PBS. This is incubated with 300 μl of pre-washed stock magnetic beads in PBS at 4° C. for a minimum of 96 hrs. This is followed by blocking with 0.1% BSA in 0.2M Tris, pH 8.5 for 24 hrs at 4° C. In an alternative protocol, Protein G sepharose beads (Sigma) are used to precipitate SEDI SOD IgG.

In an alternative protocol, other antibodies that bind to epitopes selectively presented or accessible in non-native forms of SOD1 are used in the immunoprecipitation experiments, including the epitopes disclosed in WO 2005/019828 (DLGKGGNEESTKTGNAGS (SEQ ID NO: 2) and NPLSRKHGGPKDEE (SEQ ID NO: 3), and antibodies thereto, raised for instance as described in U.S. Patent Application No. 60/778,379, filed Mar. 3, 2006, and the epitopes disclosed in Khare et al. (8) IKGLTEGLHGF (SEQ ID NO: 5) and HCIIGRTLWH (SEQ ID NO: 6).

Example 17

Immunoprecipitation and Detection of Misfolded SOD1 from Brain Tissue

Brain tissues from a normal human patient, a wildtype mouse, a transgenic mouse over-expressing wildtype human SOD1 and a G93A model mouse for ALS, expressing a misfolded form of SOD1 were obtained. The samples were immediately frozen on dry ice and weighed. Frozen tissue was cut into smaller pieces and homogenized (10% w/v) in lysis buffer (100 mM NaCl, 10 mM EDTA, 10 mM Tris, 0.5% deoxycholate, 0.5% NP-40, pH 7.4) and 1× Roche EDTA-free Complete Protease Inhibitor (Roche) solution with a pellet-pestle homogenizer. This homogenate was centrifuged at 2000×g; the supernatant was referred to as the 'soluble fraction' and the pellet fraction was referred to as the 'insoluble fraction'. Tissue homogenates were immediately aliquoted and frozen at −80° C. prior to use. For experiments with the insoluble fraction, the pellet was resuspended in lysis buffer. Protein concentration was determined using the BCA protein assay (Pierce). 100 µg of protein, diluted to 1 ml with PBS containing 1× protease inhibitors was immunoprecipitated with 5-10 µg of a monoclonal antibody that bound to DLGKGGNEESTKTGNAGS (SEQ ID NO: 2), an epitope selectively presented or accessible in non-native forms of SOD1, coupled to Dynabeads M-280 Tosyl-activated magnetic beads (Dynal Biotech, Oslo, Norway) according to the manufacturer's instructions.

For immunoblotting, an antibody directed to DLGKGGNEESTKTGNAGS (SEQ ID NO: 2) was used to detect SOD1 from cellular proteins of brain tissue samples that have been resolved by gel electrophoresis.

Figure 4:
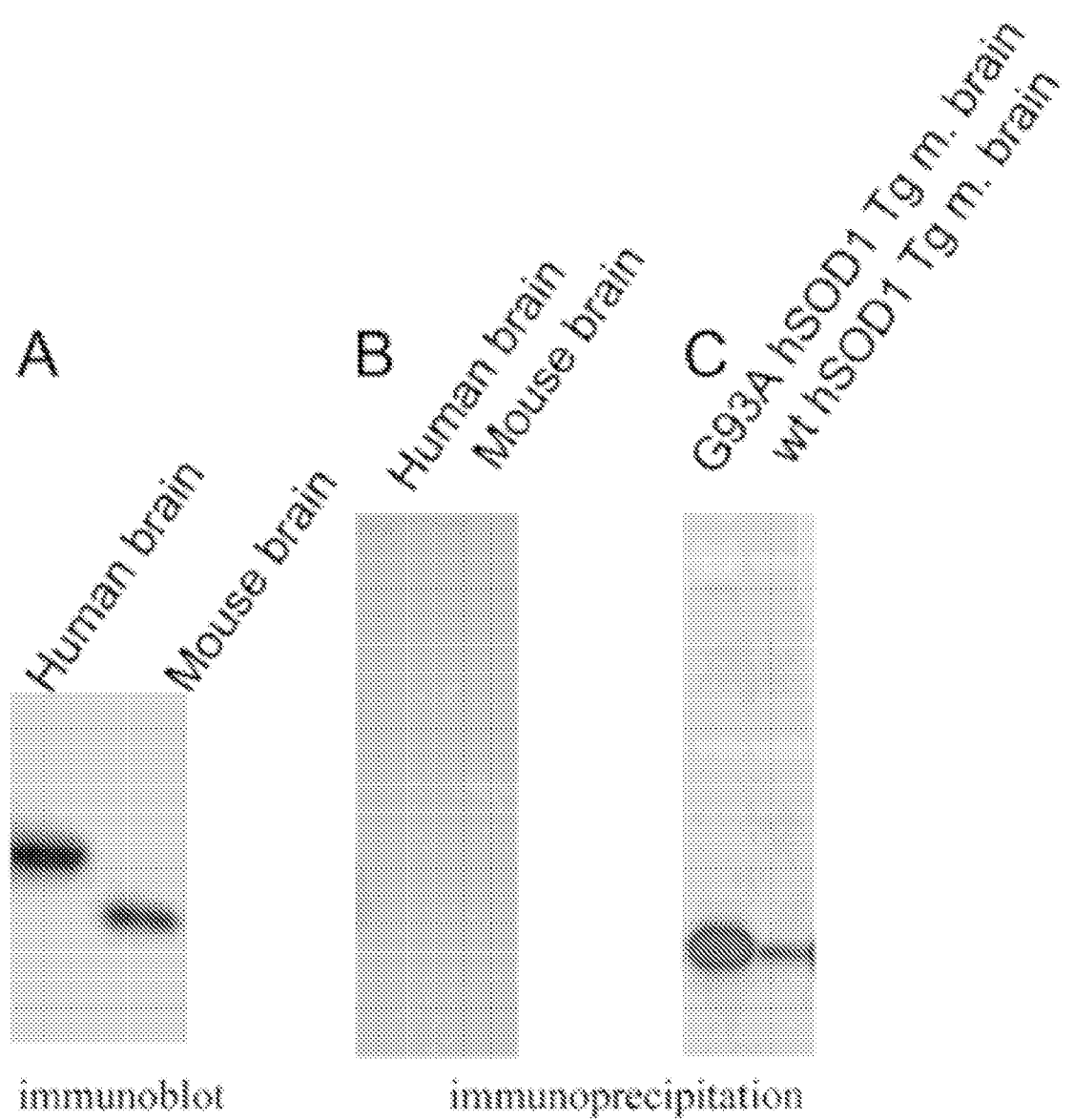
FIG. 4A is an immunoblot showing that DSE2 recognizes denatured human and mouse SOD1.
FIG. 4B is an immunoblot of immunoprecipitated SOD1 from normal human and murine brain demonstrating that anti-DSE2 antibody does not immunoprecipitate native SOD1.
FIG. 4C is an immunoblot of immunoprecipitated SOD1 from transgenic mice overexpressing wild-type and mutant human SOD1.

As demonstrated in FIG. 4, an antibody directed to DLGKGGNEESTKTGNAGS (SEQ ID NO: 2), (DSE2) immunoprecipitated a misfolded form of SOD1 in brain tissues of G93A mutant mice, and to a much lesser extent over-expressed wildtype human SOD1. This antibody did not immunoprecipitate native forms of mouse or human SOD1. However, the antibody directed to DSE2 recognized denatured human and mouse SOD1 by direct immunoblotting.

In an alternative protocol, other antibodies that bind to epitopes selectively presented or accessible in non-native forms of SOD1 are used in the immunoprecipitation experiments, including the epitopes disclosed in WO 2005/019828 (NPLSRKHGGPKDEE) (SEQ ID NO: 3), and antibodies thereto, raised for instance as described in U.S. Patent Application No. 60/778,379, filed Mar. 3, 2006, and the epitopes disclosed in Khare et al. (8) IKGLTEGLHGF (SEQ ID NO: 5) and HCIIGRTLWH (SEQ ID NO: 6).

Example 18

Immunohistochemistry of Brain Tissue

Brain tissue from patients diagnosed with Alzheimer's disease, Parkinson's disease or ALS, and matched-controls are obtained. The samples are incubated with 10% methanol free phosphate buffered formalin (Fisher Scientific). The tissue samples are dissected, paraffin-embedded and 6 µm sections cut either longitudinally or transversely using a rotary microtome. All sections for immunohistochemistry are treated with 3% $H_2O_2$ (v/v) and 10 mM sodium citrate buffer, pH 6.0 prior to labeling. Antibodies that bind to epitopes selectively presented or accessible in non-native forms of SOD1 are used. In all cases primary antibodies are left to react overnight at 4° C. Sections are developed using the DakoCytomation Envison™ System according to the manufacturer's instructions using 3,3'-diaminobenzidine (DAB) as chromagen. For double-labeling the DakoCytomation Envison™ DoubleStain kit is used with nitro-blue tetrazolium (NBT) as chromagen. Stained sections are visualized using a Leica DM 6000 microscope and digital images are obtained with a Micropublisher 3.3 RTV digital color camera (Qimaging).

Example 19

Immunohistochemistry of Brain Tissue from Alzheimer's Disease

Tissues were prepared by formalin fixing and were embedded in paraffin. Tissues were sectioned (4 microns), mounted on charged microscope slides and heated in a tissue drying oven for 45 minutes at 60° C. Slides were deparaffinized by washing slides in xylene (3×5 mins) and rehydrated by washing slides in decreasing concentrations of alcohol (3×3 mins using 100% alcohol; 2×3 mins using 95% alcohol; 1×3 mins using 80% alcohol) and distilled water. Slides were steamed in 0.01 M sodium citrate buffer, at pH 6.0 at 99-100° C. for 20 mins and incubated at RT for 20 mins. Slides were reinsed in 1×TBS with Tween (TBST) for 1 minute at RT.

Slides were incubated with a protein block for 20 mins, probed with primary antibody for 45 minutes, and rinsed with TBST. Slides were incubated with a biotinylated secondary antibody for 30 min and then rinsed with TBST. Slides were next incubated in alkaline phosphatase streptavidin for 30 minutes, rinsed in TBST and incubated with substrate for 30 mins. After rinsing in distilled water, slides were examined by microscopy.

Figure 5:
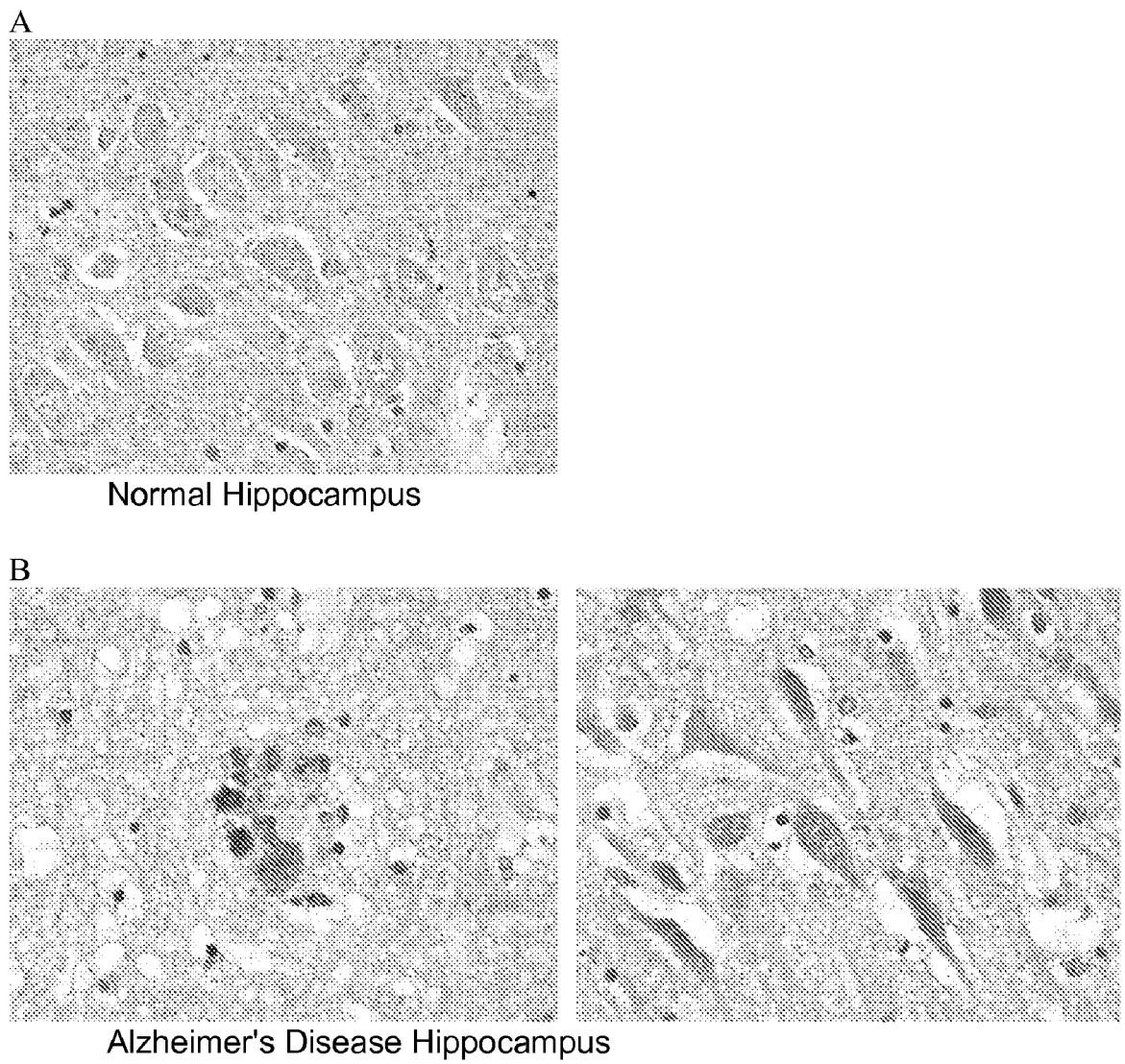
FIG. 5A is a human brain section of normal hippocampus in a 52-year-old female stained with an antibody to DSE2.
FIG. 5B is a composite of human hippocampus sections from a 78-year-old female with late-stage Alzheimer's disease probed with anti-DSE2 monoclonal antibody.

Brain hippocampus tissue from the autopsy of a 78 year old female patient diagnosed with Alzheimer's disease and -control normal hippocampus tissue from a 52 year old female were obtained. The samples were incubated with 10% methanol free phosphate buffered formalin (Fisher Scientific). The tissue samples were dissected, paraffin-embedded and 6 µm sections cut either longitudinally or transversely using a rotary microtome. All sections for immunohistochemistry were treated with 3% $H_2O_2$ (v/v) and 10 mM sodium citrate buffer, pH 6.0 prior to labeling. An antibody specific for the Alzheimer's disease-specific eptiope DLGKGGNEESTKTGNAGS (SEQ ID NO: 2), (DSE2) was used as the primary antibody to stain the tissue sections at a concentration of 5 µg/ml (FIG. 5). The antibodies were left to react overnight at 4° C. Sections were developed using the DakoCytomation Envison™ System according to the manufacturer's instructions using 3,3'-diaminobenzidine (DAB) as chromagen. For double-labeling the DakoCytomation Envison™ DoubleStain kit was used with nitro-blue tetrazolium (NBT) as chromagen. Stained sections were visualized using a Leica DM 6000 microscope and digital images were obtained with a Micropublisher 3.3 RTV digital color camera (Qimaging). The hippocampus section obtained from a 78-year-old female with late-stage Alzheimer's disease showed strong staining of senile plaques in the Alzheimer's brain with the antibody directed against DSE2 (FIG. 5B, left panel), as well as increased staining within subsets of neurons in the Alzheimer's hippocampus section (FIG. 5B, right panel) compared to the normal hippocampus (FIG. 5A).

These data demonstrate misfolded SOD1 is present intracellularly and extracellularly in brains of Alzheimer's patients and that the antibody directed against the DSE2 epitope CDLGKGGNEESTKTGNAGS (SEQ ID NO: 11) recognizes misfolded SOD1 proteins found in the brains of Alzheimer's disease patients.

Example 20

Immunohistochemistry of Brain Tissue from Parkinson's Disease

Tissues were prepared by formalin fixing and were embedded in paraffin. Tissues were sectioned (4 microns), mounted on charged microscope slides and heated in a tissue drying oven for 45 minutes at 60° C. Slides were deparaffinized by washing slides in xylene (3×5 mins) and rehydrated by washing slides in decreasing concentrations of alcohol (3×3 mins using 100% alcohol; 2×3 mins using 95% alcohol; 1×3 mins using 80% alcohol) and distilled water. Slides were steamed in 0.01 M sodium citrate buffer, at pH 6.0 at 99-100° C. for 20 mins and incubated at RT for 20 mins. Slides were reinsed in 1×TBS with Tween (TBST) for 1 minute at RT.

Slides were incubated with a protein block for 20 mins, probed with primary antibody for 45 minutes, and rinsed with TBST. Slides were incubated with a biotinylated secondary antibody for 30 min and then rinsed with TBST. Slides were next incubated in alkaline phosphatase streptavidin for 30 minutes, rinsed in TBST and incubated with substrate for 30 mins. After rinsing in distilled water, slides were examined by microscopy.

Figure 6:
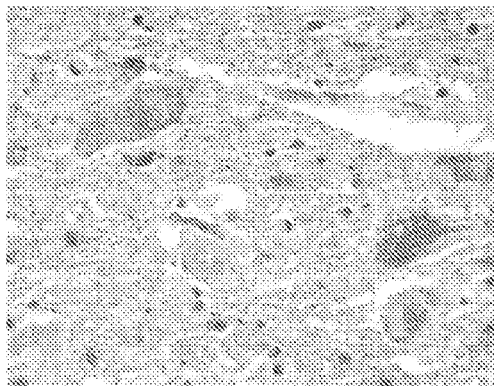
FIG. 6 (A-F) is a composite of brain sections from a 79-year old female with dementia probed with anti-DSE2 monoclonal antibody.
Figure 6:
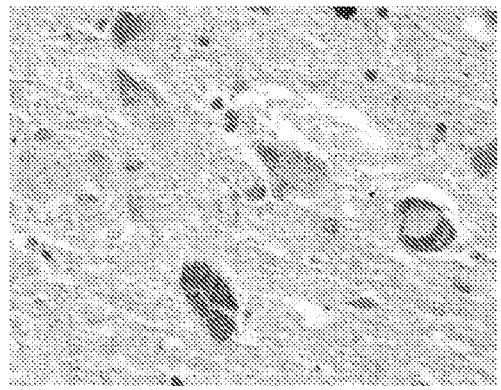
Figure 6:
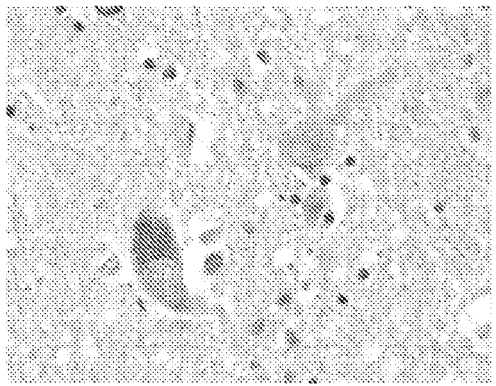
Figure 6:
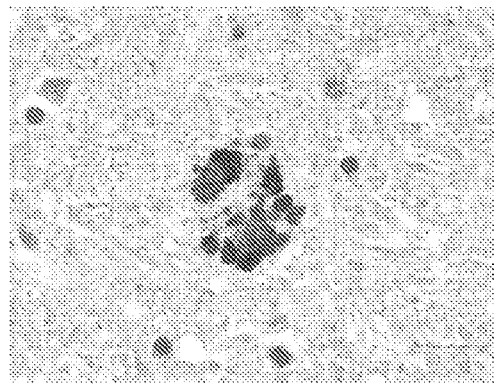

A brain sample was obtained from a 79-year-old female with dementia. The H&E-stained section (FIG. 6, panel A) showed substantia nigra with dopaminergic neurons that showed occasional Lewy bodies consistent with Parkinson's disease. The anti-DSE2 antibody showed mostly negative to rare faint staining in pigmented and non-pigmented neurons within the substantia nigra (FIG. 6, panel B, C, D, and E). Lewy bodies were negative (FIG. 6, panel B). Adjacent neuropil was faintly positive, and astrocytes were faintly to occasionally moderately positive. Corpora amylacea were strongly positive. This sample showed rare senile plaques in the adjacent gray matter that were strongly positive (FIG. 6, panel F). Adjacent serial sections were evaluated in the absence of primary antibody as a control and were all negative.

These data demonstrate misfolded SOD1 is present in brains of Parkinson's patients and that the antibody directed against the DSE2 epitope DLGKGGNEESTKTGNAGS (SEQ ID NO: 2) recognizes misfolded SOD1 proteins found in the brains of Parkinsons's disease patients.

Example 21

Immunoreactivity of SOD1 DSE2 in Disease

The inventors have detected DSE2 immunoreactivity in all types of ALS (sporadic forms, as well as SOD1 familial ALS and familial ALS without SOD1 mutations). Immunoreactivity is detectable as discrete dense deposits within some spinal cord motor neurons, including motor axons in the ventral root, as well as extracellular punctuate deposits within the anterior horns of the spinal cord, and within motor tract axons.

Moreover, DSE2 immunoreactivity is detectable intracellularly in hippocampal neurons in AD but not normal aged-matched individuals. Moreover, DSE2 immunoreactivity is also noted in regionally diffuse in senile plaques and punctuate deposits extracellularly in the hippocampus. Extracellular misfolded SOD1 in neurodegenerative diseases is clearly a target for immunotherapy, which may "neutralize" the toxic activity of the misfolded species by accelerating degradation by microglia, and/or by blocking abnormal enzymatic activity of this misfolded protein.

Example 22 a) ALS-Specific Epitope Immunization of ALS Model Mice

This study shows that vaccination with specific peptide sequences from the enzyme superoxide dismutase one (SOD1) prevents the neurodegenerative disease amyotrophic lateral sclerosis (ALS).

Transgenic mice expressing human mutant SOD1 G93A and G37R are immunized IP with KLH-coupled amyotrophic lateral sclerosis-specific epitope and control peptides every month prior to motor neuron disease onset (4 months and 6 months, respectively). Delay or abrogation of SOD aggregation and disease onset occurs for therapeutically active epitopes, and potential autoimmune manifestations for the amyotrophic lateral sclerosis-specific epitopes and control epitopes are monitored.

These methods are used with G93A and G37R model mice. G93A and G37R model mice express certain mutant forms of the human SOD1 protein and develop an ALS-like disease clinically and neuropathologically. Seventy-two of each model mice are used for this study. Seven different ALS-specific peptide epitopes to non-native forms of SOD1 are tested and compared to 2 control groups (one untreated, and one treated with adjuvant alone). Each group consisted of 8 animals.

Four-week old hemizygous transgenic mice (transgene and copy number confirmed by PCR and southern blot) are randomized into one of nine groups for immunization: no immunization (NI); Keyhole limpet hemocyanin (KLH) alone plus adjuvant; or one of seven SOD1 DSE peptide sequences. All peptides are synthesized, purified and coupled to KLH using SMCC-Sulfolink. All mice are immunized initially via intraperitoneal (IP) injection with 100 µg of KLH-coupled peptide or KLH alone, emulsified 1:1 in Freund's complete adjuvant (FCA), in a total volume injected of 100 µl. Three weeks later the mice are given a subcutaneous injection of KLH-coupled peptide emulsified in incomplete Freund's adjuvant (IFA). Thereafter, mice are given monthly subcutaneous injections of KLH-coupled peptide emulsified in IFA. After 4 immunizations, 100 µl of blood is collected from the saphenous vein, and plasma antibody titers are determined.

Animals are weighed 2-3 times per week. Leg extension reflex is assessed when animals are lifted by the base of the tail and removed from their cage for weighing. Reduction in leg extension is an early deficit observed in mutant SOD1 transgenic mice. Mice behaviour is monitored weekly using open field testing (EthoVision, Noldus Information Technology, Leesburg, Va., USA) and gait analysis is done weekly using DigiGait. Initial behavioral and gait assessments are completed just prior to the first immunization and serve as baseline data.

Brain, spinal cord and other non-CNS organ systems are analyzed postmortem for morphological and biochemical indices of neurodegeneration.

Animals are weighed and monitored regularly for adverse effects such as signs of pain and distress that might be a result of the immunizations. Autoimmunity is also monitored.

Vaccination with ALS-specific peptide epitopes prevents the neurodegenerative disease amyotrophic lateral sclerosis (ALS). Delay or abrogation of SOD aggregation and disease onset occurs for therapeutically active epitopes, and not for controls.

b) ALS-Specific Epitope Immunization of ALS Model Mice.

This study shows that vaccination with specific peptide sequences from the enzyme superoxide dismutase one (SOD1) prevents the neurodegenerative disease amyotrophic lateral sclerosis (ALS).

The method used is similar to the method described above in part a). The G93A SOD1 transgenic mice used included what have been termed long survivors and short survivors. During breeding of transgenic animals it was determined that a line of mice experienced a spontaneous partial genetic deletion of the G93A SOD1 transgene array resulting in a line with a lower copy number of the transgene. These mice live longer than mice having a higher copy of transgene insertions.

Results with DSE-comprising vaccines are provided in Table 10B below, noting whether the host animal was either a short survivor (G93A transgenic, T) or a long survivor (G93A transgenic, F).

Figure 7A:
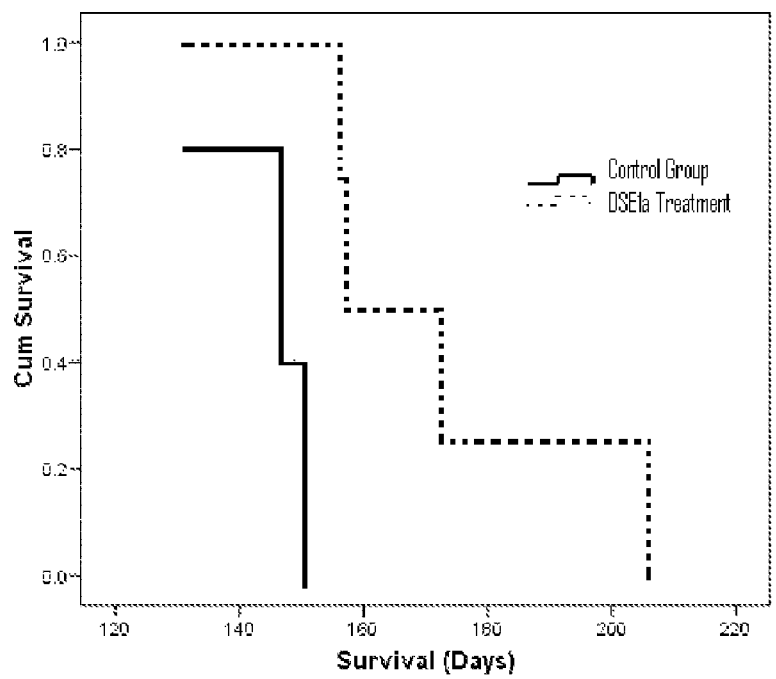
FIG. 7A is a graph illustrating that mice vaccinated with compositions comprising DSE1a peptide exhibit statistically significant enhancement of survival.
Figure 7B:
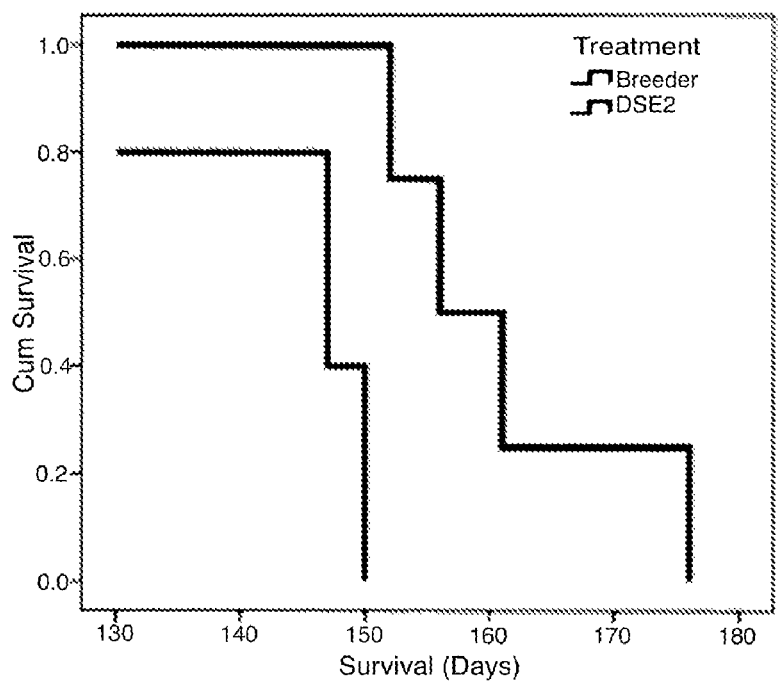
FIG. 7B is a graph illustrating that mice vaccinated with compositions comprising a DSE2 peptide exhibit statistically significant enhancement of survival.

The results demonstrate that mice vaccinated with compositions comprising DSE1a or DSE2 epitope amino acid sequence exhibited statistically significant enhancement of survival in the short-surviving mice (see FIGS. 7A and 7B respectively). In addition, mice receiving DSE1 vaccine showed a significant enhanced weight gain during the treatment period, relative to untreated controls. It is anticipated that significant effects will be evident in the other treatment groups when the number of animals is increased to allow for statistical evaluation.

Vaccination with ALS-specific peptide epitopes prevents the neurodegenerative disease amyotrophic lateral sclerosis (ALS). Delay or abrogation of SOD aggregation and disease onset occurs for therapeutically active epitopes, and not for controls.

Table 10B. Survival and Weight of Animals Vaccinated with DSE Comprising Vaccines

TABLE 10B

Survival and Weight of Animals Vaccinated with DSE Comprising Vaccines

| GROUP | ID | SEX | Short (T)/Long (F) Survivor | Survival (Days) | Weight at Death |
|---|---|---|---|---|---|
| DSE1a | 3-1-5 | M | F | 163 | 19.7 |
| DSE1a | 6-1-5 | M | T | 206 | 20.0 |
| DSE1a | 10-1-7 | M | T | 157 | 20.3 |
| DSE1a | 15-1-1 | M | F | 194 | 18.9 |
| DSE1a | 12-1-6 | F | T | 156 | 14.4 |
| DSE1a | 12-1-8 | F | T | 173 | 14.1 |
| DSE1a | 15-1-7 | F | F | 210 | 16.4 |
| DSE2 | 6-1-6 | M | T | 152 | 21.0 |
| DSE2 | 10-1-9 | M | T | 156 | 20.5 |
| DSE2 | 15-1-2 | M | F | 190 | 22.4 |
| DSE2 | 10-1-11 | F | T | 176 | 15.5 |
| DSE2 | 12-1-4 | F | T | 161 | 16.9 |
| DSE2 | 13-1-5 | F | F | 174 | 16.7 |
| DSE5 | 6-1-7 | M | T | 149 | 18.8 |
| DSE5 | 11-1-11 | M | T | 150 | 17.7 |
| DSE5 | 15-1-5 | M | F | 195 | 19.6 |
| DSE5 | 5-1-11 | F | F | 191 | 16.8 |
| DSE5 | 9-1-12 | F | F | 193 | 15.6 |
| DSE5 | 14-1-14 | F | F | 210 | 17.7 |
| DSE1a, 2, 5 | 5-1-5 | M | F | 191 | 24.7 |
| DSE1a, 2, 5 | 8-1-3 | M | F | 200 | 21.9 |
| DSE1a, 2, 5 | 9-1-5 | M | F | 207 | 22.2 |
| DSE1a, 2, 5 | 11-1-2 | M | T | 148 | 20.3 |
| DSE1a, 2, 5 | 6-1-8 | F | T | 158 | 15.9 |
| DSE1a, 2, 5 | 10-1-13 | F | T | 147 | 15.6 |
| DSE1a, 2, 5 | 12-1-10 | F | T | 171 | 14.8 |
| DSE1 | 3-1-1 | M | F | 190 | 19.0 |
| DSE1 | 9-1-7 | M | F | 193 | 19.4 |
| DSE1 | 14-1-3 | M | F | 212 | 22.5 |
| DSE1 | 8-1-5 | F | F | 209 | 15.1 |
| DSE1 | 10-1-14 | F | T | 167 | 15.5 |
| DSE1 | 14-1-10 | F | F | 212 | 18.1 |
| ADJ + NaCl | 2-1-3 | M | F | 162 | 21.6 |
| ADJ + NaCl | 8-1-2 | M | F | 174 | 21.9 |
| ADJ + NaCl | 9-1-3 | M | F | 216 | 21.3 |
| ADJ + NaCl | 5-1-8 | F | F | 178 | 15.1 |
| ADJ + NaCl | 9-1-13 | F | F | 171 | 16.9 |
| ADJ + KLH | 5-1-4 | M | F | 208 | 21.0 |
| ADJ + KLH | 9-1-2 | M | F | 199 | 20.6 |
| ADJ + KLH | 10-1-10 | M | T | 145 | 17.0 |
| ADJ + KLH | 8-1-10 | F | F | 193 | 15.5 |
| no treat | 5-1-3 | M | F | 187 | 19.4 |
| no treat | 8-1-4 | M | F | 191 | 20.4 |
| no treat | 14-1-4 | M | F | 187 | 23.2 |
| no treat | 6-1-13 | F | T | 167 | 15.3 |
| no treat | 9-1-15 | F | F | 182 | 12.9 |
| no treat | 14-1-13 | F | F | 210 | 17.7 |
| wt control | 13-1-3 | F | F | 125 | NA |

Example 23

ALS-Specific Epitope Immunization of ALS Model Mice

Four-week old G93A or G37R model are randomized into one of seven groups for immunization: saline; Keyhole limpet hemocyanin (KLH); DSE1; DSE1a; DSE2; DSE5; and DSE1a+DSE2+DSE5. All peptides are conjugated to KLH. All immunization are administered in conjunction with a pharmaceutically acceptable excipient.

Animals are assessed for changes in leg extension reflex, behaviour and gait. Brain, spinal cord and other non-CNS organ systems are analyzed postmortem for morphological and biochemical indices of neurodegeneration.

Vaccination with a nucleic acid encoding an ALS specific epitope prevents the neurodegenerative disease amyotrophic lateral sclerosis (ALS). Delay or abrogation of SOD aggregation and disease onset occurs for therapeutically active nucleic acids, and not for controls.

Example 24

Immunization of ALS Model Mice with Nucleic Acid

Four-week old G93A and G37R model mice are randomized for immunization with a nucleic acids encoding an ALS-specific epitope or an unrelated control nucleic acid. All nucleic acids are administered with a pharmaceutically acceptable excipient.

Animals are assessed for changes in leg extension reflex, behaviour and gait. Brain, spinal cord and other non-CNS organ systems are analyzed postmortem for morphological and biochemical indices of neurodegeneration.

Vaccination with a nucleic acid encoding an ALS specific epitope prevents the neurodegenerative disease amyotrophic lateral sclerosis (ALS). Delay or abrogation of SOD aggregation and disease onset occurs for therapeutically active nucleic acids, and not for controls.

Example 25

ALS-Specific Epitope Antibody Infusion of ALS Model Mice

G93A and G37R mice are infused intravenously (IV) with monoclonal antibodies directed against the amyotrophic lateral sclerosis-specific epitopes upon disease onset, to more closely model ALS immunotherapy. Slowing or arrest of SOD aggregation and disease progression occurs for therapeutically active antibodies, with no effect from isotype control antibodies. Autoimmunity is monitored for the amyotrophic lateral sclerosis-specific epitope and control antibodies, including native-exposed epitope.

G93A and G37R model mice express certain mutant forms of the human SOD1 protein and develop an ALS-like disease clinically and neuropathologically. Thirty-two mice of each strain are used for this study, with 8 mice randomized to each of 2 antibodies directed to an epitope selectively presented or accessible in non-native forms of SOD1 treatment groups and 2 control groups. Eight-week old mice are randomized into one of 4 groups: 1. An antibody directed to an epitope selectively presented or accessible in non-native forms of SOD1 injected intraperitoneal (IP); 2. An antibody directed to an epitope selectively presented or accessible in non-native forms of SOD1 infused intra-cerebroventricular (ICV); 3. PBS injected IP (control); and 4. Phosphate buffered saline (PBS) infused ICV (control).

Mice receive weekly IP injections of 1 ml of purified antibody in PBS (250 µL/ml) or PBS alone. For ICV infusion, mice are anaesthetized with isoflurane gas delivered by a nosepiece, and implanted with mini-osmotic pumps (Alzet model no. 2004; length: 3 cm, total volume: 200 uL, flow rate: 0.25 uL/hr). This pump provides steady infusion of 0.125 ug/hr (a total of 25 ug per week) for at least 4 weeks. Pumps containing either purified DSE2 antibody or PBS are fitted to a brain infusion kit (Alzet brain infusion kit 3), using a cannula placed in the third ventricle. Pumps are replaced after 4 weeks of use.

Mice are weighed and assessed for motor function and behaviour prior to IP injections or implantation of pumps to serve as baseline data. Thereafter these tests are performed once per week. Tests include:

a.) HINDLIMB EXTENSION REFLEX: Reduction in hindlimb extension when animals are lifted by the tail is an early deficit observed in mutant SOD1 transgenic mice. Animals are lifted by the base of the tail and hindlimb extension and postural reflexes and scored. Score 3 indicates full extension and normal postural reflex. Score 2 indicates moderate extension and normal postural reflex. Score 1 indicates poor extension and postural reflex. Score 0 indicates no hindlimb movement.

b.) OPEN FIELD TESTING: Open field testing are done weekly using EthoVision Pro Version 3.1 (Noldus Information Technology, Leesburg, Va., USA). Animals are placed in an enclosed circular arena (50 cm diameter) with an open top and recorded for approximately 5 minutes with an overhead digital video camera. A number of behavioural parameters are quantified offline. Four animals are monitored simultaneously in separate arenas.

c.) GAIT ANALYSIS: Gait analysis are done weekly using DigiGait (Mouse Specifics, Boston, Mass., USA). Changes in paw placement and stride length are reported as being the earliest functional changes observed in G93A B6.Cg-Tg SOD1 transgenic mice, as assessed using DigiGait.

At 12 weeks of age, 100 µl of blood are collected from the mice via the saphenous vein and plasma antibody titers are determined. For ICV treated mice, blood is collected under anaesthesia when pumps are replaced. IP treated mice are also anaesthetized with isoflurane to facilitate blood collection.

Animals are weighed and monitored regularly for adverse effects such as signs of pain and distress for the duration of the study. Animals that appear to be in pain are administered Buprenorphine.

Brain, spinal cord and other non-CNS organ systems are analyzed postmortem for morphological and biochemical indices of neurodegeneration Injection or infusion of antibodies directed to an epitope selectively presented or accessible in non-native forms of SOD1 is effective in treating the neurodegenerative disease amyotrophic lateral sclerosis (ALS). Treatment of G93A and G37R model mice these mice via injection or infusion of antibodies directed to an epitope selectively presented or accessible in non-native forms of SOD1 have: neutralized and cleared mutant SOD1; prevented the formation of SOD1 aggregates; delayed the onset of disease; and/or slowed progression of the disease.

Example 26

Treatment of G93A Mice with DSE2 Antibody

G93A model mice were infused with a monoclonal antibodies directed against the DSE2 peptide sequence. G93A model mice express a mutant forms of the human SOD1 protein and develop an ALS-like disease clinically and neuropathologically. The antibody was administered either by intracebroventricular (ICV) infusion, using a brain catheter (Alzet® Catheters) and a subcutaneously implanted pump (Alzet® Osmotic Pumps), or by intraperitoneal injection of anti-DSE2 antibody.

For ICV infusion, 8 animals were randomly assigned to either the treatment group (4 animals) or the control group (4 animals). For treatment, Alzet pumps were filled with 200 ul antibody solution (0.5 to 0.6 mg/ml) in saline, or saline alone for control. Antibody was delivered at a flow rate of 0.125 ug/hr for 4 weeks. 2 additional mice were infused by intraperitoneal (IP) injection with 1 mg anti-DSE2 antibody, followed by 3 additional injections of 1 mg anti-DSE2 antibody in saline solution in weekly intervals. 2 mice were control injected with saline solution without antibody.

Disease progression in treated and untreated mice was monitored using gait analysis (DigiGait, Mouse Specifics Inc, Boston, Mass.). Digigait analysis allows for highly accurate measurement of changes in gait parameters in this mouse model that allow for a very accurate and objective assessment of disease progression (Wooley C M, Sher R B, Kale A, Frankel W N, Cox G A, Seburn K L.; Gait analysis detects early changes in transgenic SOD1(G93A) mice. Muscle Nerve. 2005 July; 32(1):43-50). As disease progresses, stride time increases. The inventors have found that the stride time is a sensitive parameter to measure disease progression.

Table 11 shows the results of stride time measurements using Digigait analysis of treated animals after 25 days of treatment (IP injection) and 28 to 35 days of treatment (ICV infusion). Stride time is measured in seconds and averaged over the length of the study and all four paws. Stride time averaged 0.3238 second in control ICV infused. Disease progression, as measured by stride time is significantly, delayed after 35 days of treatment. Stride time is less in treated animals and is reduced to 0.2988 seconds. Stride time is also improved in IP injected mice. Stride time averaged 0.3366 s for control animals and improved to 0.3206 s after 28 days treatment.

For comparison and to demonstrate the effect of disease progression, the stride time for untreated mice at an average of 66 and 122 days of age was determined (animal age in the same range as treatment groups). At 66 days, untreated mice have an average stride time of 0.3254 s (STDEV 0.0313). At 122 days stride time has increased to 0.3492 s (STDEV 0.0288) Clearly, in the absence of treatment, this parameter increases with high statistical significance. The inventors found that both methods of treatment reverse the lengthening of the stride time that is observed in the untreated animals over time. This demonstrates the efficacy of this antibody treatment to reverse the disease associated phenotype of the ALS mouse model.

TABLE 11

Delay in Disease Progression: Stride Time of Animals Treated with Disease Specific SOD1 Antibodies

| Study | Group | | Stride Time (s) |
|---|---|---|---|
| ICV Infusion | Treatment | Average | 0.2988 s |
| | | STDEV | 0.0044 |
| | Control | Average | 0.3238 s |
| | | STDEV | 0.0449 |
| | | P value | 4.30E−02 |
| IP Injection | Treatment | Average | 0.3206 s |
| | | STDEV | 0.0044 |
| | Control | Average | 0.3366 s |
| | | STDEV | 0.0148 |
| | | P value | 1.82E−02 |
| Disease Progression | 66 days | Average | 0.3254 s |
| | | STDEV | 0.0313 |
| | 122 days | Average | 0.3492 s |
| | | STDEV | 0.0288 |
| | | P value | 1.04E−05 |

Example 27

Immunization of TgCRND8 Transgenic Mice

The TgCRND8 mouse is a murine model of Alzheimer's disease. These mice express a mutant (K670N/M671L and V717F) human βAPP695 transgene under the regulation of the Syrian hamster prion promoter on a C3H/B6 strain background. These mice have spatial learning defects at 3 months of age that are accompanied by both increasing levels of SDS-soluble Aβ and increasing numbers of Aβ-containing amyloid plaques in the brain. See Janus C et al. (65).

TgCRND8 mice are immunized IP with KLH-coupled to an epitope selectively presented or accessible in non-native forms of SOD1 or a control peptide at 6, 8, 12, 16 and 20 weeks.

The mice are tested in a reference memory version of the Morris water maze test at 11, 15, 19 and 23 weeks (See Janus C et al. (65); Janus C (66); Gass P et al. (67); and Wehner J M (68)).

Delay or abrogation of SOD1 aggregation and disease onset occurs for therapeutically active epitope, and autoimmune manifestations are monitored.

In addition to SOD1 aggregation, deposition of cerebral fibrillar Aβ is assessed (See Janus C et al. (65)).

Example 28

Antibody Infusion of TgCRND8 Transgenic Mice

TgCRND8 mice are infused with antibodies that bind to epitopes selectively presented or accessible in non-native forms of SOD1 or isotype control antibodies. As described above, the mice are tested in a reference memory version of the Morris water maze test.

Slowing or arrest of SOD1 aggregation and disease progression occurs for therapeutically active antibodies, with no effect from isotype control antibodies. Autoimmunity is monitored. In addition to SOD1 aggregation, deposition of cerebral fibrillar Aβ is assessed (See Janus C et al. (65)).

Example 29

Immunization of TgCRND8 Transgenic Mice with Nucleic Acid

The TgCRND8 mouse is a murine model of Alzheimer's disease. These mice express a mutant (K670N/M671L and V717F) human βAPP695 transgene under the regulation of the Syrian hamster prion promoter on a C3H/B6 strain background. These mice have spatial learning defects at 3 months of age that are accompanied by both increasing levels of SDS-soluble Aβ and increasing numbers of Aβ-containing amyloid plaques in the brain. See Janus C et al. (65).

TgCRND8 mice are immunized IP with KLH-coupled to a nucleic acid encoding an epitope selectively presented or accessible in non-native forms of SOD1 or a control nucleic acid at 6, 8, 12, 16 and 20 weeks.

The mice are tested in a reference memory version of the Morris water maze test at 11, 15, 19 and 23 weeks (See Janus C et al. (65); Janus C (66); Gass P et al. (67); and Wehner J M (68)). In addition to SOD1 aggregation, deposition of cerebral fibrillar Aβ can be assessed (See Janus C et al. (65)).

Vaccination with a nucleic acid encoding an epitope selectively presented or accessible in non-native forms of SOD1 prevents Alzheimer's disease. Delay or abrogation of SOD1 aggregation and disease onset occurs for therapeutically active nucleic acid, and not for controls.

Example 30

Immunization of Hα-Syn Tg Mice

Heterozygous transgenic mice expressing hα-syn under regulatory control of the platelet-derived growth factor-β promoter are used (Masliah E et al. (69)). These animals are used because they are a model for Parkinson's disease and Lewy Body disease (Masliah E et al. 70)).

The hα-syn tg mice are immunized IP with KLH-coupled to an epitope selectively presented or accessible in non-native forms of SOD1 or a control peptide at 2, 6, 8, 12, 16 and 20 weeks.

Delay or abrogation of SOD1 aggregation and disease onset occurs for therapeutically active epitope, and autoimmune manifestations are monitored. The progression of the disease is assessed by monitoring the accumulation of hα-syn in the brain of the mice and clinical features of neurological involvement (See Masliah E et al. (70)).

Example 31

Immunization of Hα-Syn Tg Mice with Nucleic Acid

Heterozygous transgenic mice expressing hα-syn under regulatory control of the platelet-derived growth factory promoter are used (Masliah E et al. (69)). These animals are used because they are a model for Parkinson's disease and Lewy Body disease (Masliah E et al. 70)).

The hα-syn transgenic mice are immunized IP with a nucleic acid encoding an epitope selectively presented or accessible in non-native forms of SOD1 or a control nucleic acid at 2, 6, 8, 12, 16 and 20 weeks.

The progression of the disease is assessed by monitoring the accumulation of hα-syn in the brain of the mice and clinical features of neurological involvement (See Masliah E et al. (70)).

Vaccination with a nucleic acid encoding an epitope selectively presented or accessible in non-native forms of SOD1 prevents Parkinson's disease. Delay or abrogation of SOD1 aggregation and disease onset occurs for therapeutically active nucleic acid, and not for controls.

Example 32

Antibody Infusion of Hα-syn tg Mice

The hα-syn tg mice are infused with antibodies that bind to epitopes selectively presented or accessible in non-native forms of SOD1 or isotype control antibodies.

Slowing or arrest of SOD1 aggregation and disease progression occurs for therapeutically active antibodies, with no effect from isotype control antibodies. Autoimmunity is monitored.

The progression of the disease is assessed by monitoring the accumulation of hα-syn in the brain of the mice and clinical features of neurological involvement (See Masliah E et al. (70)).

Example 33

Administration of Isolated Peptides to ALS Patients

Compositions comprising ALS-specific epitopes such as GGGRLAC*GVIGIGSG (SEQ ID NO: 65), (DSE1a), DLGKGGNEESTKTGNAGS (SEQ ID NO: 2), (DSE2) and IKGLTEGLHGF (SEQ ID NO: 5), (DSE5) are administered to human ALS patients. The compositions are administered to ALS patients.

Patients are monitored for indications of slowing or arrest of SOD aggregation and disease progression.

Subjects are monitored regularly for adverse effects such as signs of pain and distress that might be a result of the immunizations. Autoimmune manifestations are monitored.

Administration of the ALS-specific epitopes GGGRLAC*GVIGIGSG (SEQ ID NO: 65), (DSE1a), DLGKGGNEESTKTGNAGS (SEQ ID NO: 2), (DSE2) and IKGLTEGLHGF (DSE5) slows the progression of ALS. Slowing or arrest of SOD1 aggregation or abrogation of disease progression occurs for therapeutically active epitopes.

Example 34

Administration to ALS Patients

Antibodies

Antibodies directed against the ALS-specific epitopes comprising of GGGRLAC*GVIGIGSG (SEQ ID NO: 65), (DSE1a), DLGKGGNEESTKTGNAGS (SEQ ID NO: 2), (DSE2) and IKGLTEGLHGF (SEQ ID NO: 5), (DSE5) are administered to human ALS patients. The antibodies are administered to the subjects at 6, 8, 12, 16 and 20 weeks.

Patients are monitored for indications of slowing or arrest of SOD aggregation and disease progression. Autoimmune manifestations are also monitored.

Subjects are monitored regularly for adverse effects such as signs of pain and distress that might be a result of the immunizations. Autoimmune manifestations are monitored.

Administration of antibodies directed against the ALS-specific epitopes GGGRLAC*GVIGIGSG (SEQ ID NO: 65), (DSE1a), DLGKGGNEESTKTGNAGS (SEQ ID NO: 2), (DSE2) and IKGLTEGLHGF (SEQ ID NO: 5), (DSE5) slows the progression of ALS. Slowing or arrest of SOD1 aggregation or abrogation of disease progression occurs for therapeutically active antibodies.

Example 35

Administration of Humanized Antibodies to ALS Patients

Humanized antibodies directed against amyotrophic lateral sclerosis-specific epitopes are administered to human ALS patients. Patients are monitored for indications of slowing or arrest of SOD aggregation and disease progression. Administration of a humanized antibody directed to a ALS disease specific epitope slows the progression ALS disease in patients. Slowing or arrest of SOD1 aggregation or abrogation of disease progression occurs for therapeutically active antibodies.

Humanized antibodies directed against the ALS-specific epitopes comprising GGGRLAC*GVIGIGSG (SEQ ID NO: 65), (DSE1a), DLGKGGNEESTKTGNAGS (SEQ ID NO: 2), (DSE2) and IKGLTEGLHGF (SEQ ID NO: 5), (DSE5) peptides are administered to human ALS patients. A pharmaceutical composition comprising 1-140 grams (up to 2 grams/kilo) of the humanized antibodies is administered by intravenous infusion to produce a local concentration that ranges from 1 to 10 micrograms per ml in the CNS. In one regimen, the formulation comprises an antibody directed against one ALS-specific epitope. In another regimen, the formulation comprises two or more humanized antibodies, each directed against a different ALS-specific epitope. The dosing regimen will vary on the physiological condition of the patients and the response of the patient to treatment. In one dosing regimen, the dosing is once every 3 or 4 weeks. In other regimens, dosing is once per week, twice per week, three times per week, or once per 2 weeks.

Example 36

Intraventricular or Intrathecal Administration of Humanized Antibodies to ALS Patients Humanized antibodies against ALS-specific epitopes are directly administered into the CNS of ALS patients by intraventricular or intrathecal infusion using an infusion pump such as the infusion pumps produced by MedTronics (Minneapolis, Minn., USA). ALS patients are infused with 0.5 to 5 mg per day of humanized antibody to obtain an end concentration of 1-10 micrograms per ml in the CNS infused at a maximal rate of 1 ml/h. In one regimen, the formulation comprises an antibody directed against one ALS-specific epitope. In another regimen, the formulation comprises two or more humanized antibodies, each directed against a different ALS-specific epitope.

When humanized antibodies are administered to ALS patients by intrathecal injection an equal volume of cerebrospinal fluid is withdrawn through the same needle used for the injection to avoid an increase in pressure due to the injection volume. Subjects are given a dose that ranges from 1% to 10% of the corresponding systemic dose. Subjects receive a single dose of the humanized antibody formulation. Alternatively, subjects receive multiple doses of the humanized antibody formulation. In one regimen, the formulation comprises an antibody directed against one ALS-specific epitope. In another regimen, the formulation comprises two or more humanized antibodies, each directed against a different ALS-specific epitope. In alternate regimens, dosing is once per week, twice per week, three times per week, once every two weeks, once every three weeks or once every month. In another regimen, the dosing varies depending on the physiological condition of the subject and the response of the subject to the treatment.

Patients are monitored for indications of slowing or arrest of SOD aggregation and disease progression. Administration of a humanized antibody directed to a ALS disease specific epitope slows the progression ALS disease in patients. Slowing or arrest of SOD1 aggregation or abrogation of disease progression occurs for therapeutically active antibodies.

Example 37

Administration to Alzheimer's Disease Patients

Epitopes

The Alzheimer's disease-specific epitope DLGKGGNEESTKTGNAGS (SEQ ID NO: 2), (DSE2) is administered to human Alzheimer's disease patients. The epitopes are administered.

Patients are monitored for indications of slowing or arrest of SOD aggregation and disease progression. In particular, the memory of the subjects is tested and their behaviour is monitored. Autoimmune manifestations are also monitored.

Subjects are monitored regularly for adverse effects such as signs of pain and distress that might be a result of the immunizations. Autoimmune manifestations are also monitored.

Administration of the Alzheimer's disease-specific epitope DLGKGGNEESTKTGNAGS (SEQ ID NO: 2), (DSE2) slows the progression of Alzheimer's disease. Slowing or arrest of SOD1 aggregation or abrogation of disease progression occurs for therapeutically active epitopes.

Example 38

Administration to Alzheimer's Disease Patients

Antibodies

An antibody directed against the Alzheimer's disease-specific epitope DLGKGGNEESTKTGNAGS (SEQ ID NO: 2), (DSE2) is administered to human Alzheimer's disease patients.

Patients are monitored for indications of slowing or arrest of SOD aggregation and disease progression. In particular, the memory of the subjects is tested and their behaviour is monitored. Autoimmune manifestations are also monitored.

Subjects are monitored regularly for adverse effects such as signs of pain and distress that might be a result of the immunizations. Autoimmune manifestations are monitored.

Administration of an antibody directed to the Alzheimer's disease-specific epitope DLGKGGNEESTKTGNAGS (SEQ ID NO: 2), (DSE2) slows the progression of Alzheimer's disease. Slowing or arrest of SOD1 aggregation or abrogation of disease progression occurs for therapeutically active antibodies.

Example 39

Administration of Humanized Antibodies to Alzheimer's Disease Patients

Humanized antibodies directed against Alzheimer's disease-specific epitopes are administered to human Alzheimer's disease patients. The humanized antibodies are administered by intravenous infusion at a concentration that ranges from 1 to 10 micrograms per ml local concentration in the CNS. In one regimen, the formulation comprises an antibody directed against one Alzheimer's disease-specific epitope. In another regimen, the formulation comprises two or more humanized antibodies, each directed against a different Alzheimer's disease-specific epitope. In one dosing regimen, the dosing is once every 3 weeks. In other regimens, dosing is once per week, twice per week, three times per week, or once per 2 weeks. Alternatively, dosing varies depending on the physiological condition of the patients and the response of the patient to treatment.

Alternatively, humanized antibodies against Alzheimer's disease-specific epitope are directly administered into the CNS of Alzheimer's disease patients by intraventricular or intrathecal infusion. MedTronics (Minneapolis, Minn., USA) provides medical devices for use in this example. The end concentration of 1-10 micrograms per ml is achieved by infusion of as much as 5 mg of the humanized antibody per day at a maximal rate of 1 ml/h. In one regimen, the formulation comprises an antibody directed against one Alzheimer's disease-specific epitope. In another regimen, the formulation comprises two or more humanized antibodies, each directed against a different Alzheimer's disease-specific epitope.

Humanized antibodies are administered to Alzheimer's disease patients by intrathecal injection. To avoid an increase in pressure due to the injection volume, an equal volume of cerebrospinal fluid is withdrawn through the same needle used for the injection. Subjects are given a dose that ranges from 1% to 10% of the corresponding systemic dose. Subjects receive a single dose of the humanized antibody formulation. Alternatively, subjects receive multiple doses of the humanized antibody formulation. In one regimen, the formulation comprises an antibody directed against one Alzheimer's disease-specific epitope. In another regimen, the formulation comprises two or more humanized antibodies, each directed against a different Alzheimer's disease-specific epitope. In alternate regimens, dosing is once per week, twice per week, three times per week, once every two weeks, once every three weeks or once every month. In another regimen, the dosing varies depending on the physiological condition of the subject and the response of the subject to the treatment.

Patients are monitored for indications of slowing or arrest of SOD aggregation and disease progression. Administration of a humanized antibody directed to a Alzheimer's disease specific epitope slows the progression of Alzheimer's disease

Example 40

Administration to Parkinson's Disease Patients

Epitopes

A Parkinson's disease specific epitope is administered to human Parkinson's disease patients.

Patients are monitored for indications of slowing or arrest of SOD aggregation and disease progression. In particular, the gait, reflex and behaviour of subjects are monitored. Autoimmune manifestations are also monitored.

Subjects are monitored regularly for adverse effects such as signs of pain and distress that might be a result of the immunizations.

Administration of a Parkinson's disease specific epitope slows the progression of Parkinson's disease. Slowing or arrest of SOD1 aggregation or abrogation of disease progression occurs for therapeutically active epitopes,

Example 41

Administration to Parkinson's Disease Patients

Antibodies

An antibody directed against a Parkinson's disease specific epitope is administered to human Parkinson's disease patients.

Patients are monitored for indications of slowing or arrest of SOD aggregation and disease progression. In particular, the gait, reflex and behaviour of subjects are monitored. Autoimmune manifestations are also monitored.

Subjects are and monitored regularly for adverse effects such as signs of pain and distress that might be a result of the immunizations. Administration of an antibody directed to a Parkinson's disease specific epitope slows the progression of Parkinson's disease in patients. Slowing or arrest of SOD1 aggregation or abrogation of disease progression occurs for therapeutically active antibodies

Example 42

Administration of Humanized Antibodies to Parkinson's Disease Patients

Humanized antibodies directed against Parkinson's disease-specific epitopes are administered to human Parkinson's disease patients. The humanized antibodies are administered by intravenous infusion at a concentration that ranges from 1 to 10 micrograms per ml local concentration in the CNS. In one regimen, the formulation comprises an antibody directed against one Parkinson's disease-specific epitope. In another regimen, the formulation comprises two or more humanized antibodies, each directed against a different Parkinson's disease-specific epitope. In one dosing regimen, the dosing is once every 3 weeks. In other regimens, dosing is once per week, twice per week, three times per week, or once per 2 weeks. Alternatively, dosing varies depending on the physiological condition of the patients and the response of the patient to treatment.

Alternatively, humanized antibodies against Parkinson's disease-specific epitopes are directly administered into the CNS of Parkinson's disease patients by intraventricular or intrathecal infusion. MedTronics (Minneapolis, Minn., USA) provides medical devices for use in this example. The end concentration of 1-10 micrograms per ml is achieved by infusion of as much as 5 mg of the humanized antibody per day at a maximal rate of 1 ml/h. In one regimen, the formulation comprises an antibody directed against one Parkinson's disease-specific epitope. In another regimen, the formulation comprises two or more humanized antibodies, each directed against a different Parkinson's disease-specific epitope.

Humanized antibodies against Parkinson's disease-specific epitopes are administered to Parkinson's disease patients by intrathecal injection. To avoid an increase in pressure due to the injection volume, an equal volume of cerebrospinal fluid is withdrawn through the same needle used for the injection. Subjects are given a dose that ranges from 1% to 10% of the corresponding systemic dose. Subjects receive a single dose of the humanized antibody formulation. Alternatively, subjects receive multiple doses of the humanized antibody formulation. In one regimen, the formulation comprises an antibody directed against one Parkinson's disease-specific epitope. In another regimen, the formulation comprises two or more humanized antibodies, each directed against a different Parkinson's disease-specific epitope. In alternate regimens, dosing is once per week, twice per week, three times per week, once every two weeks, once every three weeks or once every month. In another regimen, the dosing varies depending on the physiological condition of the subject and the response of the subject to the treatment.

Patients are monitored for indications of slowing or arrest of SOD aggregation and disease progression. Administration of a humanized antibody directed to a Parkinson's disease specific epitope slows the progression of Parkinson's disease in patients. Slowing or arrest of SOD1 aggregation or abrogation of disease progression occurs for therapeutically active antibodies.

Example 43

Breeding of ALS Mice Models G93A and G37R

Founder hemizygous male G93A and G37R animals will be bred with wild-type female mice of the same background strain (C57BL/6). Females were not bred more than 6 times. Heterozygous G93A males were retired as breeders at 3 months of age, heterozygous G37R mice were retired as breeders at 6 months of age.

Fifteen hemizygous G93A (or G37R) male mice and 30 C57BL/6 female mice formed 15 breeding trios. Two female mice were initially housed together, and estrus were induced by exposing the females to the dirty bedding of their mate (Whitten effect). The next day, the females were introduced into the male cages (2 females per male). Females were checked each morning for plugs.

Offspring were identified with ear punching at 3 weeks of age, and the punched tissue was used for genotyping. and to determine transgene copy number. If ear punches did not provide sufficient material for genotyping and testing for transgene copy number, then tail clipping was performed.

Weaning took place when offspring were 3 weeks old, and hemizygous mice were randomized to experimental treatment groups.

After weaning, animals were kept 4 per cage.

A similar breeding program was used for both strains, with appropriate adjustments for survival of hemizygous animals that develop disease phenotypes (G93A survival ~145 days, G37R survival ~335 days). G93A heterozygote mice developed hindlimb predominant weakness at about age 100 days. Weakness progressed to a point of hindlimb paralysis, and animals were not be able to feed or drink (i.e. unable to reach their food and water). This point was observed around 145 days. At this point, animals were euthanized. Animals were euthanized earlier, if their body weight decreased by 20%, or if they displayed other signs of serious morbidity.

The G37R transgene caused similar clinical signs as the G93A transgene, however age at onset of weakness in heterozygotes was about 300 days, from which point weakness progressed to hindlimb paralysis. Endpoints were the same as for the G93A mice, however endpoints were usually met around 335 days in the G37R (line 29) transgenic.

Breeding mice were weighed weekly and were euthanized if they lost 15% or more of their body weight. However, weight loss less than 15% combined with other signs of serious morbidity ie. ruffled fur, hunched appearance, obvious dehydration, etc., were considered a humane endpoint for these animals.

Example 44

Development of ALS Propagation Models

In ALS, as in prion disease, neuronal death "spreads" throughout the neuroaxis, implicating a pathological mechanism for propagation of the pathological process from cell to cell. A model is developed of SOD1 misfolding propagation in cell-free systems, in cellular assays in vitro, and in animals based on similar model systems in prion disease. These models provide more "disease relevant" systems for testing immunotherapies, and will circumvent the potential false negative and false positive outcomes of current models.

Biological deposits of hybridoma cell lines were made in accordance with the Budapest Treaty and are available from the International Depository Authority of Canada 1015 Arlington Street Winnipeg, Canada R3E 3R2.

Example 45

Immunohistochemical Analysis of Patient Disease Tissues

Methods

A mouse monoclonal antibody to DSE2 (10E11C11) was evaluated by immunohistochemistry on human formalin-fixed, paraffin-embedded sections of normal tissues, including tissues from young and old individuals, as well as disease tissue. An antibody concentration of 3 ug/ml was selected based on serial dilutions and previous experience with the antibody. Antibody DSE2 was used as the primary antibody and the principal detection system consisted of a Vector anti-mouse secondary (BA-2000) and a Vector ABC-AP kit (AK-5000) with a Vector Red substrate kit (SK-5100) which produced a fuchsia-colored deposit). Tissues were also stained with positive control antibodies CD31 and vimentin, to ensure the tissue antigens were preserved and accessible for immunohistochemical analysis. The negative control consisted of performing the entire immunohistochemical procedure on adjacent sections in the absence of primary antibody. Slides were imaged with a DVC 1310C digital camera coupled to a Nikon microscope.

Brain, cortex, ischemic stroke

A sample of brain was obtained from a patient of unknown age and sex. The H&E-stained (hematoxylin and eosin stained) section showed largely non-cortical tissue with recent ischemic infarction associated with perivascular hemorrhage consistent with reperfusion. There was neutrophilic and histocytic infiltration of the injured tissue.

Antibody DSE2 showed strong staining that formed beaded patterns along processes consistent with axons in the ischemic area, with strong staining of aggregates within the parenchyma and around vessels. Compared to normal brain, stroke samples showed increased staining of injured axons and diminished staining of neurons.

A second sample of brain, obtained at autopsy from a 66 year old female with recent ischemia infarction and areas of selective neuronal necrosis, was also stained using the DSE2 antibody. The necrotic area had reduced neuropil staining with sparsely distributed focal strong staining areas, some of which had the appearance of processes. There was faint staining of many of the ischemic neurons and astrocytes within the infracted area.

A third sample of brain, taken at autopsy from a 45 year old male and showing recent infarction, was assessed using the DSE2 antibody and revealed, generally, a reduced staining of neurons and neuropil, and increased staining of injured axons.

Brain, multiple sclerosis

Samples of cerebral cortex were obtained at autopsy from two female patients, ages 51 and 53. Each sample showed areas of demyelination within the white matter. Compared to normal brain, both samples showed increased DSE2 nuclear staining of glial cells and endothelia, including paranuclear staining in one of the samples.

Colon, ulcerative colitis

A sample of colon was obtained at surgery from a 63 year old male. The H&E stained section showed ulceration and reactive epithelial changes with chronic active inflammation, consistent with ulcerative colitis. There were regions of moderate to strong staining of reactive surface and superficial glandular epithelial cells. Staining was increased and more diffuse than in normal tissue.

In a second sample, obtained from at surgery from a 52 year old male and showing ulceration and reactive epithelial changes with chronic active inflammation consistent with ulcerative colitis, there were regions of moderate staining of reactive surface and superficial glandular epithelial cells. Staining was more diffuse than in normal tissue.

In a third sample, obtained at surgery from a 13 year old male and showing colon with chronic active mucosal inflammation with crypt abscesses consistent with ulcerative colitis, glandular cells showed focal moderate paranuclear staining. *Muscularis propria* and *myenteric plexus* showed blush staining. Compared to normal samples, there was increased staining of reactive surface epithelium.

By comparison, samples of normal colon showed either no staining or faint staining at some locations, but were generally negative for DSE2 immunoreactivity.

Heart, myocardial infarct

A sample of heart was obtained at autopsy from an 80 year old female who died of coronary arteriosclerosis. The H&E stained section showed myocardium with areas of ischemic necrosis focally accompanied by neutrophil infiltration. Cardiac myocytes showed blush staining with DSE2 antibody, including recently infracted myocardium. Moderate DSE2 granular positively was present admixed with acute inflammatory infiltrate in this area. Compared to normal heart, this sample showed increased staining of myocytes adjacent to areas of infarction. There were regions of moderate to strong staining of reactive surface and superficial glandular epithelial cells. Staining was increased and more diffuse than in normal tissue.

In a second sample, obtained from at autopsy from a person of unknown age and gender, H&E staining showed myocardium with areas of ischemic necrosis accompanied by regions of neutrophilic infiltration. Compared to normal heart, this sample showed increased DSE2 staining of myocytes bordering areas of infarction.

A third sample obtained at autopsy from a male patient of unknown age showed patchy subendocardial regions of ischemic necrosis, with focal adjacent old fibrosis and surrounding myocytolysis. There was loss of staining of DSE2 the necrotic areas, with increased staining of a rim around the surrounding myocardium. Uninvolved myocardium showed negative to faint staining. Vessels and fat were negative.

It will thus be appreciated that antibodies to a misfolded epitope of SOD1 reveal the presence of misfolded SOD1 in a variety of tissues and structures internal thereto, including tissues associated with diseases associated with inflammation neurodegeneration and/or with ischemia and infarction.

Example 46

Administration to Stroke Patients

Antibodies

An antibody or a binding fragment thereof directed against a non-native form of SOD1 is administered to a patient that is experiencing, has experienced or is at risk of experiencing stroke.

An antibody is administered by intravenous infusion with 100 micrograms to 10 mg per infusion giving approximately at a concentration that ranges from 1 to 10 micrograms per ml local concentration in the CNS. In other protocols, the antibody dose is escalated. In one regimen antibody is administered by intravenous infusion at an initial dose of 3 mg per infusion and escalated gradually to 30 mg infusion per day up to 3 times a week for a total dose of 90 mg. In another protocol the initial does is 5 mg. In another protocol, the total dose administered is 100 mg. In another protocol up to 5 grams are infused via intravenous infusion. In one regimen, the formulation comprises an antibody or binding fragment thereof directed against one non-native SOD1 disease-specific epitope such as an antibody or binding fragment thereof directed against DSE2. In another regimen, the formulation comprises two or more humanized antibodies, each directed against a different non-native SOD1 disease-specific epitope such as an antibody directed against DSE2 and another antibody directed against DSE1a. The formulation is optionally administered prior to ischemia in a patient at risk of experiencing a stroke, or during an ischemic attack including the period of reperfusion, such as that following recanalization of blocked arteries treated with intravenous or intraarterial infusion of tissue plasminogen activator. In one dosing regimen, the dosing is a single bolus. In a different dosing regimen, the dosing is once every 3 weeks. In other regimens, dosing is once per week, twice per week, three times per week, or once per 2 weeks. Alternatively, dosing varies depending on the physiological condition of the patients and the response of the patient to treatment.

Patients are monitored for indications of slowing or arrest of non-native SOD1 cytotoxicity and stroke severity. Patients are monitored for behaviour such as increased use of impaired limbs, and/or recovery of pre-stroke physical and mental abilities. As well patients are optionally monitored for reduction of infarct size using imaging techniques such as magnetic resonance imaging.

Subjects are and monitored regularly for adverse effects such as signs of pain and distress that might be a result of the antibody administration. Administration of an antibody or fragment thereof directed to a non-native form of SOD1 reduces the cytotoxicity of non-native forms of SOD1 and may reduce the necrotic lesion in patients who have suffered a stroke. Slowing or arrest of misfolded SOD1 cytotoxicity and disease severity occurs for therapeutically active antibodies and binding fragments thereof.

Example 47

Administration of Humanized Antibodies to Stroke Patients

A humanized antibody or binding fragments thereof directed against an epitope present in non-native forms of SOD1 is administered to a patient who is experiencing, has experienced or is at risk of experiencing a stroke. The humanized antibody is administered by intravenous infusion with 100 micrograms to 10 mg per infusion giving approximately at a concentration that ranges from 1 to 10 micrograms per ml local concentration in the CNS. In other protocols, the antibody dose is escalated. In one regimen antibody is administered by intravenous infusion at an initial dose of 3 mg per infusion and escalated gradually to 30 mg infusion per day up to 3 times a week for a total dose of 90 mg. In another protocol the initial does is 5 mg. In another protocol, the total dose administered is 100 mg. In another protocol up to 5 grams are infused via intravenous infusion. In one regimen, the formulation comprises an antibody or binding fragment thereof directed against one non-native SOD1 disease-specific epitope such as an antibody or binding fragment thereof directed against DSE2. In another regimen, the formulation comprises two or more humanized antibodies, each directed against a different non-native SOD1 disease-specific epitope such as an antibody directed against DSE2 and another antibody directed against DSE1a. The formulation is optionally administered prior to ischemia in a patient at risk of experiencing a stroke, or during an ischemic attack including the period of reperfusion, such as that following recanalization of blocked arteries treated with intravenous or intraarterial infusion of tissue plasminogen activator. In one dosing regimen, the dosing is a single bolus. In a different dosing regimen, the dosing is once every 3 weeks. In other regimens, dosing is once per week, twice per week, three times per week, or once per 2 weeks. Alternatively, dosing varies depending on the physiological condition of the patients and the response of the patient to treatment.

Alternatively, humanized antibodies against non-native SOD1 disease-specific epitopes are directly administered into the stroke site by intrathecal or intraventricular infusion or by an implantable pump. MedTronics (Minneapolis, Minn., USA) provides medical devices for use in this example. The end concentration of 1-10 micrograms per ml is achieved by infusion of as much as 10 mg of the humanized antibody per day at a maximal rate of 1 ml/h In one regimen, the formulation comprises an antibody directed against one non-native SOD1 disease specific epitope. In another regimen, the formulation comprises two or more humanized antibodies, each directed against a different SOD1 disease-specific epitope.

Humanized antibodies against non-native SOD1 disease-specific epitopes are administered to stroke patients by intrathecal injection. To avoid an increase in pressure due to the injection volume, an equal volume of cerebrospinal fluid is withdrawn through the same needle used for the injection. Subjects are given a dose that ranges from 1% to 10% of the corresponding systemic dose. Subjects receive a single dose of the humanized antibody formulation. Alternatively, subjects receive multiple doses of the humanized antibody formulation. In one regimen, the formulation comprises an antibody directed against one non-native SOD1 disease-specific epitope. In another regimen, the formulation comprises two or more humanized antibodies, each directed against a different non-native SOD1 disease-specific epitope. In alternate regimens, dosing is a single bolus, once per week, twice per week, three times per week, once every two weeks, once every three weeks or once every month. In another regimen, the dosing varies depending on the physiological condition of the subject and the response of the subject to the treatment.

Patients are monitored for indications of slowing or arrest of SOD1 cytotoxicity and disease severity. Administration of a humanized antibody directed to a non-native SOD1 disease specific epitope slows the severity of stroke disease in patients. Slowing or arrest of SOD1 cytotoxicity or abrogation of disease severity occurs for therapeutically active antibodies.

Example 48

Administration to Myocardial Infarction Patients

Antibodies

An antibody or a binding fragment thereof directed against a non-native form of SOD1 is administered to a patient that is experiencing, has experienced or is at risk of experiencing myocardial infarction.

An antibody is administered by intravenous infusion at a concentration that ranges from 1 to 10 micrograms per ml local concentration in the heart In other protocols, the antibody dose is escalated. In one regimen antibody is administered by intravenous infusion at an initial dose of 3 mg per infusion and escalated gradually to 30 mg infusion per day up to 3 times a week for a total dose of 90 mg. In another protocol the initial does is 5 mg. In another protocol, the total dose administered is 100 mg. In another protocol up to 5 grams are infused via intravenous infusion. In one regimen, the formulation comprises an antibody or binding fragment thereof directed against one non-native SOD1 disease-specific epitope such as an antibody or binding fragment thereof directed against DSE2. In another regimen, the formulation comprises two or more humanized antibodies, each directed against a different non-native SOD1 disease-specific epitope such as an antibody directed against DSE2 and another antibody directed against DSE1a. The formulation is optionally administered prior to ischemia in a patient at risk of experiencing a heart attack, or during an ischemic attack including the period of reperfusion. In one dosing regimen, the dosing is a single bolus. In a different dosing regimen, the dosing is once every 3 weeks. In other regimens, dosing is once per week, twice per week, three times per week, or once per 2 weeks. Alternatively, dosing varies depending on the physiological condition of the patients and the response of the patient to treatment.

Patients are monitored for indications of slowing or arrest of non-native SOD1 cytotoxicity and cardiac rehabilitation. Patients are monitored for reduction of infarcted and injured tissue by blood markers, such as troponin, and electrophysiological indicators such as q-waves, ST segment elevation/depression, and arrhythmias. As well patients are optionally monitored for reduction of infarct size using imaging techniques and assessment of cardiac output.

Subjects are and monitored regularly for adverse effects such as signs of pain and distress that might be a result of the antibody administration. Administration of an antibody or fragment thereof directed to a non-native form of SOD1 reduces the cytotoxicity of non-native forms of SOD1 and may reduce the necrotic lesion in patients who have suffered a myocardial infarction. Slowing or arrest of misfolded SOD1 cytotoxicity and disease severity occurs for therapeutically active antibodies and binding fragments thereof.

Example 49

Administration of Humanized Antibodies to Myocardial Infarction Patients

A humanized antibody or binding fragments thereof directed against an epitope present in non-native forms of SOD1 is administered to a patient who is experiencing, has experienced or is at risk of experiencing a myocardial infarction. The humanized antibody is administered by intravenous infusion at a concentration that ranges from 1 to 10 micrograms per ml local concentration in the heart. In other protocols, the antibody dose is escalated. In one regimen antibody is administered by intravenous infusion at an initial dose of 3 mg per infusion and escalated gradually to 30 mg infusion per day up to 3 times a week for a total dose of 90 mg. In another protocol the initial does is 5 mg. In another protocol, the total dose administered is 100 mg. In another protocol up to 5 grams are infused via intravenous infusion. In one regimen, the formulation comprises an antibody or binding fragment thereof directed against one non-native SOD1 disease-specific epitope such as an antibody or binding fragment thereof directed against DSE2. In another regimen, the formulation comprises two or more humanized antibodies, each directed against a different non-native SOD1 disease-specific epitope such as an antibody directed against DSE2 and another antibody directed against DSE1a. The formulation is optionally administered prior to an ischemic attack in a patient at risk of experiencing a heart attack, or during an ischemic attack including the period of reperfusion. In one dosing regimen, the dosing is a single bolus. In a different dosing regimen, the dosing is once every 3 weeks. In other regimens, dosing is once per week, twice per week, three times per week, or once per 2 weeks. Alternatively, dosing varies depending on the physiological condition of the patients and the response of the patient to treatment.

Alternatively, humanized antibodies against non-native SOD1 disease-specific epitopes are directly administered into the heart by intraarterial infusion, particularly concurrent with infusion of tissue plasminogen activator. In another regimen, the formulation comprises two or more humanized antibodies, each directed against a different SOD1 disease-specific epitope.

Humanized antibodies against non-native SOD1 disease-specific epitopes are administered to heart attack patients by intraarterial injection. Subjects are given a dose that ranges from 1% to 10% of the corresponding systemic dose. Subjects receive a single dose of the humanized antibody formulation. Alternatively, subjects receive multiple doses of the humanized antibody formulation. In one regimen, the formulation comprises an antibody directed against one non-native SOD1 disease-specific epitope. In another regimen, the formulation comprises two or more humanized antibodies, each directed against a different non-native SOD1 disease-specific epitope. In alternate regimens, dosing is a single bolus, once per week, twice per week, three times per week, once every two weeks, once every three weeks or once every month. In another regimen, the dosing varies depending on the physiological condition of the subject and the response of the subject to the treatment.

Patients are monitored for indications of slowing or arrest of SOD1 cytotoxicity and disease severity. Administration of a humanized antibody directed to a non-native SOD1 disease specific epitope slows the severity of myocardial infarction in patients. Slowing or arrest of SOD1 cytotoxicity or abrogation of disease severity occurs for therapeutically active antibodies.

Example 50

Administration to Inflammatory Bowel Disease Patients

Epitopes

A vaccination composition comprising epitope present in non-native forms of SOD1 is administered to a patient with inflammatory bowel disease (IBD). The patient may be diagnosed with ulcerative colitis, Crohn's disease or a less common form of IBD.

The dosing regimen optionally comprises a single vaccination, or repeated vaccinations. Standard vaccination protocols may be used.

Patients are optionally monitored for production of antibodies to non-native forms of SOD1 and are monitored for indications of slowing or arrest of misfolded SOD1 cytotoxicity and disease. For example patients are monitored for reduction in the frequency and severity of clinical attacks of IBD as determined by pain, diarrhea, weight loss, and other clinical parameters.

Subjects are also monitored regularly for adverse effects such as signs of pain and distress that might be a result of the immunizations. Autoimmune manifestations are also monitored.

Administration of a non-native SOD1 disease specific epitope slows the progression of IBD and/or improves the management of IBD. Slowing or arrest of SOD1 cytotoxicity or abrogation of disease progression occurs for therapeutically active epitopes.

Example 51

Administration to Inflammatory Bowel Disease Patients

Antibodies

An antibody or binding fragment thereof, directed against a non-native SOD1 disease specific epitope is administered to a patient with Inflammatory Bowel Disease (IBD). The patient may be diagnosed with ulcerative colitis, Crohn's disease or a less common form of IBD.

An antibody or binding fragment thereof is administered by intravenous infusion at a concentration that ranges from 1 to 10 micrograms per ml local concentration in the bowel. In other protocols, the antibody dose is escalated. In one regimen antibody is administered by intravenous infusion at an initial dose of 3 mg per infusion and escalated gradually to 30 mg infusion per day up to 3 times a week for a total dose of 90 mg. In another protocol the initial does is 5 mg. In another protocol, the total dose administered is 100 mg. In another protocol up to 5 grams are infused via intravenous infusion. In one regimen, the formulation comprises an antibody or binding fragment thereof directed against one non-native SOD1 disease-specific epitope such as an antibody or binding fragment thereof directed against DSE2. In another regimen, the formulation comprises two or more antibodies, each directed against a different non-native SOD1 disease-specific epitope such as an antibody directed against DSE2 and another antibody directed against DSE1a. The formulation is optionally administered prior to a clinical attack, during an attack or subsequent to an attack. In one dosing regimen, the dosing is a single bolus. In a different dosing regimen, the dosing is once every 3 weeks. In other regimens, dosing is once per week, twice per week, three times per week, or once per 2 weeks. Alternatively, dosing varies depending on the physiological condition of the patients and the response of the patient to treatment.

Patients are monitored for indications of slowing or arrest of misfolded SOD1 cytotoxicity and disease. For example patients are monitored for reduction in the frequency and severity of clinical attacks of IBD as determined by pain, diarrhea, weight loss, and other clinical parameters.

Subjects are also monitored regularly for adverse effects such as signs of pain and distress that might be a result of the antibody administration.

Administration of an antibody or a binding fragment thereof specific for non-native SOD1 disease specific epitope slows the progression of IBD and/or improves the management of IBD. Slowing or arrest of SOD1 cytotoxicity or abrogation of disease progression occurs for therapeutically active epitopes.

Example 52

Administration of Humanized Antibodies to Inflammatory Bowel Disease Patients

A composition comprising a humanized antibody or binding fragment thereof directed against a non-native SOD1 epitope is administered to an Inflammatory Bowel disease (IBD) patient. The composition comprising the humanized antibody is administered by intravenous infusion at a concentration that ranges from 1 to 10 micrograms per ml local concentration in the bowel. In other protocols, the antibody dose is escalated. In one regimen antibody is administered by intravenous infusion at an initial dose of 3 mg per infusion and escalated gradually to 30 mg infusion per day up to 3 times a week for a total dose of 90 mg. In another protocol the initial does is 5 mg. In another protocol, the total dose administered is 100 mg. In another protocol up to 5 grams are infused via intravenous infusion. In one regimen, the formulation comprises an antibody directed against one non-native SOD1 disease-specific epitope. In another regimen, the formulation comprises two or more humanized antibodies, each directed against a different non-native SOD1 disease-specific epitope. In one dosing regimen, the dosing is once every 3 weeks. In other regimens, dosing is once per week, twice per week, three times per week, or once per 2 weeks. Alternatively, dosing varies depending on the physiological condition of the patients and the response of the patient to treatment.

Alternatively, a composition comprising humanized antibodies against non-native SOD1 disease-specific epitopes are directly administered into the bowel of IBD. The end concentration of 1-10 micrograms per ml is achieved by infusion of as much as 5 mg of the humanized antibody per day at a maximal rate of 1 ml/h. In one regimen, the formulation comprises an antibody directed against one non-native SOD1 disease-specific epitope. In another regimen, the formulation comprises two or more humanized antibodies, each directed against a different non-native SOD1 disease-specific epitope.

Humanized antibodies against non-native SOD1 disease-specific epitopes are administered to IBD patients in one regimen by enema. Subjects are given a dose that ranges from 1% to 10% of the corresponding systemic dose. Subjects receive a single dose of the humanized antibody formulation. Alternatively, subjects receive multiple doses of the humanized antibody formulation. In one regimen, the formulation comprises an antibody directed against one non-native SOD1 disease-specific epitope. In another regimen, the formulation comprises two or more humanized antibodies, each directed against a different non-native SOD1 disease-specific epitope. In alternate regimens, dosing is once per week, twice per week, three times per week, once every two weeks, once every three weeks or once every month. In another regimen, the dosing varies depending on the physiological condition of the subject and the response of the subject to the treatment.

Patients are monitored for indications of slowing or arrest of misfolded SOD1 cytotoxicity and disease. For example patients are monitored for reduction in the frequency and severity of clinical attacks of IBD as determined by pain, diarrhea, weight loss, and other clinical parameters.

Administration of an antibody specific for non-native SOD1 disease specific epitope slows the progression of IBD and/or improves the management of IBD. Slowing or arrest of SOD1 cytotoxicity or abrogation of disease progression occurs for therapeutically active epitopes.

Example 53

Administration to an Atherosclerosis Patient

Epitopes

A vaccination composition comprising epitope present in non-native forms of SOD1 is administered to a patient with atherosclerosis.

The dosing regimen optionally comprises a single vaccination, or repeated vaccinations. Standard vaccination protocols may be used.

Patients are optionally monitored for production of antibodies to non-native forms of SOD1 and are monitored for indications of slowing or arrest of misfolded SOD1 cytotoxicity and disease. For example patients are monitored for reduction in vascular events, such as infarction, thrombosis and/or embolus, or by evidence of improved artery lumina by angiography, computerized tomography angiography, magnetic resonance angiography, and/or Doppler ultrasound assessment of accessible arteries such as the common carotid arteries.

Subjects are also monitored regularly for adverse effects such as signs of pain and distress that might be a result of the immunizations. Autoimmune manifestations are also monitored.

Administration of a non-native SOD1 disease specific epitope slows the progression of atherosclerosis and/or improves the management of atherosclerosis. Slowing or arrest of SOD1 cytotoxicity or abrogation of disease progression occurs for therapeutically active epitopes.

Example 54

Administration to Atherosclerosis Patients

Antibodies

An antibody or binding fragment thereof, directed against a non-native SOD1 disease specific epitope is administered to a patient with atherosclerosis.

An antibody or binding fragment thereof is administered by intravenous infusion at a concentration that ranges from 1 to 10 micrograms per ml in the circulatory system. In other protocols, the antibody dose is escalated. In one regimen antibody is administered by intravenous infusion at an initial dose of 3 mg per infusion and escalated gradually to 30 mg infusion per day up to 3 times a week for a total dose of 90 mg. In another protocol the initial does is 5 mg. In another protocol, the total dose administered is 100 mg. In another protocol up to 5 grams are infused via intravenous infusion. In one regimen, the formulation comprises an antibody or binding fragment thereof directed against one non-native SOD1 disease-specific epitope such as an antibody or binding fragment thereof directed against DSE2. In another regimen, the formulation comprises two or more antibodies, each directed against a different non-native SOD1 disease-specific epitope such as an antibody directed against DSE2 and another antibody directed against DSE1a. In one dosing regimen, the dosing is a single bolus. In a different dosing regimen, the dosing is once every 3 weeks. In other regimens, dosing is once per week, twice per week, three times per week, or once per 2 weeks. Alternatively, dosing varies depending on the physiological condition of the patients and the response of the patient to treatment.

Patients are monitored for indications of slowing or arrest of misfolded SOD1 cytotoxicity and disease. For example patients are for reduction in vascular events, such as infarction, thrombosis and/or embolus, or by evidence of improved artery lumina by angiography, computerized tomography angiography, magnetic resonance angiography, and/or Doppler ultrasound assessment of accessible arteries such as the common carotid arteries.

Subjects are also monitored regularly for adverse effects such as signs of pain and distress that might be a result of the antibody administration.

Administration of an antibody or a binding fragment thereof specific for non-native SOD1 disease specific epitope slows the progression of atherosclerosis. Slowing or arrest of SOD1 cytotoxicity or abrogation of disease progression occurs for therapeutically active epitopes.

Example 55

Administration of Humanized Antibodies to Atherosclerosis Patients

A composition comprising a humanized antibody or binding fragment thereof directed against a non-native SOD1 epitope is administered to an atherosclerosis patient. The composition comprising the humanized antibody is administered by intravenous infusion at a concentration that ranges from 1 to 10 micrograms per ml local concentration in the bowel. In other protocols, the antibody dose is escalated. In one regimen antibody is administered by intravenous infusion at an initial dose of 3 mg per infusion and escalated gradually to 30 mg infusion per day up to 3 times a week for a total dose of 90 mg. In another protocol the initial does is 5 mg. In another protocol, the total dose administered is 100 mg. In another protocol up to 5 grams are infused via intravenous infusion. In one regimen, the formulation comprises an antibody directed against one non-native SOD1 disease-specific epitope. In another regimen, the formulation comprises two or more humanized antibodies, each directed against a different non-native SOD1 disease-specific epitope. In one dosing regimen, the dosing is once every 3 weeks. In other regimens, dosing is once per week, twice per week, three times per week, or once per 2 weeks. Alternatively, dosing varies depending on the physiological condition of the patients and the response of the patient to treatment.

Subjects receive a single dose of the humanized antibody formulation. Alternatively, subjects receive multiple doses of the humanized antibody formulation. In one regimen, the formulation comprises an antibody directed against one non-native SOD1 disease-specific epitope. In another regimen, the formulation comprises two or more humanized antibodies, each directed against a different non-native SOD1 disease-specific epitope. In alternate regimens, dosing is once per week, twice per week, three times per week, once every two weeks, once every three weeks or once every month. In another regimen, the dosing varies depending on the physiological condition of the subject and the response of the subject to the treatment.

Patients are monitored for indications of slowing or arrest of misfolded SOD1 cytotoxicity and disease. For example patients are for reduction in vascular events, such as infarction, thrombosis and/or embolus, or by evidence of improved artery lumina by angiography, computerized tomography angiography, magnetic resonance angiography, and/or Doppler ultrasound assessment of accessible arteries such as the common carotid arteries.

Administration of an antibody specific for non-native SOD1 disease specific epitope slows the progression of atherosclerosis. Slowing or arrest of SOD1 cytotoxicity or abrogation of disease progression occurs for therapeutically active epitopes.

Example 56

Administration to a Multiple Sclerosis Patients

Epitope

A vaccination composition comprising epitope present in non-native forms of SOD1 is administered to a patient with multiple sclerosis (MS).

The dosing regimen optionally comprises a single vaccination, or repeated vaccinations. Standard vaccination protocols may be used.

Patients are optionally monitored for production of antibodies to non-native forms of SOD1 and are monitored for indications of slowing or arrest of misfolded SOD1 cytotoxicity and disease. For example patients are monitored for reduction in the frequency and severity of MS relapses, as determined by the commonly applied disability scales, and/or neuroimaging evidence of amelioration, such as reduced plaque burden by magnetic resonance imaging, or enhanced neuronal function as evidenced by brain N-acetylaspartate levels by magnetic resonance spectroscopy.

Subjects are also monitored regularly for adverse effects such as signs of pain and distress that might be a result of the immunizations. Autoimmune manifestations are also monitored.

Administration of a non-native SOD1 disease specific epitope slows the progression of atherosclerosis and/or improves the management of atherosclerosis. Slowing or arrest of SOD1 cytotoxicity or abrogation of disease progression occurs for therapeutically active epitopes.

Example 57

Administration to MS Patients

Antibodies

An antibody or binding fragment thereof, directed against a non-native SOD1 disease specific epitope is administered to a patient with multiple sclerosis (MS).

An antibody or binding fragment thereof is administered by intravenous infusion at a concentration that ranges from 1 to 10 micrograms per ml. In other protocols, the antibody dose is escalated. In one regimen antibody is administered by intravenous infusion at an initial dose of 3 mg per infusion and escalated gradually to 30 mg infusion per day up to 3 times a week for a total dose of 90 mg. In another protocol the initial does is 5 mg. In another protocol, the total dose administered is 100 mg. In another protocol up to 5 grams are infused via intravenous infusion. In one regimen, the formulation comprises an antibody or binding fragment thereof directed against one non-native SOD1 disease-specific epitope such as an antibody or binding fragment thereof directed against DSE2. In another regimen, the formulation comprises two or more antibodies, each directed against a different non-native SOD1 disease-specific epitope such as an antibody directed against DSE2 and another antibody directed against DSE1a. In one dosing regimen, the dosing is a single bolus. In a different dosing regimen, the dosing is once every 3 weeks. In other regimens, dosing is once per week, twice per week, three times per week, or once per 2 weeks. Alternatively, dosing varies depending on the physiological condition of the patients and the response of the patient to treatment.

Patients are monitored for indications of slowing or arrest of misfolded SOD1 cytotoxicity and disease. For example patients are monitored for reduction in the frequency and severity of MS relapses, as determined by the commonly applied disability scales, and/or neuroimaging evidence of amelioration, such as reduced plaque burden by magnetic resonance imaging, or enhanced neuronal function as evidenced by brain N-acetylaspartate levels by magnetic resonance spectroscopy Subjects are also monitored regularly for adverse effects such as signs of pain and distress that might be a result of the antibody administration.

Administration of an antibody or a binding fragment thereof specific for non-native SOD1 disease specific epitope slows the progression of MS. Slowing or arrest of SOD1 cytotoxicity or abrogation of disease progression occurs for therapeutically active epitopes.

Example 58

Administration of Humanized Antibodies to Multiple Sclerosis Patients

A composition comprising a humanized antibody or binding fragment thereof directed against a non-native SOD1 epitope is administered to an multiple sclerosis (MS) patient. The composition comprising the humanized antibody is administered by intravenous infusion at a concentration that ranges from 1 to 10 micrograms per ml local concentration. In other protocols, the antibody dose is escalated. In one regimen antibody is administered by intravenous infusion at an initial dose of 3 mg per infusion and escalated gradually to 30 mg infusion per day up to 3 times a week for a total dose of 90 mg. In another protocol the initial does is 5 mg. In another protocol, the total dose administered is 100 mg. In another protocol up to 5 grams are infused via intravenous infusion. In one regimen, the formulation comprises an antibody directed against one non-native SOD1 disease-specific epitope. In another regimen, the formulation comprises two or more humanized antibodies, each directed against a different non-native SOD1 disease-specific epitope. In one dosing regimen, the dosing is once every 3 weeks. In other regimens, dosing is once per week, twice per week, three times per week, or once per 2 weeks. Alternatively, dosing varies depending on the physiological condition of the patients and the response of the patient to treatment.

Subjects receive a single dose of the humanized antibody formulation. Alternatively, subjects receive multiple doses of the humanized antibody formulation. In one regimen, the formulation comprises an antibody directed against one non-native SOD1 disease-specific epitope. In another regimen, the formulation comprises two or more humanized antibodies, each directed against a different non-native SOD1 disease-specific epitope. In alternate regimens, dosing is once per week, twice per week, three times per week, once every two weeks, once every three weeks or once every month. In another regimen, the dosing varies depending on the physiological condition of the subject and the response of the subject to the treatment.

Alternatively, humanized antibodies against non-native SOD1 disease-specific epitopes are directly administered into the CNS by intrathecal or intraventricular infusion or by an implantable pump. MedTronics (Minneapolis, Minn., USA) provides medical devices for use in this example. The end concentration of 1-10 micrograms per ml is achieved by infusion of as much as 5 mg of the humanized antibody per day at a maximal rate of 1 ml/h. In one regimen, the formulation comprises an antibody directed against one non-native SOD1 disease specific epitope. In another regimen, the formulation comprises two or more humanized antibodies, each directed against a different SOD1 disease-specific epitope.

Humanized antibodies against non-native SOD1 disease-specific epitopes are administered to MS patients by intrathecal injection. To avoid an increase in pressure due to the injection volume, an equal volume of cerebrospinal fluid is withdrawn through the same needle used for the injection. Subjects are given a dose that ranges from 1% to 10% of the corresponding systemic dose. Subjects receive a single dose of the humanized antibody formulation. Alternatively, subjects receive multiple doses of the humanized antibody formulation. In one regimen, the formulation comprises an antibody directed against one non-native SOD1 disease-specific epitope. In another regimen, the formulation comprises two or more humanized antibodies, each directed against a different non-native SOD1 disease-specific epitope. In alternate regimens, dosing is a single bolus, once per week, twice per week, three times per week, once every two weeks, once every three weeks or once every month. In another regimen, the dosing varies depending on the physiological condition of the subject and the response of the subject to the treatment.

Patients are monitored for indications of slowing or arrest of misfolded SOD1 cytotoxicity and disease. For example patients are monitored for reduction in the frequency and severity of MS relapses, as determined by the commonly applied disability scales, and/or neuroimaging evidence of amelioration, such as reduced plaque burden by magnetic resonance imaging, or enhanced neuronal function as evidenced by brain N-acetylaspartate levels by magnetic resonance spectroscopy Administration of an antibody specific for non-native SOD1 disease specific epitope slows the progression of MS and/or reduces the frequency or intensity of attacks. Slowing or arrest of SOD1 cytotoxicity or abrogation of disease progression occurs for therapeutically active epitopes.

Example 59

Immunoreactivity of DSE2 Antibodies

This example demonstrates that disease specific epitopes in SOD1 are exposed due to changes in non-native SOD1 structure or conformation; and/or due to epitope amino acid modifications such as oxidation.

Western blot analysis using a denaturing gel was performed on protein extracts derived from G93A SOD1 transgenic mouse brain, wild type mouse brain and purified erythrocyte SOD1 protein. Denaturing gels result in denaturation or loss of native protein folding putatively exposing epitopes that are not seen in properly folded or native SOD1. FIG. 9 demonstrates that antibodies that recognize the DSE2 epitope (antibody clone 3H1 in FIG. 9A and 8D1 in FIG. 9B) detect denatured human and mouse SOD1 on the immunoblot membrane, indicating that detection of this epitope in disease (e.g by immunohistochemistry in AD brains) is due to partial loss of native structure or native conformation of SOD1 which exposes the epitope in the non-native forms of SOD1.

Western blot analysis was performed on protein extracts derived from Alzheimer human brain, normal human brain and recombinant human SOD1 protein. FIG. 10A demonstrates that antibodies raised against the non-native SOD1 epitope DSE5 (clone 5C6) recognizes misfolded SOD1 in AD brain homogenates (lane 2) but not human normal brain (lane 1), suggesting that this antibody reacts with the DSE5 sequence which is stable to denaturation on immunoblotting, such as an oxidative posttranslational modification. As the epitope is not recognized in normal brain homogenates, this indicates that the epitope recognized in AD brain homogenates is stably modified in AD brain. FIGS. 10B and 10C respectively demonstrate that antibody clones 8D1 and 3H1 are unable to distinguish between misfolded SOD1 in AD brain homogenates (lane 2) and native SOD1 in normal brain (lane1), consistent with the immunoblotting data above demonstrating that denaturation of mouse or human SOD1 renders the DSE2 epitope accessible to antibody binding. FIG. 10D demonstrates that antibodies raised against non-native modified SOD1 epitope DSE1a, detect non-native forms of SOD1 present in AD brain homogenates (lane1) but not native forms of SOD1 present in normal brains. Similar to results with the DSE5 antibody, these findings suggest that binding of SOD1 DSE1a monoclonal antibody 10C12 is dominated by the cysteic acid within the sequence, and that this oxidative event occurs endogenously preferentially in brain SOD1 in diseases such as Alzheimer's disease. _Disease-selective covalent modifications of SOD1 in Alzheimer's disease, and in other diseases characterized by misfolded SOD1, provide stable targets for immunotherapy of these diseases.

While the present invention has been described with reference to what are presently considered to be the preferred examples, it is to be understood that the invention is not limited to the disclosed examples. To the contrary, the invention is intended to cover various modifications and equivalent arrangements included within the spirit and scope of the appended claims.

All publications, patents and patent applications are herein incorporated by reference in their entirety to the same extent

FULL CITATIONS FOR REFERENCES REFERRED TO IN THE SPECIFICATION

1. Urushitani M, Sik A, Sakurai T, Nukina N, Takahashi R, Julien J P. Chromogranin-mediated secretion of mutant superoxide dismutase proteins linked to amyotrophic lateral sclerosis. *Nat. Neurosci.* 2006 January; 9(1):108-18.
2. Turner B J, Atkin J D, Farg M A, Zang da W, Rembach A, Lopes E C, Patch J D, Hill A F, Cheema S S Impaired extracellular secretion of mutant superoxide dismutase 1 associates with neurotoxicity in familial amyotrophic lateral sclerosis *J Neurosci.* 2005 Jan. 5; 25(1):108-17).
3. Cashman N R, Griffin J K, Zou W-Q, Allele-selective recruitment and disease progression in familial amyotrophic lateral sclerosis. *Neurology,* 2002.
4. Cashman N R and Caughey B. Prion diseases—close to effective therapy? *Nature Reviews in Drug Discovery.* 2004 October; 3(10):874-84.
5. Rakhit R, Robertson J, Vande Velde C, Horne P, Ruth D M, Griffin J, Cleveland D W, Cashman N R, Chakrabartty A. An immunological epitope selective for pathological monomer/misfolded SOD1 in ALS. Nature Medicine, 2007 (in the press)
6. Paramithiotis E, Pinard M, Lawton T, LaBoissiere S, Leathers V L, Zou W-Q, Estey L A., Kondejewski L H, Francoeur G P, Papadopoulos M, Haghighat A, Spatz S J, Tonelli Q, Ledebur H C, Chakrabartty A, Cashman N R. A prion protein epitope selective for the pathologically misfolded conformation. *Nature Medicine* 9:893-9, 2003.
7. Lehto, M. T., Ashman, D. A. & Cashman, N. R. Treatment of ScN2a cells with prion-specific YYR antibodies. *Proc. First Intl Conf. Network Excellence: Neuroprion* (Paris, 2004).
8. Khare et al, PROTEINS: Structure, Function and Bioinformatics, 61:617-632 (2005).
9. Thompson, J D, Higgins D G, Gibson T J, 1994, *Nucleic Acids Res.* 22(22): 4673-4680.
10. Henikoff S, and Henikoff J. G., 1992, *Proc. Natl. Acad. Sci. USA* 89: 10915-10919.
11. Needleman and Wunsch. *J. Mol. Biol.,* 1970, 48:443.
12. Smith and Waterman. *Adv. Appl. Math.* 1981, 2:482.
13. Carillo and Lipton *SIAM J. Applied Math.* 1988, 48:1073.
14. Computational Molecular Biology, Lesk, e.d. Oxford University Press, New York, 1988, *Biocomputing: Informatics and Genomics Projects.*
15. Devereux et al., *Nucleic Acids Res.,* 1984, 12:387.
16. Altschul et al., *J. Molec. Biol.,* 1990: 215:403.
17. Remington's Pharmaceutical Sciences, 20th ed., Mack Publishing Company, Easton, Pa., USA, 2000.
18. Merrifield, *J. Am. Chem. Assoc.* 85:2149-2154 (1964).
19. Houbenweyl, Methods of Organic Chemistry, ed. E. Wansch, Vol. 15, pts. I and II, Thieme, Stuttgart (1987).
20. Goeddel, Gene Expression Technology: Methods in Enzymology 185, Academic Press, San Diego, Calif. 1990.
21. Sambrook et al. Molecular Cloning: A Laboratory Manual, 2nd Edition, Cold Spring Harbor Laboratory press (1989).
22. Chang et al., *Nature* 275:615 (1978).
23. Nichols and Yanofsky, *Meth. in Enzymology* 101:155, 1983.
24. Russell et al., *Gene* 20: 231, 1982.
25. Bolivar et al., *Gene* 2:9S, 1977.
26. Messing, *Meth in Enzymology* 101:20-77, 1983.
27. Vieira and Messing, *Gene* 19:259-268 (1982).
28. Amann et al., *Gene* 69:301-315 (1988).
29. Studier et al., Gene Expression Technology: Methods in Enzymology 185, Academic Press, San Diego, Calif., 60-89 (1990).
30. Baldari et al., *Embo J.* 6:229-234 (1987).
31. Kurjan and Herskowitz, *Cell* 30:933-943 (1982).
32. Schultz et al., *Gene* 54:113-123 (1987).
33. Hinnen et al., *Proc. Natl. Acad. Sci. USA* 75:1929 (1978).
34. Itoh et al., *J. Bacteriology* 153:163 (1983).
35. Cullen et al. *Bio/Technology* 5:369 (1987).
36. Seed, B., *Nature* 329:840 (1987).
37. Kaufman et al., *EMBO J.* 6:187-195 (1987).
38. Sinkar et al., *J. Biosci (Bangalore)* 11:47-58 (1987).
39. Zambryski et al., Genetic Engineering, Principles and Methods, Hollaender and Setlow (eds.), Vol. VI, pp. 253-278, Plenum Press, New York (1984).
40. Smith et al., *Mol. Cell. Biol.* 3:2156-2165 (1983).
41. Lucklow, V. A., and Summers, M. D., *Virology* 170:31-39 (1989).
42. Kohler and Milstein *Nature* 256:495-497 (1975).
43. Kozbor et al., *Immunol. Today* 4:72 (1983).
44. Cole et al., *Methods Enzymol,* 121:140-67 (1986).
45. Huse et al., *Science* 246:1275 (1989).
46. Ward et al., *Nature* 341:544-546 (1989).
47. McCafferty et al., *Nature* 348:552-554 (1990).
48. Dobson C M. (2004) Experimental investigation of protein folding and misfolding. Methods. 34(1):4-14. Review.
49. Prusiner S B. (2001) Shattuck lecture—neurodegenerative diseases and prions. N Engl J. Med. 344:1516-26.
50. Selkoe D J, Schenk D. (2003) Alzheimer's disease: molecular understanding predicts amyloid-based therapeutics. Annu Rev Pharmacol Toxicol. 43:545-84.
51. St George-Hyslop P H, Petit A. (2005) Molecular biology and genetics of Alzheimer's disease. C R Biol. 328(2):119-30.
52. Puglielli L, Tanzi R E, Kovacs D M. (2003) Alzheimer's disease: the cholesterol connection. Nat. Neurosci. 6:345-51.
53. Mehta P D, Pirttila T, Mehta S P. (2000) Plasma and cerebrospinal fluid levels of amyloid beta proteins 1-40 and 1-42 in Alzheimer disease. Arch Neurol. 57:100-5.
54. Clark C M, Xie S, Chittams J et al. (2003) Cerebrospinal fluid tau and beta-amyloid: how well do these biomarkers reflect autopsy-confirmed dementia diagnoses? Arch Neurol. 60:1696-702.
55. Green A J. (2002) Cerebrospinal fluid brain-derived proteins in the diagnosis of Alzheimer's disease and Creutzfeldt-Jakob disease. Neuropathol Appl Neurobiol. 28:427-40.
56. Schenk D, Barbour R, Dunn W, Gordon G, Grajeda H, Guido T, Hu K, Huang J, Johnson-Wood K, Khan K, Kholodenko D, Lee M, Liao Z, Lieberburg I, Motter R, Mutter L, Soriano F, Shopp G, Vasquez N, Vandevert C, Walker S, Wogulis M, Yednock T, Games D, Seubert P. (1999) Immunization with amyloid-beta attenuates Alzheimer-disease-like pathology in the PDAPP mouse. Nature. 400(6740):173-7.
57. Gilman S, Koller M, Black R S, Jenkins L, Griffith S G, Fox N C, Eisner L, Kirby L, Rovira M B, Forette F, Orgogozo J M; AN1792(QS-21)-201 Study Team. (2005) Clinical effects of Abeta immunization (AN1792) in patients with AD in an interrupted trial. Neurology. 64(9): 1553-62.
58. Fox N C, Black R S, Gilman S, Rossor M N, Griffith S G, Jenkins L, Koller M; AN1792(QS-21)-201 Study Team.

(2005) Effects of Abeta immunization (AN1792) on MRI measures of cerebral volume in Alzheimer disease. Neurology. 64(9):1563-72.
59. Olanow C W. (2004) The scientific basis for the current treatment of Parkinson's disease. Annu Rev Med 55:41-60.
60. Iwatsubo T. (2003) Aggregation of alpha-synuclein in the pathogenesis of Parkinson's disease. J Neurol 250 Suppl 3:III11-4.
61. Eriksen J L, Dawson T M, Dickson D W, Petrucelli L. (2003) Caught in the ac: alpha-synuclein is the culprit in Parkinson's disease. Neuron 40:453-6.
62. McKeith I, Mintzer J, Aarsland D et al. (2004) Dementia with Lewy bodies. Lancet Neurol 3:19-28.
63. Masliah E, Rockenstein E, Adame A, Alford M, Crews L, Hashimoto M, Seubert P, Lee M, Goldstein J, Chilcote T, Games D, Schenk D. (2005) Effects of alpha-synuclein immunization in a mouse model of Parkinson's disease. Neuron. 46(6):857-68.
64. Choi J, Rees H D, Weintraub S T, et al. (2005) Oxidative modifications and aggregation of Cu,Zn-superoxide dismutase associated with Alzheimer and Parkinson diseases. J. Bio. Chem.; 280(12): 11648-11655.
65. Janus, C. et al. (2000) Nature 408:979-982.
66. Janus, C. (2000) Neurobiology of Aging 21: 541-549.
67. Gass, P. et al. (1998) Learn Mem. 5:274-288.
68. Wehner, J. M. (1990) Brain Research 523: 181-187).
69. Masliah, E. et al. (2000) Science 287:1265-1269.
70. Masliah, E. et al. (2005) Neuron 46:857-868.
71. Kayed, R. et al. Common structure of soluble amyloid oligomers implies common mechanism of pathogenesis. Science 300, 486-9 (2003).
72. Deng, H. X. et al. Amyotrophic lateral sclerosis and structural defects in Cu,Zn superoxide dismutase. Science 261, 1047-51 (1993).
73. Andersen P M. Genetics of sporadic ALS. Amyotroph Lateral Schler Other Motor Neuron Disord. Suppl1:S37-41 (2001).
74. Trojanowski et al 2000 Ann NY Acad Sci 924:62-7.
75. Calne et al 1989; Can J Neurol Sci 16:547-50.
76. Shaw et al., 2002. Cell Mol Biol 48:127-36.
77. Olivieri et al 2001. J Neurochem 76:224-33.
78. Shimohama et al 1999. Rinsho Shinkeigaku 39:4-6.
79. Keller et al 1998. Rev Neurosci 9:105-16.
80. Simonian et al 1996. Annu Rev Pharmacol Toxicol 36:83-106.
81. Imam et al 2001. Ann NY Acad Sci 939:366-80).
82. Lazoura, E and Apostolopoulos, V. Rational Peptide-based vaccine design for cancer immunotherapeutic applications Curr Med Chem. (2005) 12:629-39.
83. Hensley K, Carney J M, Mattson M P, Aksenova M, Harris M, Wu J F, Floyd R A, Butterfield D A. A model for b-amyloid aggregation and neurotoxicity based on free radical generation by the peptide: Relevance to Alzheimer disease. Proc Natl Acad Sci USA 91: 3270-3274 (1994).
84. Elam J S, Taylor A B, Strange R, Antonyuk S, Doucette P A, Rodriguez J A, Hasnain S S, Hayward L J, Valentine J S, Yeates T O, Hart P J. Nat Struct Biol (2003) 10:461-7.
85. Kolaskar, A S and Tongaonkar P C, FEBS Lett. (1990) 276:172-4

---

I claim:

1. A method for treating familial Amyotrophic Lateral Sclerosis (ALS) mediated by a misfolded form of human superoxide dismutase 1 (SOD1) in a subject in need of treatment, the method comprising administering to the subject a composition comprising a pharmaceutically acceptable vehicle and an exogenous antibody or binding fragment thereof that binds selectively to all or part of SEQ ID NO:77, wherein administering said antibody treats the condition.

2. The method according to any claim 1, wherein the misfolded form of human SOD1 comprises SOD1 monomer and/or an aggregate comprising SOD1 monomer.

3. The method according to claim 2, wherein the human SOD1 monomer comprises a misfolded wild type SOD1 monomer.

4. The method according to claim 1, wherein the misfolded form of human SOD1 comprises a misfolded SOD1 dimer and/or aggregates of misfolded SOD1 dimer.

5. The method according to claim 4, wherein the misfolded SOD1 dimer is wild type SOD1 dimer.

6. The method according to claim 1, wherein the exogenous antibody or binding fragment thereof binds at least 5 amino acids of SEQ ID NO:77.

7. The method of claim 1 wherein the exogenous antibody or binding fragment thereof binds selectively to all or part of SEQ ID NO:77, wherein one or more of lysine (K), phenylalanine (F) and histidine (H) is oxidized and/or phenylalanine (F) is nitrated.

8. The method of claim 1 wherein the exogenous antibody or binding fragment thereof binds selectively to all or part of SEQ ID NO:5.

9. The method of claim 6, wherein the at least 5 amino acids of SEQ ID NO:77 comprises LHGF.

10. The method of claim 9, wherein the LHGF is comprised in the sequence LHGFHVH (SEQ ID NO:71).

11. The method of claim 1, wherein the exogenous antibody is the C56 antibody produced by the hybridoma deposited with International Depository of Canada under accession number 280207-01.

* * * * *